US009775829B2

(12) United States Patent
Teegarden et al.

(10) Patent No.: US 9,775,829 B2
(45) Date of Patent: *Oct. 3, 2017

(54) DIARYL AND ARYLHETEROARYL UREA DERIVATIVES AS MODULATORS OF THE 5-HT2A SEROTONIN RECEPTOR USEFUL FOR THE PROPHYLAXIS AND TREATMENT OF DISORDERS RELATED THERETO

(71) Applicant: Arena Pharmaceuticals, Inc., San Diego, CA (US)

(72) Inventors: Bradley Teegarden, San Diego, CA (US); Honnappa Jayakumar, San Diego, CA (US); Hongmei Li, Warren, NJ (US); Sonja Strah-Pleynet, Newton, MA (US); Peter I. Dosa, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/013,057

(22) Filed: Feb. 2, 2016

(65) Prior Publication Data
US 2016/0374990 A1 Dec. 29, 2016

Related U.S. Application Data

(60) Continuation of application No. 14/332,207, filed on Jul. 15, 2014, now Pat. No. 9,273,035, which is a division of application No. 13/619,137, filed on Sep. 14, 2012, now Pat. No. 8,871,797, which is a division of application No. 10/895,789, filed on Jul. 21, 2004, now Pat. No. 8,754,238.

(Continued)

(51) Int. Cl.
| | | |
|---|---|---|
| A61K 31/415 | (2006.01) |
| C07D 231/12 | (2006.01) |
| C07D 231/16 | (2006.01) |
| C07D 405/12 | (2006.01) |
| C07D 401/12 | (2006.01) |
| A61K 31/4155 | (2006.01) |
| A61K 31/454 | (2006.01) |
| A61K 31/496 | (2006.01) |
| A61K 31/5377 | (2006.01) |

(52) U.S. Cl.
CPC ........ *A61K 31/415* (2013.01); *A61K 31/4155* (2013.01); *A61K 31/454* (2013.01); *A61K 31/496* (2013.01); *A61K 31/5377* (2013.01); *C07D 231/12* (2013.01); *C07D 231/16* (2013.01); *C07D 401/12* (2013.01); *C07D 405/12* (2013.01)

(58) Field of Classification Search
CPC ............................ A61K 31/415; C07D 231/12
See application file for complete search history.

(56) References Cited

U.S. PATENT DOCUMENTS

| 4,099,012 A | 7/1978 | Gschwend |
| 4,405,644 A | 9/1983 | Kabbe et al. |

(Continued)

FOREIGN PATENT DOCUMENTS

| CA | 2135253 | 5/1996 |
| CA | 2169231 A1 | 8/1996 |

(Continued)

OTHER PUBLICATIONS

"Arena Pharmaceuticals Announces Preliminary Results of Phase 2b Clinical Trial of APD125 for the Treatment of Insomnia" PRNewswire—First Call via COMTEX News Network, Press Release dated Dec. 9, 2008.

(Continued)

*Primary Examiner* — Robert Havlin
(74) *Attorney, Agent, or Firm* — Pepper Hamilton LLP

(57) ABSTRACT

The present invention relates to certain pyrazole derivatives of Formula (I) and pharmaceutical compositions thereof that modulate the activity of the 5-HT$_{2A}$ serotonin receptor.

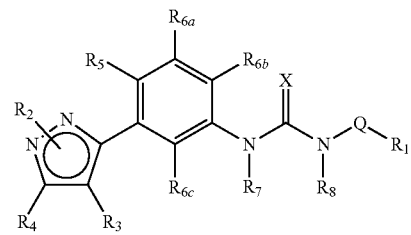

(I)

Compounds and pharmaceutical compositions thereof are directed to methods useful in the prophylaxis or treatment of platelet aggreagation, coronary artery disease, myocardial infarction, transient ischemic attack, angina, stroke, atrial fibrillation, reducing the risk of blood clot formation, asthma or symptoms thereof, agitation or a symptom, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, and sleep disorders, sleep disorders, diabetic-related disorders and the like.

The present invention also relates to the method of prophylaxis or treatment of 5-HT$_{2A}$ serotonin receptor mediated disorders in combination with a dopamine D2 receptor antagonist such as haloperidol, administered separately or together.

16 Claims, 34 Drawing Sheets

Related U.S. Application Data

(60) Provisional application No. 60/503,586, filed on Sep. 16, 2003, provisional application No. 60/489,572, filed on Jul. 22, 2003.

(56) References Cited

U.S. PATENT DOCUMENTS

| | | |
|---|---|---|
| 4,409,231 A | 10/1983 | Stenzel et al. |
| 4,482,534 A | 11/1984 | Blank |
| 4,555,399 A | 11/1985 | Hsiao |
| 4,985,352 A | 1/1991 | Julius et al. |
| 5,077,409 A | 12/1991 | Wissner |
| 5,128,351 A | 7/1992 | Wissner |
| 5,346,906 A | 9/1994 | Baker et al. |
| 5,523,280 A | 6/1996 | Chene et al. |
| 5,576,338 A | 11/1996 | Friesen et al. |
| 5,596,001 A | 1/1997 | Hamanaka |
| 5,661,024 A | 8/1997 | Kao et al. |
| 5,856,326 A | 1/1999 | Anthony et al. |
| 5,861,431 A | 1/1999 | Hildebrand et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,083 A | 2/2000 | Carr et al. |
| 6,028,085 A | 2/2000 | Bromidge |
| 6,054,472 A | 4/2000 | Armistead et al. |
| 6,107,324 A | 8/2000 | Behan et al. |
| 6,110,498 A | 8/2000 | Rudnic et al. |
| 6,140,509 A | 10/2000 | Behan et al. |
| 6,150,393 A | 11/2000 | Behan et al. |
| 6,172,084 B1 | 1/2001 | Cuny et al. |
| 6,180,138 B1 | 1/2001 | Engh et al. |
| 6,187,805 B1 | 2/2001 | Pineiro et al. |
| 6,204,285 B1 | 3/2001 | Fabiano et al. |
| 6,207,679 B1 | 3/2001 | Cuny et al. |
| 6,271,261 B1 | 8/2001 | Widdowson |
| 6,284,269 B1 | 9/2001 | Struengmann et al. |
| 6,297,261 B1 | 10/2001 | Christophersen et al. |
| 6,310,212 B1 | 10/2001 | Yuan et al. |
| 6,316,450 B1 | 11/2001 | Bromidge et al. |
| 6,358,698 B1 | 3/2002 | Weiner et al. |
| 6,376,670 B1 | 4/2002 | Cuny et al. |
| 6,380,199 B1 | 4/2002 | Reavill et al. |
| 6,383,762 B1 | 5/2002 | Kao et al. |
| 6,403,808 B1 | 6/2002 | Glennon et al. |
| 6,417,393 B1 | 7/2002 | Christophersen et al. |
| 6,420,541 B1 | 7/2002 | Behan et al. |
| 6,469,006 B1 | 10/2002 | Blair et al. |
| 6,479,480 B1 | 11/2002 | Moyes et al. |
| 6,479,519 B1 | 11/2002 | Astles et al. |
| 6,489,488 B2 | 12/2002 | Glennon et al. |
| 6,518,297 B2 | 2/2003 | Glennon et al. |
| 6,531,291 B1 | 3/2003 | Kabbash et al. |
| 6,541,209 B1 | 4/2003 | Behan et al. |
| 6,541,477 B2 | 4/2003 | Goehring et al. |
| 6,548,504 B1 | 4/2003 | Bromidge et al. |
| 6,608,085 B1 | 8/2003 | Gillespie et al. |
| 6,627,661 B2 | 9/2003 | Reavill et al. |
| 6,696,475 B2 | 2/2004 | Dahl et al. |
| 6,706,749 B2 | 3/2004 | Dahl et al. |
| 6,753,442 B1 | 6/2004 | Benedini et al. |
| 6,784,183 B2 | 8/2004 | Lavielle et al. |
| 6,787,535 B2 | 9/2004 | Beard et al. |
| 6,846,919 B2 | 1/2005 | Behan et al. |
| 6,849,644 B2 | 2/2005 | Bromidge et al. |
| 7,084,169 B2 | 8/2006 | Zhao |
| 7,087,750 B2 | 8/2006 | Caldirola et al. |
| 7,091,236 B1 | 8/2006 | Roberts et al. |
| 7,098,233 B2 | 8/2006 | Di Cesare et al. |
| 7,262,188 B2 | 8/2007 | MacDonald et al. |
| 7,368,539 B2 | 5/2008 | Behan et al. |
| 7,452,888 B2 | 11/2008 | Ahmed et al. |
| 7,601,837 B2 | 10/2009 | Ahmed et al. |
| 7,754,724 B2 | 7/2010 | Lorsbach et al. |
| 7,799,774 B2 | 9/2010 | Ahmed et al. |
| 7,943,639 B2 | 5/2011 | Johansson et al. |
| 7,977,337 B2 | 7/2011 | Ahmed et al. |
| 8,236,947 B2 | 8/2012 | Ahmed et al. |
| 8,404,690 B2 | 3/2013 | Page et al. |
| 8,481,535 B2 | 7/2013 | Gharbaoui et al. |
| 9,029,379 B2 | 5/2015 | Korenberg et al. |
| 9,034,911 B2 | 5/2015 | Selvey et al. |
| 9,084,742 B2 | 7/2015 | Chuang et al. |
| 2001/0022963 A1 | 9/2001 | Klaveness et al. |
| 2001/0051719 A1 | 12/2001 | Bromidge et al. |
| 2002/0025965 A1 | 2/2002 | Lavielle et al. |
| 2002/0025967 A1 | 2/2002 | Smith |
| 2002/0098548 A1 | 7/2002 | Kao et al. |
| 2002/0115670 A1 | 8/2002 | Kelly et al. |
| 2003/0037274 A1 | 2/2003 | Shikata et al. |
| 2003/0144505 A1 | 7/2003 | Bromidge et al. |
| 2004/0024210 A1 | 2/2004 | Johansson et al. |
| 2004/0034036 A1 | 2/2004 | Bromidge et al. |
| 2004/0077654 A1 | 4/2004 | Bouillot et al. |
| 2004/0082644 A1 | 4/2004 | Korsten |
| 2004/0092528 A1 | 5/2004 | Kelly et al. |
| 2004/0102636 A1 | 5/2004 | Miller et al. |
| 2004/0122076 A1 | 6/2004 | Bobb et al. |
| 2004/0132742 A1 | 7/2004 | Bromidge et al. |
| 2004/0167030 A1 | 8/2004 | Bernotas et al. |
| 2005/0054691 A1 | 3/2005 | Potter et al. |
| 2005/0080124 A1 | 4/2005 | Teegarden et al. |
| 2005/0090485 A1 | 4/2005 | Bromidge et al. |
| 2005/0090496 A1 | 4/2005 | Ahmed et al. |
| 2005/0124628 A1 | 6/2005 | Ahmend et al. |
| 2005/0176705 A1 | 8/2005 | Bromidge |
| 2005/0176759 A1 | 8/2005 | Ahmed et al. |
| 2005/0215526 A1 | 9/2005 | Hulme et al. |
| 2005/0267097 A1 | 12/2005 | Pinto et al. |
| 2006/0014705 A1 | 1/2006 | Howitz et al. |
| 2006/0018839 A1 | 1/2006 | Ieni et al. |
| 2006/0035888 A1 | 2/2006 | Jonas et al. |
| 2006/0063754 A1 | 3/2006 | Edgar et al. |
| 2006/0142241 A1 | 6/2006 | Yooh |
| 2006/0148818 A1 | 7/2006 | Johansson et al. |
| 2006/0172992 A1 | 8/2006 | Yokoyama et al. |
| 2006/0205792 A1 | 9/2006 | Wong et al. |
| 2006/0229335 A1 | 10/2006 | Teegarden et al. |
| 2006/0287334 A1 | 12/2006 | Johnson et al. |
| 2007/0004750 A1 | 1/2007 | Lorsbach et al. |
| 2007/0027139 A1 | 2/2007 | Johnson et al. |
| 2007/0032504 A1 | 2/2007 | Gladwin |
| 2007/0037827 A1 | 2/2007 | Nunes et al. |
| 2007/0043058 A1 | 2/2007 | Bang-Andersen et al. |
| 2007/0072857 A1 | 3/2007 | Teegarden et al. |
| 2007/0078134 A1 | 4/2007 | Teegarden et al. |
| 2007/0167431 A1 | 7/2007 | Comery et al. |
| 2007/0191345 A1 | 8/2007 | Ahmed et al. |
| 2007/0207994 A1 | 9/2007 | Teegarden et al. |
| 2007/0244086 A1 | 10/2007 | Teegarden et al. |
| 2007/0249603 A1 | 10/2007 | Johnson et al. |
| 2007/0275979 A1 | 11/2007 | MacDonald et al. |
| 2007/0293539 A1 | 12/2007 | Lansbury et al. |
| 2007/0293685 A1 | 12/2007 | Fitch et al. |
| 2008/0015223 A1 | 1/2008 | Strah-Pleynet et al. |
| 2008/0114014 A1 | 5/2008 | Rich |
| 2008/0194836 A1 | 8/2008 | Gharbaoui et al. |
| 2008/0200530 A1 | 8/2008 | Unett et al. |
| 2008/0255359 A1 | 10/2008 | Wade |
| 2009/0036682 A1 | 2/2009 | Ahmed et al. |
| 2009/0053306 A1 | 2/2009 | Agarwal et al. |
| 2009/0076254 A1 | 3/2009 | Behan et al. |
| 2009/0186895 A1 | 7/2009 | Teegarden et al. |
| 2009/0197935 A1 | 8/2009 | Teegarden et al. |
| 2009/0298841 A1 | 12/2009 | Ahmed et al. |
| 2010/0004264 A1 | 1/2010 | Xiong et al. |
| 2010/0041672 A1 | 2/2010 | Bruton et al. |
| 2010/0069367 A1 | 3/2010 | Boren et al. |
| 2010/0226855 A1 | 9/2010 | Nangia et al. |
| 2010/0240653 A1 | 9/2010 | Santora et al. |
| 2010/0267691 A1 | 10/2010 | Chuang et al. |

(56) References Cited

U.S. PATENT DOCUMENTS

| | | |
|---|---|---|
| 2010/0305107 A1 | 12/2010 | Ahmed et al. |
| 2011/0021538 A1 | 1/2011 | Krishnan et al. |
| 2011/0178094 A1 | 7/2011 | Holm et al. |
| 2011/0207790 A1 | 8/2011 | Carlos et al. |
| 2011/0207791 A1 | 8/2011 | Selvey et al. |
| 2011/0237792 A1 | 9/2011 | Ahmed et al. |
| 2011/0263592 A1 | 10/2011 | Xiong et al. |
| 2012/0088785 A1 | 4/2012 | Rich |
| 2013/0172379 A1 | 7/2013 | Rich |
| 2013/0172398 A1 | 7/2013 | Rich |
| 2013/0217700 A1 | 8/2013 | Xiong et al. |
| 2013/0237541 A1 | 9/2013 | Teegarden et al. |
| 2014/0073681 A1 | 3/2014 | Schmidt |
| 2014/0142140 A1 | 5/2014 | Bird |
| 2015/0031897 A1 | 1/2015 | Rich |
| 2015/0045372 A1 | 2/2015 | Krishnan et al. |
| 2015/0073141 A1 | 3/2015 | Teegarden et al. |
| 2015/0210648 A1 | 7/2015 | Carlos et al. |
| 2015/0233698 A1 | 8/2015 | Huang et al. |
| 2015/0320742 A1 | 11/2015 | Chuang et al. |
| 2016/0067216 A1 | 3/2016 | Selvey et al. |
| 2016/0075660 A1 | 3/2016 | Xiong et al. |
| 2016/0324851 A1 | 11/2016 | Friedhoff et al. |
| 2016/0324852 A1 | 11/2016 | Friedhoff et al. |

FOREIGN PATENT DOCUMENTS

| | | |
|---|---|---|
| DE | 102004061593 | 6/2006 |
| EP | 0030023 A2 | 6/1981 |
| EP | 0371431 | 11/1989 |
| EP | 0605981 B1 | 2/1996 |
| EP | 0818449 A1 | 1/1998 |
| EP | 0631176 B1 | 12/2000 |
| EP | 1108720 | 6/2001 |
| EP | 0867477 B1 | 5/2002 |
| EP | 1558582 | 8/2005 |
| EP | 1683516 | 1/2006 |
| EP | 1695966 A1 | 8/2006 |
| EP | 1734039 | 12/2006 |
| EP | 1667975 B1 | 11/2007 |
| EP | 1497266 B1 | 6/2008 |
| EP | 1824830 B1 | 7/2010 |
| EP | 1727803 B1 | 3/2012 |
| EP | 1956004 B1 | 6/2012 |
| EP | 2120950 B1 | 7/2012 |
| EP | 2190844 B1 | 4/2013 |
| EP | 2066641 B1 | 6/2014 |
| FR | 2722369 A | 1/1996 |
| GB | 1147379 | 4/1969 |
| GB | 2341549 A | 3/2000 |
| JP | 02262627 | 10/1990 |
| JP | 2001/244773 A | 9/2001 |
| JP | 2005-531518 A | 10/2005 |
| JP | 04334357 B2 | 3/2010 |
| WO | WO 95/11592 A1 | 5/1995 |
| WO | WO96/02138 | 2/1996 |
| WO | WO96/10559 | 4/1996 |
| WO | WO96/23783 | 8/1996 |
| WO | WO 96/32931 | 10/1996 |
| WO | WO97/03967 | 2/1997 |
| WO | WO 97/32858 A1 | 9/1997 |
| WO | WO97/45111 | 12/1997 |
| WO | WO98/24785 | 6/1998 |
| WO | WO 98/27081 A1 | 6/1998 |
| WO | WO 98/47874 A1 | 10/1998 |
| WO | WO 98/54157 A1 | 12/1998 |
| WO | WO 98/54158 A1 | 12/1998 |
| WO | WO 98/57931 A2 | 12/1998 |
| WO | WO 98/57952 A1 | 12/1998 |
| WO | WO99/06354 | 2/1999 |
| WO | WO99/32436 | 7/1999 |
| WO | WO99/32463 | 7/1999 |
| WO | WO 99/32927 | 7/1999 |
| WO | WO 99/42465 A2 | 8/1999 |
| WO | WO 99/47516 A1 | 9/1999 |
| WO | WO99/52927 | 10/1999 |
| WO | WO 99/65906 A1 | 12/1999 |
| WO | WO 00/12073 A1 | 3/2000 |
| WO | WO 00/13681 | 3/2000 |
| WO | WO 00/34265 A2 | 6/2000 |
| WO | WO 00/42026 A1 | 7/2000 |
| WO | WO 00/57877 | 10/2000 |
| WO | WO00/57877 | 10/2000 |
| WO | WO 00/58303 A1 | 10/2000 |
| WO | WO 00/58313 A1 | 10/2000 |
| WO | WO 00/63203 A1 | 10/2000 |
| WO | WO00/64866 | 11/2000 |
| WO | WO 01/07436 | 2/2001 |
| WO | WO 01/16108 A2 | 3/2001 |
| WO | WO 01/17963 A2 | 3/2001 |
| WO | WO01/21160 | 3/2001 |
| WO | WO01/29008 | 4/2001 |
| WO | WO 01/29008 | 4/2001 |
| WO | WO 01/32646 A2 | 5/2001 |
| WO | WO 01/32660 A1 | 5/2001 |
| WO | WO 01/40217 A1 | 6/2001 |
| WO | WO 01/46166 | 6/2001 |
| WO | WO 01/64676 | 9/2001 |
| WO | WO 01/98279 A2 | 12/2001 |
| WO | WO 02/08178 A1 | 1/2002 |
| WO | WO 02/20489 A2 | 3/2002 |
| WO | WO 02/28837 A1 | 4/2002 |
| WO | WO 02/36562 A2 | 5/2002 |
| WO | WO02/39987 | 5/2002 |
| WO | WO 02/44170 A2 | 6/2002 |
| WO | WO02/051833 | 7/2002 |
| WO | WO02/076464 | 10/2002 |
| WO | WO 02/078693 A2 | 10/2002 |
| WO | WO 02/089811 A1 | 11/2002 |
| WO | WO 02/098857 A1 | 12/2002 |
| WO | WO 02/102774 A1 | 12/2002 |
| WO | WO 03/002097 | 1/2003 |
| WO | WO 03/011284 A1 | 2/2003 |
| WO | WO 03/013510 A1 | 2/2003 |
| WO | WO 03/014097 A1 | 2/2003 |
| WO | WO 03/020707 A1 | 3/2003 |
| WO | WO 03/035061 A1 | 5/2003 |
| WO | WO 03/037872 A1 | 5/2003 |
| WO | WO03/062206 | 7/2003 |
| WO | WO 03/066056 A1 | 8/2003 |
| WO | WO 03/072558 A2 | 9/2003 |
| WO | WO 03/080580 A2 | 10/2003 |
| WO | WO 03/080608 A2 | 10/2003 |
| WO | WO 03/095434 A1 | 11/2003 |
| WO | WO 03/104193 A1 | 12/2003 |
| WO | WO 04/000828 A1 | 12/2003 |
| WO | WO 2004/026830 A1 | 4/2004 |
| WO | WO 2004/026831 A1 | 4/2004 |
| WO | WO2004/028450 | 4/2004 |
| WO | WO 2004/035047 A1 | 4/2004 |
| WO | WO 2004/041792 A1 | 5/2004 |
| WO | WO2004/045118 | 5/2004 |
| WO | WO 2004/046110 | 6/2004 |
| WO | WO 2004/050085 A1 | 6/2004 |
| WO | WO2004/058722 | 7/2004 |
| WO | WO2004/071426 | 8/2004 |
| WO | WO 2004/074243 A2 | 9/2004 |
| WO | WO 2004/078176 A1 | 9/2004 |
| WO | WO 2004/080969 A1 | 9/2004 |
| WO | WO2004/085433 | 10/2004 |
| WO | WO2004/096771 | 11/2004 |
| WO | WO2005/012254 | 2/2005 |
| WO | WO 2005/021530 A1 | 3/2005 |
| WO | WO 2005/021545 A | 3/2005 |
| WO | WO 2005/026125 A1 | 3/2005 |
| WO | WO 2005/030724 A2 | 4/2005 |
| WO | WO 2005/040124 A1 | 5/2005 |
| WO | WO 2005/066157 A1 | 7/2005 |
| WO | WO2005/077345 | 8/2005 |
| WO | WO 2005/095346 A1 | 10/2005 |
| WO | WO2005/103011 | 11/2005 |
| WO | WO 2005/113539 A1 | 12/2005 |
| WO | WO 2005/121140 A1 | 12/2005 |
| WO | WO2006/018662 | 2/2006 |

(56) References Cited

FOREIGN PATENT DOCUMENTS

| | | |
|---|---|---|
| WO | WO 2006/038006 A2 | 4/2006 |
| WO | WO2006/049734 | 5/2006 |
| WO | WO2006/049941 | 5/2006 |
| WO | WO 2006/053785 A1 | 5/2006 |
| WO | WO2006/055734 | 5/2006 |
| WO | WO2006/059149 | 6/2006 |
| WO | WO2006/060654 | 6/2006 |
| WO | WO2006/070394 | 7/2006 |
| WO | WO2006/076592 | 7/2006 |
| WO | WO2006/078610 | 7/2006 |
| WO | WO2006/079637 | 8/2006 |
| WO | WO2006/081335 | 8/2006 |
| WO | WO2006/086705 | 8/2006 |
| WO | WO2006/089871 | 8/2006 |
| WO | WO2006/095205 | 9/2006 |
| WO | WO2006/097766 | 9/2006 |
| WO | WO2006/100519 | 9/2006 |
| WO | WO2006/112464 | 10/2006 |
| WO | WO2006/116614 | 11/2006 |
| WO | WO2007/002559 | 1/2007 |
| WO | WO2007/026959 | 3/2007 |
| WO | WO 2007/039219 A1 | 4/2007 |
| WO | WO 2007/039220 A1 | 4/2007 |
| WO | WO 2007/039238 A1 | 4/2007 |
| WO | WO 2007/041409 A1 | 4/2007 |
| WO | WO2007/120600 | 10/2007 |
| WO | WO2007/129111 | 11/2007 |
| WO | WO2007/136680 | 11/2007 |
| WO | WO2007/136703 | 11/2007 |
| WO | WO2007/136875 | 11/2007 |
| WO | WO2008/027483 | 3/2008 |
| WO | WO2008/042388 | 4/2008 |
| WO | WO2008/054748 | 5/2008 |
| WO | WO 2008/113818 A1 | 9/2008 |
| WO | WO2009/023253 | 2/2009 |
| WO | WO 2009/074607 A1 | 6/2009 |
| WO | WO2009/123714 | 10/2009 |
| WO | WO2010/062321 | 6/2010 |
| WO | WO 2010/062323 | 6/2010 |
| WO | WO 2014/065437 | 5/2014 |
| WO | WO 2014/085362 | 6/2014 |
| WO | WO 2015/012554 | 1/2015 |
| WO | WO 2017/011767 | 1/2017 |

OTHER PUBLICATIONS

"QuaSAR—Quantitative Structure Activity Relationships of Analgesics, Narcotic Antagonists, and Hallucinogens," *Research Monograph 22*, 1978, NIDA, Barnett and Willette (eds.).
Adams et al; "Antithrombotic and Vascular effects of AR246686, a novel 5-HT$_{2A}$ receptor antagonist" 2007 EJM, pp. 1-22.
Affolter, H., "CA2+ as Messenger of 5HT2-Receptor Stimulation in Human Blood Platelets," *Naunyn Schmiedebergs Arch. Pharmacol.*, 1984, vol. 325(4), 337-42.
Al-Shamma et al., "Nelotanserin, a Novel Selective Human 5-Hydroxytryptamine$_{2A}$ Inverse Agonist for the Treatment of Insomnia," *J. Pharmacol. Exp. Ther.*, 2010, 332:281-290.
Al-Shamma et al; "The Selective Serotonin 5HT$_{2A}$ Inverse Agonist APD125 Promotes Sleep Onset and Consolidation in Male Wistar Rats During the Normal Active Phase" 2004 APSS (abstract).
Al-Shamma; "APD125: A 5-HT$_{2A}$ Inverse Agonist for the Treatment of Sleep Maintenance Insomnia" 2008 DDST; pp. 1-7.
Al-Shamma; "The Selective Serotonin $_5$-HT$_{2A}$ Inverse Agonist APD125 Promotes Sleep Onset and Consolidation" Jun. 22, 2005 APSS slides, pp. 1-5.
Andrzejewska-Buczko et al., "[Serotonin in diabetic retinopathy]," Klin Oczna. Feb. 1996;98(2):101-4 (abstract only provided).
Barluenga, Jr. et al., "A New and Specific Method for the Monomethylation of Primary Amines," *J. Chem. Soc. Chem. Commun.*, 1984, 20, 1334-1335.
Batey et al., "An Efficient New Protocol for the Formation of Unsymmetrical Tri- and Tretrasubstituted Ureas," *Tetra. Lett.*, 1998, 39, 6267-6270.
Berge et al., "Pharmaceutical salts," J. of Pharmaceutical Sciences (1977) 66(1):1-19.
Bernatowicz et al., "A Comparison of Acid Labile Linkage Agents for the Synthesis of Peptide C-Terminal Amides," *Tetra. Lett.*, 1989, 30(35), 4645-4648.
Blier et al., "Putative mechanisms of action of antidepressant drugs in affective and anxiety disorders and pain," *Journal of Psychiatry and Neuroscience*, 2001, vol. 26(1), 37-43.
Bryn et al., Pharm. Res., v. 12 (1995), n. 7, p. 945-54.
Burger, A., "Isosterism and bioisosterism in drug design," Prog. Drug Res. 37 (1991), pp. 287-371.
Byrn, Solid-State Chemistry of Drugs, 2$^{nd}$ ed. (1999), Chapter 11—Hydrates and Solvates, 233-247.
Cameron et al., "The effects of 5-hydroxytryptamine 5-HT2 receptor antagonists on nerve conduction velocity and endoneurial perfusion in diabetic rats.," Naunyn Schmiedebergs Arch Pharmacol., Jun. 2003;367(6):607-14.
Carter et al., "Carbobenzoxy Chloride and Derivatives," *Org. Syn. Coll.*, 1955, vol. 3, 167-169.
Casey et al., "Constitutively active mutant 5HT2, serotonin receptors: inverse agonist activity of classical 5HT$_{2A}$ antagonists," Society for Neuroscience Abstracts, vol. 22, p. 699.10.
Catalán et al., "New Ultraviolet Stabilizers: 3- and 5-(2'-Hydroxyphenyl)pyrazoles," *J. Am. Chem. Soc.*, 114, 5039-5048 (1992).
Cazzola and Matera, "5-HT modifiers as a potential treatment of asthma," TIPS, 21:13-6 (2000).
Chambers et al., *Bioog. Med. Chem. Lett.*, (2002), 12, 1997-1999.
Chang et al., "Mechanism of the ocular hypotensive action of ketanserin," J. Ocul Pharmacol., Summer 1985;1(2):137-47.
Cohen-Mansfield et al., "Agitated behaviors in the elderly. I. A conceptual review," J Am Geriatr Soc., Oct. 1986;34(10):711-21.
Collier et al., "Radiosynthesis and in-vivo evaluation of the psuedopeptide 6-opioid antagonist [$_{125}$I]-ITIPP(Ψ)" ]. Labeled Compd. Radiopharrn., 1999, vol. 42, pp. S264-S266.
De Bie et al., "Modulation of airway hyperresponsiveness and eosinophilia by selective histamine and 5-HT receptor antagonists in a mouse model of allergic asthma," British Journal of Pharmacology, 1998, vol. 124, 857-864.
Dosa et al., "Synthesis and SAR of solubilized pyrazole derivatives as 5-HT$_{2A}$ inverse-agonists for platelet aggregration," 232$^{nd}$ ACS National Meeting, Sep. 2006, Medi 431, 1 page, abstract.
Dosa et al; "Solubilized phenyl-pyrazole ureas as potent, selective 5-HT$_{2A}$ inverse-agonists and their application as antiplatelet agents," 2010, BMCL; pp. 1-15.
Dosa et al; "Synthesis and SAR of Pyridinyl-Pyrazole Derivatives as Selective 5HT$_{2A}$ Inverse-Agonists for Platelet Aggregation" 2008 ACS, 235$^{th}$ ACS National Meeting, MEDI 44, poster.
Dosa et al; "Synthesis and SAR of Solubilized Pyrazole Derivatives as 5HT$_{2A}$ Inverse-Agonists for Platelet Aggregation" 2006 ACS; 232nd ACS National Meeting, MEDI 431, poster.
Elliott et al., "4-Oxospiro[benzopyran-2,4'-piperidines] as Class III Antiarrhythmic Agents. Pharmacological Studies on 3,4-Dihydro-1'-[2-(benzofurazan-5-yl)-ethyl]-6methanesulfonamidospiro[(2H)-1-benzopyran-2,4'-piperidin]-4-one (L-691,121)", *J. Med. Chem.*, 35:3973-3976 (1992).
Elphick et al., "The human polyomavirus, JCV, uses serotonin to infect cells," *Science*, 2004, vol. 306, 1380-3.
Glennon et al., *J. Med. Chem.*, 1982, 25(10), 1163-68.
Greene et al., Protecting Groups in Organic Synthesis, 3rd Edition, 1999 (Wiley).
Grotewiel et al., "Receptors Exhibit Constitutive Activity that is Blocked by Inverse Agonists," *Faseb J.*, Abstract 353, 8(7), May 21-25, 1994 (1 page).
Grunder et al., Time course of 5-HT2A receptor occupancy in the human brain after a single oral dose of the putative antipsychotic drug MDL 100,907 measured by positron emission tomography, Neuropsychopharmacology. Sep. 1997;17(3):175-85.
Gutsche et al., "2-Phenylcycloheptanone," *Org. Syn. Coll.*, 1963, vol. 4, 780-783.
Halberstadt et al., Neuropsychopharmacology (2009) 34, 1958-1967.

(56) References Cited

OTHER PUBLICATIONS

Herrick-Davis et al., "Activating mutations of the serotonin 5-HT2C receptor," J. Neurochem, Sep. 1997;69(3):1138-44.
Herrick-Davis et al., "Constitutively active 5HT2C serotonin receptor created by site-directed mutagenesis," Society for Neuroscience Abstracts, vol. 22, p. 699.18.
Higuchi et al., "Pro-Drugs as Novel Delivery Systems," vol. 14 of the ACS Symposium Series; and in Bioreversible Carriers in Drug Design, ed. Edward B. Roche, American Pharmaceutical Association and Pergamon Press, 1987.
Hittner et al; "A Selective 5-HT$_{2A}$ Receptor Inverse Agonist with Preclinical Antipsychotic Profile in Rats" 2000 NEURO, poster.
Holtje, H. "Pharmacophore Identification and Receptor Mapping," The Practice of Medicinal Chemistry, $2^{nd}$ ed., 2003, Wermuth (editor), Academic Press, Chap. 24, pp. 387-403.
Ieni and Meyerson, "The 5-HT$_{1A}$ Receptor Probe[$^3$H]8-OH-DPAT Labels. The 5-HT Transporter in Human Platelets," Life Sciences, 1988, vol. 42, 311-320.
Ikeguchi and Kuroda, "Mianserin Treatment of Patients with Pyschosis Induced by Antiparkinsonian Drugs," Eur. Arch. Psych. Clin. Neurosci., 1995, 244, 320-324.
Jayakumar et al; "Synthesis and SAR of Alkoxyphenyl Pyrazole as 5-HT$_{2A}$ Inverse Agonists" 2006, ACS, $232^{nd}$ ACS National Meeting, MEDI 430, poster.
Jayakumar et al; "Synthesis and SAR of Novel-Phenyl-Pyrazole Urea derivatives" 2006 ACS, abstract.
Jayakumar et al; "Synthesis and SAR of Substituted Diphenylamines as 5HT$_{2A}$ Inverse-Agonists" 2004 ACS, meeting abstract.
Jayakumar et al; "Synthesis and SAR of Substituted Diphenylamines as 5HT$_{2A}$ Inverse-Agonists" 2005 ACS, $229^{th}$ ACS National Meeting, MEDI 049, poster.
Julius et al., "The 5HT2 Receptor Defines a Family of Structurally Distinct but Functionally Conserved Serotonin Receptors," Proc. Natl. Acad. Sci. USA, 1990, vol. 87, 928-932.
Kanayama et al,. "New treatment of lumbar disc herniation using 5-hydroxytryptamine$_{2a}$ receptor inhibitor: a randomized controlled trial," Journal of Neurosurgery: Spine, 2005, vol. 2, 441-6.
Katz et al., "Comparison of risperidone and placebo for psychosis and behavioral disturbances associated with dementia: a randomized, double-blind trial. Risperidone Study Group," J Clin Psychiatry. Feb. 1999;60(2):107-15.
Kitagawa et al., "Beckmann Rearrangement of O-4 Pentenyl Oxime through N-Bromosuccinimide-Mediated Activating Process", Chem. Pharm. Bull., 45(1) 32-35 (1997).
Konig et al., "A New Method for Synthesis of Peptides: Activation of the Carboxyl Group with Dicyclohexylcarbodiimide using 1-Hydroxybenzotriazoles as Additives," Chem. Ber., 1970, 103, 788-798 (English abstract included).
Koss et al., "Assessing patterns of agitation in Alzheimer's disease patients with the Cohen-Mansfield Agitation Inventory. The Alzheimer's Disease Cooperative Study," Alzheimer Dis Assoc Disord. 1997;11 Suppl 2:,545-50.
Krystal et al; "The effects of APD125, a selective serotonin 5-HT2A, on sleep quality and sleep maintenance in a subjective study in patients with primary insomnia," 2009, Sleep; pp. 1-23.
Kubinyi (3D QSAR in Drug Design: Ligand-Protein Interactions and Molecular Similarity, vol. 2-3, Springer, 1998, 800 pages). p. 243 provided.
Landolt et al., "Serotonin-2 receptors and human sleep: effect of a selective antagonist on EEG power spectra," Neuropsychopharmacology, 1999 8ep;21(3):455-66.
Le Bas et al., "Radioiodinated analogs of EP 00652218 for the exploration of the tachykinin NK1 receptor by spect," J. Labeled Compd. Radiopharm., 2001, vol. 44, pp. S280-S282.
Luthringer et al; "Pharmacokinetic and Pharmacodynamic Effects of the Selective 5HT$_{2A}$ Inverse Agonist APD125 in Healthy Adults" 2005 APSS, abstract.
Mandel, J., "Statistical Analysis of Experimental Data," Chapter 3, pp. 28-57, Toronto, Ontario, (1964).

Mandel, J., "Statistical Analysis of Experimental Data," Chapter 9, pp. 204-207, Toronto, Ontario, (1964).
Marchini, et al., "Sodium Borohydride-Carboxylic Acid Systems. Useful Reagents for the Alkylation of Amines," J. Org. Chem., 1975, 40(23), 3453-3456.
Mastropasqua et al, "Ocular hypotensive effect of ketanserin in patients with primary open angle glaucoma," Acta Ophthalmol Scand Suppl., 1997(224):24-5.
Menzaghi et al; "AR116081, A Novel Selective 5-HT2A Inverse Agonist as a Putative Atypical Antipsychotic: Comparative Studies with Clozapine and Haloperidol" 2000 CINP, poster.
Menzaghi et al; "AR118081, A Novel High Affinity 5-HT2A Receptor Inverse Agonist With In Vivo Efficacy" Nov. 1999 Neuro, poster.
Menzaghi et al; "Identification of Novel Selective 5-HT2A Inverse Agonists as Putative Atypical Antipsychotics Using Constitutively Activated Human 5-HT Receptors" Jun. 2000 ASPET, poster.
Menzaghi et al; "Therapeutic Potential of Selective Serotonin 5HT2A Receptor Inverse Agonists: Pre-Clinical Evaluation of AR116081 as Antipsychotics in Rodents" 2002 FESN, abstract.
Mizuki et al., "Effects of Mianserin on Negative Symptoms in Schizophrenia," Int. Clinical Psychopharmacology, 1990, 5: 83-95.
Morissette et al., Advanced Drug Delivery Review 56 (2004) 275-300.
Muto et al., "Protective effects of sarpogrelate, a 5HT$_{2A}$ antagonist, against postischemic myocardial dysfunction in guinea-pig hearts," Molecular and Cellular Biochemistry, 2005, vol. 272, 119-32.
National Institutes of Health, National Heart, Lung and Blood Institute, "Facts about Insomnia," NIH Publication No. 95, 1995, 3801, p. 1-4.
Newton and Elliot, "Mianserin-Induced Down-Regulation of Human 5-Hydroxytryptamine$_{2A}$ and 5-Hydroxytryptamine$_{2c}$ Receptors Stably Expressed in the Human Neuroblastoma Cell Line SH-SY5Y," Journal of Neurochemistry, 1997, 69: 1031-1038.
Nichols et al., J. Med. Chem., 1991, 34, 276-81.
Nishiyama, T., "Effects of 5HT$_{2A}$ receptor antagonist, sarpogrelate on thermal or inflammatory pain," European Journal of Pharmacology, 2005, vol. 516, 18-22.
Nomura et al., "5-HT$_{2A}$ receptor antagonist increases circulating adiponectin in patients with type 2 diabetes," Blood Coagulation and Fibrinolysis, 2005, vol. 16(6), 423-8.
Pietraszek et al., "Blood serotonergic mechanisms in type 2 (non-insulin-dependent) diabetes mellitus," Thromb Res., Jun. 15, 1992;66(6):765-74.
Prosser et al., "Selective serotonin 5-HT$_{2A}$ inverse agonists promote sleep consolidation in male Wistar rats during the normal inactive phase," #29, Arena Pharmaceuticals, Inc., APSS Meeting Jun. 2004) 1 page.
Remington, The Science and Practice of Pharmacy, 20th Edition, 2000 (Lippincott Williams & Wilkins).
Rosenberg et al; "APD125, a selective serotonin 5-HT$_{2A}$ receptor inverse agonist, significantly improves the key parameters of sleep maintenance in patients with primary insomnia", 2007, AASM, abstract.
Rosenberg et al; "APD125, a selective serotonin 5-HT$_{2A}$ receptor inverse agonist, significantly improves sleep maintenance in primary insomnia", 2008, APA; pp. 1-37.
Rosenberg et al; APD125, a selective serotonin 5-HT2A receptor inverse agonist, significantly improves the key PSG parameters of sleep maintenance in patients with primary insomnia 2008 Sleep, poster.
Roth et al; "APD125, a selective serotonin 5-HT2A receptor inverse agonist, significantly improves the key parameters of sleep maintenance in patients with primary insomnia" 2008 APSS pp. 1-19.
Sahgal, A. (ed.), "Practical behavioural neuroscience: problems, pitfalls and suggestions," in Behavioral Neuroscience: A Practical Approach, IRL Press, New York, 1993, vol. 1, 1-8.
Satomura et al., "Sarpogrelate, a specific 5HT2-receptor antagonist, improves the coronary microcirculation in coronary artery disease," Clin Cardiol. Jan. 2002; 25(1):28-32.
Sawnyok et al., "Antidepressants as analgesics: an overview of central and peripheral mechanisms of action," Journal of Psychiatry and Neurosciences, 2001, vol. 26(1), 21-9.

(56) References Cited

OTHER PUBLICATIONS

Schmidt et al., "The Role of 5-HT$_{2A}$ Receptors in Antipsychotic Activity," *Life Sciences*, 1995, 56(25), 2209-2222.

Shan et al; "Investigation of Non-Aqueous Vehicles for a Poorly Soluble Compound Intended for Softgel Dosage Form Development" 2005, APSS, abstract.

Shan et al; "Physicochemical Characterization During Salt Selection Process" 2005 AAPS, poster.

Shan et al; "Physicochemical Characterization During Salt Selection Process" 2006 AAPS, poster.

Sharpley et al., Slow wave sleep in humans: role of 5-HT2A and 5-HT2C receptors. Neuropharmacology. Mar.-Apr. 1994;33(3-4):467-71.

Sheehan and Cruickshank, "1-Ethyl-3-(3-Dimethylamiono)Proplycarbodiimide Hydrochloride and Methiodide," *Org. Syn. Coll.*, 1973, vol. 5, 555-558.

Shibata et al., "Adiponectin protects against myocardial ischemiareperfusion injury through AMPK- and COX-2 dependent mechanisms," *Nature Medicine*, advanced online Publications: pp. 1-8, Published Online Sep. 11, 2005.

Smith et al., Test-retest variability of serotonin 5-HT2A receptor binding measured with positron emission tomography and [18F]altanserin in the human brain, Synapse, Dec. 1998;30(4):380-92.

Sorenson et al., "Characterization of the 5-HT2 Receptor Antagonist MDL 100907 as Putative Atypical Antipsychotic: Behavioral, Electrophysiological and Neurochemical Studies," *J. Pharacol. Exp. Ther.*, 1993 266(2), 684-691.

Speer et al; "Influence of Digestive Enzymes Combined with Sodium Lauryl Sulfate on Dissolution of Cross-linked Gelatin Capsules" 2005 AAPS, poster.

Speer et al; "Influence of Digestive Enzymes on Dissolution of a Poorly Water Soluble Compound From Cross-Linked Gelatin Capsules in Sodium Lauryl Sulfate Medium" 2005 AAPS, abstract.

Speer et al; "Intrinsic Dissolution Characterization of Different Morphic Forms of a Poorly Water Soluble Compound," 2006, AAPS, abstract.

Staley et al., Comparison of [(18)F]altanserin and [(18)F]deuteroaltanserin for PET imaging of serotonin(2A) receptors in baboon brain: pharmacological studies., Nucl Med Biol., Apr. 2001;28(3):271-9.

Storey et al., "Automation of Solid Form Screening Procedures in the Pharmaceutical Industry—How to Avoid the Bottlenecks," *Crystallography Reviews*, 2004, vol. 10, No. 1, pp. 45-56.

Strah-Pleynet et al., "Discovery and SAR of novel 5-HT$_{2A}$, inverse-agonists," 227th ACS National Meeting, MED1 270, Arena Pharmaceuticals Inc. (Mar. 2004), 1 page, poster.

Strah-Pleynet et al; "5HT$_{2A}$ Receptor Inverse Agonists: Design and SAR of Novel Pyrazole Derivatives", 2006, meeting abstract.

Strah-Pleynet et al; "5-HT$_{2A}$ Receptor Inverse-Agonists: Design and Structure-Activity Relationship of Novel Pyrazole Derivatives" 2005 ACS, 231st ACS National Meeting, MEDI 145, poster.

Strah-Pleynet et al; "Bioisosteric Modifications of Urea Derivatives as 5HT$_{2A}$ Inverse-Agonists" 2004 ACS, meeting abstract.

Strah-Pleynet et al; "Bioisosteric Modifications of Urea Derivatives as 5HT$_{2A}$ Inverse-Agonists" 2005 ACS, meeting poster.

Strah-Pleynet et al; "Discovery and SAR of Novel 5-HT2A Inverse-Agonists" 2004 ACS, 227th ACS National Meeting, MEDI 270, abstract.

Street et al., "Olanzapine treatment of psychotic and behavioral symptoms in patients with Alzheimer disease in nursing care facilities: a double-blind, randomized, placebo-controlled trial. The HGEU Study Group.," Arch Gen Psychiatry. Oct. 2000; 57(10):968-76.

Takahashi et al., "Sarpogrelate hydrochloride, a serotonin2A receptor antagonist, reduces albuminuria in diabetic patients with early-stage diabetic nephropathy," Diabetes Res Clin Pract. Nov. 2002;58(2):123-9.

Takenaka et al., "The effect of anplag (sarpogrelate HCI), novel selective 5-HT$_2$ antagonist on intraocular pressure in glaucoma patients," Investig Ophthalmol Iris Sci, 36(4):S724 (3390-377).

Talvik-Lotfi et al., "High 5HT2A receptor occupancy in M100907-treated schizophrenic patients," Phychopharmacology (2000) 148:400-403.

Tang et al., *Bioorg. Med. Chem. Letters.*, 2003, 13, 2985-88.

Teegarden et al., "Discovery of 1-[3-(4-Bromo-2-methyl-2H-pyrazol-3-yl)-4-methoxyphenyl]-3-(2,4-difluorophenyl(urea(Nelotanserin) and Related 5-Hydroxytryptamine$_{2A}$ Inverse Agonists for the Treatment of Insomnia", *J. Med. Chem.* 2003, vol. 53, pp. 1923-1936.

Teegarden et al; "5HT$_{2A}$ Inverse-Agonists for the Treatment of Insomnia" 2008 CTMC, pp. 1-28.

Teegarden et al; "Discovery of 1-[3-(4-Bromo-2-methyl-2H-pyrazol-3-yl)-4-methoxy-phenyl]-3-(2,4-difluoro-phenyl)-urea (APD125) and Related 5-HT$_{2A}$ Inverse Agonists for the Treatment of Insomnia" 2009 JMC; pp. 1-50.

The International Classification of Sleep Disorders, Revised Diagnostic and Coding Manual, American Academy of Sleep Medicine (2001) pp. 1-336 (also includes table of contents and glossary).

Topliss, "J. Med. Chem.", 1977, v. 20, n. 4, p. 463-469.

van Zwieten, P. A., "Receptors Involved in the Regulation of Vascular Tone," Arzneimittelforschung. 1985, vol. 35(12A): 1904-9.

Verstraete, M., "Prevention of atherosclerotic complications: controlled trial of ketanserin," *British Medical Journal*, 1989, vol. 298, 424-30.

Vikenes et al., "Serotonin is associated with coronary artery disease and cardiac events," *Circulation*, 1999, vol. 100, 483-9.

Vippagunta et al., "Crystalline solids," *Advanced Drug Delivery Reviews*, 48:3-26 (2001).

Wermuth, The Practice of Medicinal Chemistry, 2d ed. (2003), 768 pages. Chpt. 9-10 provided.

Westkaemper and Glennon, *Curr. Topics Med. Chem.*, 2002, 2, 575-598.

White, E., "Deamination of Amines. 2-Phenylethyl Benzoate Via the Nitrosoamide Decomposition," *Org. Syn. Coll.* 1973, vol. 5, 336-339.

Wikström et al., "Synthesis and Pharmacological Testing of 1, 2, 3, 4, 10, 14b-Hexahydro-6-methoxy-2-methyldibenzo[c,f]pyrazino[1,2-a]azepin and Its Enantiomers in Comparison with the Two Antidepressants Mianserin and Mirtazapine," *J. Med. Chem.*, 2002, vol. 45, 3280-3285.

Wilson et al, "LY53857, a 5HT2 receptor antagonist, delays occlusion and inhibits platelet aggregation in a rabbit model of carotid artery occlusion," Thromb Haemost. Sep. 2, 1991;66(3):355-60.

Winokur et al., "Acute effects of mirtazapine on sleep continuity and sleep architecture in depressed patients: a pilot study," Biol Psychiatry, Jul. 1, 2000;48(1):75-8.

Xiong et al; "Discovery and SAR of Highly Selective 5-HT$_{2A}$ Receptor Subtype Inverse-Agonists for Inhibition of Platelet Aggregation" 2008 ACS, 235th National Meeting, MEDI 45, poster.

Xiong et al; "Synthesis and in Vivo Evaluation of Phenethylpiperazine Amides: Selective 5-Hydroxytryptamine$_{2A}$ Receptor Antagonists for the Treatment of Insomnia," Journal of Medical Chemistry, 2010, vol. 53, 5696-5706.

Yevich and Yocca, *Curr. Med. Chem.*, 1997, 4(5), 295-312.

Zhu et al., "Synthesis and mode of action of [125]I- and $^3$H-labeled Thieno[2,3-c]pyridine antagonists of cell adhesion molecule expression," J. Org. Chem. (200) 67:943-948.

"The Merck Manual of Diagnosis and Therapy", Merck Research Laboratories, pp. 1769-1781 (2006).

Ahmed et al., "Bicylic heteroarylpiperazines as selective brain penetrant 5-HT6 receptor antagonists," (2005) *Bioorganic & Medicinal Chem. Letters*, 15:4867-4871.

Ancelin, et al. "Non-degenerative mild cognitive impairment in elderly people and use of anticholinergic drugs: longitudinal cohort study" (Feb. 1, 2006) *BMJ*, doi:10.1136/bmj.38740.439664.DE.

Anonymous "Drug treats severe Alzheimer's". http://newsvote.bbc.co.uk/mpapps/pagetools/print/news.bbc.co.uk/2/hi/health/4832574.stm. Mar. 23, 2006.

(56) References Cited

OTHER PUBLICATIONS

Anonymous "Prevention of Atherosclerotic Complications: Controlled Trial of Ketanserin" (1989) *Br. Med. J.* 298:424-430.
Antinori et al. "Diagnosis of AIDS-related Focal Brain Lesions: A decision-making analysis based on clinical and neuroadiiologic characteristics combined with polymerase chain reaction assays in CSF" (1997) *Neurology* 48:687-694.
ARICEPT® Label Jul. 2015.
Aschenbrenner et al., Drug Therapy in Nursing, 2009, TOC.
Bentley et al. "5-HT$_6$ Antisense Oligonucleotide I.C.V. Affects Rat Performance in the Water Maze and Feeding" (1997) *Journal of Psychopharma. (Supplement)* A64:255 (abstract).
Bentley et al. "Effect of the 5-HT6 Antagonist, Ro 04-6790 on Food Consumption in Rats Trained to a Fixed Feeding Regime" (1999) *British Journal of Pharmacol.* 126(Suppl.):66 (abstract).
Bentley et al., "Investigation of stretching behavior induced by the selective 5-HT6 receptor antagonist, Ro 04-6790, in rats" (1999) *British Journal of Pharmacol.* 126:1537-1542.
Berger et al. "Progressive Multifocal Leukoencephalopathy" (1999) *Seminars in Neurology* 19:193-200.
Birks et al. "Donepezil for dementia due to Alzheimer's disease", The Cochrane Library. http://onlinelibrary.wiley.com/store/10.1002/14651858.CD001190.pub2/asset/CD001190.pdf?v=1&t=h5uxf9xk&s=991bffcda40d23d5edf561ab6543198f531af16d [retrieved Aug. 14, 2012).
Bos et al. "5-HT6 receptor antagonists lead optimization and biological evaluation of N-aryl and B-heteroaryl 4-amino-benzene sulfonamides" (2001) *Eur. J. Med. Chem.* 36(2):165-178.
Bourson et al. "Determination of the Role of the 5-HT6 Receptor in the Rat Brain: A Study Using Antisense Oligonucelotides" (1995) *The Journal of Pharmacology & Experimental Therapeutics* 274(1): 173-180.
Bourson et al. "Involvement of 5-HT6 receptors in nigro-striatal function in rodents" (1998) *British J. of Pharmacol.* 125:1562-1566.
Branchek et al. "5-HT6 Receptors as Emerging Targets for Drug Discovery" (2000) *Annu. Rev. Pharmcol. Toxicol.* 40: 319-334.
Bromidge et al. "Phenyl Benzenesulfonamides are Novel and Selective 5-HT6 Antagonists: Identification of N-(2,50Dibromo-3-fluorophenyl)-4-methoxy-3-piperazin-1-ylbenzensulfonamide (SB-357134)" (2001) *Bioorganic & Medicinal Chemistry Letters* 11:55-58.
Burla et al. "SIR2004: an improved tool for crystal structure determination and refinement" (2005) *J. Appl. Cryst.* 38: 381-388 (abstract).
Buysse et al. "The Pittsburgh Sleep Quality Index: A New Instrument for Psychiatric Practice and Researach" (1989) *Psychiatry Research* 28(2):193-213.
Callahan et al. "Characterization of the Selective 5-HT6 Receptor Antagonist SB 271046 in Behavioral Models of Cognition", 34th Annual Scientific Meeting of the Soc. for Neurosci., San Diego. Oct. 2004.
Campbell et al. "Use of anticholinergics and the risk of cognitive impairment in an African American population" (2010) *Neurology* 75:152-159.
Carnahan et al. "The Concurrent Use of Anticholinergics and Cholinesterase Inhibitors: Rare Event or Common Practice?" (2004) JAGS 52(12):2082-2087 (abstract).
Castaneda-Corral et al. "Role of Peripheral and Spinal 5-HT6 Receptors According to the Rat Formalin Test" (2009) *Neuroscience* 162:444-452.
Cazzola et al. "Central 5-HT$_{1A}$ Receptors and Vagal Tone to the Airways" (2000) *Trends Pharmacol. Sci.* 21:201-202.
Chang et al. "Mechanism of the ocular hypotensive action of ketanserin" (Summer 1985) *J. Ocul Pharmacol.* 1(2):137-147.
Chang-Fong et al. "1,2,3,4-Tetrahydrocarbazoles as 5-HT6 serotonin receptor ligands" (2004) *Bioorg. Med. Chem. Lett.* 14(8):1961-1964.

Chew et al. "Serum Anticholinergic Activity and Cognition in Patients with Moderate-to-Severe Dementia" (Jun. 2005) *Am J Geriatr Psychiatry* 13:6 (abstract).
Chuang et al. "5-HT6 Receptor Antagonist SB-742457 as a Novel Cognitive Enhancing Agent for Alzheimer's Disease" (2006) *Alzheimer's & Dementia, The Journal of the Alzheimer's Association*, 2(3/Supp. 1):S631-S632.
Clinical Trial Protocol Summaries (Five studies). http://www.gsk-clinicalstudyregister.com/quick-search-list.jsp?item=SB742457&type=Compound&letterrange=Q-U&studyType=All&phase=All&population=All&marketing=All (accessed Mar. 9, 2012).
Collins et al. "N-Phenylamidines as Selective Inhibitors of Human Neuronal Nitric Oxide Sythase: Structure-Activity Studies and Demonstration of in Vivo Activity" (1998) *J. Med. Chem., Amer. Chem. Soc.* 41(15):2858-2871.
Cooke "Glycopyrrolate in Bladder Dysfunction", Jan. 1, 1983 *South African Medical Journal* 63(1):3 (abstract).
CUVPOSA glycopyrrolate oral solution Product Information Sheet, Rev. Jul. 2010.
Database Beilstein [Online] Beilstein Institute for Organic Chem., Frankfurt-Main, DE; XP002535545 Database Accession No. 5926580 (BRN), the whole document.
Davies et al. "Drug discovery targets: 5-HT$_6$ receptor" (2005) *Drugs of the Future* 30(5):479-495.
Defilippi et al. "Drug Interactions with Cholinesterase Inhibitors" (2003) *Drugs Aging* 20(6):437-444 (abstract).
Deuchar et al. "The role of 5-hydroxytryptamine in the control of pulmonary vascular tone in a rabbit model of pulmonary hypertension secondary to left ventricular dysfunction" (2005) *Pulm. Pharmacol. Ther.* 18(1):23-31.
Diagnostic and Statistical Manual of Mental Disorders, Fourth Edition, Text Revision: DSM-IV-TR, Washington, DC, American Psychiatric Association, 2000 (abstract).
Douaud et al. "Preventing Alzheimer's disease-related gray matter atrophy by B-vitamin treatment" (2013) *PNAS* 110:9523-9528.
Drinka "Antimuscarinic Drugs for Overactive Bladder and Their Potential Effects on Cognitive Function in Older Patients" 2006 *JAGS* 54(6):1004-1005 (abstract).
East et al. "5HT6 receptor binding sites in schizophrenia and following antipsychotic drug administration: Autoradiographic studies with 125ISB-258585" (2002) *Synapse* 45:191-199.
Edwards et al. "Risk of delirium with concomitant use of tolterodine and and acetycholinesterase inhibitors". 2002 *J Amer Geriatric Society* 50(6):1165-1166 (abstract).
European Search Report for EP05025004.2 dated Jun. 30, 2006.
European Search Report for EP08157490.7 dated Jul. 8, 2008.
European Search Report for EP12170019.9 dated Aug. 16, 2012.
Ferguson "Modulation of lymphatic smooth muscle contraction responses by the endothelium" (1992) *Journal of Surgical Research* 52:359-363 (abstract).
File "Anxiolytic Action of a Neurokinin, Receptor Antagonist in the Social Interaction Test" (Nov. 1997) *Pharmacol. Biochem. Behav.* 58(3):747-752.
File "The Use of Social Interaction as a Method for Detecting Anxiolytic Activity of Chlordiazepoxide-llike Drugs" (Jun. 1980) *J. Neuro. Methods* 2(3):219-238.
Foley et al. "The 5-HT6 Receptor Antagonist SB-271046 Reverses Scopolamine-Disrupted Consolidation of a Passive Avoidance Task and Ameliorates Spatial Task Deficits in Aged Rats" (2004) *Neuropsychopharmacology* 29:93-100.
Fujita et al. "Sarpogrelate Treatment Reduces Restenosis After Coronary Stenting" (2003) *Am. Heart J.* 145:e16.
Fujiwara "Augmented Responses to 5-HT2-Receptor-Mediated Vascoconstrictions in Atherosclerotic Rabbit Common Carotid Arteries" (1995) *Journal of Cardiovascular Pharmacology* 26:503-510.
Fullerton et al. "A phase 2 clinical trial of PF-05212377 (SAM-760) in subjects with mild to moderate Alzheimer's Disease with existing neuropsychiatric symptoms on a stable daily dose of Donepezil" Pfizer AAIC 2016 Poster Presentation, Cambridge, MA.

(56) References Cited

OTHER PUBLICATIONS

Garcia-Alloza et al. "Differential Involvement of 5-HT IB/ID and 5-HT6 Receptors in Cognitive and Non-cognitive Symptoms in Alzheimer's Disease" (2004) *Neuropsychopharmacology* 29:410-416.
Gardner "Distress Vocalization in Rat Pups a Simple Screening Method for Anxiolytic Drugs" (Nov. 1985) *J. Pharma. Meth.* 14(3):181-187 (Nov. 1985).
Geldmacher "Donepezil (Aricept®) for treatment of Alzheimer's disease and other dementing conditions" (2004) *Expert Rev. Neurotherapeutics* 4(1):5-16.
Gill et al. "A Prescribing Cascade Involving Cholinesterase Inhibitors and Anticholinergic Drugs" (2005) *Arch Intern Med* 165:808-813.
Gish et al. "Memorandum: Age-dependent manifestations of central anticholinergic effects" Department of Health and Human Services Public Health Service Food and Drug Administration Center for Drug Evaluation and Research, Mar. 5, 2007.
Glaxosmithkline Clinical Trial, http://www.gsk-clinicalstudyregister.com/result_comp_list.jsp?compound=SB742457&studyType=All&phase=All&population=All&marketing=All. Sep. 21, 2011.
Glaxosmithkline Pharmacology Study Report—A study in healthy volunteers to characterise [$^{11}$C]GSK215083A as a positron emission tomography (PET) tracer ligand for the 5-HT$_6$ receptor and to assess the occupancy at the 5-HT$_6$ receptor of SB-742457 in the brain using PET and a tracer dose of [$^{11}$C]GSK215083A (Sep. 24, 2009).
Glaxosmithkline, A Dose Ranging Study to Investigate the Efficacy and Safety of SB-742457 in Alzheimer's Disease NCT ID No. NCT00224497 (Verified 2007) Clinical Study.
Glaxosmithkline, SB-742457 and Donepezil in Alzheimer's Disease. NCT ID No. NCT00348192 (2006) Clinical Study.
Glennon et al. "2-Substituted Tryptamines: Agents with Selectivity for 5-HT6 Serotonin Receptors" (2000) J. Med. Chem., 43: 1011-1018.
Gottlieb et al. "NMR Chemical Shifts of Common Laboratory Solvents as Trace Impurities" (1997) *J. Org. Chem.* 62:7512-7515.
Griesser "The Importance of Solvates, in Polymorphism in the Pharmaceutical Industry" 211-233; Rolf Hilfiker, ed., 2006.
Guillory "Generation of Polymorphs, Hydrates, Solvates, and Amorphous Solids, in Polymorphism in the Pharmaceutical Industry" (1999) Harry G. Britain ed. 183-226, 202-209.
Guy "Clinical Global Impression (CGI)—Severity of Depression Rating Scale" ECDEU Assessment Manual for Psychopharmacology (Rev. Ed. U.S. Dept. Of Health, Education and Welvare, Bethesda, MD 1976).
Hamilton "A Rating Scale for Depression" (1960) *J. Neurol. Neurosurg. Psychiat.* 23:56-62.
Hamilton "Development of a Rating Scale for Primary Depressive Illness" (Dec. 1967) *Br. J. Clin. Psych.* 6(4):278-296.
Hashimoto et al. "Urinary Incontinence: an Unrecognised Adverse Effect with Donepezil" (Aug. 12, 2000) *The Lancet* 356:568 (abstract).
Hayashi et al. "Sarpogrelate HC1, a selective 5-HT2A Antagonist, Retards the Progression of Atherosclerosis Through a Novel Mechanism" (2003) *Atherosclerosis* 168:23-31.
Helm et al. "GABAb receptor antagonist SGS742 improves spatial memory and reduces protein binding to the cAMP response element (CRE) in the hippocampus" (2005) *Neuropharmacology* 48:956-964.
Hirst et al. "Characterization of [25I]-SB-258585 binding to human recombinant and native 5-HT6 receptors in rat, pig and human brain tissue" (2000) *British Journal of Pharmacology* 130:1597-1605.
Hirst et al. "Differences in the Central Nervous System Distribution and Pharmacology of the Mouse 5-Hydroxytryptamine-6 Receptor Compared with Rat and Human Receptors Investigated by Radioligand Binding, Site-Directed Mutagenesis, and Molecular Building" (2003) *Mol. Pharmacol.* 64:1295-1308.
Holenz et al. "Medicinal Chemistry Driven Approaches Toward Novel and Selective Serontonin 5-HT6 Receptor Ligands" (2005) *J. Med. Chem.* 48(6):1781-1795.
Horibe et al. "Sarpogrelate, a 5-HT2 Receptor Blocker, may Have a Preconditioning-Like Effect in Patients with Coronary Artery Disease" (2004) *Circulation Research* 68:68-72.
Ibach et al. "Acetylcholinesterase Inhibition in Alzheimer's Disease" (2004) *Current Pharmaceutical Design* 10:231-251.
Iliff et al. "A Paravascular Pathway Facilitates CSF Flow Through the Brain Parenchyma and the Clearance of Interstitial Solutes, Including Amyloid β." (2012) *Sci. Transl. Med.* 4(147):147ra111.
International Preliminary Report on Patentability for International Application No. PCT/US2005/041726 dated Sep. 21, 2006 by Authorized Officer Stefan Hartinger.
International Preliminary Report on Patentability for International Application No. PCT/US2007/011810 dated Jul. 16, 2008 by Authorized Officer Bart De Jong.
International Preliminary Report on Patentability; PCT/US2007/021182 dated Nov. 4, 2008 by Authorized Officer P. Lauro.
International Search Report and Written Opinion for PCT/EP008/067225 dated Mar. 23, 2009.
International Search Report and Written Opinion for PCT/EP2004/010843 dated Mar. 14, 2005.
International Search Report and Written Opinion for PCT/EP2005/012463 dated Feb. 20, 2006.
International Search Report and Written Opinion for PCT/EP2006/009460 dated Dec. 14, 2006.
International Search Report and Written Opinion for PCT/EP2008/053285 dated Jul. 29, 2008.
International Search Report and Written Opinion for PCT/US2004/023488 dated Oct. 12, 2004.
International Search Report and Written Opinion for PCT/US2004/023880 dated Nov. 15, 2004.
International Search Report and Written Opinion for PCT/US2007/021182 dated Mar. 14, 2005.
International Search Report and Written Opinion for PCT/US2008/009740 dated Feb. 18, 2009.
International Search Report and Written Opinion for PCT/US2009/005811 dated Jul. 8, 2010.
International Search Report and Written Opinion for PCT/US2009/005809 dated Apr. 28, 2010.
International Search Report and Written Opinion for PCT/US2009/002019 dated Dec. 14, 2009.
International Search Report and Written Opinion for PCT/US2016/031359 dated Jul. 29, 2016.
International Search Report and Written Opinion for PCT/US2016/037090 dated Sep. 9, 2016.
International Search Report for International Application No. PCT/US2006/002721 dated Feb. 20, 2007.
International Search Report for International Application No. PCT/US2005/041726 dated May 18, 2006 by Authorized Officer Stefan Hartinger.
International Search Report for International Application No. PCT/US2006/001516 dated Jun. 7, 2006.
International Search Report for International Application No. PCT/US2007/011810 dated Oct. 30, 2007 by Authorized Officer Bart De Jong.
International Search Report for PCT/EP2003/003197 dated Dec. 11, 2003.
Isaac et al. "6-Bicyclopiperazinyl-1-arylsulfonylindoles and 6-Bicyclopiperidinyl-1-arylsulfonylindoles Derivatives as Novel, Potent, and Selective 5-HT6 Receptor Antagonists" (2000) *Bioorganic & Med. Chem. Letters* 10:1719-1721.
Janos et al. "Overactive bladder medicines and cognitive testing" (Nov. 2008) *Int J Clin Pract* 62(11):1637-1642 (abstract).
Jeon et al. "The synthesis of a new pyrazolylimidazolinone via 1,3-dipolar cycloaddition reaction of N-methyl sydnone with methyl propiolate" (1998) *Bull. Korean Chem. Soc.* 19(7):725-726.
Jewart et al. "Cognitive, Behavioral and Physiological Changes in Alzheimer Disease Patients as a Function of Incontinence Medications" (Apr. 2005) *Am J Geriatr Psychiatry* 13(4):324-328 (abstract).

(56) References Cited

OTHER PUBLICATIONS

Jhee et al. "Centrally Acting Antiemetics Mitigate Nausea and Vomiting in Patients with Alzheimer's Disease Who Receive Rivastigmine" (Mar./Apr. 2002) *Clinical Neuropharmacology* 25(2):122-123 (abstract).

Johnell et al. "Concurrent Use of Anticholinergic Drugs and Cholinesterase Inhibitors" (2008) *Drugs Aging* 25(10):871-877 (abstract).

Johnson et al. "5-HT6 receptor antagonists: Prospects for the treatment of cognitive disorders including dementia" (2008) *Current Opinion in Drug Discovery and Development* 11(5): 642-654.

Kaduszkiewicz et al. "Cholinesterase inhibitors for patients with Alzheimer's disease: systematic review of randomised clinical trials" (2005) *BMJ online* 331-321.

Kan et al. "Association of the HTR6 Polymorphism C267T With Late-Onset Alzheimer's Disease in Chinese" (1995) *J. Pharmacol. & Exp. Therapeutics* 274:173-180.

Kaneniwa et al. "Solubilization of Water-Insoluble Organic Powders by Ball-Milling in the Presence of Polyvinylpyrrolidone" (1975) *Chem. Pharm. Bull.* 23(11):2973-2986.

Kay et al. "Antimuscarinic Drugs for Overactive Bladder and Their Potential Effects on Cognitive Function in Older Patients" (2005) *JAGS* 53:2195-2201 (abstract).

Kay et al. "Preserving cognitive function for patients with overactive bladder: evidence for a differential effect with darifenacin" (Nov. 2008) *Int J Clin Pract.* 62(11):1792-1800.

Khoshkhoo et al. "Crystallization of polymorphs: the effect of solvent" (1993) *J. Phys. DD Appl.Phys.* 26:B90-B93.

Khullar et al. "Prevalence of Faecal Incontinence Among Women with Urinary Incontinence" (1998) *Br. J. Obstet. Gynaecol.* 105:1211-1213.

Krieger et al. "Novel Immunosuppressants" (2004) *Pediatr. Transplantation* 8:594-599.

Levin et al. "Direct measurement of the anticholinergic activity of a series of pharmacological compounds on the canine and rabbit urinary bladder" (1982) *J. Urology* 128(2):396-398 (abstract).

Lewy Body Dementia Association, Inc., treatment options page, http://www.lbda.org/content/treatment-options, at least as early as Apr. 10, 2015.

Liang et al. "Olanzapine in the treatment of schizophrenia: a open trial clinical study" (1999) *Chinese Journal of Psychiatry* vol. 04, Title page/TOC only.

Lieben et al. "The Selective 5-HT6 Receptor Antagonist Ro4368554 Restores Memory Performance in Cholinergic and Serotonergic Models of Memory Deficiency in the Rat" (2005) *Neuropsychopharmacology* 30: 2169-2179.

Liem-Moolenaar et al. "Central Nervous System Effects of the Interaction Between Risperidone (single dose) and the 5-HT6 Antagonist SB742457 (repeated doses) in Healthy Men" (2010) *Br. J. Clin. Pharma.* 71(6):907-916.

Lightowler et al. "Anxiolytic-like Effect of Paroxetine in a Rat Social Interaction Test" Oct. 1994) *Pharmacol. Biochem. Behav.* 49(2):281-285 (abstract).

Lindner et al. "An Assessment of the Effects of Serontonin 6 (5-HT6) Receptor Antagonists in Rodent Models of Learning" (2003) *J. Pharmacol. Exp. Ther.* 307(2): 682-691.

Lombardo et al CTAD Poster Presentation Figure 4 entitled "Phase 1 PET Study to Evaluate the Receptor Occupancy of RVT-101" Sep. 21, 2011.

London Stock Exchange Announcement—GlaxoSmithKline (GSK) plc, Issued on Thursday, Dec. 13, 2007, New York, New York.

Lopez et al. "Predictors of progression in patients with AD and Lewy bodies" (2000) *Neurology* 54:1774-1779 (abstract).

Lu et al. "Chronic Exposure to Anticholinergic Medications Adversely Affects the Course of Alzheimer Disease" (Jul.-Aug. 2003) *Am J Geriatr Psychiatry* 11(4):458-461 (abstract).

Maher-Edwards et al "Double-blind, controlled phase II study of a 5-HT6 receptor antagonist, SB-742457, in Alzheimer's disease" (2010) *Current Alzheimer Research* 7:374-385.

Maher-Edwards et al. "SB-742457 and donepezil in Alzheimer disease: a randomized, placebo-controlled study" (2011) *Int. J. Geriatr. Psychiatry* 26:536-544.

Major et al. "Establishment of a Line of Human Fetal Glial Cells That Supports JC Virus Multiplication" (1985) *PNAS USA* 82:1257-1261.

Marcos "Serotonin-Induced Smooth Muscle Hyperplasia in Various Forms of Human Pulmonary Hypertension" (2004) *Circ. Res.* 94(9):1263-1270.

Martarello et al. "Radiolabelling and in vivo evaluation of [11C]GSK215083 as a potential PET radioligand for the 5-HT6 receptor in the porcine brain" (2005) *J. Label Compd. Radiopharm.* 48:S7.

Martarello et al.. "Radiolabelling and in vivo evaluation of [11C]GSK215083 as potential PET radioligand for the 5-HT6 receptor in the porcine brain" (2005) *Journal of Cerebral Blood Flow & Metabolism* 25:S598.

McKeith et al. "Efficacy of rivastigmine in dementia with Lewy bodies: a randomised, double-blind, placebo-controlled international study" (2000) *The Lancet* 356:2031-2036 (abstract).

MedlinePlus, MedlinePlus Medical Encyclopedia, 2009, pp. 1-5 (abstract).

Mestre et al. "5-Hydroxytryptamine 2A receptor antagonists as potential treatment for psychiatric disorders" (2013) *Expert Opin. Investig Drugs* 22(4):411-421.

Miao et al. "Ketanserin Stabilizes Blood Pressure in Conscious Spontaneously Hypertensive Rats" (2003) *Clin. Exp. Pharmacol. Physiol.* 30(3):189-193.

Mitchell et al. "5-HT6 receptors: a novel target for cognitive enhancement" (2005) *Pharmacol & Therapeutics* 108:320-333.

Montgomery et al. "A New Depression Scale Designed to be Sensitive to Change" (Apr. 1979) *Br. J. Psychiatry* 134(4):382-389.

Morairty et al. "Selective 5HT2A and 5HT6 Receptor Antagonists Promote Sleep in Rats" (2008) *Sleep* 31(1).

Mueller "Drug Immunosuppression Therapy for Adult Heart Transplantation. Part 1: Immune Response to Allograft and Mechanism of Action of Immunosuppressents" (2004) *Ann. Thorac. Surg.* 77:354-362.

Müller, Inorganic Structural Chemistry, Apr. 15, 1993, John Wiley and Sons, 274 pages, pp. 14-15.

Nordberg et al. "Cholinesterase Inhibitors in the Treatment of Alzheimer's Disease" (1998) *Drug Safety* 19(6):465-480.

Office Action for U.S. Appl. No. 11/883,043, mailed on Sep. 8, 2009.

Oken "Antihistamines, a Possible Risk Factor for Alzheimer's Disease" (1995) *Medical Hypotheses* 44:47-48 (abstract).

Olichney et al. "Cognitive Decline is Faster in Lewy Body Variant than in Alzheimer's Disease" (1998) *Neurology* 51:351-357 (abstract).

Ono Pharmaceutical Co., Ltd. "Launch of Rivistach.RTM. Patch, for the Treatment of Dementia of Alzheimer's Type" (2011) 2 pages.

Otwinowski et al. "Processing of x-ray diffraction data collected in oscillation mode" (1997) *Methods Enzymology* 276:307-326 (abstract).

Parker et al. "Human Kinetic Modeling of the 5HT6 PET Radioligand 11C-GSK215083 and Its Utility for Determining Occupancy at Both 5HT6 and 5HT2A Receptors by SB742457 as a Potential Therapeutic Mechanism of Aaction in Alzheimer Disease" (2015) *J. Nucl. Med.* 56:1901-1909.

Pawlak et al. "A Potent 5-Hydroxytryptamine Receptor (5-HT2A) Antagonist, DV-7028, Delays Arterial Thrombosis Development in Rats" (1998) *Thrombosis Research* 90:259-270.

Phase 1 Study, result summary. Study AZ3105822, a single-blind, randomized, placebo-controlled study to evaluate the effect of repeated dosing of an investigational product on the pharmacokinetics and pharmacodynamics of Warfarin in healthy adult subjects. http://www.gsk-clinicalstudyregister.com/result_detail.jsp?protocolId=105822&studyId=BC2066FF-1606-487D-B093-189458F0AE76&compound=SB742457 (undated).

Phase 2, Study 1, result summary. Study AZ3110865, a study comparing SB-74257 or donepezil versus placebo in subjects with mild-to-moderate Alzheimer's disease. http:...www.gsk-clinical studyregister.com/result_detail.jsp?protocolId=AZ3110865&studyId=242C4974-9729-4D30-8F91-327CF0631014&compound=SB742457 (undated).

(56) References Cited

OTHER PUBLICATIONS

Phase 2, Study 2, result summary. Study AZ3110866, a fixed dose study of SB-742457 versus placebo when added to existing donepezil treatment in subjects with mild-to-moderate Alzheimer's disease. http://www.gsk-clinicalstudyresgister.com/result_detail.jsp?protocolId=AZ3110866&studyId=B8176D5B-C331-4621-9303-2BBF51E4690B&compound=SB742457 (undated).
Pineiro-Nunez et al., "Discovery and SAR studies of 2,6-difluorobenzenesulfonic acid 1-methyl-3-(methylopiperidin-4-yl)-1H-indol-5-yl ester, a novel and potent 5-HT6 antagonist treatment of cognitive deficit", 299$^{th}$ ACS Natl. Mtg., Mar. 13-17, San Diego, Abst. Medi 282 (2005).
Porsolt et al. "Behavioral despair in mice: a primary screening test for antidepressants" (1977) *Arch. Int. Pharmac. Ther.* 229(2):327-336 abstract.
Portegies et al. "Guidelines for the Diagnosis and Management of Neuroogical Complications of HIV Infection" (2004) *Eur. J. Neurol.* 11:297-304.
Product Information Sheet, Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Sanctura.RTM. (trospium chloride), Rev. Jan. 2011.
Product Information Sheet, VESIcare.RTM. (solifenacin succinate) tablets, Rev. Apr. 2010.
Przyklenk et al. "Targeted inhibition of the serotonin 5HT2A receptor improves coronary patency in an in vivo model of recurrent thrombosis" (2010) *J. Thromb Haemost.* 8(2):331-340.
Querbes et al. "A JC Virus-Induced Signal is Required for Infection ofGlial Cells by a Clathrin- and eps15-Dependent Pathway" (2004) *J. Virology* 78:250-256.
Raschetti et al. "Cholinesterase Inhibitors in Mild Cognitive Impairment: A Systematic Review of Randomised Trials" (2007) *PloS Med.* 4(11):1818-1828.
Ray et al. "Central Anticholinergic Hypersensitivity in Aging" (Apr.-Jun. 1992) *Journal of Geriatric Psychiatry and Neurology* 5:72-77 (abstract).
Remington's Pharmaceutical Science, 15$^{th}$ ed, Mack Publishing Company, Easton, PA (Jun. 1976) (abstract).
Riemer et al. "Influence of the 5-HT6 Receptor on Acetylcholine Release in the Cortex: Pharmacological Characterization of 4-(2-Bromo-6-pyrrolidin-1-ylpyridine-4-sulfonyl)phenylamine, a Potent and Selective 5-HT6 Receptor Antagonist" (2003) *Brief Articles, J. Med. Chem.* 46:1273-1276.
Roberts et al. "The distribution of 5-HT6 receptors in rat brain: an autoradiographic binding study using the radiolabeled 5-HT6 receptor antagonist 125ISB-258585" (2002) *Brain Research* 934:49-57.
Robichaud et al. "Ch. 2: Recent Advances in Selective Serotonin Receptor Modulation" (2000) *Annual Reports in Medicinal Chemistry* 36:11-20.
Robinul RTM. glycopyrrolate tablets Product Information Sheet, Rev. Apr. 2010.
Roche Bioreversible Carriers in Drug Design ed (1987) (TOC only).
Roe et al. "Use of Anticholinergic Medications by Older Adults with Dementia" (2002) *JAGS* 50:836-842 (abstract).
Rogers et al. "5-HT6 Receptor Antagonists Enhance Retention of a Water Maze Task in the Rat" (2001) *Psychopharmacology* 158:114-119.
Rojas-Fernandez "Successful Use of Donepezil for the Treatment of Dementia with Lewy Bodies" (2001) *Annals of Pharmacotherapy* 35(2):202-205.
Roth et al. "Serotonin receptors represent highly favorable molecular targets for cognitive enhancement in schizophrenia and other disorders" (2004) *Psychopharmacology* 174:17-24.
Rudolph et al. "The Anticholinergic Risk Scale and Anticholinergic Adverse Effects in Older Persons" (Mar. 10, 2008) *Arch Intern Med* 168(5):508-513.

Russell et al. "N-Arylsulfonylindole Derivivatives as Serotonin 5-HT6 Receptor Ligands" (2001) *J. Med. Chem.* 44(23):3881-3895.
Shua-Haim et al. "Safety, Tolerability, and Caregiver's Impressions of Combination Therapy With Rivastigmine and Memantine for the Treatment of Alzheimer's Disease" (2004) *Neurobiology & Aging* S205: p. 1-377.
Silva et al. "Chronic treatment with mianserin prevents DOCA-salt hypertension in rats—evidence for the involvement of central 5-HT2 receptors" (2005) *J. Pharmacol.* 518(2-3):152-157, 2005.
Singh et al. "Immunosuppresive-aassociated Leukoencephalopathy in Organ Transplant Recipients" (2000) *Transplantation* 69:467-472.
Sink et al. "Dual Use of Bladder Anticholinergics and Cholinesterase Inhibitors: Long-Term Functional and Cognitive Outcomes" (2008) *JAGS* 56:847-853.
Sleight et al. "Characterization of Ro 04-6790 and Ro 63-0563: potent and selective antagonists at human and rat 5-HT6 receptors" (1998) *British Journal of Phamacol.* 124:556-562.
Stadler et al. "5-HT6 antagonists: a novel approach for the symptomatic treatment of Alzheimer's Disease", 37$^{th}$ IUPAC Cong. Aug. 14-19, 1999, Berlin, Abst. MM-7.
Teramura-Gronblad et al. "Use of Anticholinergic Drugs and Cholinesterase Inhibitors and Their Association with Psychological Well-Being Among Frail Older Adults in Residential Care Facilities" (2011) *Ann Pharmacotherapy* 45:596-602 (abstract).
Terry et al. "The Cholinergic Hypothesis of Age and Alzheimer's Disease-Related Cognitive Deficits: Recent Challenges and Their Implications for Novel Drug Development" (2003) *JPET* 306(3):821-827.
Thome et al. "Association analysis of HTR6 and HTR2A polymorphisms in sporadic Alzheimer's disease" (2001) *Journal of Neural Transmission* 108:1175-1180.
Totterdell "Synaptic Circutry of Interactions Between Limbic and Dopaminergic Afferents to the Ventral Striatum" (2004) *International Journal of Neuropsychopharmacology* 7:S14 SP.11.01.
Tsai et al. "Association Analysis of the 5-HT6 Receptor Polymorphism C267T in Alzheimer's Disease" (1999) *Neuroscience Letters* 276:138-139.
Tsao et al. "Transient Memory Impairment and Hallucinations Associated with Tolterodine Use" (Dec. 4, 2003) *New England Journal of Medicine* 349(23):2274-2275 (abstract).
Upton et al. "5-HT$_6$ Receptor antagonists as novel cognitive enhancing agents for Alzheimer's Disease" (2008) *Neurotherapeutics* 5(3):458-469.
Vacante et al. "Extension of JC Virus Host Range to Monkey Cells by Insertion of a Simian Virus 40 Enhancer into the JC Virus Regulatory Region" *Virology* 170:353-361.
Van Eijk et al. "Effect of rivastigmine as an adjunct to usual care with haloperidol on duration of delirium and mortality in critically ill patients: a multicentre, double-blind, placebo-controlled randomised trial" (2010) *The Lancet* 376:1829-1837 (abstract).
Vanover et al. "Role of 5-HT2A receptor antagonists in the treatment of insomnia" (2010) *Nature and Science of Sleep* 2:139-150.
Vasilevskii "Oxidative Iodination of Substituted N-Methylpyrazoles," (1980) *Bull. Acad. Sci. USSR* 29(5):778-784.
Vasilevsky et al. "Study of the Heterocyclization of vic-Substituted Hydrazides of Actylenylpyrazolecarboxylic Acids into N-Amino Pyrazolpyridinones" (2002) *J. Hetercycl. Chem.* 39:1229-1233.
Verdejo et al. "Tratamiento con propantelina de la incontinencia urinaria por inestabilidad vesical en pacientes ancianos" (1992) *Anales de Medicina* 9(3):1160120.
Williams et al. "Survival and mortality differences between dementia with Lewy bodies vs Alzheimer disease" (1935) *Neurology* 67:1935-1941 (abstract).
Willner "Animal Models as Simulations of Depression" (1991) *Trends Pharmacol. Sci.* 12(4): 131-136 (abstract).
Woolley et al. "5-HT6 Receptors" (2004) *Current Drug Targets—CNS & Neurological Disorders* 3:59-79.
Woolley et al. "A role for 5-HT6 Receptors in Retention of Spatial Learning in the Morris Water Maze" (2001) *Neuropharmacology* 41:210-219.

(56) References Cited

OTHER PUBLICATIONS

Woolley et al. "Reversal of a cholinergic-induced deficit in a rodent model of recognition memory by the selective 5-HT6 receptor antagonist, Ro 04-6790" (2003) *Psychopharmacology* 170:358-367.

Yamada et al. "Phase I/II trial of didanosine (2',2'-dideoxyinosine) in hemophiliac patients with AIDS or AIDS-related complex" (1993) *Clin. Diagn. Virol.* 1:245-256.

Yamashita et al. "Conjunctive effects of the 5HT2 receptor antagonist, sarpogrelate, on thrombolysis with modified tissue plasminogen activator in different laser-induced thrombosis models" (2000) *Haemostatis* 30:321-332 (abstract).

Gillman, The serotonin syndrome and its treatment, *Journal of Phychopharmacology* (1999), 31(1):100-109.

Kalueff et al., Hypolocomotion, anxiety and serotonin syndrome-like behavior contribute to the complex phenotype of serotonin transporter knockout mice, *Genes, Brain and Behavior* (2007), 6:389-400.

Mastropasqua et al. "Ocular hypotensive effect of ketanserin in patients with primary open angle glaucoma" (1997) *Acta Ophthalmol Scand Suppl.* (224):24-5.

FIG. 3A

ATGGATATTCTTTGTGAAGAAAATACTTCTTTGAGCTCAACTACGAACTCCCTAATGCAATTA

AATGATGACAACAGGCTCTACAGTAATGACTTTAACTCCGGAGAAGCTAACACTTCTGATGCA

TTTAACTGGACAGTCGACTCTGAAAATCGAACCAACCTTTCCTGTGAAGGGTGCCTCTCACCG

TCGTGTCTCTCCTTACTTCATCTCCAGGAAAAAAACTGGTCTGCTTTACTGACAGCCGTAGTGA

TTATTCTAACTATTGCTGGAAACATACTCGTCATCATGGCAGTGTCCCTAGAGAAAAAGCTGC

AGAATGCCACCAACTATTTCCTGATGTCACTTGCCATAGCTGATATGCTGCTGGGTTTCCTTGT

CATGCCCGTGTCCATGTTAACCATCCTGTATGGGTACCGGTGGCCTCTGCCGAGCAAGCTTTGT

GCAGTCTGGATTTACCTGGACGTGCTCTTCTCCACGGCCTCCATCATGCACCTCTGCGCCATCT

CGCTGGACCGCTACGTCGCCATCCAGAATCCCATCCACCACAGCCGCTTCAACTCCAGAACTA

AGGCATTTCTGAAAATCATTGCTGTTTGGACCATATCAGTAGGTATATCCATGCCAATACCAG

TCTTTGGGCTACAGGACGATTCGAAGGTCTTTAAGGAGGGGAGTTGCTTACTCGCCGATGATA

ACTTTGTCCTGATCGGCTCTTTTGTGTCATTTTTCATTCCCTTAACCATCATGGTGATCACCTAC

TTTCTAACTATCAAGTCACTCCAGAAAGAAGCTACTTTGTGTGTAAGTGATCTTGGCACACGG

GCCAAATTAGCTTCTTTCAGCTTCCTCCCTCAGAGTTCTTTGTCTTCAGAAAAGCTCTTCCAGC

GGTCGATCCATAGGGAGCCAGGGTCCTACACAGGCAGGAGGACTATGCAGTCCATCAGCAAT

GAGCAAAAGGCATGCAAGGTGCTGGGCATCGTCTTCTTCCTGTTTGTGGTGATGTGGTGCCCT

TTCTTCATCACAAACATCATGGCCGTCATCTGCAAAGAGTCCTGCAATGAGGATGTCATTGGG

GCCCTGCTCAATGTGTTTGTTTGGATCGGTTATCTCTCTTCAGCAGTCAACCCACTAGTCTACA

CACTGTTCAACAAGACCTATAGGTCAGCCTTTTCACGGTATATTCAGTGTCAGTACAAGGAAA

ACAAAAAACCATTGCAGTTAATTTTAGTGAACACAATACCGGCTTTGGCCTACAAGTCTAGCC

AACTTCAAATGGGACAAAAAAAGAATTCAAAGCAAGATGCCAAGACAACAGATAATGACTGC

TCAATGGTTGCTCTAGGAAAGCAGTATTCTGAAGAGGCTTCTAAAGACAATAGCGACGGAGT

GAATGAAAAGGTGAGCTGTGTGTGA

FIG. 3B

MDILCEENTSLSSTTNSLMQLNDDNRLYSNDFNSGEANTSDAFNWTVDSENRTNLSCEGCLSPSCL
SLLHLQEKNWSALLTAVVIILTIAGNILVIMAVSLEKKLQNATNYFLMSLAIADMLLGFLVMPVSM
LTILYGYRWPLPSKLCAVWIYLDVLFSTASIMHLCAISLDRYVAIQNPIHHSRFNSRTKAFLKIIAVW
TISVGISMPIPVFGLQDDSKVFKEGSCLLADDNFVLIGSFVSFFIPLTIMVITYFLTIKSLQKEATLCVS
DLGTRAKLASFSFLPQSSLSSEKLFQRSIHREPGSYTGRRTMQSISNEQKACKVLGIVFFLFVVMWC
PFFITNIMAVICKESCNEDVIGALLNVFVWIGYLSSAVNPLVYTLFNKTYRSAFSRYIQCQYKENKK
PLQLILVNTIPALAYKSSQLQMGQKKNSKQDAKTTDNDCSMVALGKQYSEEASKDNSDGVNEKV
SCV

FIG. 4B

MVNLRNAVESFLVHLIGLLVWQCDISVSPVAAIVTDIFNTSDGGRFKFPDGVQNWPALSIVIIILMTIGGN
ILVIMAVSMEKKLHNATNYFLMSLAIADMLVGLLVMPLSLLAILYDYVWPLPRYLCPVWISLDVLFSTASI
MHLCAISLDRYVAIRNPIEHSRFNSRTKAIMKIAIVWAISIGVSVPIPVIGLRDEEKVFVNNTTCVLNDPN
FVLIGSFVAFFIPLTIMVITYCLTIYVLRRQALMLLHGHTEEPPGLSLDFLKCCKRNTAEEENSANPNQDQ
NARRRKKKERRPRGTMQAINNERKASKVLGIVFFVFLIMWCPFFITNILSVLCEKSCNQKLMEKLLNVFVW
IGYVCSGINPLVYTLFNKTYRRAFSNYLRCNYKVEKKPPVRQIPRVAATALSGRELNVNIYRHTNEPVIEK
ASDNEPGIEMQVENLELPVNPSSVVSERISSV

*FIG. 4A*

ATGGTGAACCTGAGGAATGCGGTGCATTCATTCCTTGTGCACCTAATTGGCCTATTGGTTTGGC

AATGTGATATTTCTGTGAGCCCAGTAGCAGCTATAGTAACTGACATTTTCAATACCTCCGATG

GTGGACGCTTCAAATTCCCAGACGGGGTACAAAACTGGCCAGCACTTTCAATCGTCATCATAA

TAATCATGACAATAGGTGGCAACATCCTTGTGATCATGGCAGTAAGCATGGAAAAGAAACTG

CACAATGCCACCAATTACTTCTTAATGTCCCTAGCCATTGCTGATATGCTAGTGGGACTACTTG

TCATGCCCCTGTCTCTCCTGGCAATCCTTTATGATTATGTCTGGCCACTACCTAGATATTTGTG

CCCCGTCTGGATTTCTTTAGATGTTTTATTTTCAACAGCGTCCATCATGCACCTCTGCGCTATAT

CGCTGGATCGGTATGTAGCAATACGTAATCCTATTGAGCATAGCCGTTTCAATTCGCGGACTA

AGGCCATCATGAAGATTGCTATTGTTTGGGCAATTTCTATAGGTGTATCAGTTCCTATCCCTGT

GATTGGACTGAGGGACGAAGAAAAGGTGTTCGTGAACAACACGACGTGCGTGCTCAACGACC

CAAATTTCGTTCTTATTGGGTCCTTCGTAGCTTTCTTCATACCGCTGACGATTATGGTGATTAC

GTATTGCCTGACCATCTACGTTCTGCGCCGACAAGCTTTGATGTTACTGCACGGCCACACCGA

GGAACCGCCTGGACTAAGTCTGGATTTCCTGAAGTGCTGCAAGAGGAATACGGCCGAGGAAG

AGAACTCTGCAAACCCTAACCAAGACCAGAACGCACGCCGAAGAAAGAAGAAGGAGAGACG

TCCTAGGGGCACCATGCAGGCTATCAACAATGAAAGAAAAGCTTCGAAAGTCCTTGGGATTG

TTTTCTTTGTGTTTCTGATCATGTGGTGCCCATTTTTCATTACCAATATTCTGTCTGTTCTTTGTG

AGAAGTCCTGTAACCAAAAGCTCATGGAAAAGCTTCTGAATGTTGTTTGTTTGGATTGGCTAG

TTTGTTCAGGAATCAATCCTCTGGTGTATACTCTGTTCAACAAAATTTACCGAAGGGCATTCTC

CAACTATTTGCGTTGCAATTATAAGGTAGAGAAAAAGCCTCCTGTCAGGCAGATTCCAAGAGT

TGCCGCCACTGCTTTGTCTGGGAGGGAGCTTAATGTTAACATTTATCGGCATACCAATGAACC

GGTGATCGAGAAAGCCAGTGACAATGAGCCCGGTATAGAGATGCAAGTTGAGAATTTAGAGT

TACCAGTAAATCCCTCCAGTGTGGTTAGCGAAAGGATTAGCAGTGTGTGA

FIG. 5A

ATGGTGAACCTGAGGAATGCGGTGCATTCATTCCTTGTGCACCTAATTGGCCTATTGGTTTGGCAAT
GTGATATTTCTGTGAGCCCAGTAGCAGCTATAGTAACTGACATTTTCAATACCTCCGATGGTGGACG
CTTCAAATTCCCAGACGGGGTACAAAACTGGCCAGCACTTTCAATCGTCATCATAATAATCATGAC
AATAGGTCGCAACATCCTTGTGATCATGGCAGTAAGCATGGAAAAGAAACTGCACAATGCCACCA
ATTACTTCTTAATGTCCCTAGCCATTGCTGATATGCTAGTGGGACTACTTGTCATGCCCCTGTCTCTC
CTGGCAATCCTTTATGATTATGTCTGGCCATCAACTAGATATTTGTGCCCGTCTGGATTTCTTTAGA
TGTTTTATTTTCAACAGCGTCCATCATGCACCTCTGCGCTATATCGCTGGATCGGTATGTAGCAATA
CGTAATTCTATTGAGCATAGCCGTTTCAATTCGCGGACTAAGGCCATCATGAAGATTGCTATTGTTT
GGGCAATTTCTATAGGTGTATCAGTTCCTATCCCTGTGATTGGACTGAGGGACGAAGAAAAGGTGT
TCGTGAACAACACGACGTGCGTGCTCAACGACCCAAATTTGCTTCTTATTGGGTCCTTCGTAGCTTT
CTTCATACCGCTGACGATTATGGTGATTACGTATTGCCTGACCATCTACGTTCTGCGCCGACAAGCT
TTGATGTTACTGCACGGCCACACCGAGGAACCGCCTGGACTAAGTCTGTATTTCCTGAACTGCTGC
AAGAGGAATACGGCCGAGGAAGAGAACTCTGCAAACCCTAACCAAGACCAGAACGCACGCCGAA
GAAAGAAGAAGGAGAGACGTCCTAGGGGCACCATGCAGGCTATCAACAATGAAAGAAAAGCTAA
GAAAGTCCTTGGGATTGTTTTCTTTGTGTTTCTGATCATGTGGTGCCCATTTTTCATTACCAATATTC
TGTCTGTTCTTTGTGAGAAGTCCTGTAACCAAAAGCTCATGGAAAAGCTCTGAATGTGTTTGTTTG
GATTGGCTATGTTTGTTCAGGATTCAATCCTCTGGTGTATACTCTGTTCAACAAAATTTACCGAAGG
GCATTCTCCAACTATTTGCGTTGCAATTATAAGGTAGAGAAAAAGCCCTCCTGTCAGGCAGATTCCA
AGAGTTGCCGCCACTGCTTTGTCTGGGAGGGAGCTTATTGTTAACATTTATCGGCATACCAATGAA
CCGGTGATCGAGAAAGCCAGTGACAATGAGCCCGGTATAGAGATGCAAGTTGAGAATTTAGAGTT
ACCAGTAAATCCCTCCAGTGTGGTTAGCGAAAGGATTAGCAGTGTGTGA

FIG. 5B

MVNLRNAVHSFLVHLIGLLVWQCDISVSPVAAIVTDIFNTSDGGRFKFPDGVQNWPALSIVIIIIMTI
GGNILVIMAVSMEKKLHNATNYFLMSLAIADMLVGLLVMPLSLLAILYDYVWPLPRYLCPVWISL
DVLFSTASIMHLCAISLDRYVAIRNPIEHSRFNSRTKAIMKIAIVWAISIGVSVPIPVIGLRDEEKVFV
NNTTCVLNDPNFVLIGSFVAFFIPLTIMVITYCLTIYVLRRQALMLLHGHTEEPPGLSDFLKCCKRN
TAEEENSANPNQDQNARRRKKKERRPBGTMQAINNERKAKKVLGIVFFVFLIMWCPFFTTNILSVL
CEKSCNQKLMEKLLNVFVWIGYVCSGINPLVYTLFNKIYRRAFSNYLRCNYKVEKKPPVRQIPRV
AATALSGRENLNVNIYRHTNEPVIEKASDNEPGIEMQVENLELPVNPSSVVSERISSV

FIG. 6B

MDILCEENTSLSSTTNSLMQLNDDNRLYSNDFNSGEANTSDAFNWTVDSENRTNLSCEGCLSPSCL
SLLHLQEKNWSALLTAVVIILLTIAGNILVIMAVSLEKKLQNATNYFLMSLAIADMILGFLVMPVSM
LTILYGYRWPLPSKLCAVWIYLDVLFSTASIMHLCAISLDRYVAIQNPIHHSRFNSRTKAFLKIIAVW
TISVGISMPIPVFGLQDDSKVFKEGSCLLADDNFVLIGSFVSFFIPLTIMVITYFLTIKVLRRQALMLL
HGHTEEPPGLSLDFLKCCKRNTAEEENSANPNQDQNARRRKKKERRPBGTMQAINNERKAS
KVLGIVFFLFVVMWCPFFTTNIMAVICKESCNEDVIGALLNVFVWIGYLSSAVNPLVYTLFNKIYR
RAFSNYLRCNYKVEKKPPVRQIPRVAATALSGRELNVNIYRHTNEPVIEKASDNEPGIEMQVE
NLELPVNPSSVVSERISSV

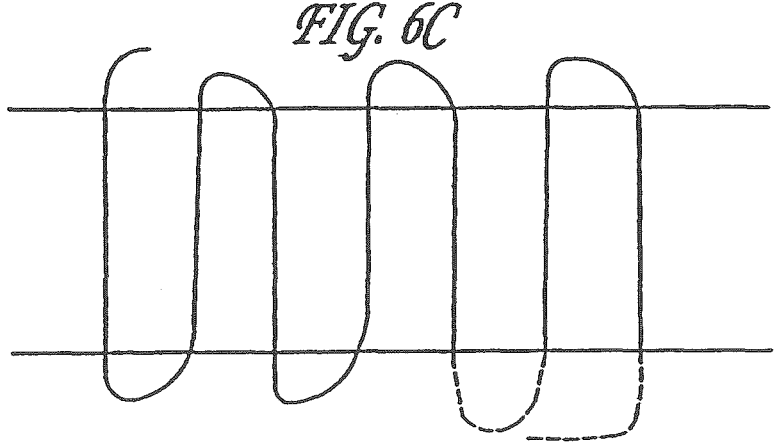

ATGGATATTCTTTGTGAAGAAAATACTTCTTTGAGCTCAACTACGAACTCCCTAATGCAATTA
AATGATGACAACAGGCTCTACAGTAATGACTTTAACTCCGGAGAAGCTAACACTTCTGATGCA
TTTAACTGGACAGTCGACTCTGAAAATCGAACCAACCTTTCCTGTGAAGGGTGCCTCTCACCG
TCGTGTCTCTCCTTACTTCATCTCAGGAAAAAAACTGGTCTGCTTTACTGACAGCCGTAGTGA
TTATTCTAACTATTGCTGGAAACATACTCGTCATCATGGCAGTGTCCCTAGAGAAAAAGCTGC
AGAATGCCACCAACTATTTCCTGATGTCACTTGCCATAGCTGATATGCTGCTGGGTTTCCTTGT
CATGCCCGTGTCCATGTTAACCATCCTGTATGGGTACCGGTGGCCTCTGCCGAGCAAGCTTTGT
GCAGTCTGGATTTACCTGGACGTGCTCTTCTCCACGGCCTCCATCATGCACCTCTGCGCCATCT
CGCTGGACCGCTACGTCGCCATCCAGAATCCCATCCACCACAGCCGCTTCAACTCCAGAACTA
AGGCATTTCTGAAAATCATTGCTGTTTGGACCATATCAGTAGGTATATCCATGCCAATACCAG
TCTTTGGGCTACAGGACGATTCGAAGGTCTTTAAGGAGGGGAGTTGCTTACTCGCCGATGATA
ACTTTGTCTGATCGGCTCTTTTGTGTCATTTTTCATTCCCTTAACCATCATGGTGATCACCTAC
TTTCTAACTATCAAGGTTCTGCGCCCGACAAGCTTTGATGTTACTGCACGGCCACACCGAG
GAACCGCCTGGACTAAGTCTGGATTTCCTGAAGTGCTGCAAGAGGAATACGGCCGAGGA
AGAGAACTCTGCAAACCCTAACCAAGACCAGAACGCACGCCGAAGAAAGAAGAAGGAG
AGACGTCCTAGGGGCACCATGCAGGCTATCAACAATGAAAGAAAAGCTTCGAAGGTACT
GGGCATCGTCTTCTTCCTGTTTGTGGTGATGTGGTGCCCTTTCTTCATCACAAACATCATGGCC
GTCATCTGCAAAGAGTCCTGCAATGAGGATGTCATTGGGGCCCTGCTCAATGTGTTTGTTTGG
ATCGGTTATCTCTCTTCAGCAGTCAACCCACTAGTCTATACTCTGTTCAACAAAATTTACCGA
AGGGCATTCTCCAACTATTTGCGTTGCAATTATAAGGTAGAGAAAAAGCCTCCTGTCAG
GCAGATTCCAAGAGTTGCCGCCACTGCTTTGTCTGGGAGGGAGCTTAATGTTAACATTT
ATCGGCATACCAATGAACCGGTGATCGAGAAAGCCAGTGACAATGAGCCCGGTATAGAG
ATGCAAGTTGAGAATTTAGAGTTACAGTAAATCCCTCCAGTGTGGTTAGCGAAAGGAT
TAGCAGTGTGTGA

FIG. 7A

ATGGATATTCTTTGTGAAGAAAATACTTCTTTGAGCTCAACTACGAACTCCCTAATGCAATTA

AATGATGACAACAGGCTCTACAGTAATGACTTTAACTCCGGAGAAGCTAACACTTCTGATGCA

TTTAACTGGACAGTCGACTCTGAAAATCGAACCAACCTTTCCTGTGAAGGGTGCCTCTCACCG

TCGTGTCTCTCCTTACTTCATCTCCAGGAAAAAAACTGGTCTGCTTTACTGACAGCCGTAGTGA

TTATTCTAACTATTGCTGGAAACATACTCGTCATCATGGCAGTGTCCCTAGAGAAAAAGCTGC

AGAATGCCACCAACTATTTCCTGATGTCACTTGCCATAGCTGATATGCTGCTGGGTTTCCTTGT

CATGCCCGTGTCCATGTTAACCATCCTGTATGGGTACCGGTGGCCTCTGCCGAGCAAGCTTTGT

GCAGTCTGGATTTACCTGGACGTGCTCTTCTCCACGGCCTCCATCATGCACCTCTGCGCCATCT

CGCTGGACCGCTACGTCGCCATCCAGAATCCCATCCACCACAGCCGCTTCAACTCCAGAACTA

AGGCATTTCTGAAAATCATTGCTGTTTGGACCATATCAGTAGGTATATCCATGCCAATACCAG

TCTTTGGGCTACAGGACGATTCGAAGGTCTTTAAGGAGGGGAGTTGCTTACTCGCCGATGATA

ACTTTGTCCTGATCGGCTCTTTTGTGTCATTTTTCATTCCCCTGACGATTATGGTGATTACGT

ATTGCCTGACCATCTACGTTCTGCGCCGACAAGCTTTGATGTTACTGCACGGCCACACC

GAGGAACCGCCTGGACTAAGTCTGGATTTCCTGAAGTGCTGCAAGAGGAATACGGCCGA

GGAAGAGAACTCTGCAAACCCTAACCAAGACCAGAACGCACGCCGAAGAAAGAAGAAG

GAGAGACGTCCTAGGGGCACCATGCAGGCTATCAACAATGAAAGAAAAGCTAAGAAAGT

CCTTGGGATTGTTTTCTTTGTGTTTCTGATCATGTGGTGCCCTTTCTTCATCACAAACATCA

TGGCCGTCATCTGCAAAGAGTCCTGCAATGAGGATGTCATTGGGGCCCTGCTCAATGTGTTTG

TTTGGATCGGTTATCTCTCTTCAGCAGTCAACCCACTAGTCTATACTCTGTTCAACAAAATTT

ACCGAAGGGCATTCTCCAACTATTTGCGTTGCAATTATAAGGTAGAGAAAAAGCCTCCT

GTCAGGCAGATTCCAAGAGTTGCCGCCACTGCTTTGTCTGGGAGGGAGCTTAATGTTAA

CATTTATCGGCATACCAATGAACCGGTGATCGAGAAAGCCAGTGACAATGAGCCCGGTA

TAGAGATGCAAGTTGAGAATTTAGAGTTACCAGTAAATCCCTCCAGTGTGGTTAGCGAA

AGGATTAGCAGTGTGTGA

FIG. 7B

MDILCEENTSLSSTTNSLMQLNDDNRLYSNDFNSGEANTSDAFNWTVDSENRTNLSCEGCLSPSCL
SLLHLQEKNWSALLTAVVIILTIAGNILVIMAVSLEKKLQNATNYFLMSLAIADMLLGFLVMPVSM
LTILYGYRWPLPSKLCAVWIYLDVLFSTASIMHLCAISLDRYVAIQNPIHHRSFNSRTKAFLKIIAVW
TISVGISMPIPVFGLQDDSKVFKEGSCLLADDNFVLIGSFVSFFIPLTIMVTTYCLTIYVLRRQALML
LHGHTEEPPGLSLDFLKCCKRNTAEEENSANPNQDQNARRRKKKERRPRGTMQAINNERKA
KKVLGIVFFVFLMWCPFFITNIMAVICKESCNEDVIGALLNVFVWIGYLSSAVNPLVYTLFNKIY
RRAFSNYLRCNYKVEKKPPVRQIPRVAATALSGRELNVNIYRHTNEPVIEKASDNEPGIEMQV
ENLELPVNPSSVVSERISSV

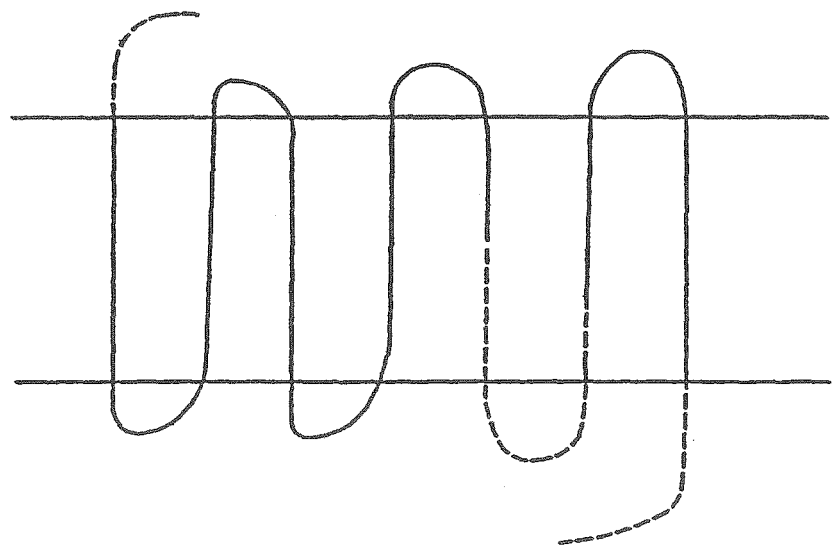

FIG. 7C

*Xho I (1312) to Sca I (3049) is identical to pRc/RSV Xho I (3045) to 4782.
*Sca I (3049) to 4070 is identical to pCDM7 Amp ScaI (2524) to 3545.
*multiple cloning site includes Hind III to Sac I of pBluescript II.
*110 to 1312 is identical to pCDM7 Amp 76 to 1278.
*Sac I and Spe I in MCS are not unique.

5HT$_{2A}$ Occupancy: Rhesus Monkey Experimental Methods

| Pretreatment | Pretreatment Time | PET Scan Time | [F-18]Altanserin Activity |
|---|---|---|---|
| Baseline | Baseline PET | --- | 16:38 | 1.90 mCi |
| 8 hour study | 0.5mg/kg Compound 1 | 8:39 AM | 16:21 | 2.10 mCi |
| 24hour study | 0.5mg/kg Compound 1 | 16:01 Day 1 | 16:15 Day 2 | 2.10 mCi |

Figure 24

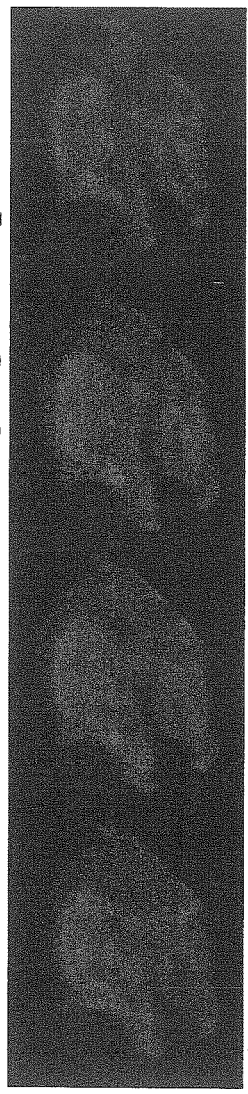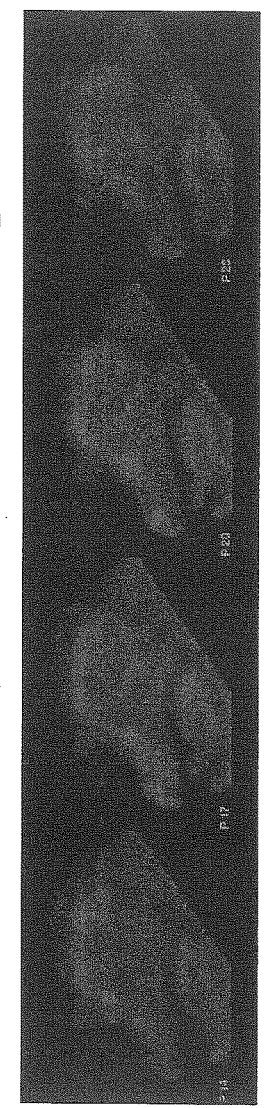
Figure 26

5HT$_{2A}$ Occupancy by Compound 1

| Region | Monkey Baseline DVR | 0.5 mg/kg Cmpd 1 -8 hrs | 0.5 mg/kg Cmpd 1 -24 hrs | % Occupancy -8 hr | % Occupancy -24 hr |
|---|---|---|---|---|---|
| Occipital Cortex | 2.59 | 1.25 | 1.36 | 84% | 77% |
| Frontal Cortex | 2.22 | 1.11 | 1.21 | 91% | 83% |
| Anterior Cingulate | 2.59 | 1.16 | 1.27 | 90% | 83% |
| Temporal Cortex | 2.27 | 1.19 | 1.27 | 85% | 79% |
| Striatum | 1.58 | 1.16 | 1.12 | 72% | 79% |

Figure 27

SEQUENCE LISTING

```
<160> NUMBER OF SEQ ID NOS: 30

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
gacctcgagg ttgcttaaga ctgaagca                                          28

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
atttctagac atatgtagct tgtaccgt                                          28

<210> SEQ ID NO 3
<211> LENGTH: 50
<212> TYPE: DNA
<213> ORGANISM: Artificial Sequence
<220> FEATURE:
<223> OTHER INFORMATION: oligonucleotide

<400> SEQUENCE: 3 ctagggcac catgcaggct atcaacaatg aaagaaaagc taagaaagtc                   50

<210> SEQ ID NO 4
<211> LENGTH: 50
<212> TYPE: DNA
<213> ORGANISM: Artificial Sequence
<220> FEATURE:
<223> OTHER INFORMATION: oligonucleotide

<400> SEQUENCE: 4
caaggacttt cttagctttt ctttcattgt tgatagcctg catggtgccc                  50

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
caaagaaagt actgggcatc gtcttcttcc t                                      31
```

```
<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tgctctagat tccagatagg tgaaaacttg                                        30

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
ccgctcgagt actgcgccga caagctttga t                                      31

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
cgatgcccag cactttcgaa gcttttcttt cattgttg                               38

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9
aaaagcttcg aaagtgctgg gcatcgtctt cttcct                                 36

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
tgctctagat tccagatagg tgaaaacttg                                        30

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
cgtgtctctc cttacttca                                                    19

<210> SEQ ID NO 12
<211> LENGTH: 36
<212> TYPE: DNA
<213> ORGANISM: Artificial Sequence
<220> FEATURE:
<223> OTHER INFORMATION: primer
```

```
<400> SEQUENCE: 12
tcggcgcagt actttgatag ttagaaagta ggtgat                              36

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
ttctaactat caaagtactg cgccgacaag ctttgatg                            38

<210> SEQ ID NO 14
<211> LENGTH: 43
<212> TYPE: DNA
<213> ORGANISM: Artificial Sequence
<220> FEATURE:
<223> OTHER INFORMATION: primer

<400> SEQUENCE: 14
ttcagcagtc aacccactag tctatactct gttcaacaaa att                      43

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
atttctagac atatgtagct tgtaccgt                                       28

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
atcacctact ttctaacta                                                 19

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ccataatcgt caggggaatg aaaaatgaca caa                                 33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
atttttcatt cccctgacga ttatggtgat tac                                 33
```

```
<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
tgatgaagaa agggcaccac atgatcagaa aca                            33

<210> SEQ ID NO 20
<211> LENGTH: 33
<212> TYPE: DNA
<213> ORGANISM: Artificial Sequence
<220> FEATURE:
<223> OTHER INFORMATION: primer

<400> SEQUENCE: 20
gatcatgtgg tgccctttct tcatcacaaa cat                            33

<210> SEQ ID NO 21
<211> LENGTH: 1416
<212> TYPE: DNA
<213> ORGANISM: Homo sapiens

<400> SEQUENCE: 21
atggatattc tttgtgaaga aaatacttct ttgagctcaa ctacgaactc cctaatgcaa      60
ttaaatgatg acaacaggct ctacagtaat gactttaact ccggagaagc taacacttct    120
gatgcattta actggacagt cgactctgaa atcgaaccaa ccttttcctg tgaagggtgc    180
ctctcaccgt cgtgtctctc cttacttcat ctccaggaaa aaaactggtc tgctttactg    240
acagccgtag tgattattct aactattgct ggaaacatac tcgtcatcat ggcagtgtcc    300
ctagagaaaa agctgcagaa tgccaccaac tatttcctga tgtcacttgc catagctgat    360
atgctgctgg gtttccttgt catgcccgtg tccatgttaa ccatcctgta tgggtaccgg    420
tggcctctgc cgagcaagct ttgtgcagtc tggatttacc tggacgtgct cttctccacg    480
gcctccatca tgcacctctg cgccatctcg ctggaccgct acgtcgccat ccagaatccc    540
atccaccaca gccgcttcaa ctccagaact aaggcatttc tgaaaatcat tgctgtttgg    600
accatatcag taggtatatc catgccaata ccagtctttg gctacaggga cgattcgaag    660 gtctcttaagg aggggagttg cttactcgcc gatgataact ttgtcctgat cggctctttt    720
gtgtcatttt tcattcccct taaccatcatg gtgatcacct actttctaac tatcaagtca    780
ctccagaaag aagctacttt gtgtgtaagt gatcttggca cacgggccaa attagcttct    840
ttcagcttcc tccctcagag ttctttgtct cagaaaagc tcttccagcg gtcgatccat    900
agggagccag ggtcctacac aggcaggagg actatgcagt ccatcagcaa tgagcaaaag    960
gcatgcaagg tgctgggcat cgtcttcttc ctgtttgtgg tgatgtggtg ccctttcttc   1020
atcacaaaca tcatggccgt catctgcaaa gagtcctgca atgaggatgt cattggggcc   1080
ctgctcaatg tgtttgtttg gatcggttat ctctcttcag cagtcaaccc actagtctac   1140
acactgttca acaagaccta taggtcagcc ttttcacggt atattcagtg tcagtacaag   1200
gaaaacaaaa aaccattgca gttaatttta gtgaacacaa taccggcttt ggcctacaag   1260
tctagccaac ttcaaatggg acaaaaaaag aattcaaagc aagatgccaa gacaacagat   1320
aatgactgct caatggttgc tctaggaaag cagtattctg aagaggcttc taaagacaat   1380
agcgacggag tgaatgaaaa ggtgagctgt gtgtga                              1416
```

```
<210> SEQ ID NO 22
<211> LENGTH: 471
<212> TYPE: PRT
<213> ORGANISM: Homo sapiens

<400> SEQUENCE: 22
```

| Met | Asp | Ile | Leu | Cys | Glu | Glu | Asn | Thr | Ser | Leu | Ser | Ser | Thr | Thr | Asn |
|---|---|---|---|---|---|---|---|---|---|---|---|---|---|---|---|
| 1 | | | | 5 | | | | | 10 | | | | | 15 | |

| Ser | Leu | Met | Gln | Leu | Asn | Asp | Asp | Asn | Arg | Leu | Tyr | Ser | Asn | Asp | Phe |
|---|---|---|---|---|---|---|---|---|---|---|---|---|---|---|---|
| | | | 20 | | | | | 25 | | | | | 30 | | |

| Asn | Ser | Gly | Glu | Ala | Asn | Thr | Ser | Asp | Ala | Phe | Asn | Trp | Thr | Val | Asp |
|---|---|---|---|---|---|---|---|---|---|---|---|---|---|---|---|
| | | | 35 | | | | | 40 | | | | | 45 | | |

| Ser | Glu | Asn | Arg | Thr | Asn | Leu | Ser | Cys | Glu | Gly | Cys | Leu | Ser | Pro | Ser |
|---|---|---|---|---|---|---|---|---|---|---|---|---|---|---|---|
| | 50 | | | | | 55 | | | | | 60 | | | | |

| Cys | Leu | Ser | Leu | Leu | His | Leu | Gln | Glu | Lys | Asn | Trp | Ser | Ala | Leu | Leu |
|---|---|---|---|---|---|---|---|---|---|---|---|---|---|---|---|
| 65 | | | | | 70 | | | | | 75 | | | | | 80 |

| Thr | Ala | Val | Val | Ile | Ile | Leu | Thr | Ile | Ala | Gly | Asn | Ile | Leu | Val | Ile |
|---|---|---|---|---|---|---|---|---|---|---|---|---|---|---|---|
| | | | | 85 | | | | | 90 | | | | | 95 | |

| Met | Ala | Val | Ser | Leu | Glu | Lys | Lys | Leu | Gln | Asn | Ala | Thr | Asn | Tyr | Phe |
|---|---|---|---|---|---|---|---|---|---|---|---|---|---|---|---|
| | | | 100 | | | | | 105 | | | | | 110 | | |

| Leu | Met | Ser | Leu | Ala | Ile | Ala | Asp | Met | Leu | Leu | Gly | Phe | Leu | Val | Met |
|---|---|---|---|---|---|---|---|---|---|---|---|---|---|---|---|
| | | 115 | | | | | 120 | | | | | 125 | | | |

| Pro | Val | Ser | Met | Leu | Thr | Ile | Leu | Tyr | Gly | Tyr | Arg | Trp | Pro | Leu | Pro |
|---|---|---|---|---|---|---|---|---|---|---|---|---|---|---|---|
| 130 | | | | | 135 | | | | | 140 | | | | | |

| Ser | Lys | Leu | Cys | Ala | Val | Trp | Ile | Tyr | Leu | Asp | Val | Leu | Phe | Ser | Thr |
|---|---|---|---|---|---|---|---|---|---|---|---|---|---|---|---|
| 145 | | | | | 150 | | | | | 155 | | | | | 160 |

| Ala | Ser | Ile | Met | His | Leu | Cys | Ala | Ile | Ser | Leu | Asp | Arg | Tyr | Val | Ala |
|---|---|---|---|---|---|---|---|---|---|---|---|---|---|---|---|
| | | | | 165 | | | | | 170 | | | | | 175 | |

| Ile | Gln | Asn | Pro | Ile | His | His | Ser | Arg | Phe | Asn | Ser | Arg | Thr | Lys | Ala |
|---|---|---|---|---|---|---|---|---|---|---|---|---|---|---|---|
| | | | 180 | | | | | 185 | | | | | 190 | | |

| Phe | Leu | Lys | Ile | Ile | Ala | Val | Trp | Thr | Ile | Ser | Val | Gly | Ile | Ser | Met |
|---|---|---|---|---|---|---|---|---|---|---|---|---|---|---|---|
| | | 195 | | | | | 200 | | | | | 205 | | | |

| Pro | Ile | Pro | Val | Phe | Gly | Leu | Gln | Asp | Asp | Ser | Lys | Val | Phe | Lys | Glu |
|---|---|---|---|---|---|---|---|---|---|---|---|---|---|---|---|
| 210 | | | | | 215 | | | | | 220 | | | | | |

| Gly | Ser | Cys | Leu | Leu | Ala | Asp | Asp | Asn | Phe | Val | Leu | Ile | Gly | Ser | Phe |
|---|---|---|---|---|---|---|---|---|---|---|---|---|---|---|---|
| 225 | | | | | 230 | | | | | 235 | | | | | 240 |

| Val | Ser | Phe | Phe | Ile | Pro | Leu | Thr | Ile | Met | Val | Ile | Thr | Tyr | Phe | Leu |
|---|---|---|---|---|---|---|---|---|---|---|---|---|---|---|---|
| | | | | 245 | | | | | 250 | | | | | 255 | |

| Thr | Ile | Lys | Ser | Leu | Gln | Lys | Glu | Ala | Thr | Leu | Cys | Val | Ser | Asp | Leu |
|---|---|---|---|---|---|---|---|---|---|---|---|---|---|---|---|
| | | | 260 | | | | | 265 | | | | | 270 | | |

| Gly | Thr | Arg | Ala | Lys | Leu | Ala | Ser | Phe | Ser | Phe | Leu | Pro | Gln | Ser | Ser |
|---|---|---|---|---|---|---|---|---|---|---|---|---|---|---|---|
| | | 275 | | | | | 280 | | | | | 285 | | | |

| Leu | Ser | Ser | Glu | Lys | Leu | Phe | Gln | Arg | Ser | Ile | His | Arg | Glu | Pro | Gly |
|---|---|---|---|---|---|---|---|---|---|---|---|---|---|---|---|
| | 290 | | | | | 295 | | | | | 300 | | | | |

| Ser | Tyr | Thr | Gly | Arg | Arg | Thr | Met | Gln | Ser | Ile | Ser | Asn | Glu | Gln | Lys |
|---|---|---|---|---|---|---|---|---|---|---|---|---|---|---|---|
| 305 | | | | | 310 | | | | | 315 | | | | | 320 |

| Ala | Cys | Lys | Val | Leu | Gly | Ile | Val | Phe | Phe | Leu | Phe | Val | Val | Met | Trp |
|---|---|---|---|---|---|---|---|---|---|---|---|---|---|---|---|
| | | | | 325 | | | | | 330 | | | | | 335 | |

| Cys | Pro | Phe | Phe | Ile | Thr | Asn | Ile | Met | Ala | Val | Ile | Cys | Lys | Glu | Ser |
|---|---|---|---|---|---|---|---|---|---|---|---|---|---|---|---|
| | | | 340 | | | | | 345 | | | | | 350 | | |

| Cys | Asn | Glu | Asp | Val | Ile | Gly | Ala | Leu | Leu | Asn | Val | Phe | Val | Trp | Ile |
|---|---|---|---|---|---|---|---|---|---|---|---|---|---|---|---|
| | | 355 | | | | | 360 | | | | | 365 | | | |

| Gly | Tyr | Leu | Ser | Ser | Ala | Val | Asn | Pro | Leu | Val | Tyr | Thr | Leu | Phe | Asn |
|---|---|---|---|---|---|---|---|---|---|---|---|---|---|---|---|
| | 370 | | | | | 375 | | | | | 380 | | | | |

```
Lys Thr Tyr Arg Ser Ala Phe Ser Arg Tyr Ile Gln Cys Gln Tyr Lys
385                 390                 395                 400

Glu Asn Lys Lys Pro Leu Gln Leu Ile Leu Val Asn Thr Ile Pro Ala
            405                 410                 415

Leu Ala Tyr Lys Ser Ser Gln Leu Gln Met Gly Gln Lys Lys Asn Ser
        420                 425                 430

Lys Gln Asp Ala Lys Thr Thr Asp Asn Asp Cys Ser Met Val Ala Leu
    435                 440                 445

Gly Lys Gln Tyr Ser Glu Glu Ala Ser Lys Asp Asn Ser Asp Gly Val
        450                 455                 460

Asn Glu Lys Val Ser Cys Val
465                 470

<210> SEQ ID NO 23
<211> LENGTH: 1377
<212> TYPE: DNA
<213> ORGANISM: Homo sapiens

<400> SEQUENCE: 23
atggtgaacc tgaggaatgc ggtgcattca ttccttgtgc acctaattgg cctattggtt      60
tggcaatgtg atatttctgt gagcccagta gcagctatag taactgacat tttcaatacc     120
tccgatggtg acgcttcaa attcccagac ggggtacaaa actggccagc actttcaatc      180
gtcatcataa aataggtggc aacatccttg tgatcatggc agtaagcatg                240
gaaaagaaac tgcacaatgc caccaattac ttcttaatgt ccctagccat tgctgatatg     300
ctagtgggac tacttgtcat gccccctgtct ctcctggcaa tccttttatga ttatgtctgg    360 ccactaccta gatatttgtg ccccgtctgg atttctttag atgttttatt ttcaacagcg    420
tccatcatgc acctctgcgc tatatcgctg gatcggtatg tagcaatacg taatcctatt    480
gagcatagcc gtttcaattc gcggactaag gccatcatga agattgctat tgtttgggca    540
atttctatag gtgtatcagt tcctatccct gtgattggac tgagggacga agaaaaggtg    600
ttcgtgaaca cacgacgtgt cgtgctcaac gacccaaatt cgttcttat tgggtccttc      660 gtagctttct tcataccgct gacgattatg gtgattacgt attgcctgac catctacgtt    720
ctgcgccgac aagctttgat gttactgcac ggccacaccg aggaaccgcc tggactaagt    780
ctggatttcc tgaagtgctg caagaggaat acggccgagg aagagaactc tgcaaaccct    840
aaccaagacc agaacgcacg ccgaagaaag aagaaggaga acgtcctag gggcaccatg     900 caggctatca acaatgaaag aaaagcttcg aaagtccttg ggattgtttt ctttgtgttt    960
ctgatcatgt ggtgcccatt tttcattacc aatattctgt ctgttctttg tgagaagtcc   1020
tgtaaccaaa agctcatgga aaagcttctg aatgtgtttg tttggattgg ctatgtttgt   1080
tcaggaatca atcctctggt gtatctctgt ttcaacaaaa tttaccgaag ggcattctcc   1140
aactatttgc gttgcaatta taaggtagag aaaaagcctc tgtcaggca gattccaaga   1200 gttgccgcca ctgctttgtc tgggagggag cttaatgtta acattttatcg gcataccaat   1260 gaaccggtga tcgagaaagc cagtgacaat gagcccggta tagagatgca agttgagaat   1320
ttagagttac cagtaaatcc ctccagtgtg gttagcgaaa ggattagcag tgtgtga      1377

<210> SEQ ID NO 24
<211> LENGTH: 458
<212> TYPE: PRT
<213> ORGANISM: Homo sapiens
```

```
<400> SEQUENCE: 24

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Arg Phe Lys Phe
        35                  40                  45

Pro Asp Gly Val Gln Asn Trp Pro Ala Leu Ser Ile Val Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
                100                 105                 110

Ala Ile Leu Tyr Asp Tyr Val Trp Pro Leu Pro Arg Tyr Leu Cys Pro
            115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
                180                 185                 190

Gly Leu Arg Asp Glu Glu Lys Val Phe Val Asn Asn Thr Thr Cys Val
            195                 200                 205

Leu Asn Asp Pro Asn Phe Val Leu Ile Gly Ser Phe Val Ala Phe Phe
210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
            275                 280                 285

Arg Lys Lys Lys Glu Arg Arg Pro Arg Gly Thr Met Gln Ala Ile Asn
290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
                340                 345                 350

Phe Val Trp Ile Gly Tyr Val Cys Ser Gly Ile Asn Pro Leu Val Tyr
            355                 360                 365

Thr Leu Phe Asn Lys Ile Tyr Arg Arg Ala Phe Ser Asn Tyr Leu Arg
        370                 375                 380

Cys Asn Tyr Lys Val Glu Lys Lys Pro Pro Val Arg Gln Ile Pro Arg
385                 390                 395                 400
```

Val Ala Ala Thr Ala Leu Ser Gly Arg Glu Leu Asn Val Asn Ile Tyr
            405                 410                 415

Arg His Thr Asn Glu Pro Val Ile Glu Lys Ala Ser Asp Asn Glu Pro
        420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
        450                 455

<210> SEQ ID NO 25
<211> LENGTH: 1377
<212> TYPE: DNA
<213> ORGANISM: Artificial Sequence
<220> FEATURE:
<223> OTHER INFORMATION: 5-HT2c receptor fragment

<400> SEQUENCE: 25

| | | |
|---|---|---|
| atggtgaacc tgaggaatgc ggtgcattca ttccttgtgc acctaattgg cctattggtt | 60 |
| tggcaatgtg atatttctgt gagcccagta gcagctatag taactgacat tttcaatacc | 120 |
| tccgatggtg gacgcttcaa attcccagac ggggtacaaa actggccagc actttcaatc | 180 |
| gtcatcataa taatcatgac aataggtggc aacatcctty tgatcatggc agtaagcatg | 240 |
| gaaaagaaac tgcacaatgc caccaattac ttcttaatgt ccctagccat tgctgatatg | 300 |
| ctagtgggac tacttgtcat gccctgtct ctcctggcaa tccttttatga ttatgtctgg | 360 |
| ccactaccta gatatttgtg cccgtctgg atttctttag atgtttttatt ttcaacagcg | 420 |
| tccatcatgc acctctgcgc tatatcgctg atcggtatg tagcaatacg taatcctatt | 480 |
| gagcatagcc gtttcaattc gcggactaag gccatcatga agattgctat tgtttgggca | 540 |
| atttctatag gtgtatcagt tcctatccct gtgattggac tgagggacga agaaaaggtg | 600 |
| ttcgtgaaca cacgacgtg cgtgctcaac gacccaaatt tcgttcttat tgggtccttc | 660 |
| gtagctttct tcataccgct gacgattatg gtgattacgt attgcctgac catctacgtt | 720 |
| ctgcgccgac aagctttgat gttactgcac ggccacaccg aggaaccgcc tggactaagt | 780 |
| ctggatttcc tgaagtgctg caagaggaat acggccgagg aagagaactc tgcaaaccct | 840 |
| aaccaagacc agaacgcacg ccgaagaaag aagaaggaga acgtcctag ggcaccatg | 900 |
| caggctatca acaatgaaag aaaagctaag aaagtccttg ggattgtttt ctttgtgttt | 960 |
| ctgatcatgt ggtgcccatt tttcattacc aatattctgt ctgttctttg tgagaagtcc | 1020 |
| tgtaaccaaa agctcatgga aaagcttctg aatgtgtttg tttggattgg ctatgtttgt | 1080 |
| tcaggaatca atcctctggt gtatactctg ttcaacaaaa tttaccgaag gcattctcc | 1140 |
| aactatttgc gttgcaatta taaggtagag aaaaagcctc ctgtcaggca gattccaaga | 1200 |
| gttgccgcca ctgctttgtc tgggagggag cttaatgtta acatttatcg gcataccaat | 1260 |
| gaaccggtga tcgagaaagc cagtgacaat gagcccggta tagagatgca agttgagaat | 1320 |
| ttagagttac cagtaaatcc ctccagtgtg gttagcgaaa ggattagcag tgtgtga | 1377 |

<210> SEQ ID NO 26
<211> LENGTH: 458
<212> TYPE: PRT
<213> ORGANISM: Artificial Sequence
<220> FEATURE:
<223> OTHER INFORMATION: 5-HT2c receptor fragment

<400> SEQUENCE: 26

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Arg Phe Lys Phe
        35                  40                  45

Pro Asp Gly Val Gln Asn Trp Pro Ala Leu Ser Ile Val Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Lys Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

```
Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455

<210> SEQ ID NO 27
<211> LENGTH: 1437
<212> TYPE: DNA
<213> ORGANISM: Artificial Sequence
<220> FEATURE:
<223> OTHER INFORMATION: 5-HT2c receptor fragment

<400> SEQUENCE: 27
atggatattc tttgtgaaga aaatacttct ttgagctcaa ctacgaactc cctaatgcaa      60
ttaaatgatg acaacaggct ctacagtaat gactttaact ccggagaagc taacacttct     120
gatgcattta actggacagt cgactctgaa aatcgaacca accttttcctg tgaagggtgc    180 ctctcaccgt cgtgtctctc cttacttcat ctccaggaaa aaaactggtc tgctttactg     240
acagccgtag tgattattct aactattgct ggaaacatac tcgtcatcat ggcagtgtcc     300
ctagagaaaa agctgcagaa tgccaccaac tatttcctga tgtcacttgc catagctgat     360
atgctgctgg gtttccttgt catgcccgtg tccatgttaa ccatcctgta tgggtaccgg     420
tggcctctgc cgagcaagct ttgtgcagtc tggatttacc tggacgtgct cttctccacg     480
gcctccatca tgcacctctg cgccatctcg ctggaccgct acgtcgccat ccagaatccc     540
atccaccaca gccgcttcaa ctccagaact aaggcatttc tgaaaatcat tgctgtttgg     600
accatatcag taggtatatc catgccaata ccagtctttg gctacaggac gattcgaag    660 gtctttaagg aggggagttg cttactcgcc gatgataact ttgtcctgat cggctctttt     720
gtgtcatttt tcattccctt aaccatcatg gtgatcacct actttctaac tatcaaggtt     780
ctgcgccgac aagctttgat gttactgcac ggccacaccg gaaccgcc tggactaagt      840 ctggatttcc tgaagtgctg caagaggaat acggccgagg aagagaactc tgcaaaccct    900
aaccaagacc agaacgcacg ccgaagaaag aagaaggaga acgtcctag ggcaccatg      960 caggctatca acaatgaaag aaaagcttcg aaggtactgg gcatcgtctt cttcctgttt    1020
gtggtgatgt ggtgccottt cttcatcaca aacatcatgg ccgtcatctg caaagagtcc    1080
tgcaatgagg atgtcattgg ggccctgctc aatgtgtttg tttggatcgg ttatctctct    1140
tcagcagtca acccactagt ctatactctg ttcaacaaaa tttaccgaag gcattctcc    1200 aactatttgc gttgcaatta taaggtagag aaaaagcctc ctgtcaggca gattccaaga    1260
gttgccgcca ctgctttgtc tgggagggag cttaatgtta acatttatcg cataccaat    1320 gaaccggtga tcgagaaagc cagtgacaat gagcccggta tagagatgca agttgagaat    1380
ttagagttac agtaaatcc ctccagtgtg gttagcgaaa ggattagcag tgtgtga     1437

<210> SEQ ID NO 28
<211> LENGTH: 478
<212> TYPE: PRT
<213> ORGANISM: Artificial Sequence
<220> FEATURE:
<223> OTHER INFORMATION: 5-HT2c receptor fragment
```

<400> SEQUENCE: 28

```
Met Asp Ile Leu Cys Glu Glu Asn Thr Ser Leu Ser Ser Thr Thr Asn
 1               5                  10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
 65                  70                  75                  80

Thr Ala Val Val Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Val Leu Arg Arg Gln Ala Leu Met Leu Leu His Gly His
            260                 265                 270

Thr Glu Glu Pro Pro Gly Leu Ser Leu Asp Phe Leu Lys Cys Cys Lys
        275                 280                 285

Arg Asn Thr Ala Glu Glu Asn Ser Ala Asn Pro Asn Gln Asp Gln
    290                 295                 300

Asn Ala Arg Arg Arg Lys Lys Lys Glu Arg Arg Pro Arg Gly Thr Met
305                 310                 315                 320

Gln Ala Ile Asn Asn Glu Arg Lys Ala Ser Lys Val Leu Gly Ile Val
                325                 330                 335

Phe Phe Leu Phe Val Val Met Trp Cys Pro Phe Phe Ile Thr Asn Ile
            340                 345                 350

Met Ala Val Ile Cys Lys Glu Ser Cys Asn Glu Asp Val Ile Gly Ala
        355                 360                 365

Leu Leu Asn Val Phe Val Trp Ile Gly Tyr Leu Ser Ser Ala Val Asn
    370                 375                 380

Pro Leu Val Tyr Thr Leu Phe Asn Lys Ile Tyr Arg Arg Ala Phe Ser
385                 390                 395                 400

Asn Tyr Leu Arg Cys Asn Tyr Lys Val Glu Lys Lys Pro Pro Val Arg
                405                 410                 415
```

```
Gln Ile Pro Arg Val Ala Ala Thr Ala Leu Ser Gly Arg Glu Leu Asn
            420                 425                 430

Val Asn Ile Tyr Arg His Thr Asn Glu Pro Val Ile Glu Lys Ala Ser
            435                 440                 445

Asp Asn Glu Pro Gly Ile Glu Met Gln Val Glu Asn Leu Glu Leu Pro
            450                 455                 460

Val Asn Pro Ser Ser Val Val Ser Glu Arg Ile Ser Ser Val
465                 470                 475

<210> SEQ ID NO 29
<211> LENGTH: 1437
<212> TYPE: DNA
<213> ORGANISM: Artificial Sequence
<220> FEATURE:
<223> OTHER INFORMATION: 5-HT2c receptor fragment

<400> SEQUENCE: 29
atggatattc tttgtgaaga aaatacttct tgagctcaa ctacgaactc cctaatgcaa      60
ttaaatgatg acaacaggct ctacagtaat gactttaact ccggagaagc taacacttct     120
gatgcattta actggacagt cgactctgaa aatcgaacca accttcctg tgaagggtgc      180 ctctcaccgt cgtgtctctc cttacttcat ctccaggaaa aaaactggtc tgctttactg     240
acagccgtag tgattattct aactattgct ggaaacatac tcgtcatcat ggcagtgtcc     300
ctagagaaaa agctgcagaa tgccaccaac tatttcctga tgtcacttgc catagctgat     360
atgctgctgg gtttccttgt catgcccgtg tccatgttaa ccatcctgta tgggtaccgg     420
tggcctctgc cgagcaagct ttgtgcagtc tggatttacc tggacgtgct cttctccacg     480
gcctccatca tgcacctctg cgccatctcg ctggaccgct acgtcgccat ccagaatccc     540
atccaccaca gccgcttcaa ctccagaact aaggcattc tgaaaatcat gctgtttgg      600 accatatcag taggtatatc catgccaata ccagtctttg gctacagga cgattcgaag     660 gtctttaagg aggggagttg cttactcgcc gatgataact ttgtcctgat cggctctttt     720
gtgtcatttt tcattcccct gacgattatg gtgattacgt attgcctgac catctacgtt     780
ctgcgccgac aagctttgat gttactgcac ggccacaccg aggaaccgcc tggactaagt     840 ctggattcc tgaagtgctg caagaggaat acggccgagg aagagaactc tgcaaaccct     900
aaccaagacc agaacgcacg ccgaagaaag aagaaggaga acgtcctag ggcaccatg      960 caggctatca acaatgaaag aaaagctaag aaagtccttg ggattgtttt ctttgtgttt    1020
ctgatcatgt ggtgccctt cttcatcaca aacatcatgg ccgtcatctg caaagagtcc    1080
tgcaatgagg atgtcattgg ggccctgctc aatgtgtttg tttggatcgg ttatctctct    1140
tcagcagtca acccactagt ctatactctg ttcaacaaaa tttaccgaag gcattctcc    1200 aactatttgc gttgcaatta taaggtagag aaaaagcctc tgtcaggca gattccaaga    1260 gttgccgcca ctgctttgtc tgggagggag cttaatgtta acatttatcg cataccaat    1320 gaaccggtga tcgagaaagc cagtgacaat gagcccggta tagagatgca agttgagaat    1380
ttagagttac cagtaaatcc ctccagtgtg gttagcgaaa ggattagcag tgtgtga      1437

<210> SEQ ID NO 30
<211> LENGTH: 478
<212> TYPE: PRT
<213> ORGANISM: Artificial Sequence
<220> FEATURE:
<223> OTHER INFORMATION: 5-HT2c receptor fragment
```

<400> SEQUENCE: 30

```
Met Asp Ile Leu Cys Glu Glu Asn Thr Ser Leu Ser Ser Thr Thr Asn
  1               5                  10                  15

Ser Leu Met Gln Leu Asn Asp Asp Asn Arg Leu Tyr Ser Asn Asp Phe
             20                  25                  30

Asn Ser Gly Glu Ala Asn Thr Ser Asp Ala Phe Asn Trp Thr Val Asp
         35                  40                  45

Ser Glu Asn Arg Thr Asn Leu Ser Cys Glu Gly Cys Leu Ser Pro Ser
     50                  55                  60

Cys Leu Ser Leu Leu His Leu Gln Glu Lys Asn Trp Ser Ala Leu Leu
 65                  70                  75                  80

Thr Ala Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Cys Leu
                245                 250                 255

Thr Ile Tyr Val Leu Arg Arg Gln Ala Leu Met Leu Leu His Gly His
            260                 265                 270

Thr Glu Glu Pro Pro Gly Leu Ser Leu Asp Phe Leu Lys Cys Cys Lys
        275                 280                 285

Arg Asn Thr Ala Glu Glu Glu Asn Ser Ala Asn Pro Asn Gln Asp Gln
    290                 295                 300

Asn Ala Arg Arg Arg Lys Lys Lys Glu Arg Arg Pro Arg Gly Thr Met
305                 310                 315                 320

Gln Ala Ile Asn Asn Glu Arg Lys Ala Lys Lys Val Leu Gly Ile Val
                325                 330                 335

Phe Phe Val Phe Leu Ile Met Trp Cys Pro Phe Phe Ile Thr Asn Ile
            340                 345                 350

Met Ala Val Ile Cys Lys Glu Ser Cys Asn Glu Asp Val Ile Gly Ala
        355                 360                 365

Leu Leu Asn Val Phe Val Trp Ile Gly Tyr Leu Ser Ser Ala Val Asn
    370                 375                 380

Pro Leu Val Tyr Thr Leu Phe Asn Lys Ile Tyr Arg Arg Ala Phe Ser
385                 390                 395                 400

Asn Tyr Leu Arg Cys Asn Tyr Lys Val Glu Lys Lys Pro Pro Val Arg
                405                 410                 415
```

-continued

```
Gln Ile Pro Arg Val Ala Ala Thr Ala Leu Ser Gly Arg Glu Leu Asn
            420                 425                 430

Val Asn Ile Tyr Arg His Thr Asn Glu Pro Val Ile Glu Lys Ala Ser
        435                 440                 445

Asp Asn Glu Pro Gly Ile Glu Met Gln Val Glu Asn Leu Glu Leu Pro
        450                 455                 460

Val Asn Pro Ser Ser Val Val Ser Glu Arg Ile Ser Ser Val
465                 470                 475
```

DIARYL AND ARYLHETEROARYL UREA DERIVATIVES AS MODULATORS OF THE 5-HT2A SEROTONIN RECEPTOR USEFUL FOR THE PROPHYLAXIS AND TREATMENT OF DISORDERS RELATED THERETO

CROSS-REFERENCE TO RELATED APPLICATIONS

This application is a continuation of U.S. application Ser. No. 14/332,207 filed on Jul. 15, 2014, which is a divisional of U.S. application Ser. No. 13/619,137, filed Sep. 14, 2012, which itself is a divisional of U.S. application Ser. No. 10/895,789, filed Jul. 21, 2004, which claims the benefit of U.S. application Ser. Nos. 60/489,572, filed Jul. 22, 2003 and 60/503,586, filed Sep. 16, 2003, the disclosures of each of which are incorporated herein by reference in their entireties.

FIELD OF THE INVENTION

The present invention relates to certain diaryl and arylheteroaryl urea derivatives of Formula (I) and pharmaceutical compositions thereof that modulate the activity of the $5\text{-HT}_{2A}$ serotonin receptor. Compounds and pharmaceutical compositions thereof are directed to methods useful in the prophylaxis or treatment of platelet aggregation, coronary artery disease, myocardial infarction, transient ischemic attack, angina, stroke, atrial fibrillation, reducing the risk of blood clot formation, asthma or symptoms thereof, agitation or a symptom, behavioral disorders, drug induced psychosis, excitative psychosis, Gilles de la Tourette's syndrome, manic disorder, organic or NOS psychosis, psychotic disorder, psychosis, acute schizophrenia, chronic schizophrenia, NOS schizophrenia and related disorders, sleep disorders, diabetic-related disorders and the like.

The present invention also relates to the method of prophylaxis or treatment of $5\text{-HT}_{2A}$ serotonin receptor mediated disorders in combination with a dopamine D2 receptor antagonist such as haloperidol, administered separately or together.

BACKGROUND OF THE INVENTION

G Protein Coupled Receptors

G Protein coupled receptors share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as, the carboxy terminus, interact with the G protein. Currently, Gq, Gs, Gi and Go are G proteins that have been identified. The general structure of G protein coupled receptors is shown in FIG. 1.

Under physiological conditions, G protein coupled receptors exist in the cell membrane in equilibrium between two different states or conformations: an "inactive" state and an "active" state. As shown schematically in FIG. 2, a receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed "constitutive receptor activation."

Serotonin Receptors

Receptors for serotonin (5-hydroxytryptamine, 5-HT) are an important class of G protein coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive compulsive disorders, schizophrenia, suicide, autism, migraine, emesis, alcoholism, and neurodegenerative disorders. With respect to antipsychotic treatment approaches focused on the serotonin receptors, these types of therapeutics can generally be divided into two classes, the "typical" and the "atypical." Both have anti-psychotic effects, but the typicals also include concomitant motor-related side effects (extra pyramidal syndromes, e.g., lip-smacking, tongue darting, locomotor movement, etc). Such side effects are thought to be associated with the compounds interacting with other receptors, such as the human dopamine D2 receptor in the nigro-striatal pathway. Therefore, an atypical treatment is preferred. Haloperidol is considered a typical anti-psychotic, and clozapine is considered an atypical anti-psychotic.

Serotonin receptors are divided into seven subfamilies, referred to as 5-HT1 through 5-HT7, inclusive. These subfamilies are further divided into subtypes. For example, the 5-HT2 subfamily is divided into three receptor subtypes: $5\text{-HT}_{2A}$, $5\text{-HT}_{2B}$, and $5\text{-HT}_{2C}$. The human $5\text{-HT}_{2C}$ receptor was first isolated and cloned in 1987, and the human $5\text{-HT}_{2A}$ receptor was first isolated and cloned in 1990. These two receptors are thought to be the site of action of hallucinogenic drugs. Additionally, antagonists to the $5\text{-HT}_{2A}$ and $5\text{-HT}_{2C}$ receptors are believed to be useful in treating depression, anxiety, psychosis, and eating disorders.

U.S. Pat. No. 4,985,352 describes the isolation, characterization, and expression of a functional cDNA clone encoding the entire human $5\text{-HT}_{1C}$ receptor (now known as the $5\text{-HT}_{2C}$ receptor). U.S. Pat. Nos. 5,661,024 and 6,541,209 describe the isolation, characterization, and expression of a functional cDNA clone encoding the entire human $5\text{-HT}_{2A}$ receptor.

Mutations of the endogenous forms of the rat $5\text{-HT}_{2A}$ and rat $5\text{-HT}_{2C}$ receptors have been reported to lead to constitutive activation of these receptors ($5\text{-HT}_{2A}$: Casey, C. et al. (1996) *Society for Neuroscience Abstracts,* 22:699.10, hereinafter "Casey"; $5\text{-HT}_{2C}$: Herrick-Davis, K., and Teitler, M. (1996) *Society for Neuroscience Abstracts,* 22:699.18, hereinafter "Herrick-Davis 1"; and Herrick-Davis. K. et al. (1997) *J. Neurochemistry* 69(3): 1138, hereinafter "Herrick-Davis-2"). Casey describes a mutation of the cysteine residue at position 322 of the rat $5\text{-HT}_{2A}$ receptor to lysine (C322K), glutamine (C322Q), and arginine (C322R) which reportedly led to constitutive activation. Herrick-Davis 1 and Herrick-Davis 2 describe mutations of the serine residue

SUMMARY OF THE INVENTION

One aspect of the present invention encompasses certain diaryl and arylheteroaryl urea derivatives as shown in Formula (I):

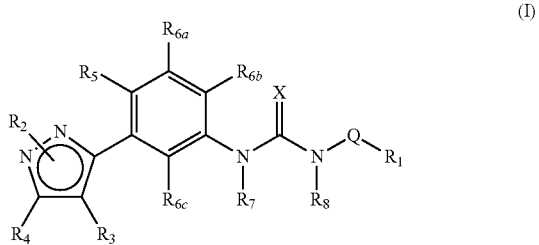

or a pharmaceutically acceptable salt, hydrate or solvate thereof;
wherein:
i) $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-5}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

ii) $R_2$ is selected from the group consisting of H, $C_{1-6}$ alkyl, $C_{2-6}$ alkenyl, $C_{2-6}$ alkynyl and $C_{3-7}$ cycloalkyl;

iii) $R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

iv) $R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

v) $R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, amino, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl are each optionally substituted with 1 to 5 further substituents selected from the group consisting of halogen and carbo-$C_{1-6}$-alkoxy;

vi) $R_{6a}$, $R_{6b}$, and $R_{6c}$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

One aspect of the present invention encompasses pharmaceutical compositions comprising a compound of the present invention and a pharmaceutically acceptable carrier.

One aspect of the present invention encompasses methods for modulating the activity of a $5HT_{2A}$ serotonin receptor by contacting the receptor with a compound according to any of the embodiments described herein or a pharmaceutical composition.

One aspect of the present invention encompasses methods for prophylaxis or treatment of platelet aggregation in an individual comprising administering to said individual in need thereof a therapeutically effective amount of a compound according to any of the embodiments described herein or a pharmaceutical composition.

One aspect of the present invention encompasses methods for prophylaxis or treatment of an indication selected from the group consisting of coronary artery disease, myocardial infarction, transient ischemic attack, angina, stroke, and atrial fibrillation in an individual comprising administering to said individual in need thereof a therapeutically effective amount of a compound according to any of the embodiments described herein or a pharmaceutical composition.

One aspect of the present invention encompasses methods for prophylaxis or treatment of reducing the risk of blood clot formation in an angioplasty or coronary bypass surgery individual comprising administering to said individual in need thereof a therapeutically effective amount of a compound according to any of the embodiments described herein or a pharmaceutical composition.

One aspect of the present invention encompasses methods for prophylaxis or treatment of reducing the risk of blood clot formation in an individual suffering from atrial fibrillation, comprising administering to said individual in need thereof a therapeutically effective amount of a compound according to any of the embodiments described herein or a pharmaceutical composition.

One aspect of the present invention encompasses methods for prophylaxis or treatment of asthma in an individual comprising administering to said individual in need thereof a therapeutically effective amount of a compound according to any of the embodiments described herein or a pharmaceutical composition.

One aspect of the present invention encompasses methods for prophylaxis or treatment of a symptom of asthma in an individual comprising administering to said individual in need thereof a therapeutically effective amount of a compound according to any of the embodiments described herein or a pharmaceutical composition.

One aspect of the present invention encompasses methods for prophylaxis or treatment of agitation or a symptom thereof in an individual comprising administering to said individual in need thereof a therapeutically effective amount of a compound according to any of the embodiments described herein or a pharmaceutical composition. In some embodiments, the individual is a cognitively intact elderly individual.

One aspect of the present invention encompasses methods for prophylaxis or treatment of agitation or a symptom thereof in an individual suffering from dementia comprising administering to said individual in need thereof a therapeutically effective amount of a compound according to any of the embodiments described herein or a pharmaceutical composition. In some embodiments, the dementia is due to a degenerative disease of the nervous system. In some embodiments, the dementia is Alzheimers disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention encompasses methods for prophylaxis or treatment of an individual suffering from at least one of the indications selected from the group consisting of behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of an individual with infantile autism, Huntington's chorea, or nausea and vomiting from chemotherapy or chemotherapeutic antibodies comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of schizophrenia in an individual comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of alleviating negative symptoms of schizophrenia induced by the administration of haloperidol to an individual suffering from said schizophrenia, comprising administering to said individual in need thereof a therapeutically effective amount of a compound according to any of the embodiments described herein or a pharmaceutical composition. In some embodiments, the haloperidol and the compound or pharmaceutical composition are administered in separate dosage forms. In some embodiments, the haloperidol and the compound or pharmaceutical composition are administered in a single dosage form.

One aspect of the present invention encompasses methods for prophylaxis or treatment of a sleep disorder in an individual comprising administering to said individual in need thereof a therapeutically effective amount of a compound according to any of the embodiments described herein or a pharmaceutical composition. In some embodiments, the sleep disorder comprises a fragmented sleep architecture. In some embodiments, the effective amount of a compound according to any of the embodiments described herein, or a pharmaceutical composition described herein, promotes sleep consolidation. In some embodiments, the effective amount of a compound according to any of the embodiments described herein, or a pharmaceutical composition described herein, increases delta power.

In some embodiments, the sleep disorder is a dyssomnia. In some embodiments, the dyssomnia is selected from the group consisting of psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome and non-24-hour sleep-wake disorder.

In some embodiments, the sleep disorder is a parasomnia. In some embodiments, the parasomnia is selected from the group consisting of confusional arousals, sleepwalking and sleep terrors, rhythmic movement disorder, sleep starts, sleep talking and nocturnal leg cramps.

In some embodiments, the sleep disorder is associated with a medical or psychiatric disorder. In some embodiments, the medical or psychiatric disorder is selected from the group consisting of psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep yl, phenetOne aspect of the present invention encompasses methods for prophylaxis or treatment of a One aspect of the present invention encompasses methods for prophylaxis or treatment of a diabetic-related disorder in an individual comprising administering to said individual in need thereof a therapeutically effective amount of a compound according to any of the embodiments described herein or a pharmaceutical composition.

In some embodiments, the diabetic-related disorder is diabetic peripheral neuropathy.

In some embodiments, the diabetic-related disorder is diabetic nephropathy.

In some embodiments, the diabetic-related disorder is diabetic retinopathy.

One aspect of the present invention encompasses processes for preparing a composition comprising admixing a compound according any embodiments described herein and pharmaceutically acceptable carrier.

One aspect of the present invention is the use of a compound for the production of a medicament for use in the prophylaxis or treatment of a $5HT_{2A}$ mediated disorder.

One embodiment of the present invention is the use of a compound for the production of a medicament for use in the prophylaxis or treatment of a $5HT_{2A}$ mediated disorder wherein the disorder is platelet aggregation.

One embodiment of the present invention is the use of a compound for the production of a medicament for use in the prophylaxis or treatment of a $5HT_{2A}$ mediated disorder wherein the disorder is selected from the group consisting of coronary artery disease, myocardial infarction, transient ischemic attack, angina, stroke, and atrial fibrillation.

One embodiment of the present invention is the use of a compound for the production of a medicament for use in the prophylaxis or treatment of a $5HT_{2A}$ mediated disorder wherein the disorder is a blood clot formation in an angioplasty or coronary bypass surgery individual.

One embodiment of the present invention is the use of a compound for the production of a medicament for use in the prophylaxis or treatment of a $5HT_{2A}$ mediated disorder wherein the disorder is a blood clot formation in an individual suffering from atrial fibrillation.

One embodiment of the present invention is the use of a compound for the production of a medicament for use in the prophylaxis or treatment of a $5HT_{2A}$ mediated disorder wherein the disorder is asthma.

One embodiment of the present invention is the use of a compound for the production of a medicament for use in the prophylaxis or treatment of a $5HT_{2A}$ mediated disorder wherein the disorder is a symptom of asthma.

One embodiment of the present invention is the use of a compound for the production of a medicament for use in the prophylaxis or treatment of a $5HT_{2A}$ mediated disorder wherein the disorder is agitation or a symptom thereof in an individual. In some embodiments the individual is a cognitively intact elderly individual.

One embodiment of the present invention is the use of a compound for the production of a medicament for use in the prophylaxis or treatment of a $5HT_{2A}$ mediated disorder wherein the disorder is agitation or a symptom thereof in an individual suffering from dementia. In some embodiments the dementia is due to a degenerative disease of the nervous system. In some embodiment the dementia is Alzheimers disease, Lewy Body, Parkinson's disease, or Huntington's disease. In some embodiments the dementia is due to diseases that affect blood vessels. In some embodiments the dementia is due to stroke or multi-infract dementia.

One embodiment of the present invention is the use of a compound for the production of a medicament for use in the prophylaxis or treatment of a $5HT_{2A}$ mediated disorder further comprising a dopamine D2 receptor antagonist wherein the disorder is selected from the group consisting of a behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia. In some embodiments the dopamine D2 receptor antagonist is haloperidol.

One embodiment of the present invention is the use of a compound for the production of a medicament for use in the prophylaxis or treatment of a $5HT_{2A}$ mediated disorder further comprising a dopamine D2 receptor antagonist wherein the disorder is infantile autism, Huntington's chorea, or nausea and vomiting from chemotherapy or chemotherapeutic antibodies. In some embodiments the dopamine D2 receptor antagonist is haloperidol.

One embodiment of the present invention is the use of a compound for the production of a medicament for use in the prophylaxis or treatment of a $5HT_{2A}$ mediated disorder further comprising a dopamine D2 receptor antagonist wherein the disorder is schizophrenia. In some embodiments the dopamine D2 receptor antagonist is haloperidol.

One embodiment of the present invention is the use of a compound for the production of a medicament for use in the prophylaxis or treatment of a $5HT_{2A}$ mediated disorder wherein the disorder is a negative symptom or symptoms of schizophrenia induced by the administration of haloperidol.

One embodiment of the present invention is the use of a compound for the production of a medicament for use in the prophylaxis or treatment of a $5HT_{2A}$ mediated disorder wherein the haloperidol and the compound or pharmaceutical composition are administered in separate dosage forms.

One embodiment of the present invention is the use of a compound for the production of a medicament for use in the prophylaxis or treatment of a $5HT_{2A}$ mediated disorder wherein the haloperidol and the compound or pharmaceutical composition are administered in a single dosage form.

One aspect of the present invention are compounds according to any of the embodiments described herein for use in a method of treatment of the human or animal body by therapy.

One aspect of the present invention are compounds according to any of the embodiments described herein for use in a method for the prophylaxis or treatment of a $5HT_{2A}$ mediated disorder, as described herein, in the human or animal body by therapy.

One aspect of the present invention are compounds according to any of the embodiments described herein for use in a method for the prophylaxis or treatment of a sleep disorder, as described herein, in the human or animal body by therapy.

One aspect of the present invention are compounds according to any of the embodiments described herein for use in a method for the prophylaxis or treatment of platelet aggregation in the human or animal body by therapy.

These and other aspects of the invention disclosed herein will be set forth in greater detail as the patent disclosure proceeds.

BRIEF DESCRIPTION OF THE DRAWINGS

In the following figures, bold typeface indicates the location of the mutation in the non-endogenous, constitutively activated receptor relative to the corresponding endogenous receptor.

FIG. 3a provides the nucleic acid sequence of the endogenous human 5-HT$_{2A}$ receptor (SEQ. ID. NO: 21).

FIG. 3b provides the corresponding amino acid sequence of the endogenous human 5-HT$_{2A}$ receptor (SEQ. ID. NO: 22).

FIG. 4a provides the nucleic acid sequence of the endogenous human 5-HT$_{2C}$ receptor (SEQ. ID. NO: 23).

FIG. 4b provides the corresponding amino acid sequence of the endogenous human 5-HT$_{2C}$ receptor (SEQ. ID. NO: 24).

FIG. 5a provides the nucleic acid sequence of a constitutively active form of the human 5-HT$_{2C}$ receptor ("AP-1 cDNA"-SEQ. ID. NO: 25).

FIG. 5b provides the corresponding amino acid sequence of the AP-1 cDNA ("AP-1"-SEQ. ID. NO: 26).

FIG. 6a provides the nucleic acid sequence of a constitutively active form of the human 5-HT$_{2A}$ receptor whereby the IC3 portion and the cytoplasmic-tail portion of the endogenous 5-HT$_{2A}$ receptor have been replaced with the IC3 portion and the cytoplasmic-tail portion of the human 5-HT$_{2C}$ receptor ("AP-3 cDNA"-SEQ. ID. NO: 27).

FIG. 6b provides the corresponding amino acid sequence of the AP-3 cDNA ("AP-3" SEQ. ID. NO: 28).

FIG. 6c provides a schematic representation of AP-3, where the dashed-lines represent the portion obtained from the human 5-HT$_{2C}$ receptor.

FIG. 7a provides the nucleic acid sequence of a constitutively active form of the human 5-HT$_{2A}$ receptor whereby (1) the region between the proline of TM5 and the proline of TM6 of the endogenous human 5-HT$_{2A}$ receptor has been replaced with the corresponding region of the human 5-HT$_{2C}$ receptor (including a S310K point mutation); and (2) the cytoplasmic-tail portion of the endogenous 5-HT$_{2A}$ receptor has been replaced with the cytoplasmic-tail portion of the endogenous human 5-HT$_{2C}$ receptor ("AP-4 cDNA"—SEQ. ID. NO:29).

FIG. 7b provides the corresponding amino acid sequence of the AP-4 cDNA ("AP-4"-SEQ. ID. NO: 30).

FIG. 7c provides a schematic representation of the mutated 5-HT$_{2A}$ receptor of FIG. 7b where the dashed-lines represent the portion obtained from the human 5-HT$_{2C}$ receptor.

FIG. 17 shows a general coupling method between a pyrazole boronic acid and an aryl triflate, it is understood that similar coupling methods can be used wherein the triflate is a halide, such as, I, Br or Cl.

FIG. 21 shows a general coupling method between a phenyl amine, as described in previous figures, and an isocyanate or thioisocyanate to give ureas and thioureas respectively.

FIG. 24 shows the experimental design of 5HT2A occupancy studies in monkeys.

FIG. 26 shows PET scan images of monkey brains 8 or 24 hours after treatment with Compound 1 compared to a baseline PET scan (sagital view).

FIG. 27 shows tabulated data for percent occupancy of 5HT2A receptors by Compound 1 in monkeys.

FIG. 29 shows a general coupling method between a pyrazole boronic acid and an aryl triflate, it is understood that similar coupling methods known in the art can also be used, and a halide, such as, I, Br or Cl, can be used in place of the triflate.

FIG. 30 illustrates the formation of pyrazoles from a variety of substituted chromen-4-ones. Also shown are alkylation and "Mitsunobu-like" examples for modifying the phenol, and illustrative reductions of the nitro to amine.

FIG. 31 illustrates the alkylation and "Mitsunobu-like" examples for modifying the phenol. It is understood that a variety of halo-alkyls and alcohols can be used in these reactions. Some representative alcohols are, 2-dimethylamino ethanol, 3-dimethylamino propanol, and the like.

FIG. 32 illustrates general methods for introducing a variety of halogens into compounds of the invention. It is understood that these halogenation reaction can also be conducted later in the synthesis, for example as the last step.

FIG. 33 shows a general coupling method between a phenyl amine, as described in previous figures, and isocyanates or thioisocyanates to give ureas and thioureas respectively. FIG. 33 also shows the general method for introducing $R_7$ and $R_8$ into compounds of the invention.

DEFINITIONS

Figure 1:
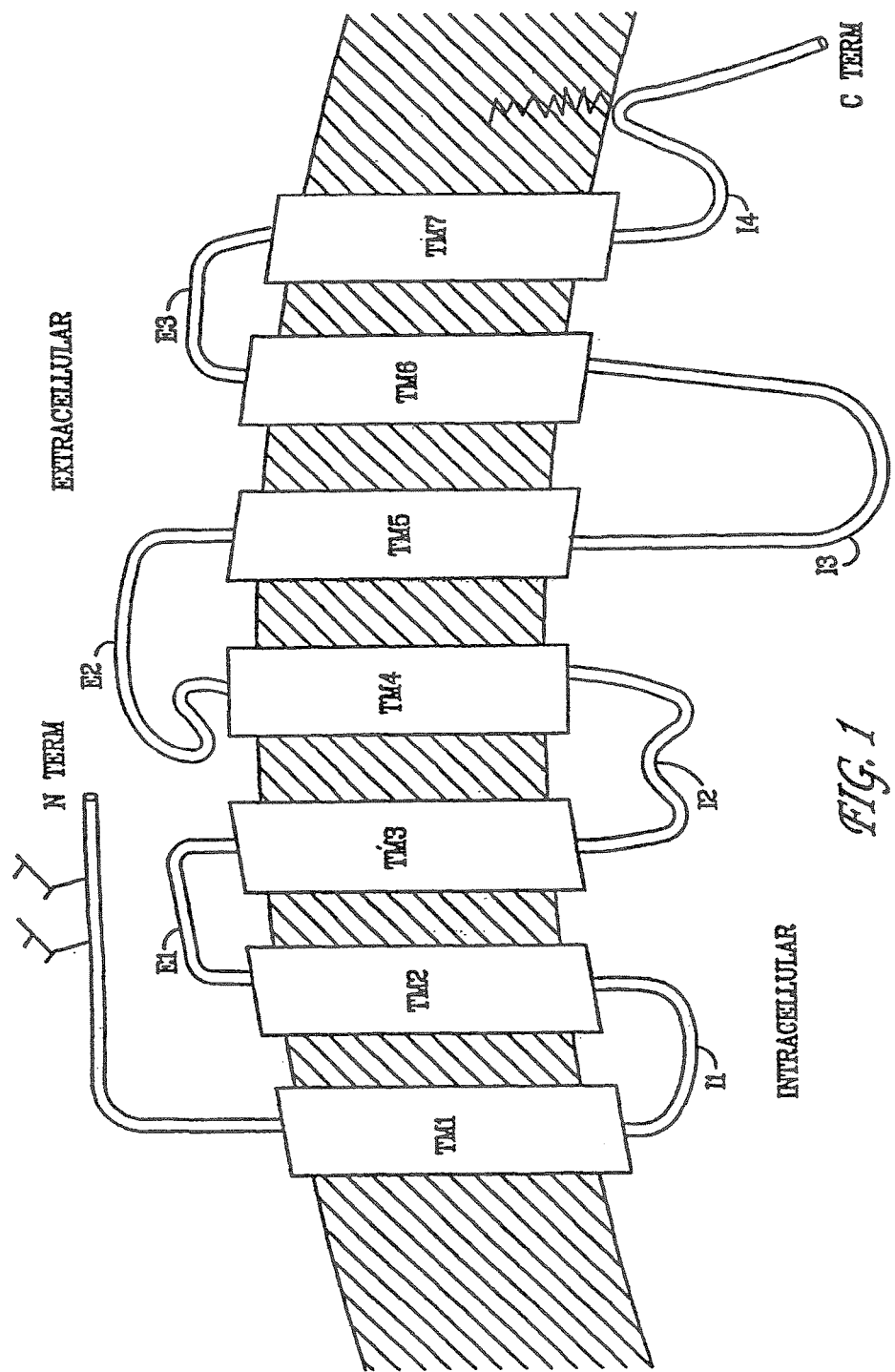
FIG. 1 shows a generalized structure of a G protein-coupled receptor with the numbers assigned to the transmembrane helices, the intracellular loops, and the extracellular loops.
Figure 2:
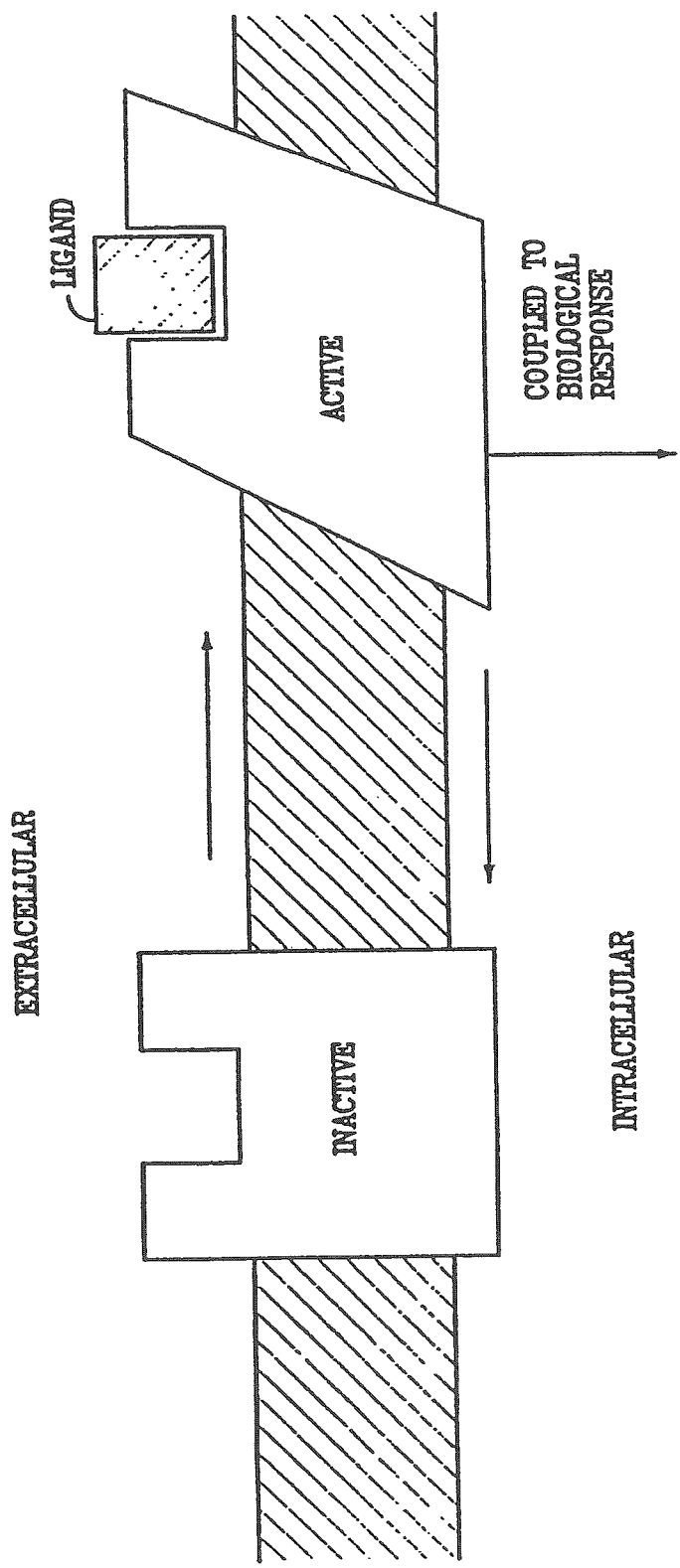
FIG. 2 schematically shows the active and inactive states for a typical G protein-coupled receptor and the linkage of the active state to the second messenger transduction pathway.

The scientific literature that has evolved around receptors has adopted a number of terms to refer to ligands having various effects on receptors. For clarity and consistency, the following definitions will be used throughout this patent document.

AGONISTS shall mean moieties that interact and activate the receptor, such as the 5-$HT_{2A}$ receptor, and initiates a physiological or pharmacological response characteristic of that receptor. For example, when moieties activate the intracellular response upon binding to the receptor, or enhance GTP binding to membranes.

AMINO ACID ABBREVIATIONS used herein are set out in TABLE 1:

TABLE 1

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

The term "$C_{1-6}$ acyl" denotes a $C_{1-6}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-6}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-6}$ alkoxy" as used herein denotes a radical alkyl, as defined herein, attached directly to an oxygen atom.

Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 4 carbons, some embodiments are 1 to 3 carbons, and some embodiments are 1 or 2 carbons. Examples of an alkyl include, but not limited to, methyl, ethyl, n-propyl, iso-propyl., n-butyl, sec-butyl, iso-butyl, t-butyl, pentyl, iso-pentyl, t-pentyl, neo-pentyl, 1-methyl butyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-6}$ alkylcarboxamido" or "$C_{1-6}$ alkylcarboxamide" denotes a single $C_{1-6}$ alkyl group attached to the nitrogen of an amide group, wherein alkyl has the same definition as found herein. The $C_{1-6}$ alkylcarboxamido may be represented by the following:

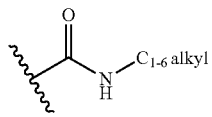 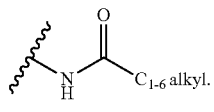

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to the variable or claim element "Q".

The term "$C_{1-6}$ alkylimino" denotes a C alkyl radical attached directly to the carbon of the —C(=NH)— group wherein the definition of alkyl has the same definition as described herein; some examples include but not limited to, 1-imino-ethyl [i.e., —C(=NH)CH$_3$], 1-imino-propyl [i.e., —C(=NH)CH$_2$CH$_3$], 1-imino-2-methyl-propyl [i.e., —C(=NH)CH(CH$_3$)$_2$], and the like.

The term "$C_{1-6}$ alkylsulfinyl" denotes a $C_{1-6}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butylsulfinyl, and the like.

The term "$C_{1-6}$ alkylsulfonamide" refers to the groups

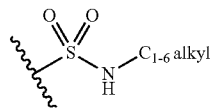 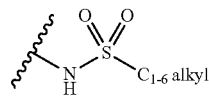

wherein $C_{1-6}$ alkyl has the same definition as described herein.

The term "$C_{1-6}$ alkylsulfonyl" denotes a $C_{1-6}$ alkyl radical attached to a sulfone radical of the formula: —S(O)$_2$— wherein the alkyl radical has the same definition as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_{1-6}$ alkylthio" denotes a $C_{1-6}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "$C_{1-6}$ alkylthiocarboxamide" denotes a thioamide of the following formulae:

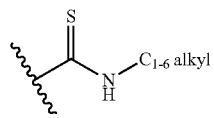 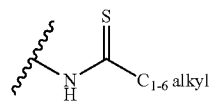

wherein $C_{1-4}$ alkyl has the same definition as described herein.

The term "$C_{1-6}$ alkylthioureyl" denotes the group of the formula: —NC(S)N— wherein one are both of the nitrogens are substituted with the same or different $C_{1-6}$ alkyl groups and alkyl has the same definition as described herein, Examples of an alkylthioureyl include, but not limited to, CH$_3$NHC(S)NH—, NH$_2$C(S)NCH$_3$—, (CH$_3$)$_2$C(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-6}$ alkylureyl" denotes the group of the formula: —NC(O)N— wherein one are both of the nitrogens are substituted with the same or different $C_{1-6}$ alkyl group wherein alkyl has the same definition as described herein. Examples of an alkylureyl include, but not limited to, CH$_3$NHC(O)NH—, NH$_2$C(O)NCH$_3$—, (CH$_3$)$_2$NC(O)N—, —(CH$_3$)$_2$NC(O)NH—, (CH$_3$)$_2$NC(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl 5-hexynyl and the like. The term "alkynyl" includes di- and tri-ynes.

The term "amino" denotes the group —NH$_2$.

The term "$C_{1-6}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 1:0 ring carbons. Examples include phenyl and naphthyl.

The term "arylalkyl" defines a $C_1$-$C_4$ alkylene, such as —CH$_2$—, —CH$_2$CH$_2$- and the like, which is further substituted with an aryl group. Examples of an "arylalkyl" include benzyl, phenethylene and the like.

The term "arylcarboxamido" denotes a single aryl group attached to the nitrogen of an amide group wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "carbo-C$_{1-6}$-alkoxy" refers to a C$_{1-6}$ alkyl ester of a carboxylic acid, wherein the alkyl group is as defined herein. Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neopentoxy, carbo-n-hexyloxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "C$_{4-7}$ cycloalkenyl" denotes a nor-aromatic ring radical containing 4 to 7 ring carbons and at least one double bond; some embodiments contain 4 to 6 carbons: some embodiments contain 4 to 5 carbons; some embodiments contain 4 carbons. Examples include cyclobutenyl, cyclopentenyl, cyclopentenyl cyclohexenyl, and the like.

The term "C$_{3-7}$ cycloalkyl" denotes a saturated ring radical containing 3 to 7 carbons; some embodiments contain 3 to 6 carbons: some embodiments contain 3 to 5 carbons; some embodiments contain 5 to 7 carbons; some embodiments contain 3 to 4 carbons. Examples include cyclopropyl, cyclobutyl, cyclopentyl, cyclopenyl, cyclohexyl, cycloheptyl and the like.

The term "C$_{2-8}$ dialkylamino" denotes an amino substituted with two of the same or different C$_{1-4}$ alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "C$_{2-4}$ dialkylamino."

The term "C$_{2-8}$ dialkylcarboxamido" or "C$_{2-8}$ dialkylcarboxamide" denotes two alkyl radicals, that are the same or different, attached to an a amide group, wherein alkyl has the same definition as described herein. A C$_{2-8}$ dialkylcarboxamido may be represented by the following groups:

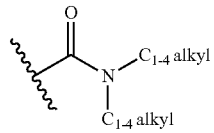 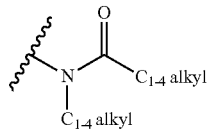

wherein C$_{1-4}$ has the same definition as described hemin Examples of a dialkylcarboxamide include, but not limited to, N,N-dimethylcarboxamide N-methyl-N-ethylcarboxamide, N,N-diethylcarboxamide, N-methyl-N-isopropylcarboxamide, and the like.

The term "C$_{2-8}$ dialkylsulfonamide" refers to one of the following groups shown below:

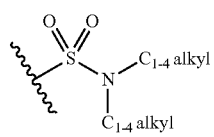 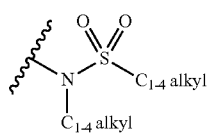

wherein C$_{1-4}$ has the same definition as described herein, for example but not limited to, methyl, ethyl, n-propyl, isopropyl, and the like.

The term "C$_{2-8}$ dialkylthiocarboxamido" or "C$_{2-8}$ dialkylthiocarbox-amide" denotes two alkyl radicals, that are the same or different, attached to a thioamide group, wherein alkyl has the same definition as described herein. A C$_{2-8}$ dialkylthiocarboxamido or C$_{2-8}$ dialkylthiocarboxamide may be represented by the following groups:

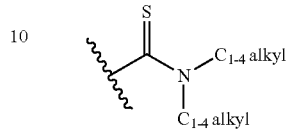 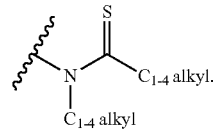

Examples of a dialkylthiocarboxamide include, but not limited to, N,N-dimethylthiocarboxamide, N-methyl-N-ethylthiocarboxamide and the like.

The term "ethynylene" refers to the carbon-carbon triple bond group as represented below:

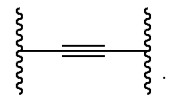 [SMILES: *C#C*]

The term "formyl" refers to the group —CHO.

The term "C$_{1-4}$ haloalkoxy" denotes a haloalkyl, as defined herein, which is directly attached to an oxygen atom. Examples include, but not limited to, difluoromethoxy trifluoromethoxy, 2,2,2-trifluoroethoxy, pentafluoroethoxy and the like.

The term "C$_{1-6}$ haloalkyl" denotes an C$_{1-6}$ alkyl group, defined herein, wherein the alkyl is substituted with one halogen up to fully substituted and a fully substituted C$_{1-6}$ haloalkyl can be represented by the formula C$_n$L$_{2n+1}$ wherein L is a halogen and "n" is 1, 2, 3 or 4; when more than one halogen is present then they may be the same or different and selected from the group consisting of F, Cl, Br and 1, preferably F. Examples of C$_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "C$_{1-6}$ haloalkylcarboxamide" denotes an alkylcarboxamide group, defined herein, wherein the alkyl is substituted with one halogen up to fully substituted represented by the formula C$_n$L$_{2n+1}$ wherein L is a halogen and "n" is 1, 2, 3 or 4, When more than one halogen is present they may be the same or different and selected from the group consisting of F, Cl, Br and I, preferably F.

The term "C$_{1-6}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoromethylsulfinyl and the like.

The term "C$_{1-6}$ haloalkylsulfonyl" denotes a haloalkyl radical attached to a sulfone group of the formula: —S(O)$_2$— wherein haloalkyl has the same definition as described herein. Examples include, but nor limited to, trifluoromethylsulfonyl, 2,2,2-trifluoroethylsulfonyl, 2,2-difluoroethylsulfonyl and the like.

The term "C$_{1-6}$ haloalkylthio" denotes a haloalkyl radical directly attached to a sulfur wherein the haloalkyl has the same meaning as described herein. Examples include, but not limited to, trifluoromethylthio (i.e., CF$_3$S—, also referred to as trifluoromethylsulfanyl, 1,1-difluoroethylthio, 2,2,2 trifluoroethylthio and the like.

The term "halogen" or "halo" denotes to a fluoro, chloro, bromo or iodo group. The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like. Other examples include, but not limited to, those in TABLE 2, TABLE 3, and the like.

The term "heterocyclic" denotes a non-aromatic carbon ring (i.e., $C_{3-7}$ cycloalkyl or $C_{4-7}$ cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl piperzin-1-yl, piperzin-4-yl, pyrrolidin-1-yl, pyrrolidin-3-yl, [1,3]-dioxolan-2-yl and the like.

The term "heterocycliccarboxamido" denotes a heterocyclic group, as defined herein, with a ring nitrogen where the ring nitrogen is bonded directly to the carbonyl forming an amide. Examples include, but not limited to,

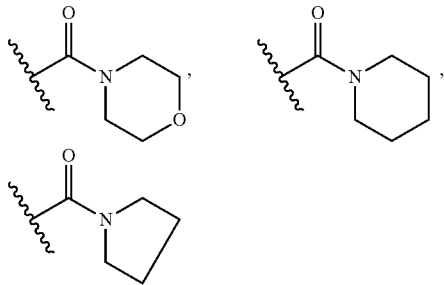

and the like.

The term "heterocyclicsulfonyl" denotes a heterocyclic group, as defined herein, with a ring nitrogen where the ring nitrogen is bonded directly to an —SO$_2$-group forming an sulfonamide. Examples include, but not limited to,

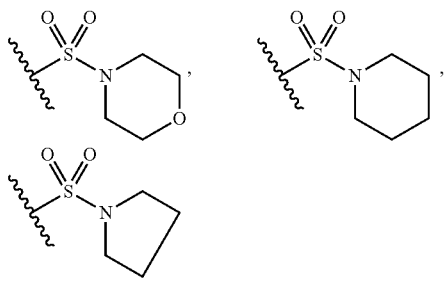

and the like.

The term "hydroxyl" refers to the group —OH.
The term "hydroxylamino" refers to the group —NHOH.
The term "nitro" refers to the group —NO$_2$.
The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

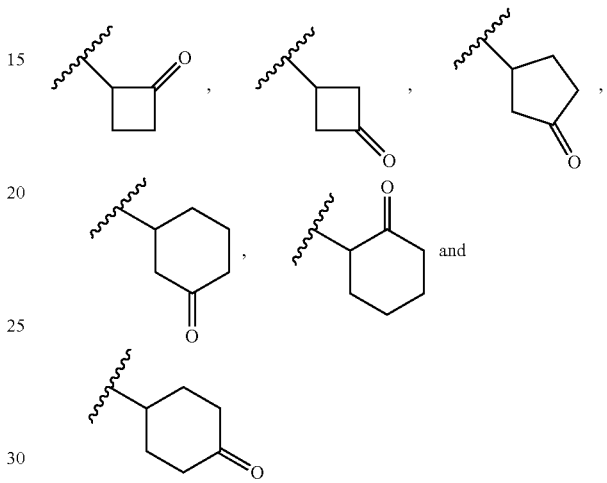

The term "perfluoroalkyl" denotes the group of the formula —$C_nF_{2n+1}$; stated differently a perfluoroalkyl is an alkyl as defined herein wherein the alkyl is fully substituted with fluorine atoms and is therefore considered a subset of haloalkyl Examples of perfluoroalkyls include CF$_3$, CF$_2$CF$_3$, CF$_2$CF$_2$CF$_3$, CF(CF$_3$)$_2$, CF$_2$CF$_2$CF$_2$CF$_3$, CF$_2$CF(CF$_3$)$_2$, CF(CF$_3$)CF$_2$CF$_3$ and the like.

The term "phenoxy" refers to the group $C_6H_5O$—.
The term "phenyl" refers to the group $C_6H_5$—.
The term "sulfonic acid" refers to the group —SO$_3$H.
The term "thiol" denotes the group —SH.

CODON shall mean a grouping of three nucleotides (or equivalents to nucleotides) which generally comprise a nucleoside [denosine (A), guanosine (G), citidine (C), uridine (U) and thymidine (T)] coupled to a phosphate group and which, when translated, encodes an amino acid.

COMPOSITION shall mean a material comprising at least two compounds or two components; for example, and without limitation, a Pharmaceutical Composition is a Composition comprising a compound of the present invention and a pharmaceutically acceptable carrier.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing the indicated moieties together, whether in an in vitro system or an in vivo system. Thus, "contacting" a 5-HT$_{2A}$ receptor with a compound of the invention includes the administration of a compound of the present invention to an individual, preferably a human, having a 5-HT$_{2A}$ receptor, as well as, for example, introducing a compound of the invention into a sample containing a cellular or more purified preparation containing a 5-HT$_{2A}$ receptor.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus.

In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

IN NEED OF PROPHYLAXIS OR TREATMENT as used herein refers to a judgment made by a caregiver (e.g. physician, nurse, nurse practitioner, etc. in the case of humans; veterinarian in the case of animals, including non-human mammals) that an individual or animal requires or will benefit from prophylaxis or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention.

In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill, therefore, the compounds of the present invention are used to alleviate, inhibit or ameliorate the disease, condition or disorder.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound. INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient; including but not limited to, salts, solvates and hydrates of compounds of Formula (I); whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Invention

One aspect of the present invention encompasses certain diaryl and arylheteroaryl urea derivatives as shown in Formula (I):

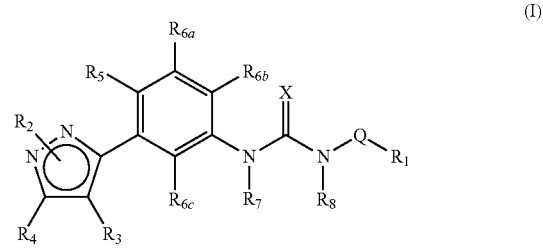

or a pharmaceutically acceptable salt, hydrate or solvate thereof; wherein $R_1$, $R_2$, $R_3$, $R_4$, $R_5$, $R_{6a}$, $R_{6b}$, $R_{6c}$, $R_7$, $R_8$, X, and Q have the same definitions as described herein, supra and infra.

Some embodiments of the present invention encompass certain diaryl and arylheteroaryl urea derivatives as shown in the following Formula

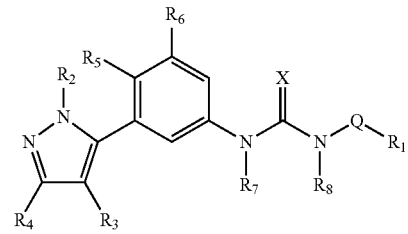

wherein:

i) $R_1$ is aryl or heteroaryl optionally substituted with $R_9$, $R_{10}$, $R_{11}$, $R_{12}$, $R_{13}$, $R_{14}$, and $R_{15}$ selected independently from the group consisting of $C_{1-6}$ aryl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkysulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

ii) $R_2$ is selected from the group consisting of $C_{1-6}$ alkyl, $C_{2-6}$ alkenyl, $C_{2-6}$ alkynyl and $C_{3-7}$ cycloalkyl;

iii) $R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

iv) $R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

v) $R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said phenyl is optionally substituted with 1 to 5 halogen atoms;

vi) $R_6$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

vii) $R_7$ and $R_8$ are independently H or $C_{1-8}$ alkyl;

viii) X is O or S; and ix) Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond; or a pharmaceutically acceptable salt, hydrate or solvate thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of the present invention may have one or more chiral centers, and therefore can exist as enantiomers and/or diastereomers. The invention is understood to extend to and embrace all such enantiomers, diastereomers and mixtures thereof, including but not limited, to racemates. Accordingly, some embodiments of the present invention pertain to compounds of the present invention that are R enantiomers. Further, some embodiments of the present invention pertain to compounds of the present invention that are S enantiomers. In examples where more than one chiral center is present, then, some embodiments of the present invention include compounds that are RS or SR enantiomers. In further embodiments, compounds of the present invention are RR or SS enantiomers. It is understood that compounds of the present invention are intended to represent all individual enantiomers and mixtures thereof, unless stated or shown otherwise.

In some embodiments, $R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, carboxamide, cyano, $C_{3-7}$ cycloalkyl, halogen, $C_{1-6}$ haloalkoxy, $C_{1-6}$ haloalkyl, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, $C_{1-6}$ alkylsulfonyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is phenyl or naphthyl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, and $R_{13}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl optionally substituted with $R_9$, $R_{10}$, $R_{11}$, $R_{12}$, and $R_{13}$, $R_{14}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylamino-ethyl)-methyl-amino [i.e., —N(CH$_3$)CH$_2$CH$_2$N(CH$_3$)$_2$], (3-dimethylamino-propyl)-methyl-amino [i.e., —N(CH$_3$)CH$_2$CH$_2$CH$_2$N(CH$_3$)$_2$], —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is phenyl and can be represented by the Formula shown below:

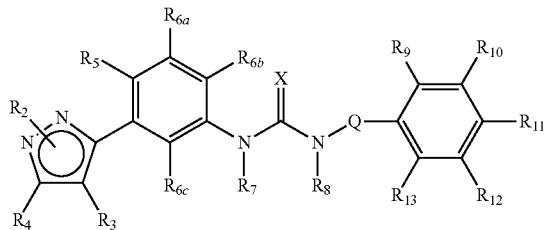

wherein each variable in the above formula has the same meaning as described herein, supra and infra. In some embodiments, $R_7$ and $R_8$ are both —H, Q is a bond, and X is O.

Some embodiments of the present invention pertain to compounds wherein $R_1$ is phenyl and can be represented by Formula (Ia) as shown below:

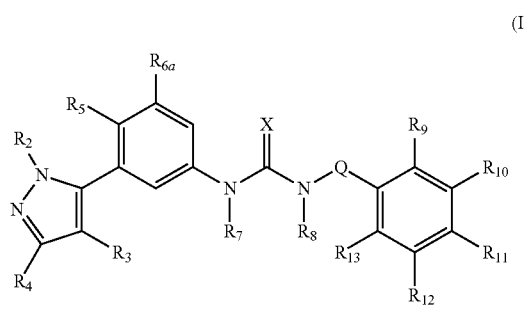

(Ia)

wherein:
$R_9$ to $R_{13}$ substituents are each selected independently from the group consisting of H, $C_{1-6}$ acyl, $C_{1-6}$ acyloxy, $C_{1-6}$ alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$ alkylamino, $C_{2-8}$ dialkylamino, carbo-$C_{1-6}$ alkoxy, carboxamide, carboxy, cyano, halogen, $C_{1-6}$ haloalkoxy, $C_{2-8}$ haloalkyl, hydroxyl, nitro and phenyl, or two adjacent substituents together with the phenyl form a $C_{5-7}$ cycloalkyl optionally comprising 1 to 2 oxygen atoms; and wherein each said $C_{1-6}$ alkyl and phenyl groups can be optionally substituted with 1 to 5 substituents selected independently front the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl; and wherein said phenyl can be optionally substituted with 1 to 5 substituents selected independently from the group consisting of $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is phenyl optionally substituted with $R_9$ to $R_{13}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl.

In some embodiments, $R_1$ is phenyl optionally substituted with $R_9$ to $R_{13}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, F, Cl, Br, I, —OCF$_3$, —OCHF$_2$, —OCF$_2$CF$_3$, —OCH$_2$CF$_3$, —CF$_3$, —CHF$_2$, —CF$_2$CF$_3$, —CH$_2$CF$_3$, nitro and phenyl.

In some embodiments, $R_1$ is phenyl optionally substituted with $R_9$ to $R_{13}$ substituents are each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl-amino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

In some embodiments, $R_1$ is phenyl optionally substituted with $R_9$, $R_{10}$, $R_{11}$, $R_{12}$ and $R_{13}$ substituents selected independently from the group consisting of —C(O)CH$_3$, —OCH$_3$, —CH$_3$, cyano, —F, —Cl, —Br, —OCF$_3$, —CF$_3$, nitro and phenyl.

Some embodiments of the present invention pertain to compounds wherein $R_1$ is naphthyl optionally substituted with $R_9$ $R_{10}$ $R_{11}$ $R_{12}$ $R_{13}$ $R_{14}$ and $R_{15}$ substituents selected independently from the group consisting of $C_{1-6}$ acyl, $C_{1-6}$ acyloxy, $C_{1-6}$ alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$ alkylamino, $C_{2-8}$ dialkylamino, carbo-$C_{1-6}$-alkoxy, carboxamide, carboxy, cyano, halogen, $C_{1-6}$ haloalkoxy, $C_{1-6}$ haloalkyl, hydroxyl and nitro; and wherein said $C_{1-6}$ alkyl can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$ and nitro.

In some embodiments, $R_1$ is naphthyl optionally substituted with $R_9$, $R_{10}$, $R_{11}$, $R_{12}$, $R_{13}$, $R_{14}$ and $R_{15}$ substituents selected independently from the group consisting of —C(O)CH$_3$, —OCH$_3$, —CH$_3$, cyano, —F, —Cl, —Br, —OCF$_3$, —CF$_3$ and nitro.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ alkoxy, $C_{1-6}$ alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl-amino-ethyl)-methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of —OCH$_3$, —CH$_3$, cyano, —F, —Cl, —Br, —OCF$_3$, and —CF$_3$.

Some embodiments of the present invention pertain to compounds wherein $R_1$ is heteroaryl optionally substituted with $R_9$, $R_{10}$, $R_{11}$, $R_{12}$, and $R_{13}$ each selected independently from the group consisting of $C_{1-6}$ acyl, $C_{1-6}$ acyloxy, $C_{1-6}$ alkoxy, $C_{1-6}$ alkyl, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, amino, $C_{1-6}$ alkylamino, $C_{2-8}$ dialkylamino, carbo-$C_{1-6}$-alkoxy, carboxamide, carboxy, cyano, halogen, $C_{1-6}$ haloalkoxy, $C_{1-6}$ haloalkyl, hydroxyl, nitro and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group; and wherein each of said $C_{1-6}$ alkyl and phenyl groups can be optionally substituted with 1 to 5 substituents selected independently from the group consisting of $C_{1-6}$ alkoxy, $C_{1-6}$ alkyl, amino, cyano, halogen, $C_{1-6}$ haloalkoxy, $C_{1-6}$ haloalkyl, hydroxyl and nitro.

In some embodiments, $R_1$ is heteroaryl optionally substituted with $R_9$, $R_{10}$, $R_{11}$, $R_{12}$ and $R_{13}$ each selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl; and wherein said phenyl can be optionally substituted with 1 to 5 substituents selected independently from the group consisting of $C_{1-6}$ alkoxy, $C_{1-6}$ alkyl, cyano, halogen, $C_{1-6}$ haloalkoxy, $C_{1-6}$ haloalkyl and nitro.

In some embodiments, $R_1$ is heteroaryl optionally substituted with $R_9$, $R_{10}$, $R_{11}$, $R_{12}$ and $R_3$ each selected independently from the group consisting of $C_{1-6}$ acyl, $C_{1-6}$ alkoxy, $C_{1-6}$ alkyl, cyano, halogen, $C_{1-6}$ haloalkoxy, $C_{1-6}$ haloalkyl, nitro and phenyl.

In some embodiments, $R_1$ is heteroaryl optionally substituted with $R_9$, $R_{10}$, $R_{11}$, $R_{12}$, and $R_{13}$ each selected independently from the group consisting of —C(O)CH$_3$, —C(O)CH$_2$CH$_3$, —C(O)CH(CH$_3$)$_2$, —C(O)CH$_2$CH$_2$CH$_3$, —C(O)CH$_2$CH(CH$_3$)$_2$, —OCH$_3$, —OCH$_2$CH$_3$, —OCH(CH$_3$)$_2$, —OCH$_2$CH$_2$CH$_3$, —OCH$_2$CH(CH$_3$)$_2$, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, cyano, —F, —Cl, —Br, —I, —OCF$_3$, —OCHF$_2$, —OCFH$_2$, —OCF$_2$CF$_3$, —OCH$_2$CF$_3$, —CF$_3$, —CHF$_2$, —CFH$_2$, —CF$_2$CF$_3$, —CH$_2$CF$_3$, nitro and phenyl.

In some embodiments, $R_1$ is heteroaryl optionally substituted with $R_9$, $R_{10}$, $R_{11}$, $R_{12}$, and $R_{13}$ each selected independently from the group consisting of —C(O)CH$_3$, —OCH$_3$, —CH$_3$, cyano, —F, —Cl, —Br, —OCF$_3$, —CF$_3$, nitro and phenyl. In some embodiments, $R_1$ is heteroaryl optionally substituted with $R_9$, $R_{10}$, $R_{11}$, $R_{12}$, and $R_{13}$ selected independently from the group consisting of H, —C(O)CH$_3$, —OCH$_3$, —CH$_3$, cyano, —F, —Cl, —Br, —OCF$_3$, —CF$_3$, nitro and phenyl.

In some embodiments $R_1$ is heteroaryl having 5-atoms in the aromatic ring examples of which are represented by the following formulae:

TABLE 2

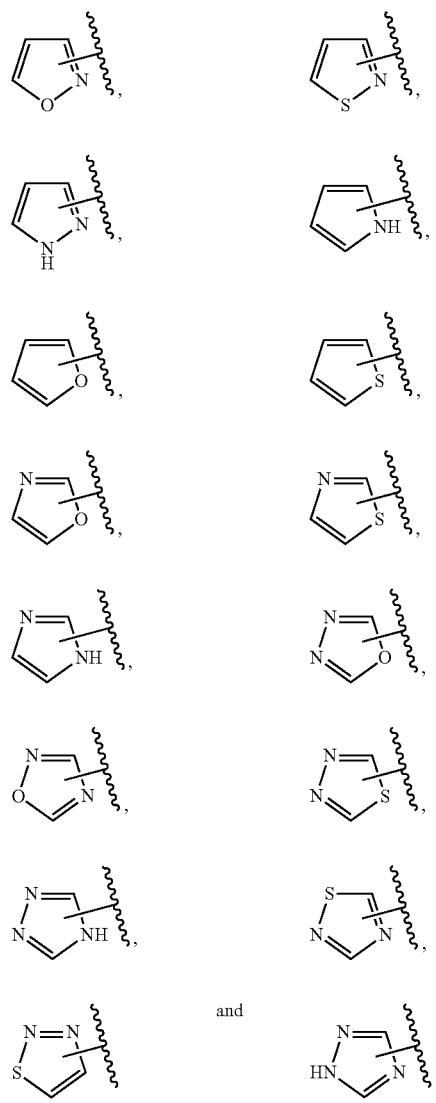

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imidazol-5-yl group).

In some embodiments, $R_1$ is a 6-membered heteroaryl, for example, a 6-membered heteroaryl as shown in TABLE 3:

TABLE 3

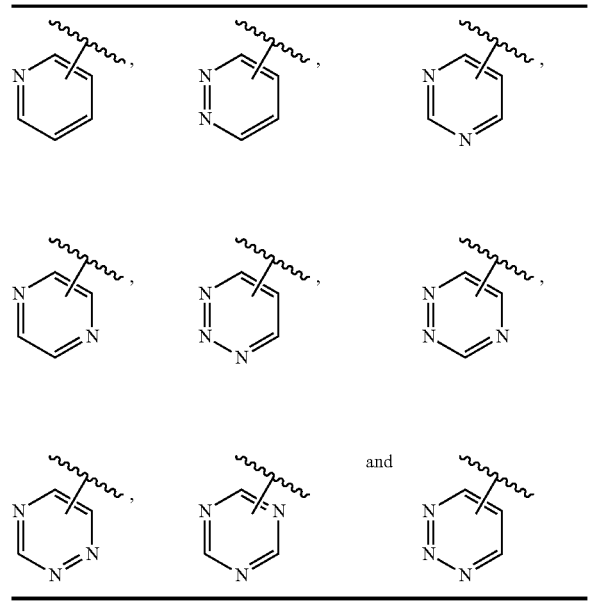

wherein the heteroaryl group is bonded at any ring carbon. In some embodiments, $R_1$ is selected from the group consisting of pyridinyl, pyridazinyl, pyrimidinyl and pyrazinyl, in some embodiments, $R_1$ is pyridinyl.

In some embodiments $R_1$ is a heteroaryl, for example but not limited to those shown in TABLE 2 and 3, optionally substituted with 1 to 3 substituents selected from the group consisting of $C_{1-6}$ acyl, $C_{1-6}$ acyloxy. $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro, phenoxy and phenyl; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro.

Some embodiments of the present invention pertain to compounds wherein $R_2$ is H or $C_{1-6}$ alkyl.

Some embodiments of the present invention pertain to compounds wherein $R_2$ is $C_{1-6}$ alkyl. In some embodiments, $R_2$ is selected from the group consisting of —CH, —CH$_2$CH$_3$, —CH(CH$_3$)$_2$, —CH$_2$CH$_2$CH$_3$, —CH$_2$CH(CH$_3$)$_2$ and —CH$_2$CH$_2$CH$_2$CH$_3$. In some embodiments, $R_2$ is —CH$_3$ or —CH(CH$_3$)$_2$.

Some embodiments of the present invention can be represented by Formulae (Ib) and (Ic) respectively as shown below:

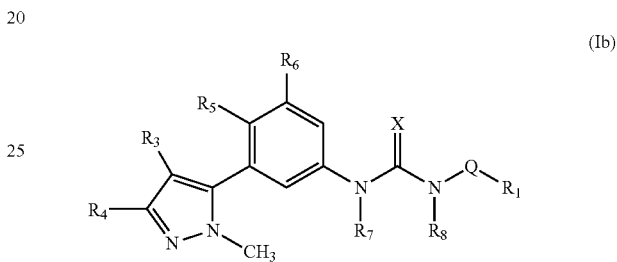

(Ib)

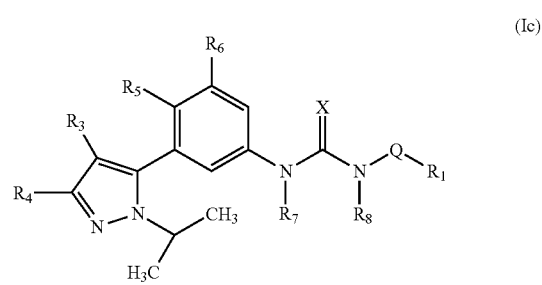

(Ic)

wherein each variable in Formulae (Ib) and (Ic) has the same meaning as described herein, supra and infra.

Some embodiments of the present invention pertain to compounds wherein $R_2$ is H.

It is understood that when $R_2$ is H, then tautomers are possible. It is well understood and appreciated in the art that pyrazoles can exist in various tautomeric forms. Two possible tautomeric forms are illustrated below:

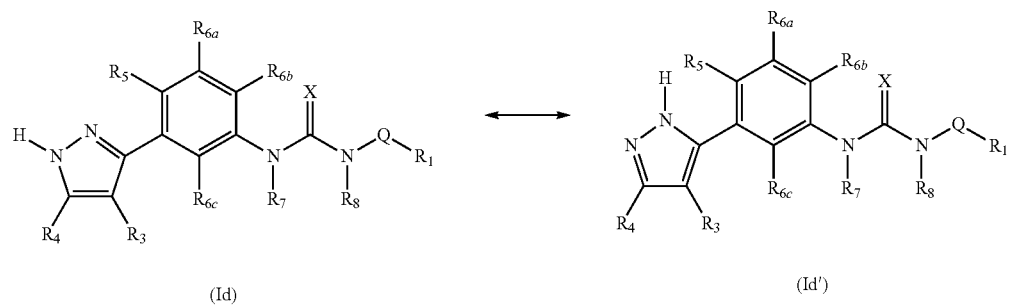

(Id)            (Id')

It is further understood that tautomeric forms can also have corresponding nomenclature for each represented tautomers, for example. Formula (Id) and Formula (Id) can be represented by the general chemical names 1H-pyrazol-3-yl and 2H-pyrazole-3-yl respectively. Therefore, the present invention includes all tautomers and, the various nomenclature designations.

Some embodiments of the present invention pertain to compounds wherein $R_2$ is $C_{2-6}$ alkenyl. In some embodiments. $R_2$ is —$CH_2CH$=$CH_2$.

Some embodiments of the present invention pertain to compounds wherein $R_2$ is $C_{2-6}$ alkenyl.

Some embodiments of the present invention pertain to compounds wherein $R_2$ is $C_{3-7}$ cycloalkyl. In some embodiments, $R_2$ is cyclopropyl.

Some embodiments of the present invention pertain to compounds wherein $R_3$ is selected from the group consisting of H, $C_{2-6}$ alkenyl, $C_{1-6}$ alkyl, $C_{1-6}$ alkylcarboxamide, $C_{2-6}$ alkynyl, carbo-$C_{1-6}$-alkoxy, carboxamide, carboxy, cyano, $C_{3-7}$ cycloalkyl, halogen, heteroaryl or phenyl; and wherein each of said $C_{2-6}$ alkenyl, $C_{1-6}$ alkyl, $C_{2-6}$ alkynyl, heteroaryl and phenyl groups can be optionally substituted with 1 to 5 substituents selected independently from the group consisting of $C_{1-6}$ alkylamino, $C_{2-8}$ dialkylamino, $C_{2-6}$ alkenyl, $C_{1-4}$ alkoxy, $C_{1-8}$ alkyl, $C_{2-6}$ alkynyl, amino, halogen, $C_{1-4}$ haloalkoxy and hydroxyl.

In some embodiments, $R_3$ is selected from the group consisting of H, $C_{2-6}$ alkenyl, $C_{1-6}$ alkyl, $C_{2-6}$ alkynyl, carbo-$C_{1-6}$-alkoxy, carboxy, cyano, $C_{3-7}$ cycloalkyl, halogen, heteroaryl or phenyl; and wherein each of said $C_{2-6}$ alkenyl, $C_{1-6}$ alkyl, $C_{2-6}$ alkynyl and phenyl groups can be optionally substituted with 1 to 5 substituents selected independently from the group consisting of $C_{2-8}$ dialkylamino, $C_{2-6}$ alkenyl, $C_{1-4}$ alkoxy, $C_{2-6}$ alkynyl, halogen, $C_{1-4}$ haloalkoxy and hydroxyl.

In some embodiments, $R_3$ is selected from the group consisting of H, —CH=$CH_2$, —$CH_3$, —$CH_2CH_3$, —CH($CH_3$)$_2$, —$CH_2CH_2CH_3$, —$CH_2CH(CH_3)_2$, —$CH_2CH_2CH_2CH_3$, —C≡CH, —C(O)OCH_3, —C(O)OCH_2CH_3, carboxy, cyano, cyclopropyl F, Cl, Br, I, thiophen-2-yl, thiophen-3-yl, phenyl, —$CH_2CH_2N(CH_3)_2$-methoxyphenyl, 3-methoxyphenyl, 4-methoxyphenyl, —CH=CH—C≡CH, 4-fluorophenyl, 4-trifluoromethoxy-phenyl, —$CH_2O$ H and —$CH_2CH_2O$ H.

Some embodiments of the present invention pertain to compounds wherein $R_3$ is H or halogen.

In some embodiments, $R_3$ is H, F, Cl or Br.

Some embodiments of the present invention pertain to compounds of Formula (Ie) as shown below:

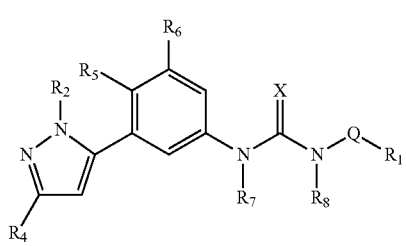

(Ie)

wherein each variable in Formula (Ie) has the same meaning as described herein, supra and infra.

Some embodiments of the present invention pertain to compounds of Formula (If) as shown below:

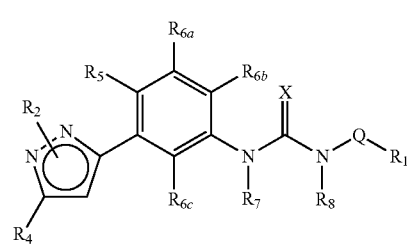

(If)

wherein each variable in Formula (If) has the same meaning as described herein, supra and infra.

Some embodiments of the present invention pertain to compounds of Formula (Ig) as shown below:

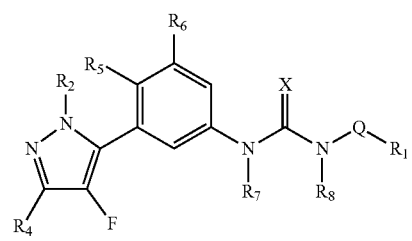

(Ig)

wherein each variable in Formula (Ig) has the same meaning as described herein, supra and infra.

Some embodiments of the present invention pertain to compounds of Formula (Ih) as shown below:

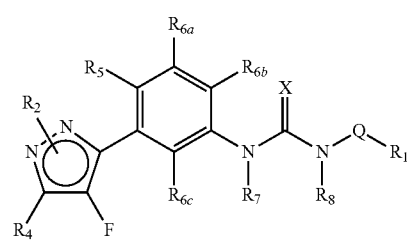

(Ih)

wherein each variable in Formula (Ih) has the same meaning as described herein, supra and infra.

Some embodiments of the present invention pertain to compounds of Formula (Ii) as shown below:

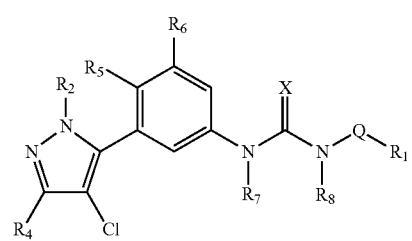

(Ii)

wherein each variable in Formula (Ii) has the same meaning as described he-rein, supra and infra.

Some embodiments of the present invention pertain to compounds of Formula (Ij) as shown below:

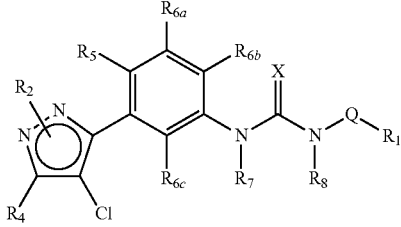
(Ij)

wherein each variable in Formula (Ij) has the same meaning as described herein, supra and infra.

Some embodiments of the present invention pertain to compounds of Formula (Ik) as shown below:

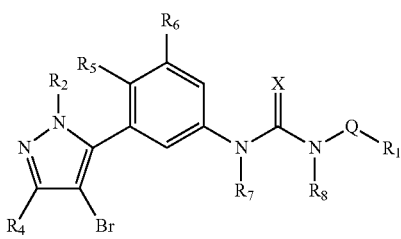
(Ik)

wherein each variable in Formula (Ik) has the same meaning as described herein, supra and infra.

Some embodiments of the present invention pertain to compounds of Formula (Ik') as shown below:

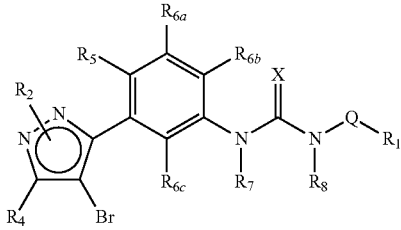
(Ik')

wherein each variable in Formula (Ik') has the same meaning as described herein, supra and infra.

Some embodiments of the present invention pertain to compounds wherein $R_4$ is selected from the group consisting of H, $C_{1-6}$ alkyl and $C_{1-6}$ haloalkyl.

In some embodiments, $R_4$ is selected from the group consisting of H, —CH$_3$, —CH$_2$CH$_3$, —CH(CH$_3$)$_2$, —CH$_2$CH$_2$CH$_3$, —CH$_2$CH(CH$_3$)$_2$, —CH$_2$CH$_2$CH$_2$CH$_3$, —CF$_3$, —CHF$_2$, —CF$_2$CF$_3$ and —CH$_2$CF$_3$.

In some embodiments, $R_4$ is selected from the group consisting of H or —CF$_3$.

Some embodiments of the present of the present invention can be represented by Formulae (Im) and (In) as shown below:

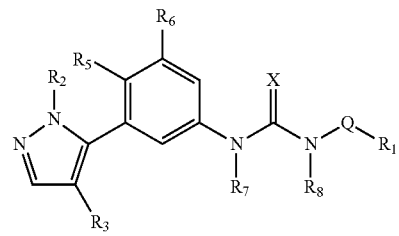
(Im)

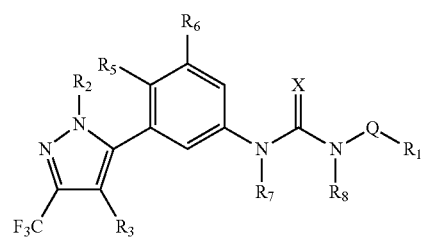
(In)

wherein each variable in Formulae (Im) and (In) has the same meaning as described herein, supra and infra.

Some embodiments of the present invention can be represented by Formulae (Io) and (Io') as shown below:

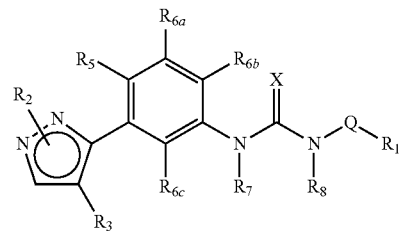
(Io)

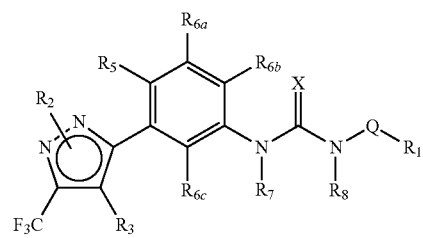
(Io')

wherein each variable in Formulae (Io) and (1&) has the same meaning as described herein, supra and infra.

Some embodiments of the present invention pertain to compounds wherein $R_5$ is selected from the group consisting of $C_{1-6}$ alkoxy, $C_{1-6}$ alkylthio, amino, $C_{1-6}$ alkylamino, $C_{2-8}$ dialkylamino, halogen, $C_{1-6}$ haloalkoxy, and hydroxyl, wherein said $C_{1-6}$ alkoxy group can be optionally substituted with 1 to 5 substituents selected independently from the group consisting of amino, $C_{1-6}$ alkylamino, $C_{2-8}$ dialkylamino, amino, carbo-$C_{1-6}$-alkoxy, carboxamide, carboxy, cyano, halogen, and phenyl, and wherein said amino and phenyl are each optionally substituted with 1 to 5 further substituents selected from the group consisting of halogen and carbo-$C_{1-6}$-alkoxy.

Some embodiments of the present invention pertain to compounds wherein $R_5$ is $C_{1-6}$ alkoxy, or hydroxyl, wherein said $C_{1-6}$ alkoxy group can be optionally substituted with 1 to 5 substituents selected independently from the group consisting of $C_{1-4}$ alkoxy, $C_{1-6}$ alkylamino, $C_{2-8}$ dialkylamino, alkylsulfinyl, $C_{1-4}$ alkylsulfonyl, $C_{1-4}$ alkylthio, amino, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and phenyl, and wherein said phenyl is optionally substituted with 1 to 5 halogen atoms.

Some embodiments of the present invention pertain to compounds wherein $R_5$ is selected from the group consisting of $C_{1-6}$ alkoxy, $C_{1-6}$ haloalkoxy, and hydroxyl, wherein said $C_{1-6}$ alkoxy group can be optionally substituted with 1 to 5 substituents selected independently from the group consisting of amino, $C_{2-8}$ dialkylamino, carboxy, and phenyl, and wherein said amino and phenyl are each optionally substituted with 1 to 5 further substituents selected from the group consisting of halogen and carbo-$C_{1-6}$-alkoxy.

In some embodiments, $R_5$ is $C_{1-6}$ alkoxy, or hydroxyl, and wherein said $C_{1-6}$ alkoxy group can be optionally substituted with 1 to 5 substituents selected independently from the group consisting of $C_{1-4}$ alkoxy, $C_{1-6}$ alkylamino, $C_{2-8}$ dialkylamino, amino, $C_{1-4}$ haloalkoxy, hydroxyl and phenyl, wherein said phenyl is optionally substituted with 1 to 5 halogen atoms.

Some embodiments of the present invention pertain to compounds wherein $R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylamino-ethoxy [i.e., —OCH$_2$CH$_2$N(CH$_3$)$_2$], 3-dimethylamino-propoxy [i.e., —OCH$_2$CH$_2$CH$_2$N(CH$_3$)$_2$], carboxymethoxy [i.e., —OCHC(O)OH], and 2-tert-butoxycarbonylamino-ethoxy [i.e., —OCH$_2$CH$_2$NHC(O)OC(CH$_3$)$_3$].

In some embodiments, $R_5$ is selected from the group consisting of —OCH$_3$, —OCH$_2$CH$_3$, —OCH(CH$_3$)$_2$, —OCH$_2$CH$_2$CH$_3$, —OCH$_2$CH(CH$_3$)$_2$, hydroxyl, —OCH$_2$CH$_2$O H, —OCH$_2$CH$_2$O CH$_3$, —OCH$_2$CH$_2$O CH$_2$CH$_3$, —OCH$_2$CH$_2$O CH(CH$_3$)$_2$, —OCH$_2$CH$_2$O CH$_2$CH$_2$CH$_3$, —OCH$_2$CH$_2$O CH$_2$CH(CH$_3$)$_2$, —OCH$_2$CH$_2$NH$_2$, —OCH$_2$CH$_2$NHCH$_3$, —OCH$_2$CH$_2$N(CH$_3$)$_2$, —OCH$_2$CH$_2$O CF$_3$, —OCH$_2$CH$_2$O CHF$_2$, —OCH$_2$CH$_2$O CFH$_2$, —OCH$_2$C$_6$H$_5$, —OCH$_2$CH$_2$C$_6$H$_5$, —OCH$_2$C$_6$H$_5$-o-Cl, —OCH$_2$C$_6$H$_5$-m-Cl and —OCH$_2$C$_6$H$_5$-p-Cl.

In some embodiments, $R_5$ is selected from the group consisting of —OCH$_3$, —OCH$_2$CH$_3$, —OCH(CH$_3$)$_2$, hydroxyl, —OCH$_2$CH$_2$N(CH$_3$)$_2$, —OCH$_2$C$_6$H$_5$, —OCH$_2$CH$_2$C$_6$H$_5$ and —OCH$_2$C$_6$H$_5$-p-Cl.

In some embodiments, $R_5$ is —OCH$_3$.

Some embodiments of the present invention pertains to compounds wherein $R_6$ is selected from the group consisting of H, $C_{1-6}$ alkoxy, carbo-$C_{1-6}$-alkoxy, carboxamide, carboxy, cyano, halogen and hydroxyl.

In some embodiments, $R_6$ is H.

Some embodiments of the present invention pertain to compounds wherein $R_{6a}$, $R_{6b}$, and $R_{6c}$ are each independently selected from the group consisting of H, $C_{1-6}$ alkoxy, $C_{1-6}$ alkyl, amino, $C_{1-6}$ alkylamino, $C_{2-8}$ dialkylamino cyano, halogen, $C_{1-6}$ haloalkoxy, $C_{1-6}$ haloalkyl, hydroxyl, and nitro.

Some embodiments of the present invention pertain to compounds wherein $R_{6a}$, $R_{6b}$ and $R_{6c}$, are each independently selected from the group consisting of H, —OCH$_3$, —CH$_3$, —N(CH$_3$)$_2$, cyano, —F, —Cl, —Br, —OCF$_3$, hydroxyl, and nitro.

Some embodiments of the present invention pertain to compounds wherein $R_{6a}$, $R_{6b}$, and $R_{6c}$ are each independently selected from the group consisting of H, $C_{1-6}$ alkoxy, carbo-$C_{1-6}$-alkoxy, carboxamide, carboxy, cyano, halogen and hydroxyl.

Some embodiments of the present invention pertain to compounds wherein $R_{6a}$, $R_{6b}$, and $R_{6c}$ are all H.

Some embodiments of the present invention pertain to compounds wherein $R_5$ is $C_{1-6}$ alkoxy and $R_{6a}$, $R_{6b}$, and $R_{6c}$, are all H.

In some embodiments, $R_5$ is —OCH$_3$.

Some embodiments of the present invention pertain to compounds represented by Formula (Ip) as shown below:

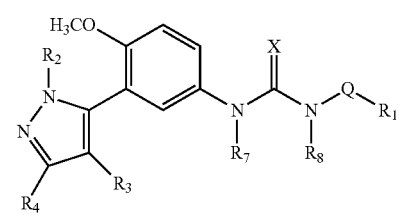

(Ip)

wherein each variable in Formula (Ip) has the same meaning as described herein, supra and infra. In some embodiments, compounds of the present invention have Formula (Ip) and Q is a bond.

Some embodiments of the present invention pertain to compounds represented by Formula (Iq) as shown below:

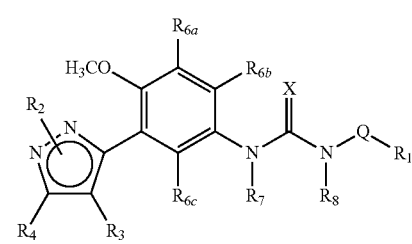

(Iq)

wherein each variable in Formula (Iq) has the same meaning as described herein, supra and infra. In some embodiments, compounds of the present invention have Formula (Iq) and Q is a bond.

Some embodiments of the present invention pertain to compounds wherein $R_7$ is H or $C_{1-8}$ alkyl.

In some embodiments, $R_7$ is selected from the group consisting of H, —CH$_3$, —CH$_2$CH$_3$, —CH(CH$_3$)$_2$, —CH$_2$CH$_2$CH$_3$, —CH$_2$CH(CH$_3$)$_2$ and —CH$_2$CH$_2$CH$_2$CH$_3$.

In some embodiments, $R_7$ is H.

Some embodiments of the present invention pertain to compounds wherein $R_8$ is H or $C_{1-8}$ alkyl.

In some embodiments, R is selected from the group consisting of H, —CH$_3$, —CH$_2$CH$_3$, —CH(CH$_3$)$_2$, —CH$_2$CH$_2$CH$_3$, —CH$_2$CH(CH$_3$)$_2$ and —CH$_2$CH$_2$CH$_2$CH$_3$.

In some embodiments, $R_8$ is H.

Some embodiments of the present invention pertain to compounds wherein both $R_7$ and $R_8$ are H.

Some embodiments of the present invention pertain to compounds represented by Formula (Ir) as shown below:

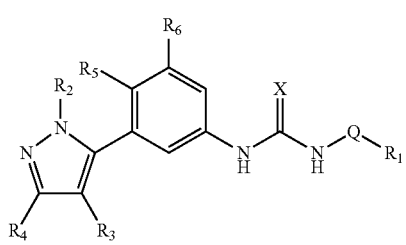

(Ir)

wherein each variable in Formula (Ir) has the same meaning as described herein, supra and infra.

Some embodiments of the present invention pertain to compounds represented by Formula (Is) as shown below:

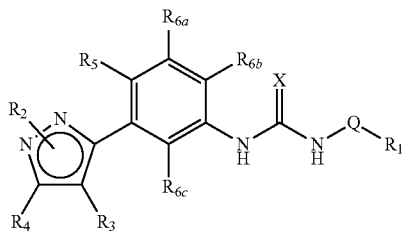

(Is)

wherein each variable in Formula (Is) has the same meaning as described herein, supra and infra.

Some embodiments of the present invention pertain to compounds wherein X is O (i.e., oxygen).

Some embodiments of the present invention pertain to compounds wherein X is S (i.e., sulfur).

Some embodiments of the present invention pertain to compounds wherein Q is $C_{1-3}$ alkylene optionally substituted with $C_{1-3}$ alkyl, $C_{1-3}$ haloalkyl, halogen and oxo.

Some embodiments of the present invention pertain to compounds wherein Q is a $C_{1-3}$ alkylene optionally substituted with oxo. As used herein, oxo refers to a double bonded oxygen. In some embodiments, Q is —C(O)— (i.e., a carbonyl).

In some embodiments, Q is —CH$_2$—.

Some embodiments of the present invention pertain to compounds wherein Q is a bond.

Some embodiments of the present invention can be represented by Formula (It) as shown below:

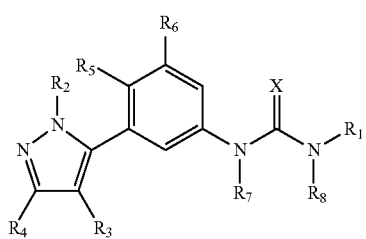

(It)

wherein each variable in Formula (It) has the same meaning as described herein, supra and infra.

Some embodiments of the present invention can be represented by Formula (Iu) as shown below:

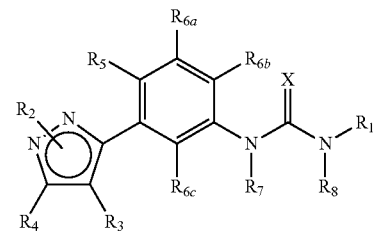

(Iu)

wherein each variable in Formula (Iu) has the same meaning as described herein, supra and infra.

In some embodiments, $R_1$ is phenyl and can be represented by Formula (Iv) as shown below:

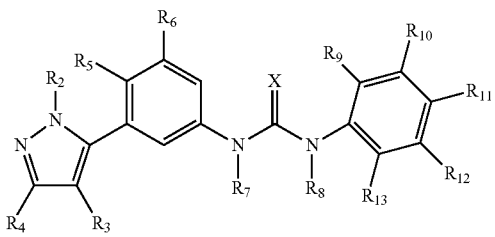

(Iv)

wherein each variable in Formula (Iv) has the same meaning as described, herein, supra and infra. In some embodiments, $R_7$ and $R_8$ are both H. In some embodiments, X is O (i.e., oxygen).

in some embodiments, $R_1$ is phenyl and can be represented by Formula (Iw) as shown below:

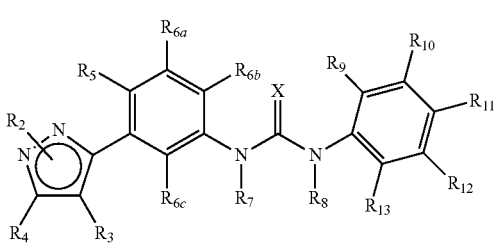

(Iw)

wherein each variable in Formula (Iw) has the same meaning as described herein, supra and infra. In some embodiments, $R_7$ and $R_8$ are both Ht In some embodiments, X is O (i.e., oxygen).

Some embodiments of the present invention pertain to compounds of Formula (IIa):

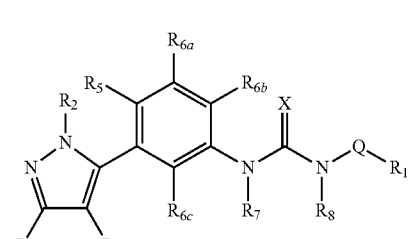

(IIa)

wherein:

$R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ alkoxy, $C_{1-6}$ alkyl, amino, $C_{1-6}$ alkylamino, $C_{2-8}$ dialkylamino, $C_{1-6}$ alkylimino, cyano, halogen, $C_{1-6}$ haloalkoxy, $C_{1-6}$ haloalkyl, heterocyclic, hydroxyl, nitro, and phenyl or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F; and wherein said $C_{1-6}$ alkyl, $C_{1-6}$ alkylimino, and heterocyclic are each optionally substituted with 1 to 5 substituents selected independently from the group consisting of $C_{1-6}$ alkyl, amino, $C_{1-6}$ alkylamino, $C_{2-8}$ dialkylamino, and hydroxyl;

$R_2$ is $C_{1-6}$ alkyl;

$R_3$ is H or halogen;

$R_4$ is selected from the group consisting of H, $C_{1-6}$ alkyl and $C_{1-6}$ haloalkyl;

$R_5$ is selected from the group consisting of $C_{1-6}$ alkoxy, $C_{1-6}$ haloalkoxy, and hydroxyl, wherein said $C_{1-6}$ alkoxy group can be optionally substituted with 1 to 5 substituents selected independently from the group consisting of amino, $C_{2-8}$ dialkylamino, carboxy, and phenyl, and wherein said amino and phenyl are each optionally substituted with 1 to 5 further substituents selected from the group consisting of halogen and carbo-$C_{1-6}$-alkoxy;

$R_{6a}$, $R_{6b}$, and $R_{6c}$ are each independently selected from the group consisting of H, $C_{1-6}$ alkoxy, $C_{1-6}$ alkyl, amino, $C_{1-6}$ alkylamino, $C_{2-8}$ dialkylamino, cyano, halogen, $C_{1-5}$ haloalkoxy, $C_{1-6}$ haloalkyl, hydroxyl, and nitro $R_7$ and $R_{88}$ are both H:

X is O; and

Q is a bond.

Some embodiments of the present invention pertain to compounds of Formula (IIa):

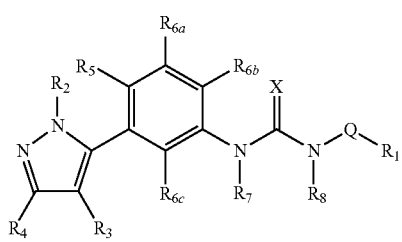

(IIa)

wherein:

$R_1$ is phenyl or naphthyl optionally substituted with $R_9$, $R_{10}$, $R_{11}$, $R_{12}$, $R_{13}$, $R_{14}$, and $R_{15}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethyl-amino-ethyl)methyl-amino, (3-dimethylamino-propyl)-methyl-amino, —C(=NOH)CH$_3$, cyano, —F, —Cl, —Br, —OCF$_3$, —CF$_3$, 4-methyl-piperazin-1-yl, morpholin-4-yl, 4-methyl-piperidin-1-yl hydroxyl, nitro, and phenyl:

$R_2$ is —CH$_3$ or —CH(CH$_3$)$_2$:

$R_3$ is H, F, Cl, or Br:

$R_4$ is —H, or —CF$_3$;

$R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylaminoethoxy, 3-dimethylamino-propoxy, carboxymethoxy, and 2-tert-butoxycarbonylamino-ethoxy;

$R_{6a}$, $R_{6b}$, and $R_{6c}$ are each independently selected from the group consisting of H, —OCH$_3$, —CH$_3$, —N(CH$_3$)$_2$, cyano, —F, —Cl, —Br, —OCF$_3$, hydroxyl, and nitro;

$R_7$ and $R_8$ are both H;

X is O; and

Q is a bond.

Some embodiments of the present invention pertain to compounds of Formula (IIa):

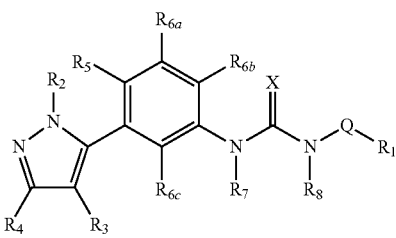

(IIa)

wherein:

$R_1$ is phenyl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —CH(OH)CH$_3$, —N(CH$_3$)$_2$, (2-dimethylaminoethyl-methyl-amino, (3-dimethylamino-propyl)-methyl-amino, —C(=NO)CH$_3$, cyano, —F, —Cl, —Br, —OCF$_3$, —CF$_3$, 4-methyl-piperazin-1-yl, morpholin-4-yl, 4-methyl-piperidin-1-yl, hydroxyl, nitro, and phenyl;

$R_2$ is —CH$_3$ or —CH(CH$_3$)$_2$;

$R_3$ is —H, —F, —Cl, or —Br;

$R_4$ is —H, or —CF$_3$;

$R_5$ is selected from the group consisting of —OCH$_3$, —OCH$_2$CH$_3$, —OCH(CH$_3$)$_2$, —OCF$_3$, hydroxyl, benzyloxy, 4-chloro-benzyloxy, phenethyloxy, 2-dimethylaminoethoxy, 3-dimethylamino-propoxy, carboxymethoxy, and 2-tert-butoxycarbonylamino-ethoxy;

$R_{6a}$, $R_{6b}$, and $R_{6c}$ are each independently selected from the group consisting of —H, —OCH$_3$, —CH$_3$, —N(CH$_3$)$_2$, cyano, —F, Cl, Br, —OCF$_3$, hydroxyl, and nitro;

$R_7$ and $R_8$ are both H;

X is O; and

Q is a bond.

Some embodiments of the present invention pertain to compounds of Formula (IIa):

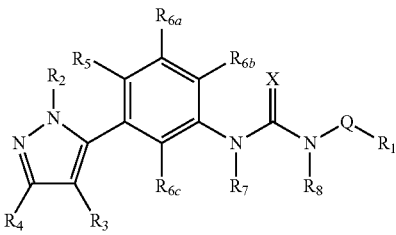

(IIa)

wherein:

$R_1$ is phenyl optionally substituted with $R_9$, $R_{10}$, $R_{11}$, $R_{12}$, and $R_{13}$ each selected independently from the group consisting of —C(O)CH$_3$, —OCH$_3$, —CH$_3$, —CH(CH$_3$)$_2$, —N(CH$_3$)$_2$, cyano, —F, —Cl, —Br, —OCF$_3$, —CF$_3$, hydroxyl, and nitro;

$R_2$ is —CH$_3$;

$R_3$ is —H, —F, —Cl, or —Br;

R₄ is —H;

R₅ is selected from the group consisting of —OCH₃, —OCH₂CH₃, —OCH(CH₃)₂, —OCF₃, hydroxyl, benzyloxy, 4-chloro-benzyloxy, phenethyloxy, 2-dimethylamino-ethoxy, 3-dimethylamino-propoxy, carboxyethoxy, and 2-tert-butoxycarbonylamino-ethoxy;

$R_{6a}$, $R_{6b}$, and $R_{6c}$ are each —H:

$R_7$ and $R_8$ are both —H;

X is O; and

Q is a bond.

Some embodiments of the present invention include compounds illustrated in TABLE A as shown below:

TABLE A

| Cmpd # | Structure | Chemical |
|---|---|---|
| 1 | 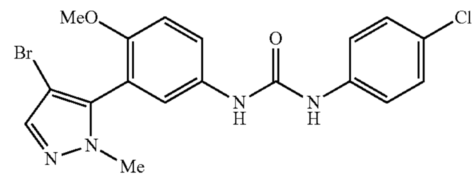 | 1-[3-(4-Bromo-2-methyl-2H-pyrazol-3-yl)-4-methoxy-phenyl]-3-(4-chloro-phenyl)-urea |
| 2 | 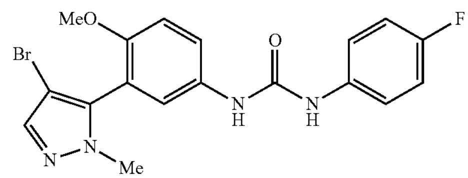 | 1-[3-(4-Bromo-2-methyl-2H-pyrazol-3-yl)-4-methoxy-phenyl]-3-(4-fluoro-phenyl)-urea |
| 3 | 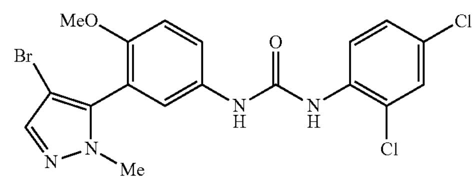 | 1-[3-(4-Bromo-2-methyl-2H-pyrazol-3-yl)-4-methoxy-phenyl]-3-(2,4-dichloro-phenyl)-urea |
| 4 | 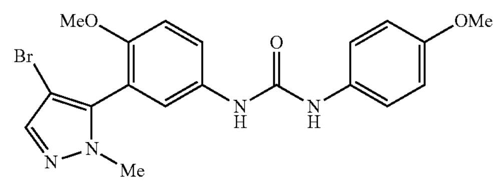 [SMILES: COc1ccc(NC(=O)Nc2ccc(OC)c(-c3c(Br)cnn3C)c2)cc1] | 1-[3-(4-Bromo-2-methyl-2H-pyrazol-3-yl)-4-methoxy-phenyl)-3-(4-methoxy-phenyl)-urea |
| 5 | 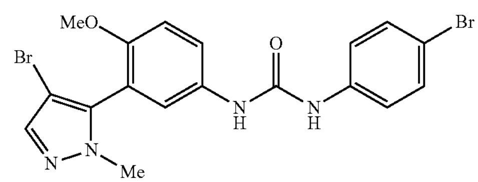 | 1-[3-(4-Bromo-2-methyl-2H-pyrazol-3-yl)-4-methoxy-phenyl]-3-(4-bromo-phenyl)-urea |
| 6 | 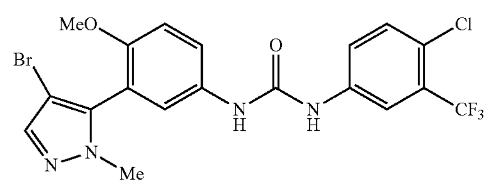 [SMILES: COc1ccc(NC(=O)Nc2ccc(Cl)c(C(F)(F)F)c2)cc1-c1c(Br)cnn1C] | 1-[3-(4-Bromo-2-methyl-2H-pyrazol-3-yl)-4-methoxy-phenyl]-3-(4-chloro-3-trifluoromethyl-phenyl)-urea |
| 7 | 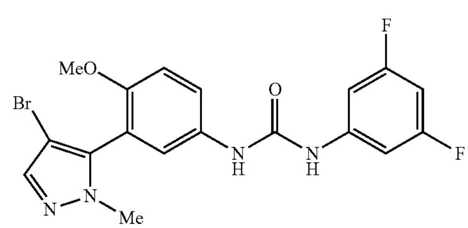 | 1-[3-(4-Bromo-2-methyl-2H-pyrazol-3-yl)-4-methoxy-phenyl]-3-(3,5-difluoro-phenyl)-urea |

TABLE A-continued

| Cmpd # | Structure | Chemical |
|---|---|---|
| 8 | 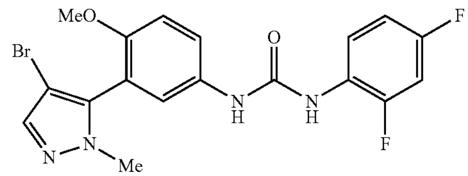 | 1-[3-(4-Bromo-2-methy)-2H-pyrarol-3-yl)-4-methoxy-phenyl]-3-(2,4-difluoro-phenyl)-urea |
| 9 | 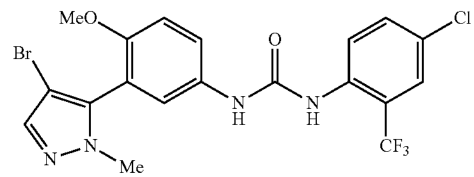 | 1-[3-(4-Bromo-2-methyl-2H-pyrazol-3-yl)-4-methoxy-phenyl]-3-(4-chloro-2-trifluoromethyl-phenyl)-urea |
| 10 | 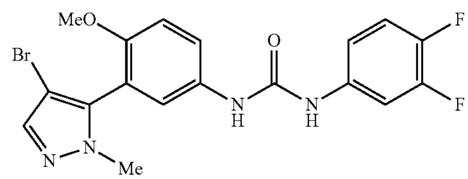 [SMILES: COc1ccc(NC(=O)Nc2ccc(F)c(F)c2)cc1-c1c(Br)cnn1C] | 1-[3-(4-Bromo-2-methyl-2H-pyrazol-3-yl)-4-methoxy-phenyl]-3-(3,4-difluoro-phenyl)-urea |
| 11 | 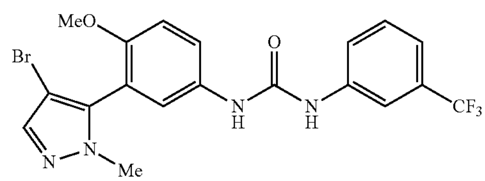 [SMILES: COc1ccc(NC(=O)Nc2cccc(C(F)(F)F)c2)cc1-c1c(Br)cnn1C] | 1-[3-(4-Bromo-2-methyl-2H-pyrazol-3-yl)-4-methoxy-phenyl]-3-(3-trifluoromethyl-phenyl)-urea |
| 12 | 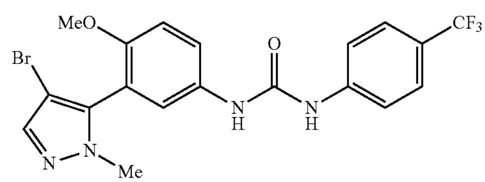 [SMILES: COc1ccc(NC(=O)Nc2ccc(C(F)(F)F)cc2)cc1-c1c(Br)cnn1C] | 1-[3-(4-Bromo-2-methyl-2H-pyrazol-3-yl)-4-methoxy-phenyl]-3-(4-trifluoromethyl-phenyl)-urea |
| 13 | 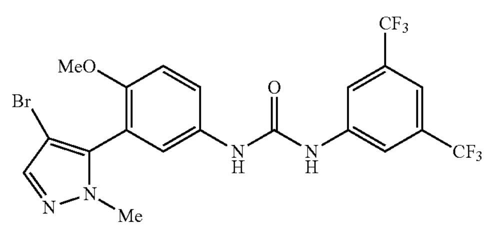 [SMILES: COc1ccc(NC(=O)Nc2cc(C(F)(F)F)cc(C(F)(F)F)c2)cc1-c1c(Br)cnn1C] | 1-(3,5-Bis-trifluoromethyl-phenyl)-3-[3-(4-bromo-2-methyl-2H-pyrazol-3-yl)-4-methoxy-phenyl]-urea |
| 14 | 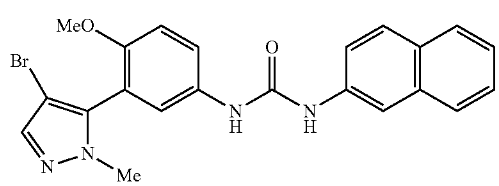 [SMILES: COc1ccc(NC(=O)Nc2ccc3ccccc3c2)cc1-c1c(Br)cnn1C] | 1-[3-(4-Bromo-2-methyl-2H-pyrazol-3-yl)-4-methoxy-phenyl]-3-naphthalen-2-yl-urea |
| 15 | 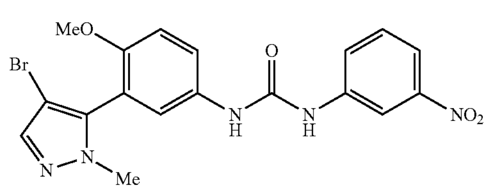 [SMILES: COc1ccc(NC(=O)Nc2cccc([N+](=O)[O-])c2)cc1-c1c(Br)cnn1C] | 1-[3-(4-Bromo-2-methyl-2H-pyrazol-3-yl)-4-methoxy-phenyl]-3-(3-nitro-phenyl)-urea |

TABLE A-continued

| Cmpd # | Structure | Chemical |
|---|---|---|
| 16 | 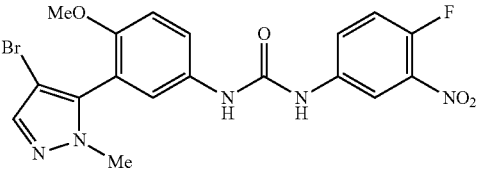 [SMILES: COc1ccc(NC(=O)Nc2ccc(F)c([N+](=O)[O-])c2)cc1-c1c(Br)cnn1C] | 1-[3-(4-Bromo-2-methyl-2H-pyrazol-3-yl)-4-methoxy-phenyl]-3-(4-fluoro-3-nitro-phenyl)-urea |
| 17 | 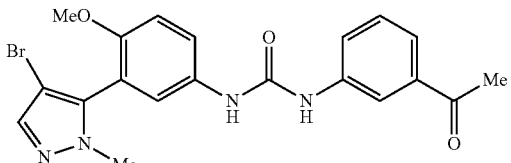 | 1-(3-Acetyl-phenyl)-3-[3-(4-bromo-2-methyl-2H-pyrazol-3-yl)-4-methoxy-phenyl]-urea |
| 18 | 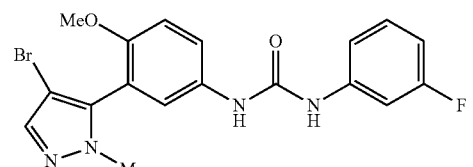 | 1-[3-(4-Bromo-2-methyl-2H-pyrazol-3-yl)-4-methoxy-phenyl]-3-(3-fluoro-phenyl)-urea |
| 19 | 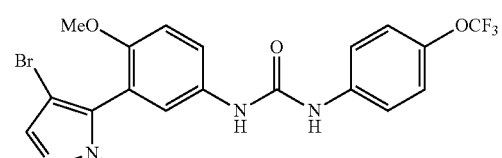 | 1-[3-(4-Bromo-2-methyl-2H-pyrazol-3-yl)-4-methoxy-phenyl]-3-(4-trifluoromethoxy-phenyl)-urea |
| 20 | 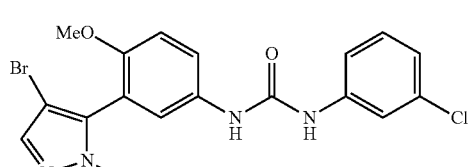 | 1-[3-(4-Bromo-2-methyl-2H-pyrazol-3-yl)-4-methoxy-phenyl]-3-(3-chloro-phenyl)-urea |
| 21 | 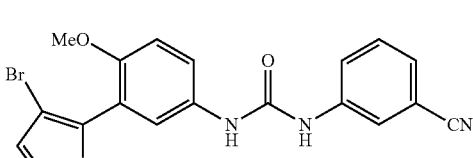 | 1-[3-(4-Bromo-2-methyl-2H-pyrazol-3-yl)-4-methoxy-phenyl]-3-(3-cyano-phenyl)-urea |
| 22 | 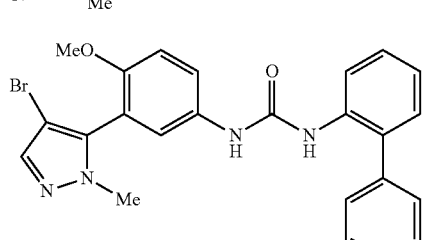 | 1-Biphenyl-2-yl-3-[3-(4-bromo-2-methyl-2H-pyrazol-3-yl)-4-methoxy-phenyl]-urea |
| 23 | 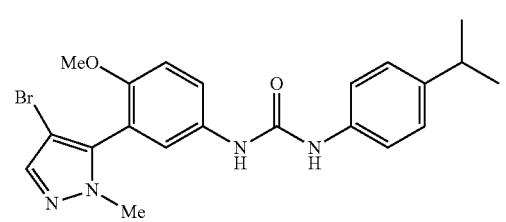 [SMILES: COc1ccc(NC(=O)Nc2ccc(C(C)C)cc2)cc1-c1c(Br)cnn1C] | 1-[3-(4-Bromo-2-methyl-2H-pyrazol-3-yl)-4-methoxy-phenyl]-3-(4-isopropyl-phenyl)-urea |

TABLE A-continued

| Cmpd # | Structure | Chemical |
|---|---|---|
| 24 | 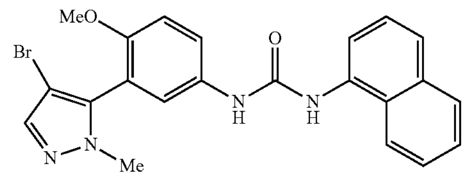 | 1-[3-(4-Bromo-2-methyl-2H-pyrazol-3-yl)-4-methoxy-phenyl]-3-naphthalen-1-yl-urea |
| 25 | 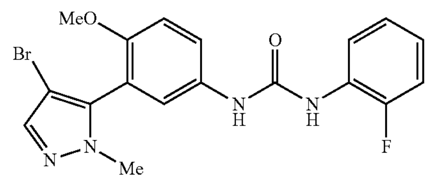 | 1-[3-(4-Bromo-2-methyl-2H-pyrazol-3-yl)-4-methoxy-phenyl]-3-(2-fluoro-phenyl)-urea |
| 26 | 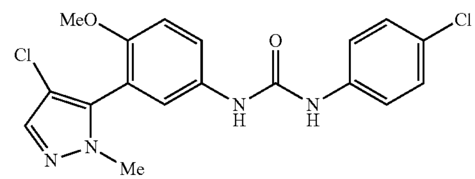 [SMILES: COc1ccc(NC(=O)Nc2ccc(Cl)cc2)cc1-c1c(Cl)cnn1C] | 1-[3-(4-Chloro-2-methyl-2H-pyrazol-3-yl)-4-methoxy-phenyl]-3-(4-chloro-phenyl)-urea |
| 27 | 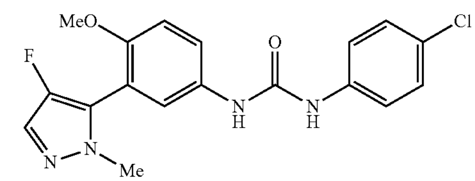 | 1-(4-Chloro-phenyl)-3-[3-(4-fluoro-2-methyl-2H-pyrazol-3-yl)-4-methoxy-phenyl]-urea |
| 28 | 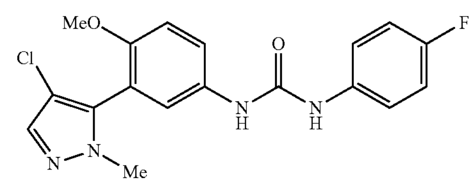 [SMILES: COc1ccc(NC(=O)Nc2ccc(F)cc2)cc1-c1c(Cl)cnn1C] | 1-[3-(4-Chloro-2-methyl-2H-pyrazol-3-yl)-4-methoxy-phenyl]-3-(4-fluoro-phenyl)-urea |
| 29 | 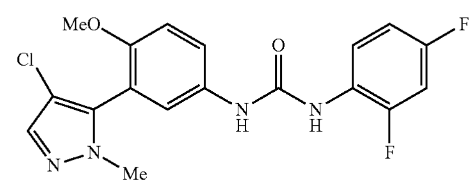 [SMILES: COc1ccc(NC(=O)Nc2ccc(F)cc2F)cc1-c1c(Cl)cnn1C] | 1-[3-(4-Chloro-2-methyl-2H-pyrazol-3-yl)-4-methoxy-phenyl]-3-(2,4-difluoro-phenyl)-urea |
| 30 | 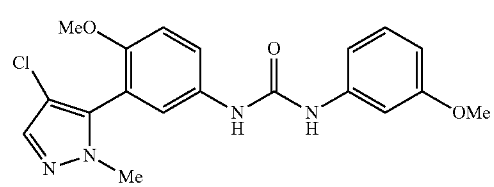 [SMILES: COc1cccc(NC(=O)Nc2ccc(OC)c(-c3c(Cl)cnn3C)c2)c1] | 1-[3-(4-Chloro-2-methyl-2H-pyrazol-3-yl)-4-methoxy-phenyl]-3-(3-methoxy-phenyl)-urea |
| 31 | 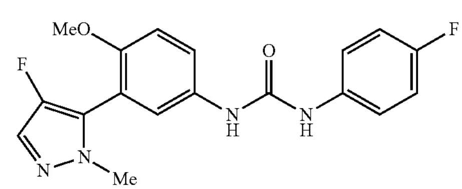 [SMILES: COc1ccc(NC(=O)Nc2ccc(F)cc2)cc1-c1c(F)cnn1C] | 1-[3-(4-Fluoro-2-methyl-2H-pyrazol-3-yl)-4-methoxy-phenyl]-3-(4-fluoro-phenyl)-urea |

TABLE A-continued

| Cmpd # | Structure | Chemical |
| --- | --- | --- |
| 32 | 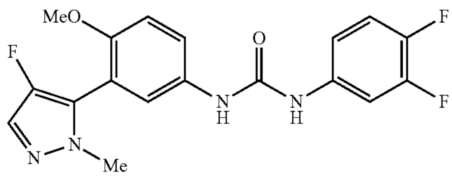 [SMILES: COc1ccc(NC(=O)Nc2ccc(F)c(F)c2)cc1-c1c(F)cnn1C] | 1-(3,4-Difluoro-phenyl)-3-[3-(4-fluoro-2-methyl-2H-pyrazol-3-yl)-4-methoxy-phenyl]-urea |
| 33 | 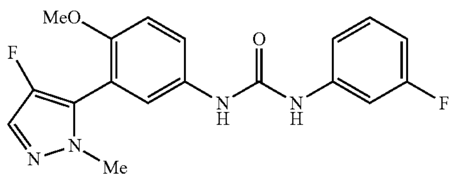 [SMILES: COc1ccc(NC(=O)Nc2cccc(F)c2)cc1-c1c(F)cnn1C] | 1-[3-(4-Fluoro-2-methyl-2H-pyrazol-3-yl)-4-methoxy-phenyl]-3-(3-fluoro-phenyl)-urea |
| 34 | 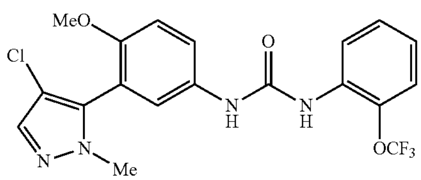 [SMILES: COc1ccc(NC(=O)Nc2ccccc2OC(F)(F)F)cc1-c1c(Cl)cnn1C] | 1-[3-(4-Chloro-2-methyl-2H-pyrazol-3-yl)-4-methoxy-phenyl]-3-(2-trifluoromethoxy-phenyl)-urea |
| 35 | 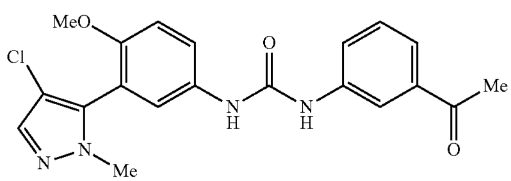 [SMILES: COc1ccc(NC(=O)Nc2cccc(C(C)=O)c2)cc1-c1c(Cl)cnn1C] | 1-(3-Acetyl-phenyl)-3-[3-(4-chloro-2-methyl-2H-pyrazol-3-yl)-4-methoxy-phenyl]-urea |
| 36 | 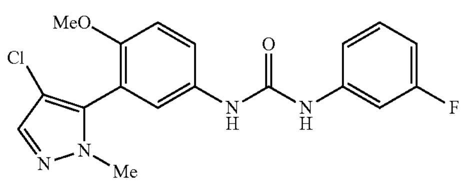 [SMILES: COc1ccc(NC(=O)Nc2cccc(F)c2)cc1-c1c(Cl)cnn1C] | 1-[3-(4-Chloro-2-methyl-2H-pyrazol-3-yl)-4-methoxy-phenyl]-3-(3-fluoro-phenyl)-urea |
| 37 | 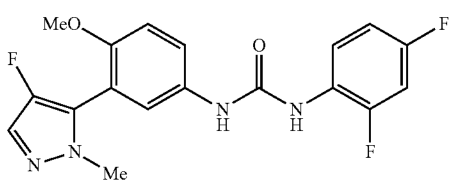 [SMILES: COc1ccc(NC(=O)Nc2ccc(F)cc2F)cc1-c1c(F)cnn1C] | 1-(2,4-Difluoro-phenyl)-3-[3-(4-fluoro-2-methyl-2H-pyrazol-3-yl)-4-methoxy-phenyl]-urea |
| 38 | 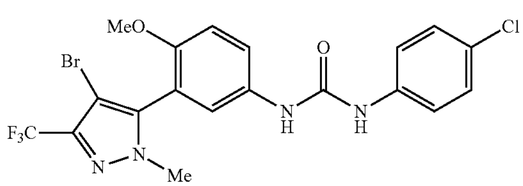 [SMILES: COc1ccc(NC(=O)Nc2ccc(Cl)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-chloro-phenyl)-urea |
| 39 | 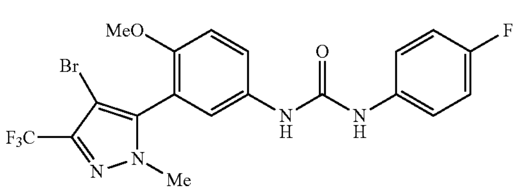 [SMILES: COc1ccc(NC(=O)Nc2ccc(F)cc2)cc1-c1c(Br)c(C(F)(F)F)nn1C] | 1-[3-(4-Bromo-2-methyl-5-trifluoromethyl-2H-pyrazol-3-yl)-4-methoxy-phenyl]-3-(4-fluoro-phenyl)-urea |

TABLE A-continued

| Cmpd # | Structure | Chemical |
|---|---|---|
| 40 | 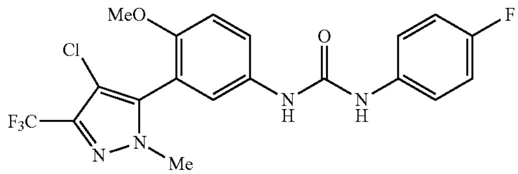 [SMILES: COc1ccc(NC(=O)Nc2ccc(F)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-fluoro-phenyl)-urea |
| 41 | 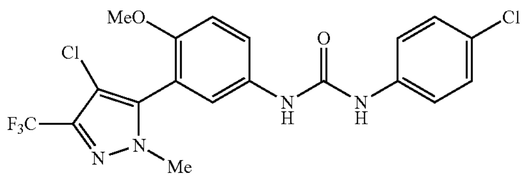 [SMILES: COc1ccc(NC(=O)Nc2ccc(Cl)cc2)cc1-c1c(Cl)c(C(F)(F)F)nn1C] | 1-[3-(4-Chloro-2-methyl-5-trifluoromethyl-2H-pyrazol-3-yl)-4-methoxy-phenyl]-3-(4-chloro-phenyl)-urea |
| 42 | 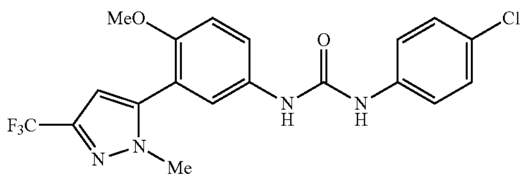 [SMILES: COc1ccc(NC(=O)Nc2ccc(Cl)cc2)cc1-c1cc(C(F)(F)F)nn1C] | 1-(4-Chloro-phenyl)-3-[4-methoxy-3-(2-methyl-5-trifluoromethyl-2H-pyrazol-3-yl)-phenyl]-urea |
| 43 | 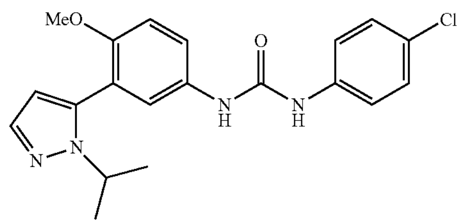 [SMILES: COc1ccc(NC(=O)Nc2ccc(Cl)cc2)cc1-c1ccnn1C(C)C] | 1-(4-Chloro-phenyl)-3-[3-(2-isopropyl-2H-pyrazol-3-yl)-4-methoxy-phenyl]-urea |
| 44 | 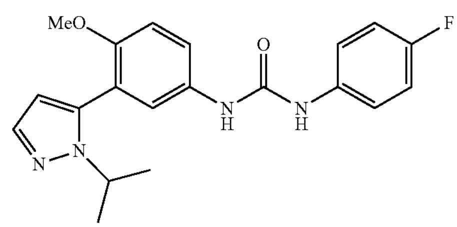 [SMILES: COc1ccc(NC(=O)Nc2ccc(F)cc2)cc1-c1ccnn1C(C)C] | 1-(4-Fluoro-phenyl)-3-[3-(2-isopropyl-2H-pyrazol-3-yl)-4-methoxy-phenyl]-urea |
| 45 | 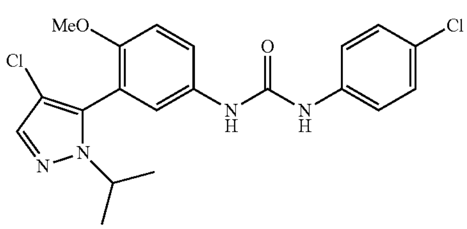 [SMILES: COc1ccc(NC(=O)Nc2ccc(Cl)cc2)cc1-c1c(Cl)cnn1C(C)C] | 1-[3-(4-Chloro-2-isopropyl-2H-pyrazol-3-yl)-4-methoxy-phenyl]-3-(4-chloro-phenyl)-urea |
| 46 | 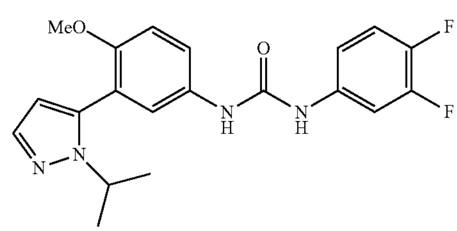 [SMILES: COc1ccc(NC(=O)Nc2ccc(F)c(F)c2)cc1-c1ccnn1C(C)C] | 1-(3,4-Difluoro-phenyl)-3-[3-(2-isopropyl-2H-pyrazol-3-yl)-4-methoxy-phenyl]-urea |

TABLE A-continued

| Cmpd # | Structure | Chemical |
|---|---|---|
| 47 | 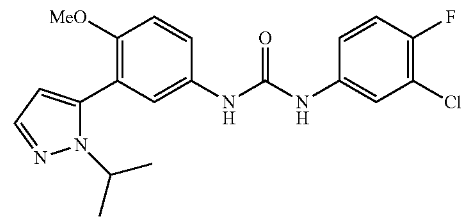 [SMILES: COc1ccc(NC(=O)Nc2ccc(F)c(Cl)c2)cc1-c1ccnn1C(C)C] | 1-(3-Chloro-4-fluoro-phenyl)-3-[3-(2-isopropyl-2H-pyrazol-3-yl)-4-methoxy-phenyl]-urea |
| 48 | 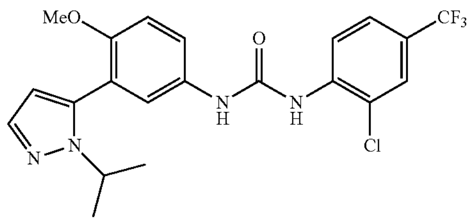 [SMILES: COc1ccc(NC(=O)Nc2ccc(C(F)(F)F)cc2Cl)cc1-c1ccnn1C(C)C] | 1-(2-Chloro-4-trifluoromethyl-phenyl)-3-[3-(2-isopropyl-2H-pyrazol-3-yl)-4-methoxy-phenyl]-urea |
| 49 | 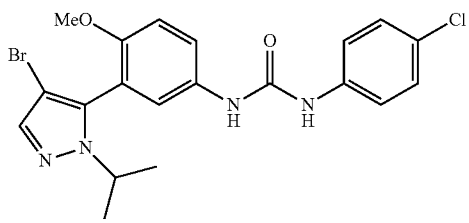 | 1-[3-(4-Bromo-2-isopropyl-2H-pyrazol-3-yl)-4-methoxy-phenyl]-3-(4-chloro-phenyl)-urea |
| 50 | 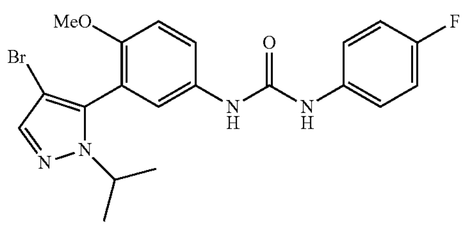 [SMILES: COc1ccc(NC(=O)Nc2ccc(F)cc2)cc1-c1c(Cl)cnn1C(C)C] | 1-[3-(4-Bromo-2-isopropyl-2H-pyrazol-3-yl)-4-methoxy-phenyl]-3-(4-fluoro-phenyl)-urea |
| 51 | 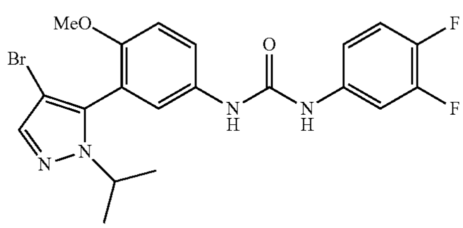 | 1-[3-(4-Bromo-2-isopropyl-2H-pyrazol-3-yl)-4-methoxy-phenyl]-3-(3,4-difluoro-phenyl)-urea |
| 52 | 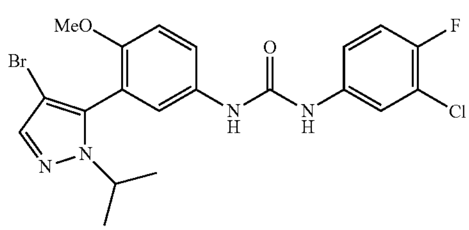 | 1-[3-(4-Bromo-2-isopropyl-2H-pyrazol-3-yl)-4-methoxy-phenyl]-3-(3-chloro-4-fluoro-phenyl)-urea |
| 53 | 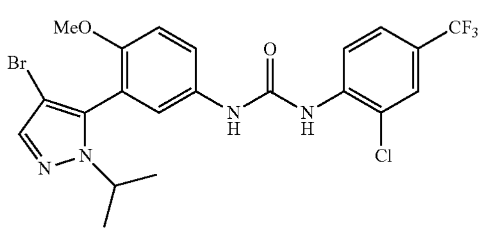 | 1-[3-(4-Bromo-2-isopropyl-2H-pyrazol-3-yl)-4-methoxy-phenyl]-3-(2-Chloro-4-trifluoromethyl-phenyl)-urea |

| Cmpd # | Structure | Chemical |
|---|---|---|
| 54 | 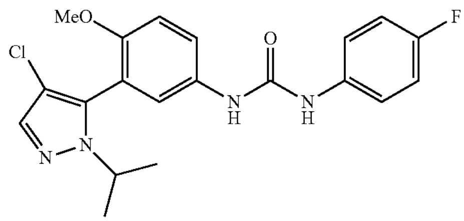 | 1-[3-(4-Chloro-2-isopropyl-2H-pyrazol-3-yl)-4-methoxy-phenyl]-3-(4-fluoro-phenyl)-urea |
| 55 | 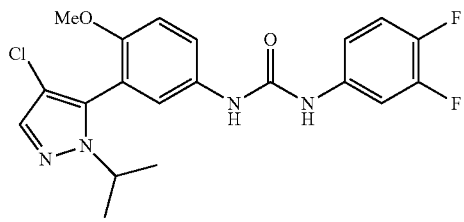 [SMILES: COc1ccc(NC(=O)Nc2ccc(F)c(F)c2)cc1-c1c(Cl)cnn1C(C)C] | 1-[3-(4-Chloro-2-isopropyl-2H-pyrazol-3-yl)-4-methoxy-phenyl]-3-(3,4-difluoro-phenyl)-urea |
| 56 | 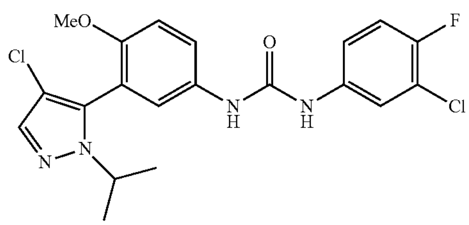 [SMILES: COc1ccc(NC(=O)Nc2ccc(F)c(Cl)c2)cc1-c1c(Cl)cnn1C(C)C] | 1-(3-Chloro-4-fluoro-phenyl)-3-[3-(4-Chloro-2-isopropyl-2H-pyrazol-3-yl)-4-methoxy-phenyl]-urea |
| 57 | 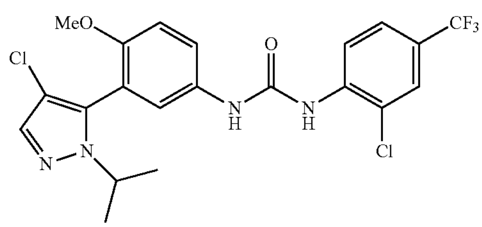 [SMILES: COc1ccc(NC(=O)Nc2ccc(C(F)(F)F)cc2Cl)cc1-c1c(Cl)cnn1C(C)C] | 1-[3-(4-Chloro-2-isopropyl-2H-pyrazol-3-yl)-4-methoxy-phenyl]-3-(2-Chloro-4-trifluoromethyl-phenyl)-urea |
| 58 | 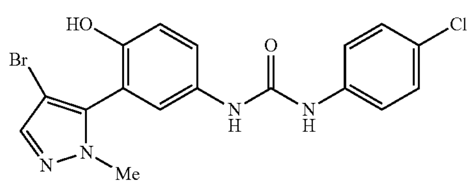 | 1-[3-(4-Bromo-2-methyl-2H-pyrazol-3-yl)-4-hydroxy-phenyl]-3-(4-chloro-phenyl)-urea |
| 59 | 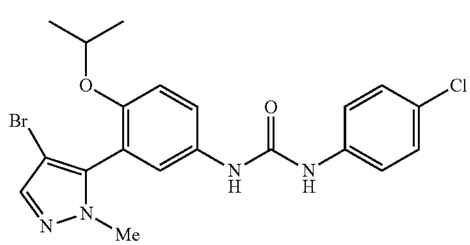 [SMILES: CC(C)Oc1ccc(NC(=O)Nc2ccc(Cl)cc2)cc1-c1c(Br)cnn1C] | 1-[3-(4-Bromo-2-methyl-2H-pyrazol-3-yl)-4-isopropoxy-phenyl]-3-(4-chloro-phenyl)-urea |
| 60 | 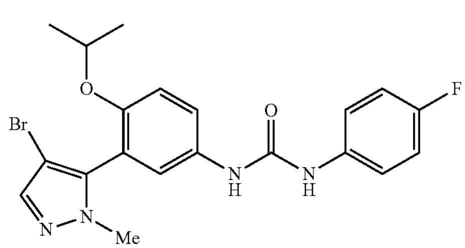 [SMILES: CC(C)Oc1ccc(NC(=O)Nc2ccc(F)cc2)cc1-c1c(Br)cnn1C] | 1-[3-(4-Bromo-2-methyl-2H-pyrazol-3-yl)-4-isopropoxy-phenyl]-3-(4-fluoro-phenyl)-urea |

TABLE A-continued

| Cmpd # | Structure | Chemical |
|---|---|---|
| 61 | 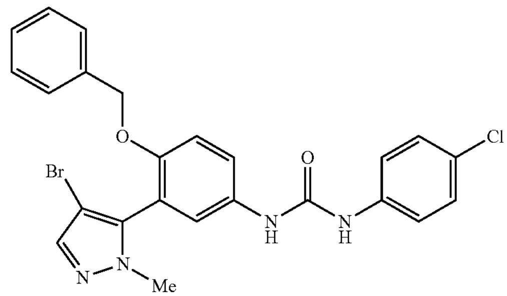 [SMILES: Cn1ncc(Br)c1-c1cc(NC(=O)Nc2ccc(Cl)cc2)ccc1OCc1ccccc1] | 1-[4-Benzyloxy-3-(4-bromo-2-methyl-2H-pyrazol-3-yl)-phenyl]-3-(4-chloro-phenyl)-urea |
| 62 | 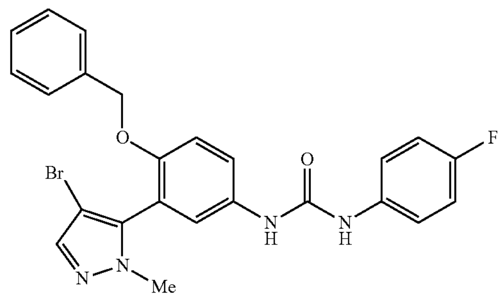 [SMILES: Cn1ncc(Br)c1-c1cc(NC(=O)Nc2ccc(F)cc2)ccc1OCc1ccccc1] | 1-[4-Benzyloxy-3-(4-bromo-2-methyl-2H-pyrazol-3-yl)-phenyl]-3-(4-fluoro-phenyl)-urea |
| 63 | 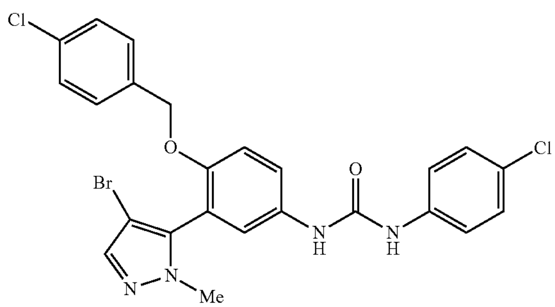 [SMILES: Cn1ncc(Br)c1-c1cc(NC(=O)Nc2ccc(Cl)cc2)ccc1OCc1ccc(Cl)cc1] | 1-[3-(4-Bromo-2-methyl-2H-pyrazol-3-yl)-4-(4-chloro-benzyloxy)-phenyl]-3-(4-chloro-phenyl)-urea |
| 64 | 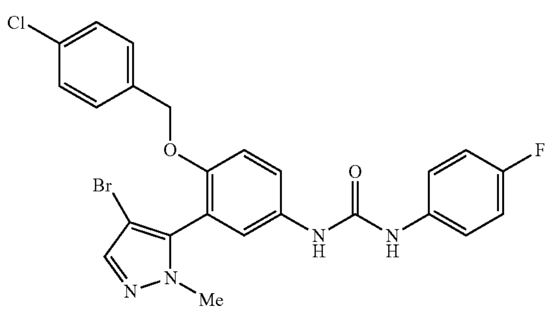 [SMILES: Cn1ncc(Br)c1-c1cc(NC(=O)Nc2ccc(F)cc2)ccc1OCc1ccc(Cl)cc1] | 1-[3-(4-Bromo-2-methyl-2H-pyrazol-3-yl)-4-(4-chloro-benzyloxy)-phenyl]-3-(4-fluoro-phenyl)-urea |
| 65 | 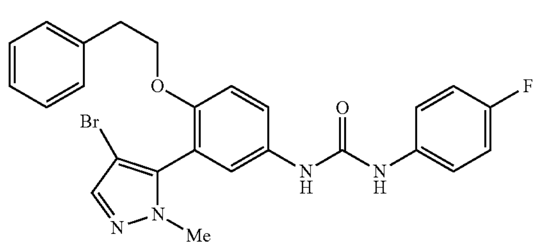 [SMILES: Cn1ncc(Br)c1-c1cc(NC(=O)Nc2ccc(F)cc2)ccc1OCCc1ccccc1] | 1-[3-(4-Bromo-2-methyl-2H-pyrazol-3-yl)-4-phenethyloxy-phenyl]-3-(4-fluoro-phenyl)-urea |

TABLE A-continued

| Cmpd # | Structure | Chemical |
|---|---|---|
| 66 | 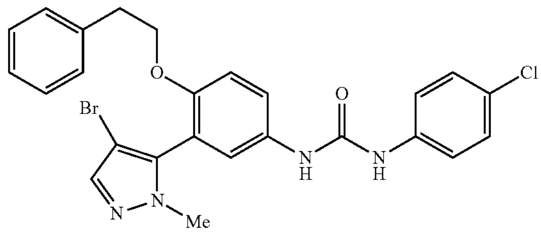 [SMILES: Cn1ncc(Br)c1-c1cc(NC(=O)Nc2ccc(Cl)cc2)ccc1OCCc1ccccc1] | 1-[3-(4-Bromo-2-methyl-2H-pyrazol-3-yl)-4-phenethyloxy-phenyl]-3-(4-chloro-phenyl)-urea |
| 67 | 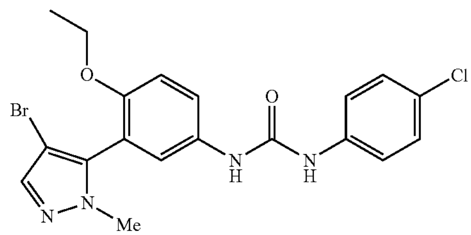 [SMILES: CCOc1ccc(NC(=O)Nc2ccc(Cl)cc2)cc1-c1c(Br)cnn1C] | 1-[3-(4-Bromo-2-methyl-2H-pyrazol-3-yl)-4-ethoxy-phenyl]-3-(4-chloro-phenyl)-urea |
| 68 | 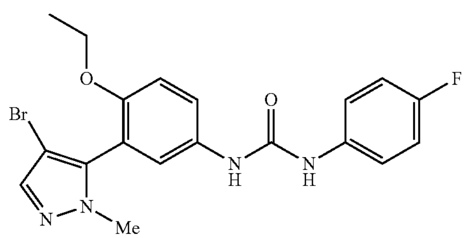 [SMILES: CCOc1ccc(NC(=O)Nc2ccc(F)cc2)cc1-c1c(Br)cnn1C] | 1-[3-(4-Bromo-2-methyl-2H-pyrazol-3-yl)-4-ethoxy-phenyl]-3-(4-fluoro-phenyl)-urea |
| 69 | 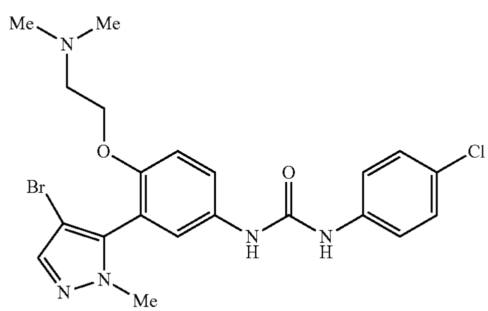 | 1-[3-(4-Bromo-2-methyl-2H-pyrazol-3-yl)-4-(2-dimethylamino-ethoxy)-phenyl]-3-(4-chloro-pheny)-urea |
| 70 | 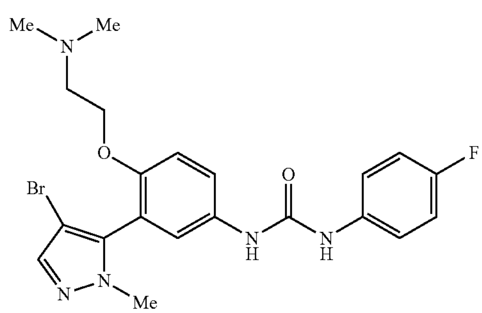 | 1-[3-(4-Bromo-2-methyl-2H-pyrazol-3-yl)-4-(2-dimethylamino-ethoxy)-phenyl]-3-(4-fluoro-phenyl)-urea |
| 71 | 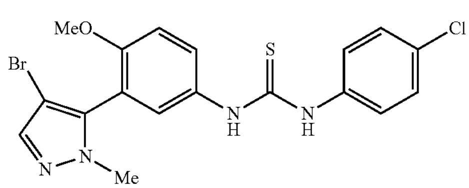 | 1-[3-(4-Bromo-2-methyl-2H-pyrazol-3-yl)-4-methoxy-phenyl]-3-(4-chloro-phenyl)-thiourea |

TABLE A-continued

| Cmpd # | Structure | Chemical |
|---|---|---|
| 72 | 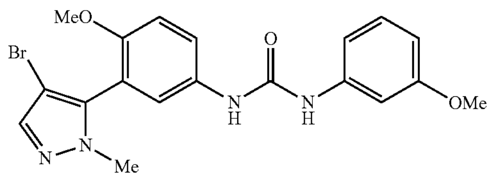 [SMILES: COc1cccc(NC(=O)Nc2ccc(OC)c(-c3c(Br)cnn3C)c2)c1] | 1-[3-4-Bromo-2-methyl-2H-pyrazol-3-yl)-4-methoxy-phenyl]-3-(3-methoxy-phenyl)-urea |
| 73 | 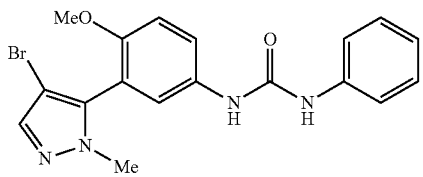 [SMILES: COc1ccc(NC(=O)Nc2ccccc2)cc1-c1c(Br)cnn1C] | 1-Benzoyl-3-[3-(4-bromo-2-methyl-2H-pyrazol-3-yl)-4-methoxy-phenyl]-urea |
| 74 | 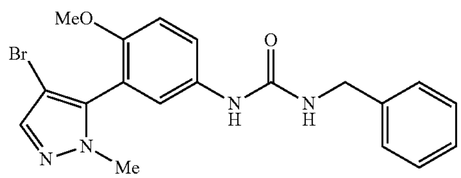 | 1-Benzyl-3-[3-(4-bromo-2-methyl-2H-pyrazol-3-yl)-4-methoxy-phenyl]-urea |
| 75 | 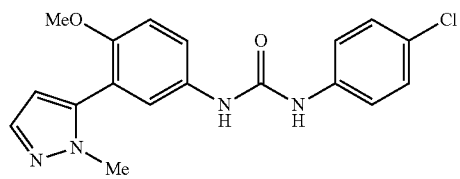 [SMILES: COc1ccc(NC(=O)Nc2ccc(Cl)cc2)cc1-c1ccnn1C] | 1-(4-Chloro-phenyl)-3-[4-methoxy-3-(2-methyl-2H-pyrazol-3-yl)-phenyl]-urea |
| 76 | 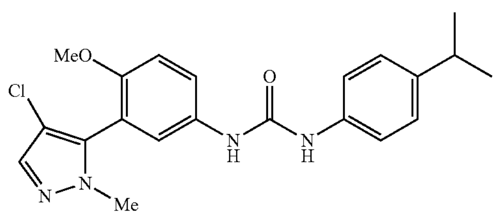 [SMILES: COc1ccc(NC(=O)Nc2ccc(C(C)C)cc2)cc1-c1c(Cl)cnn1C] | 1-[3-(4-Chloro-2-methyl-2H-pyrazol-3-yl)-4-methoxy-phenyl]-3-(4-isopropyl-phenyl)-urea |
| 77 | 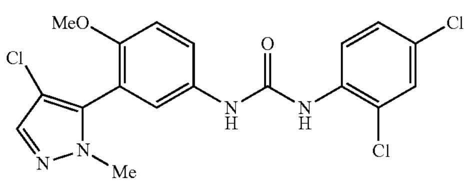 [SMILES: COc1ccc(NC(=O)Nc2ccc(Cl)cc2Cl)cc1-c1c(Cl)cnn1C] | 1-[3-(4-Chloro-2-methyl-2H-pyrazol-3-yl)-4-methoxy-phenyl]-3-(2,4-dichloro-phenyl)-urea |
| 78 | 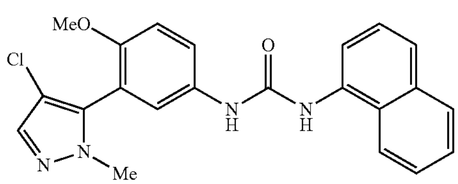 [SMILES: COc1ccc(NC(=O)Nc2cccc3ccccc23)cc1-c1c(Cl)cnn1C] | 1-[3-(4-Chloro-2-methyl-2H-pyrazol-3-yl)-4-methoxy-phenyl]-3-naphthalen-1-yl-urea |
| 79 | 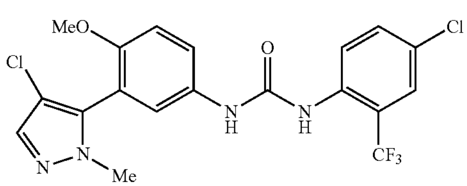 [SMILES: COc1ccc(NC(=O)Nc2ccc(Cl)cc2C(F)(F)F)cc1-c1c(Cl)cnn1C] | 1-[3-(4-Chloro-2-methyl-2H-pyrazol-3-yl)-4-methoxy-phenyl]-3-(4-chloro-2-trifluoromethyl-phenyl)-urea |

TABLE A-continued

| Cmpd # | Structure | Chemical |
|---|---|---|
| 80 | 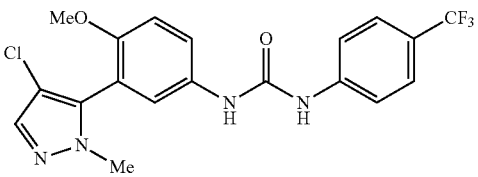 [SMILES: COc1ccc(NC(=O)Nc2ccc(C(F)(F)F)cc2)cc1-c1c(Cl)cnn1C] | 1-[3-(4-Chloro-2-methyl-2H-pyrazol-3-yl)-4-methoxy-phenyl]-3-(4-trifluoromethyl-phenyl)-urea |
| 81 | 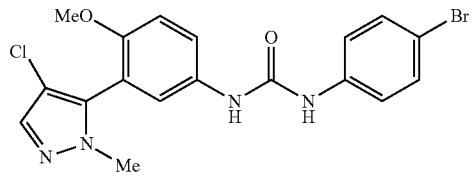 [SMILES: COc1ccc(NC(=O)Nc2ccc(Br)cc2)cc1-c1c(Cl)cnn1C] | 1-(4-Bromo-phenyl)-3-[3-(4-chloro-2-methyl-2H-pyrazol-3-yl)-4-methox-phenyl]-urea |
| 82 | 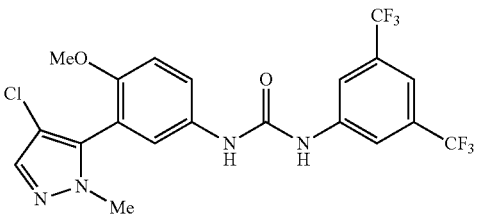 [SMILES: COc1ccc(NC(=O)Nc2cc(C(F)(F)F)cc(C(F)(F)F)c2)cc1-c1c(Cl)cnn1C] | 1-(3,5-Bis-trifluoromethyl-phenyl)-3-[3-(4-chloro-2-methyl-2H-pyrazol-3-yl)-4-methoxy-phenyl]-urea |
| 83 | 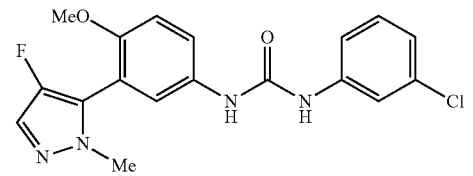 [SMILES: COc1ccc(NC(=O)Nc2cccc(Cl)c2)cc1-c1c(F)cnn1C] | 1-(3-Chloro-phenyl)-3-[3-(4-fluoro-2-methyl-2H-pyrazol-3-yl)-4-methoxy-phenyl]-urea |
| 84 | 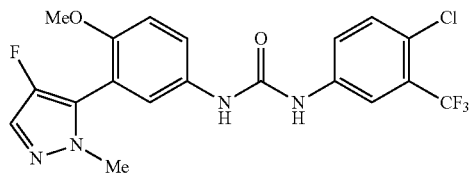 [SMILES: COc1ccc(NC(=O)Nc2ccc(Cl)c(C(F)(F)F)c2)cc1-c1c(F)cnn1C] | 1-(4-Chloro-3-trifluoromethyl-phenyl)-3-[3-(4-fluoro-2-methyl-2H-pyrazol-3-yl)-4-methoxy-phenyl]-urea |
| 85 | 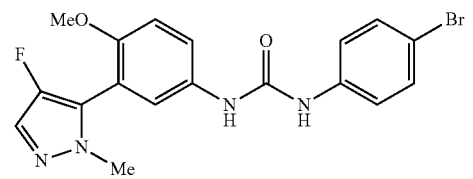 [SMILES: COc1ccc(NC(=O)Nc2ccc(Br)cc2)cc1-c1c(F)cnn1C] | 1-(4-Bromo-phenyl)-3-[3-(4-fluoro-2-methyl-2H-pyrazol-3-yl)-4-methoxy-phenyl]-urea |
| 86 | 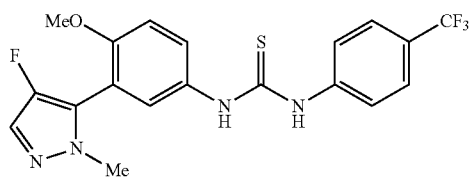 [SMILES: COc1ccc(NC(=S)Nc2ccc(C(F)(F)F)cc2)cc1-c1c(F)cnn1C] | 1-[3-(4-Fluoro-2-methyl-2H-pyrazol-3-yl)-4-methoxy-phenyl]-3-(4-trifluoromethyl-phenyl)-thiourea |
| 87 | 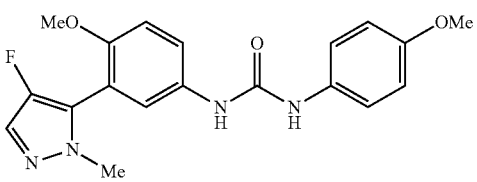 [SMILES: COc1ccc(NC(=O)Nc2ccc(OC)c(-c3c(F)cnn3C)c2)cc1] | 1-[3-(4-Fluoro-2-methyl-2H-pyrazol-3-yl)-4-methoxy-phenyl]-3-(4-methoxy-phenyl)-urea |

TABLE A-continued

| Cmpd # | Structure | Chemical |
|---|---|---|
| 88 | 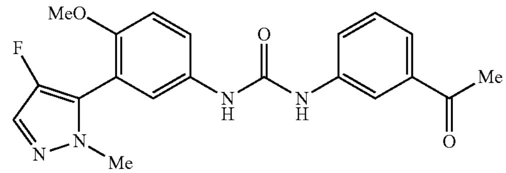 [SMILES: COc1ccc(NC(=O)Nc2cccc(C(C)=O)c2)cc1-c1c(F)cnn1C] | 1-(3-Acetyl-phenyl)-3-[3-(4-fluoro-2-methyl-2H-pyrazol-3-yl)-4-methoxy-phenyl]-urea |
| 89 | 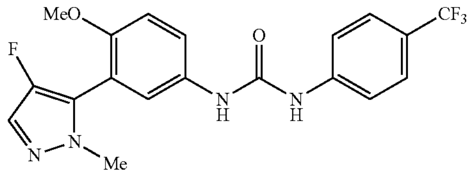 [SMILES: COc1ccc(NC(=O)Nc2ccc(C(F)(F)F)cc2)cc1-c1c(F)cnn1C] | 1-[3-(4-Fluoro-2-methyl-2H-pyrazol-3-yl)-4-methoxy-phenyl]-3-(4-trifluoromethyl-phenyl)-urea |
| 90 | 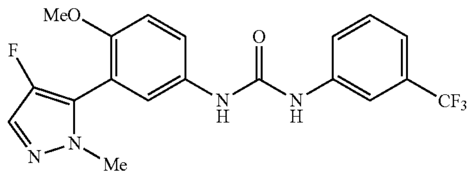 [SMILES: COc1ccc(NC(=O)Nc2cccc(C(F)(F)F)c2)cc1-c1c(F)cnn1C] | 1-[3-(4-Fluoro-2-methyl-2H-pyrazol-3-yl)-4-methoxy-phenyl]-3-(3-trifluoromethyl-phenyl)-urea |
| 91 | 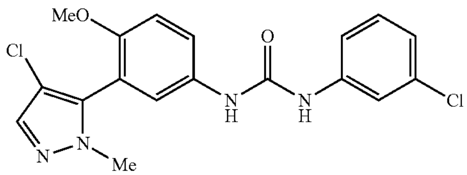 [SMILES: COc1ccc(NC(=O)Nc2cccc(Cl)c2)cc1-c1c(Cl)cnn1C] | 1-[3-(4-Chloro-2-methyl-2H-pyrazol-3-yl)-4-methoxy-phenyl]-3-(3-chloro-phenyl)-urea |
| 92 | 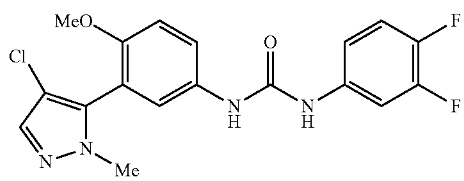 [SMILES: COc1ccc(NC(=O)Nc2ccc(F)c(F)c2)cc1-c1c(Cl)cnn1C] | 1-[3-(4-Chloro-2-methyl-2H-pyrazol-3-yl)-4-methoxy-phenyl]-3-(3,4-difluoro-phenyl)-urea |
| 93 | 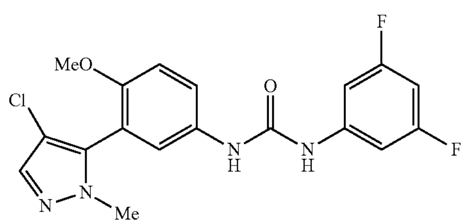 [SMILES: COc1ccc(NC(=O)Nc2cc(F)cc(F)c2)cc1-c1c(Cl)cnn1C] | 1-[3-(4-Chloro-2-methyl-2H-pyrazol-3-yl)-4-methoxy-phenyl]-3-(3,5-(difluoro-phenyl)-urea |
| 94 | 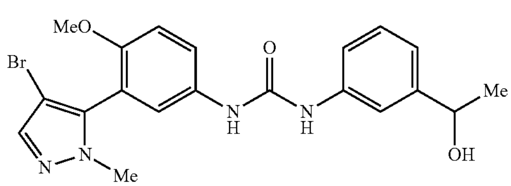 [SMILES: COc1ccc(NC(=O)Nc2cccc(C(C)O)c2)cc1-c1c(Br)cnn1C] | 1-[3-(4-Bromo-2-methyl-2H-pyrazol-3-yl)-4-methoxy-phenyl]-3-[3-(1-hydroxy-ethyl)-phenyl]-urea |
| 95 | 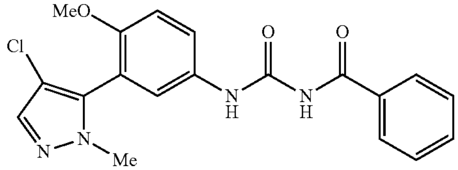 [SMILES: COc1ccc(NC(=O)NC(=O)c2ccccc2)cc1-c1c(Cl)cnn1C] | 1-Benzoyl-3-[3-(4-chloro-2-methyl-2H-pyrazol-3-yl)-4-methoxy-phenyl]-urea |

TABLE A-continued

| Cmpd # | Structure | Chemical |
|---|---|---|
| 96 | 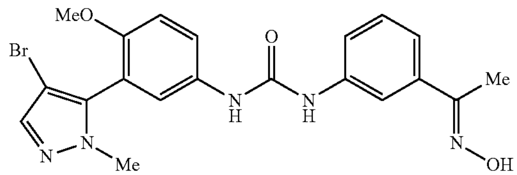 [SMILES: COc1ccc(NC(=O)Nc2cccc(/C(C)=N/O)c2)cc1-c1c(Br)cnn1C] | 1-[3-(4-Bromo-2-methyl-2H-pyrazol-3-yl)-4-methoxy-phenyl]-3-[3-(1-hydroxyimino-ethyl)-phenyl]-urea |
| 97 | 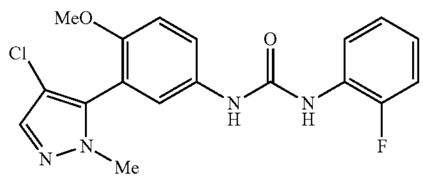 [SMILES: COc1ccc(NC(=O)Nc2ccccc2F)cc1-c1c(Cl)cnn1C] | 1-[3-(4-Chloro-2-methyl-2H-pyrazol-3-yl)-4-methoxy-phenyl]-3-(2-fluoro-phenyl)-urea |
| 98 | 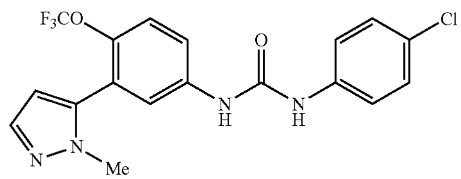 [SMILES: Cn1nccc1-c1cc(NC(=O)Nc2ccc(Cl)cc2)ccc1OC(F)(F)F] | 1-(4-Chloro-phenyl)-3-[3-(2-methyl-2H-pyrazol-3-yl)-4-trifluoromethoxy-phenyl]-urea |
| 99 | 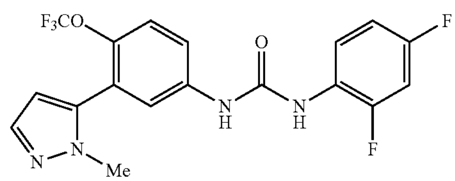 [SMILES: Cn1nccc1-c1cc(NC(=O)Nc2ccc(F)cc2F)ccc1OC(F)(F)F] | 1-(2,4-Difluoro-phenyl)-3-[3-(2-methyl-2H-pyrazol-3-yl)-4-trifluoromethoxy-phenyl]-urea |
| 100 | 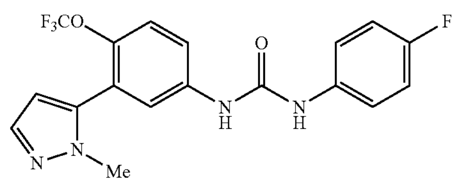 [SMILES: Cn1nccc1-c1cc(NC(=O)Nc2ccc(F)cc2)ccc1OC(F)(F)F] | 1-(4-Fluoro-phenyl)-3-[3-(2-methyl-2H-pyrazol-3-yl)-4-trifluoromethoxy-phenyl]-urea |
| 101 | 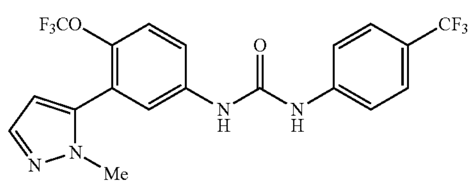 [SMILES: Cn1nccc1-c1cc(NC(=O)Nc2ccc(C(F)(F)F)cc2)ccc1OC(F)(F)F] | 1-[3-(2-Methyl-2H-pyrazol-3-yl)-4-trifluoromethoxy-phenyl]-3-(4-trifluoromethyl-phenyl)-urea |
| 102 | 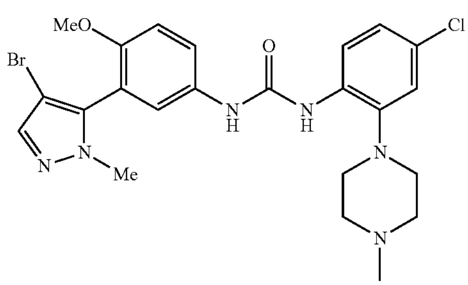 [SMILES: COc1ccc(NC(=O)Nc2ccc(Cl)cc2N2CCN(C)CC2)cc1-c1c(Br)cnn1C] | 1-[3-(4-Bromo-2-methyl-2H-pyrazol-3-yl)-4-methoxy-phenyl]-3-[4-chloro-2-(4-methyl-piperazin-1-yl)-phenyl]-urea |
| 103 | 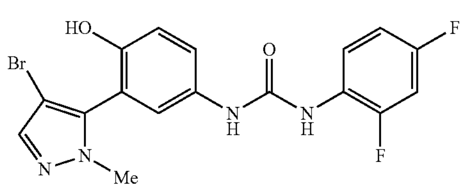 | 1-[3-(4-Bromo-2-methyl-2H-pyrazol-3-yl)-4-hydroxy-phenyl]-3-(2,4-difluoro-phenyl)-urea |

TABLE A-continued

| Cmpd # | Structure | Chemical |
|---|---|---|
| 104 | 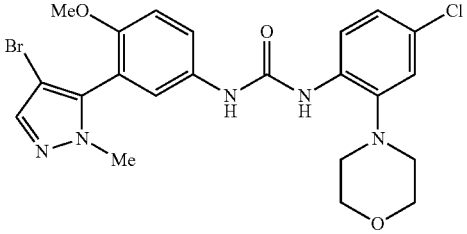 [SMILES: COc1ccc(NC(=O)Nc2ccc(Cl)cc2N2CCOCC2)cc1-c1c(Br)cnn1C] | 1-[3-(4-Bromo-2-methyl-2H-pyrazol-3-yl)-4-methoxy-phenyl]-3-(4-chloro-2-morpholin-4-yl-phenyl)-urea |
| 105 | 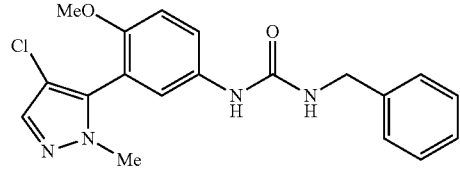 [SMILES: COc1ccc(NC(=O)NCc2ccccc2)cc1-c1c(Cl)cnn1C] | 1-Benzyl-3-[3-(4-chloro-2-methyl-2H-pyrazol-3-yl)-4-methoxy-phenyl]-urea |
| 106 | 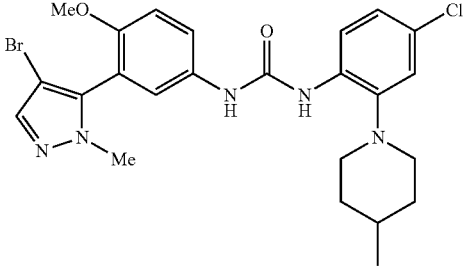 [SMILES: COc1ccc(NC(=O)Nc2ccc(Cl)cc2N2CCC(C)CC2)cc1-c1c(Br)cnn1C] | 1-[3-(4-Bromo-2-methyl-2H-pyrazol-3-yl)-4-methoxy-phenyl]-3-[4-chloro-2-(4-(methyl-piperidin-1-yl)-phenyl]-urea |
| 107 | 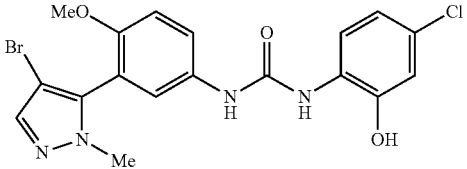 [SMILES: COc1ccc(NC(=O)Nc2ccc(Cl)cc2O)cc1-c1c(Br)cnn1C] | 1-[3-(4-Bromo-2-methyl-2H-pyrazol-3-yl)-4-methoxy-phenyl]-3-(4-chloro-2-hydroxy-phenyl)-ureu |
| 108 | 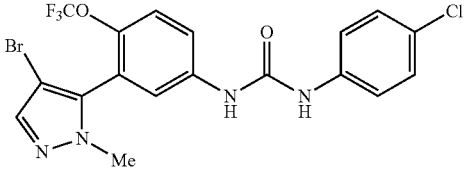 [SMILES: Cn1ncc(Br)c1-c1cc(NC(=O)Nc2ccc(Cl)cc2)ccc1OC(F)(F)F] | 1-[3-(4-Bromo-2-methyl-2H-pyrazol-3-yl)-4-trifluoromethoxy-phenyl]-3-(4-chloro-phenyl)-urea |
| 109 | 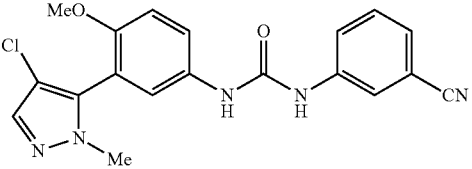 [SMILES: COc1ccc(NC(=O)Nc2cccc(C#N)c2)cc1-c1c(Cl)cnn1C] | 1-[3-(4-Chloro-2-methyl-2H-pyrazol-3-yl)-4-methoxy-phenyl]-3-(3-cyano-phenyl)-urea |
| 110 | 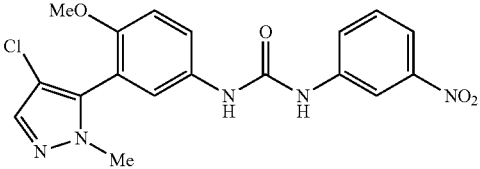 [SMILES: COc1ccc(NC(=O)Nc2cccc([N+](=O)[O-])c2)cc1-c1c(Cl)cnn1C] | 1-[3-(4-Chloro-2-methyl-2H-pyrazol-3-yl)-4-methoxy-phenyl]-3-(3-nitro-phenyl)-urea |

TABLE A-continued

| Cmpd # | Structure | Chemical |
|---|---|---|
| 111 | 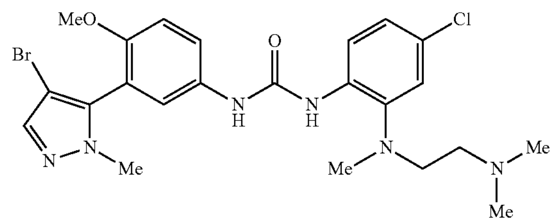 [SMILES: COc1ccc(NC(=O)Nc2ccc(Cl)cc2N(C)CCN(C)C)cc1-c1c(Br)cnn1C] | 1-[3-(4-Bromo-2-methyl-2H-pyrazol-3-yl)-4-methoxy-phenyl]-3-{4-chloro-2-[(2-dimethylamino-ethyl)-methyl-amino]-phenyl}-urea |
| 112 | 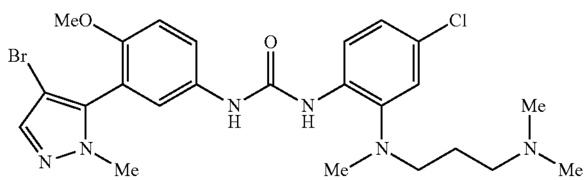 [SMILES: COc1ccc(NC(=O)Nc2ccc(Cl)cc2N(C)CCCN(C)C)cc1-c1c(Br)cnn1C] | 1-[3-(4-Bromo-2-methyl-2H-pyrazol-3-yl)-4-methoxy-phenyl]-3-{4-chloro-2-[(3-dimethylamino-propyl)-methyl-amino]-phenyl}-urea |
| 113 | 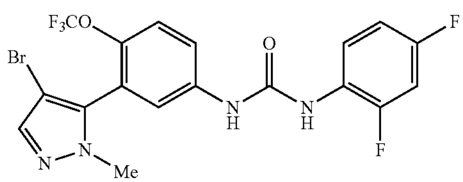 | 1-[3-(4-Bromo-2-methyl-2H-pyrazol-3-yl)-4-trifluoromethoxy-phenyl]-3-(2,4-difluoro-phenyl)-urea |
| 114 | 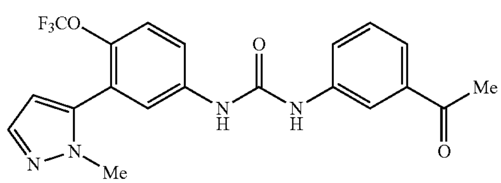 [SMILES: CC(=O)c1cccc(NC(=O)Nc2ccc(OC(F)(F)F)c(-c3ccnn3C)c2)c1] | 1-(3-Acetyl-phenyl)-3-[3-(2-methyl-2H-pyrazol-3-yl)-4-trifluoromethoxy-phenyl]-urea |
| 115 | 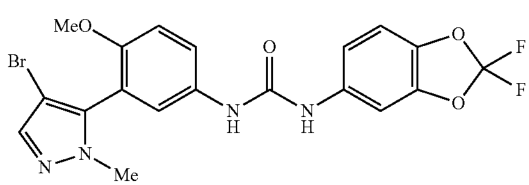 [SMILES: COc1ccc(NC(=O)Nc2ccc3c(c2)OC(F)(F)O3)cc1-c1c(Br)cnn1C] | 1-[3-(4-Bromo-2-methyl-2H-pyrazol-3-yl)-4-methoxy-phenyl]-3-(2,2-difluoro-benzo[1,3]dioxol-5-yl)-urea |
| 116 | 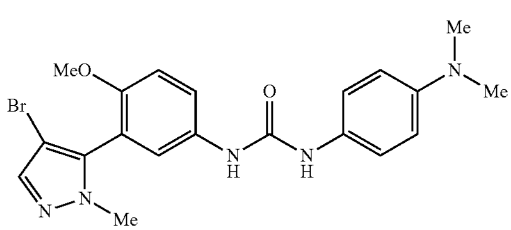 [SMILES: COc1ccc(NC(=O)Nc2ccc(N(C)C)cc2)cc1-c1c(Br)cnn1C] | 1-[3-(4-Bromo-2-methyl-2H-pyrazol-3-yl)-4-methoxy-phenyl]-3-(4-dimethylamino-phenyl)-urea |
| 117 | 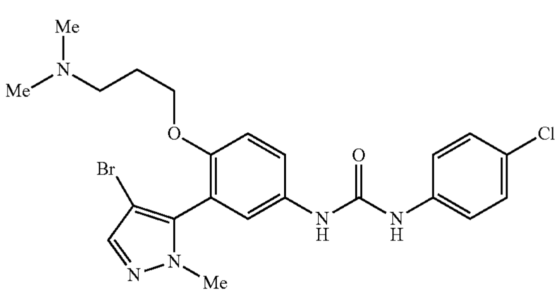 [SMILES: CN(C)CCCOc1ccc(NC(=O)Nc2ccc(Cl)cc2)cc1-c1c(Br)cnn1C] | 1-[3-(4-Bromo-2-methyl-2H-pyrazol-3-yl)-4-(3-dimethylamino-propoxy)-phenyl]-3-(4-chloro-phenyl)-urea |

TABLE A-continued

| Cmpd # | Structure | Chemical |
|---|---|---|
| 118 | 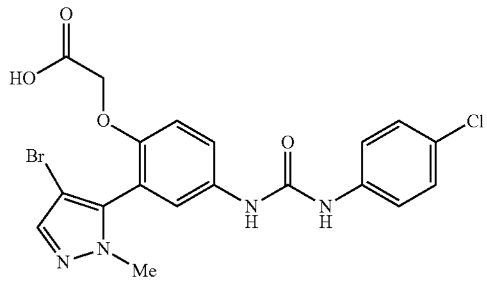 [SMILES: Cn1ncc(Br)c1-c1cc(NC(=O)Nc2ccc(Cl)cc2)ccc1OCC(=O)O] | [2-(4-Bromo-2-methyl-2H-pyrazol-3-yl)-4-[3-(4-chloro-phenyl)-ureido]-phenoxy]-acetic acid |
| 119 | 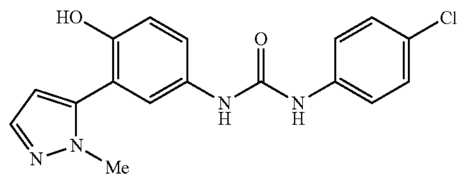 [SMILES: Cn1nccc1-c1cc(NC(=O)Nc2ccc(Cl)cc2)ccc1O] | 1-(4-Chloro-phenyl)-3-[4-hydroxy-3-(2-methyl-2H-pyrazol-3-yl)-phenyl]-urea |
| 120 | 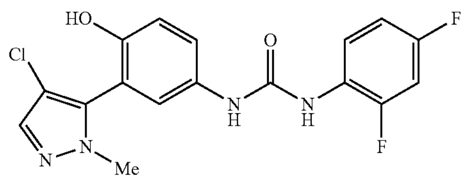 [SMILES: Cn1ncc(Cl)c1-c1cc(NC(=O)Nc2ccc(F)cc2F)ccc1O] | 1-[3-(4-Chloro-2-methyl-2H-pyrazol-3-yl)-4-hydroxy-phenyl]-3-(2,4-difluoro-phenyl)-urea |
| 121 | 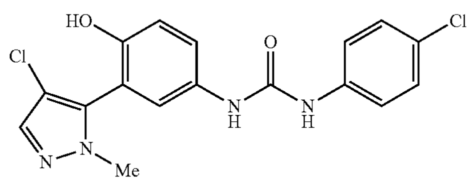 | 1-[3-(4-Chloro-2-methyl-2H-pyrazol-3-yl)-4-hydroxy-phenyl]-3-(4-chloro-phenyl)-urea |
| 122 | 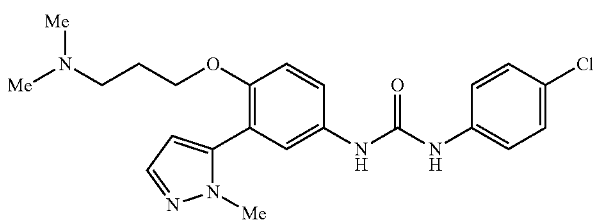 [SMILES: CN(C)CCCOc1ccc(NC(=O)Nc2ccc(Cl)cc2)cc1-c1ccnn1C] | 1-(4-Chloro-phenyl)-3-[4-(3-dimethylamino-propoxy)-3-(2-methyl-2H-pyrazol-3-yl)-phenyl]-urea |
| 123 | 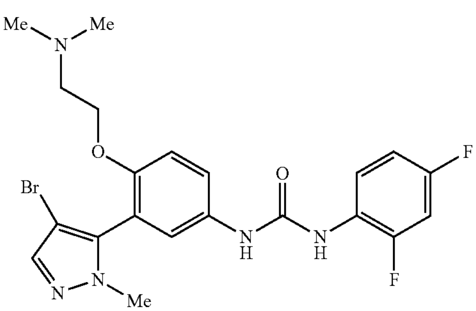 | 1-[3-(4-Bromo-2-methyl-2H-pyrazol-3-yl)-4-(2-dimethylamino-ethoxy)-phenyl]-3-(2,4-difluoro-phenyl)-urea |
| 124 | 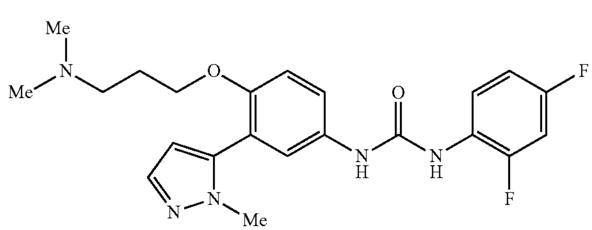 [SMILES: CN(C)CCCOc1ccc(NC(=O)Nc2ccc(F)cc2F)cc1-c1ccnn1C] | 1-(2,4-Difluoro-phenyl)-3-[4-(3-dimethylamino-propoxy)-3-(2-methyl-2H-pyrazol-3-yl)-phenyl]-urea |

TABLE A-continued

| Cmpd # | Structure | Chemical |
|---|---|---|
| 125 | 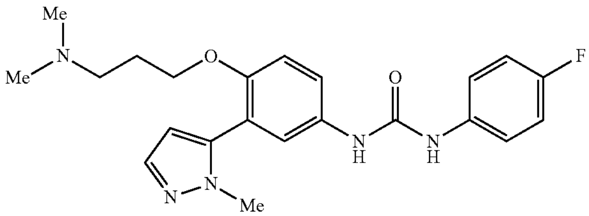 [SMILES: CN(C)CCCOc1ccc(NC(=O)Nc2ccc(F)cc2)cc1-c1ccnn1C] | 1-[4-(3-Dimethylamino-propoxy)-3-(2-methyl-2H-pyrazol-3-yl)-phenyl]-3-(4-fluoro-phenyl)-urea |
| 126 | 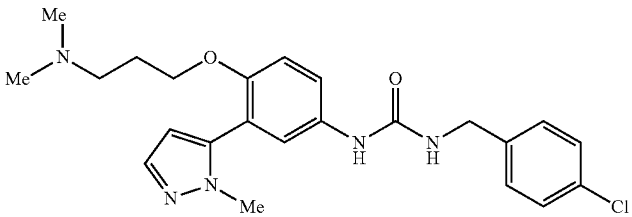 [SMILES: CN(C)CCCOc1ccc(NC(=O)NCc2ccc(Cl)cc2)cc1-c1ccnn1C] | 1-(4-Chloro-benzyl)-3-[4-(3-dimethylamino-propoxy)-3-(2-methyl-2H-pyrazol-3-yl)-phenyl]-urea |
| 127 | 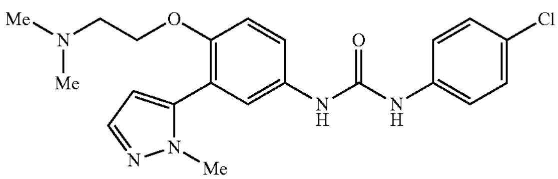 [SMILES: CN(C)CCOc1ccc(NC(=O)Nc2ccc(Cl)cc2)cc1-c1ccnn1C] | 1-(4-Chloro-phenyl)-3-[4-(2-dimethylamino-ethoxy)-3-(2-methyl-2H-pyrazol-3-yl)-phenyl]-urea |
| 128 | 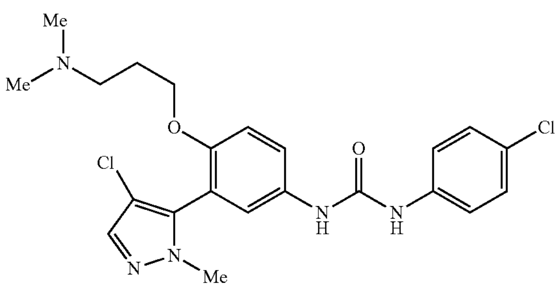 [SMILES: CN(C)CCCOc1ccc(NC(=O)Nc2ccc(Cl)cc2)cc1-c1c(Cl)cnn1C] | 1-[3-(4-Chloro-2-methyl-2H-pyrazol-3-yl)-4-(3-dimethylamino-propoxy)-phenyl]-3-(4-chloro-phenyl)-urea |
| 129 | 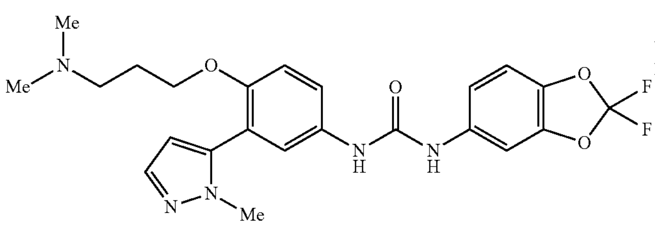 [SMILES: CN(C)CCCOc1ccc(NC(=O)Nc2ccc3c(c2)OC(F)(F)O3)cc1-c1ccnn1C] | 1-(2,2-Difluoro-benzo[1,3]dioxol-5-yl)-3-[4-(3-dimethylamino-propoxy)-3-(2-methyl-2H-pyrazol-3-yl)-phenyl]-urea |
| 130 | 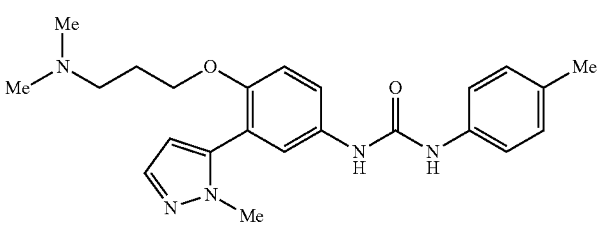 [SMILES: Cc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-p-tolyl-urea |
| 131 | 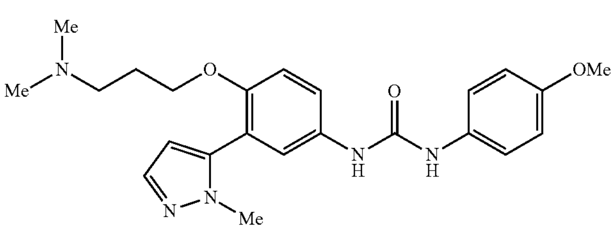 [SMILES: COc1ccc(NC(=O)Nc2ccc(OCCCN(C)C)c(-c3ccnn3C)c2)cc1] | 1-[4-(3-Dimethylamino-propoxy)-3-(2-methyl-2H-pyrazol-3-yl)-phenyl]-3-(4-methoxy-phenyl)-urea |

TABLE A-continued

| Cmpd # | Structure | Chemical |
|---|---|---|
| 132 | 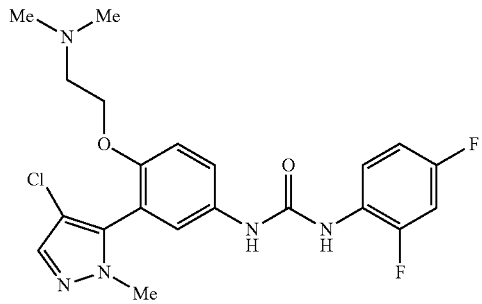 [SMILES: CN(C)CCOc1ccc(NC(=O)Nc2ccc(F)cc2F)cc1-c1c(Cl)cnn1C] | 1-[3-(4-Chloro-2-methyl-2H-pyrazol-3-yl)-4-(2-dimethylamino-ethoxy)-phenyl]-3-(2,4-difluoro-phenyl)-urea |
| 133 | 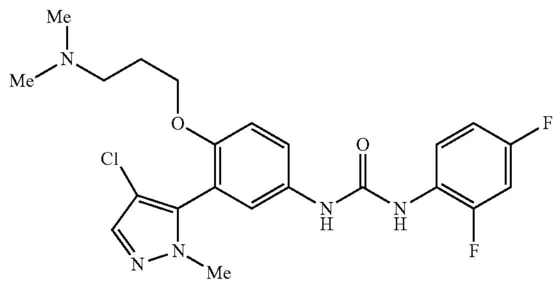 [SMILES: CN(C)CCCOc1ccc(NC(=O)Nc2ccc(F)cc2F)cc1-c1c(Cl)cnn1C] | 1-[3-(4-Chloro-2-methyl-2H-pyrazol-3-yl)-4-(3-dimethylamino-propoxy)-phenyl]-3-(2,4-difluoro-phenyl)-urea |
| 134 | 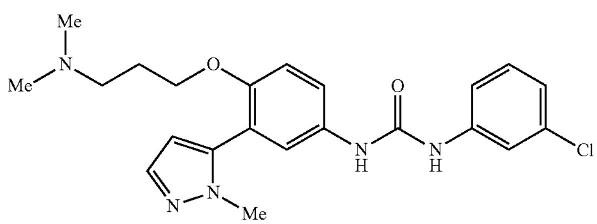 [SMILES: CN(C)CCCOc1ccc(NC(=O)Nc2cccc(Cl)c2)cc1-c1ccnn1C] | 1-(3-Chloro-phenyl)-3-[4-(3-dimethylamino-propoxy)-3-(2-methyl-2H-pyrazol-3-yl)-phenyl]-urea |
| 135 | 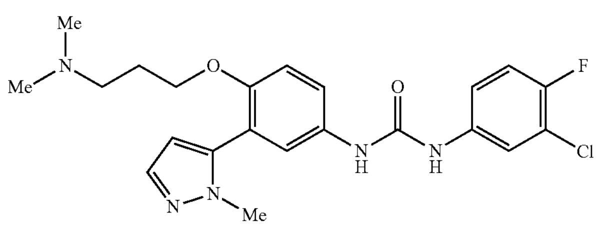 [SMILES: CN(C)CCCOc1ccc(NC(=O)Nc2ccc(F)c(Cl)c2)cc1-c1ccnn1C] | 1-(3-Chloro-4-fluoro-phenyl)-3-[4-(3-dimethylamino-propoxy)-3-(2-methyl-2H-pyrazol-3-yl)-phenyl]-urea |
| 136 | 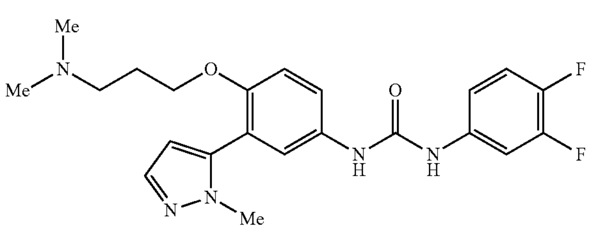 [SMILES: CN(C)CCCOc1ccc(NC(=O)Nc2ccc(F)c(F)c2)cc1-c1ccnn1C] | 1-(3,4-Difluoro-phenyl)-3-[4-(3-dimethylamino-propoxy)-3-(2-methyl-2H-pyrazol-3-yl)-phenyl]-urea |
| 137 | 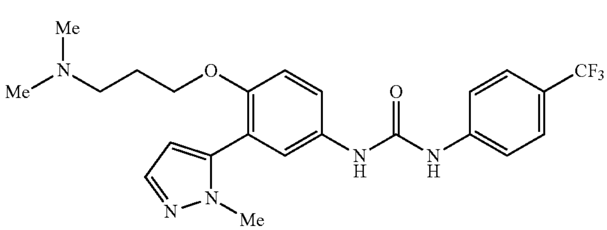 [SMILES: CN(C)CCCOc1ccc(NC(=O)Nc2ccc(C(F)(F)F)cc2)cc1-c1ccnn1C] | 1-[4-(3-Dimethylamino-proproxy)-3-(2-methyl-2H-pyrazol-3-yl)-phenyl]-3-(4-trifluoromethyl-phenyl)-urea |

TABLE A-continued

| Cmpd # | Structure | Chemical |
|---|---|---|
| 138 | 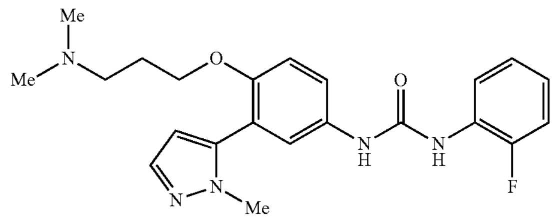 [SMILES: CN(C)CCCOc1ccc(NC(=O)Nc2ccccc2F)cc1-c1ccnn1C] | 1-[4-(3-Dimethylamino-propoxy)-3-(2-methyl-2H-pyrazol-3-yl)-phenyl]-3-(2-fluoro-phenyl)-urea |
| 139 | 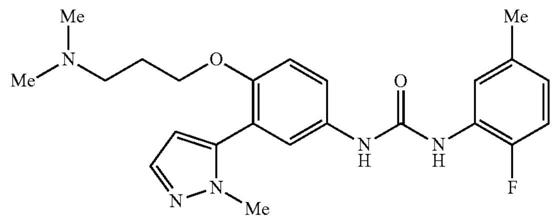 [SMILES: Cc1ccc(F)c(NC(=O)Nc2ccc(OCCCN(C)C)c(-c3ccnn3C)c2)c1] | 1-[4-(3-Dimethylamino-propoxy)-3-(2-methyl-2H-pyrazol-3-yl)-phenyl]-3-(2-fluoro-5-methyl-phenyl)-urea |
| 140 | 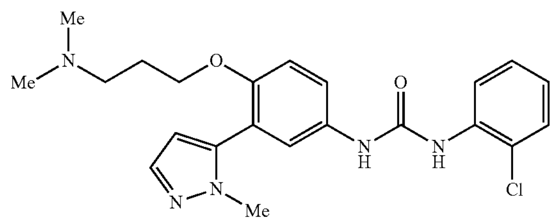 [SMILES: CN(C)CCCOc1ccc(NC(=O)Nc2ccccc2Cl)cc1-c1ccnn1C] | 1-(2-Chloro-phenyl)-3-[4-(3-dimethylamino-propoxy)-3-(2-methyl-2H-pyrazol-3-yl)-phenyl]-urea |
| 141 | 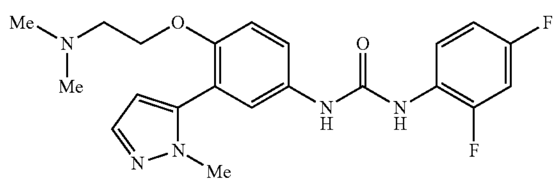 [SMILES: CN(C)CCOc1ccc(NC(=O)Nc2ccc(F)cc2F)cc1-c1ccnn1C] | 1-(2,4-Difluoro-phenyl)-3-[4-(2-dimethylamino-ethoxy)-3-(2-methyl-2H-pyrazol-3-yl)-phenyl]-urea |
| 142 | 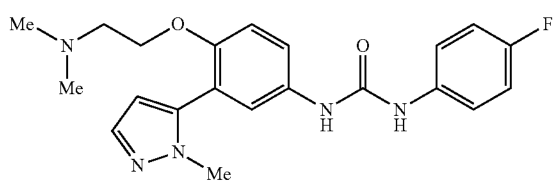 [SMILES: CN(C)CCOc1ccc(NC(=O)Nc2ccc(F)cc2)cc1-c1ccnn1C] | 1-[4-(2-Dimethylamino-ethoxy)-3-(2-methyl-2H-pyrazol-3-yl)-phenyl]-3-(4-fluoro-phenyl)-urea |
| 143 | 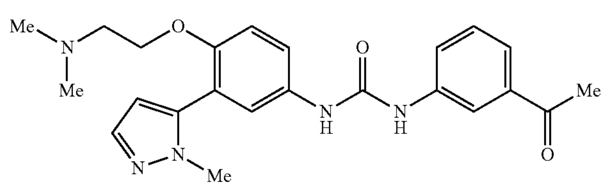 [SMILES: CC(=O)c1cccc(NC(=O)Nc2ccc(OCCN(C)C)c(-c3ccnn3C)c2)c1] | 1-(3-Acetyl-phenyl)-3-[4-(2-dimethylamino-ethoxy)-3-(2-methyl-2H-pyrazol-3-yl)-phenyl]-urea |
| 144 | 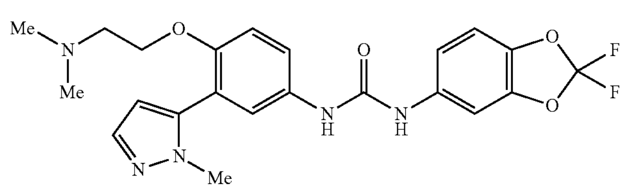 [SMILES: CN(C)CCOc1ccc(NC(=O)Nc2ccc3c(c2)OC(F)(F)O3)cc1-c1ccnn1C] | 1-(2,2-Difluoro-benzo[1,3]dioxol-5-yl)-3-[4-(2-dimethylamino-ethoxy)-3-(2-methyl-2H-pyrazol-3-yl)-phenyl]-urea |

TABLE A-continued

| Cmpd # | Structure | Chemical |
|---|---|---|
| 145 | 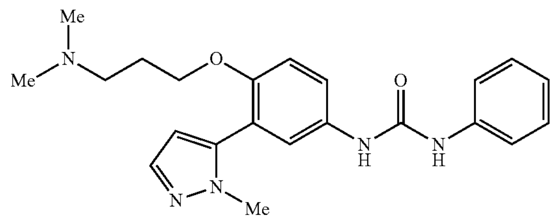 [SMILES: CN(C)CCCOc1ccc(NC(=O)Nc2ccccc2)cc1-c1ccnn1C] | 1-[4-(3-Dimethylamino-propoxy)-3-(2-methyl-2H-pyrazol-3-yl)-phenyl]-3-phenyl-urea |
| 146 | 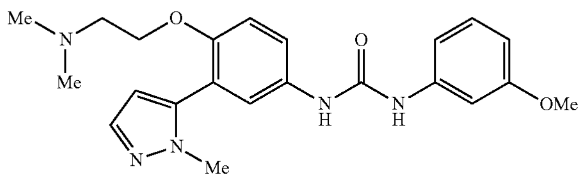 [SMILES: COc1cccc(NC(=O)Nc2ccc(OCCN(C)C)c(-c3ccnn3C)c2)c1] | 1-[4-(2-Dimethylamino-ethoxy)-3-(2-methyl-2H-pyrazol-3-yl)-phenyl]-3-(3-methoxy-phenyl)-urea |
| 147 | 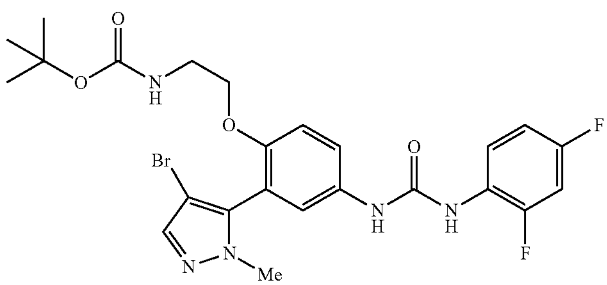 [SMILES: Cn1ncc(Br)c1-c1cc(NC(=O)Nc2ccc(F)cc2F)ccc1OCCNC(=O)OC(C)(C)C] | (2-{2-(4-Bromo-2-methyl-2H-pyrazol-3-yl)-4-[3-(2,4-difluoro-phenyl)-ureido]-phenoxy}-ethyl)-carbamic acid tert-butyl ester |
| 148 | 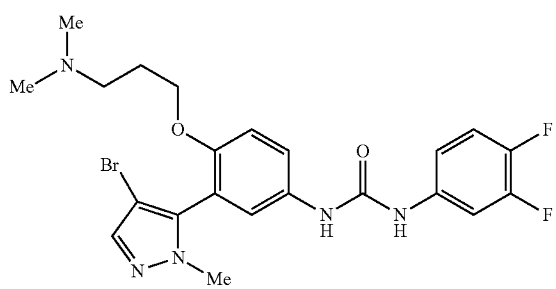 [SMILES: CN(C)CCCOc1ccc(NC(=O)Nc2ccc(F)c(F)c2)cc1-c1c(Br)cnn1C] | 1-[3-(4-Bromo-2-methyl-2H-pyrazol-3-yl)-4-(3-dimethylamino-propoxy)-phenyl]-3-(3,4-difluoro-phenyl)-urea |
| 149 | 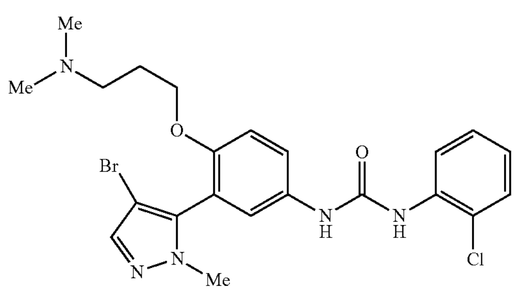 [SMILES: CN(C)CCCOc1ccc(NC(=O)Nc2ccccc2Cl)cc1-c1c(Br)cnn1C] | 1-[3-(4-Bromo-2-methyl-2H-pyrazol-3-yl)-4-(3-dimethylamino-propoxy)-phenyl]-3-(2-chloro-phenyl)-urea |
| 150 | 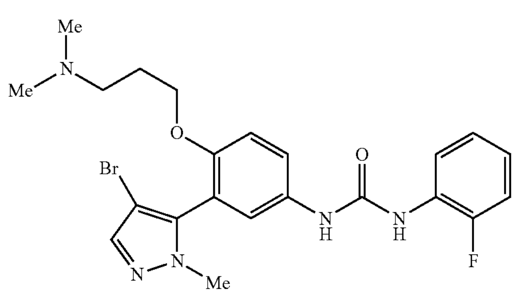 [SMILES: CN(C)CCCOc1ccc(NC(=O)Nc2ccccc2F)cc1-c1c(Br)cnn1C] | 1-[3-(4-Bromo-2-methyl-2H-pyrazol-3-yl)-4-(3-dimethylamino-propoxy)-phenyl]-3-(2-fluoro-phenyl)-urea |

| Cmpd # | Structure | Chemical |
|---|---|---|
| 151 | 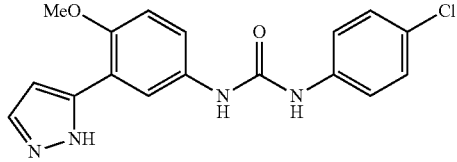 [SMILES: COc1ccc(NC(=O)Nc2ccc(Cl)cc2)cc1-c1ccn[nH]1] | 1-(4-Chloro-phenyl)-3-[4-methoxy-3-(2H-pyrazol-3-yl)-phenyl]-urea |
| 152 | 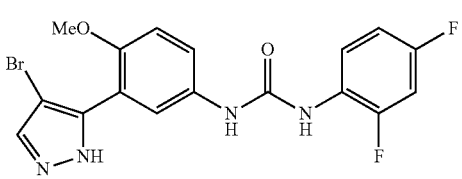 [SMILES: COc1ccc(NC(=O)Nc2ccc(F)cc2F)cc1-c1[nH]ncc1Br] | 1-[3-(4-Bromo-2H-pyrazol-3-yl)-4-methoxy-phenyl]-3-(2,4-difluoro-phenyl)-urea |
| 153 | 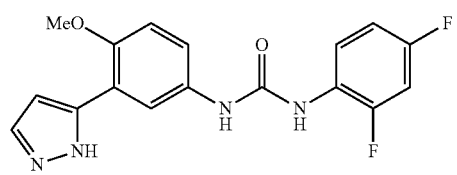 [SMILES: COc1ccc(NC(=O)Nc2ccc(F)cc2F)cc1-c1ccn[nH]1] | 1-(2,4-Difluoro-phenyl)-3-[4-methoxy-3-(2H-pyrazol-3-yl)-phenyl]-urea |
| 154 | 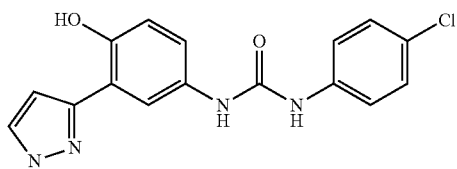 | 1-(4-Chloro-phenyl)-3-[4-hydroxy-3-(1-methyl-1H-pyrazol-3-yl)-phenyl]-urea |
| 155 | 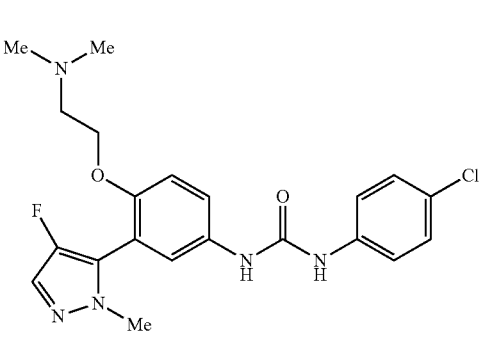 [SMILES: CN(C)CCOc1ccc(NC(=O)Nc2ccc(Cl)cc2)cc1-c1c(F)cnn1C] | 1-(4-Chloro-phenyl)-3-[4-(2-dimethylamino-ethoxy)-3-(4-fluoro-2-methyl-2H-pyrazol-3-yl)-phenyl]-urea |
| 156 | 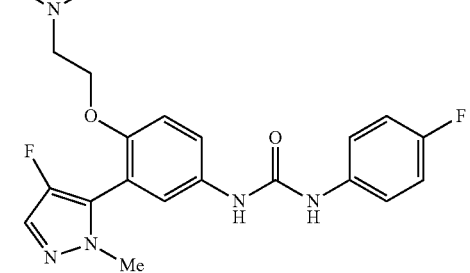 | 1-[4-(2-Dimethylamino-ethoxy)-3-(4-fluoro-2-methyl-2H-pyrazol-3-yl)-phenyl]-3-(4-fluoro-phenyl)-urea |

TABLE A-continued

| Cmpd # | Structure | Chemical |
|---|---|---|
| 157 | 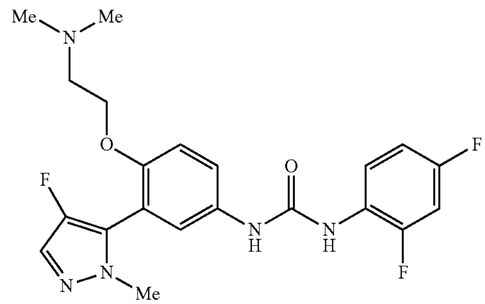 [SMILES: CN(C)CCOc1ccc(NC(=O)Nc2ccc(F)cc2F)cc1-c1c(F)cnn1C] | 1-(2,4-Difluoro-phenyl)-3-[4-(2-dimethylamino-ethoxy)-3-(4-fluoro-2-methyl-2H-pyrazol-3-yl)-phenyl]-urea |
| 158 | 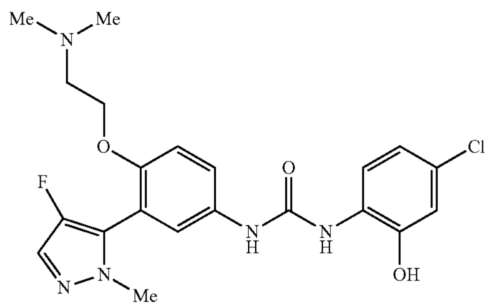 [SMILES: CN(C)CCOc1ccc(NC(=O)Nc2ccc(Cl)cc2O)cc1-c1c(F)cnn1C] | 1-(4-Chloro-2-hydroxy-phenyl)-3-[4-(2-dimethylamino-ethoxy)-3-(4-fluoro-2-methyl-2H-pyrazol-3-yl)-phenyl]-urea |
| 159 | 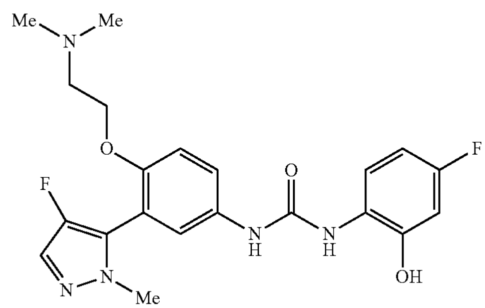 [SMILES: CN(C)CCOc1ccc(NC(=O)Nc2ccc(F)cc2O)cc1-c1c(F)cnn1C] | 1-[4-(2-Dimethylamino-ethoxy)-3-(4-fluoro-2-methyl-2H-pyrazol-3-yl)-phenyl]-3-(4-fluoro-2-hydroxy-phenyl)-urea |
| 160 | 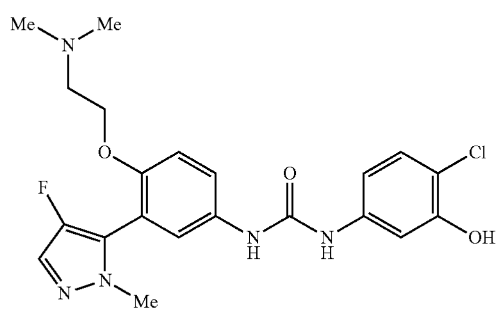 [SMILES: CN(C)CCOc1ccc(NC(=O)Nc2ccc(Cl)c(O)c2)cc1-c1c(F)cnn1C] | 1-(4-Chloro-3-hydroxy-phenyl)-3-[4-(2-dimethylamino-ethoxy)-3-(4-fluoro-2-methyl-2H-pyrazol-3-yl)-phenyl]-urea |
| 161 | 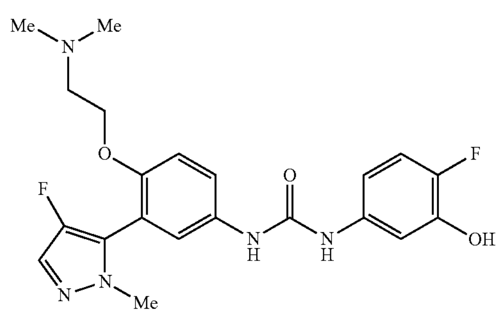 [SMILES: CN(C)CCOc1ccc(NC(=O)Nc2ccc(F)c(O)c2)cc1-c1c(F)cnn1C] | 1-[4-(2-Dimethylamino-ethoxy)-3-(4-fluoro-2-methyl-2H-pyrazol-3-yl)-phenyl]-3-(4-fluoro-3-hydroxy-phenyl)-urea |

| Cmpd # | Structure | Chemical |
|---|---|---|
| 162 | 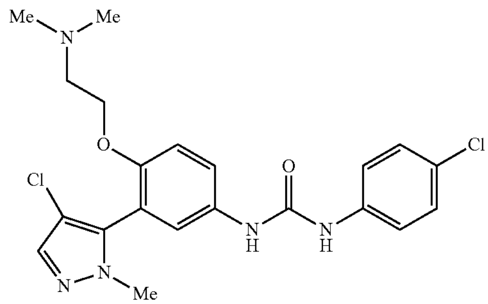 [SMILES: CN(C)CCOc1ccc(NC(=O)Nc2ccc(Cl)cc2)cc1-c1c(Cl)cnn1C] | 1-[3-(4-Chloro-2-methyl-2H-pyrazol-3-yl)-4-(2-dimethylamino-ethoxy)-phenyl]-3-(4-chloro-phenyl)-urea |
| 163 | 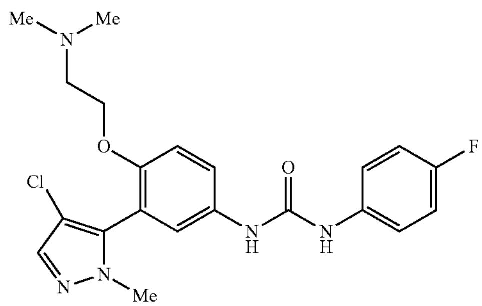 [SMILES: CN(C)CCOc1ccc(NC(=O)Nc2ccc(F)cc2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-phenyl)-urea |
| 164 | 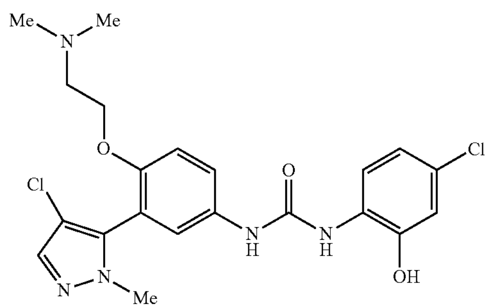 [SMILES: CN(C)CCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(2-dimethylamino-ethoxy)-phenyl]-urea |
| 165 | 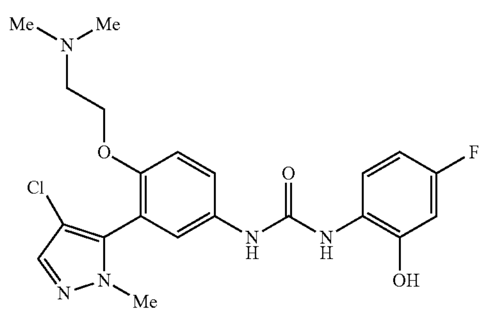 | 1-[3-(4-Chloro-2-methyl-2H-pyrazol-3-yl)-4-(2-dimethylamino-ethoxy)-phenyl]-3-(4-fluoro-2-hydroxy-phenyl)-urea |
| 166 | 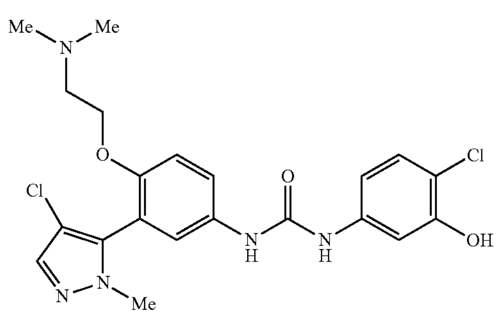 [SMILES: CN(C)CCOc1ccc(NC(=O)Nc2ccc(Cl)c(O)c2)cc1-c1c(Cl)cnn1C] | 1-(4-Chloro-3-hydroxy-phenyl)-3-[3-(4-chloro)-2-methyl-2H-pyrazol-3-yl)-4-(2-dimethylamino-ethoxy)-phenyl]-urea |

TABLE A-continued

| Cmpd # | Structure | Chemical |
|---|---|---|
| 167 | 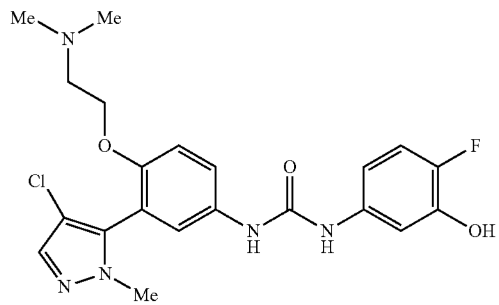 [SMILES: CN(C)CCOc1ccc(NC(=O)Nc2ccc(F)c(O)c2)cc1-c1c(Cl)cnn1C] | 1-[3-(4-Chloro-2-methyl-2H-pyrazol-3-yl)-4-(2-dimethylamino-ethoxy)-phenyl]-3-(4-fluoro-3-hydroxy-phenyl)-urea |
| 168 | 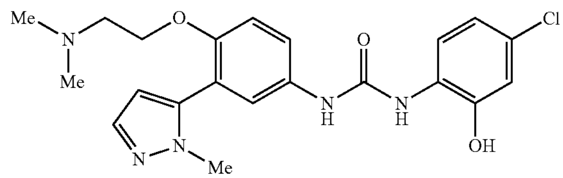 [SMILES: CN(C)CCOc1ccc(NC(=O)Nc2ccc(Cl)cc2O)cc1-c1ccnn1C] | 1-(4-Chloro-2-hydroxy-phenyl)-3-[4-(2-dimethylamino-ethoxy)-3-(2-methyl-2H-pyrazol-3-yl)-phenyl]-urea |
| 169 | 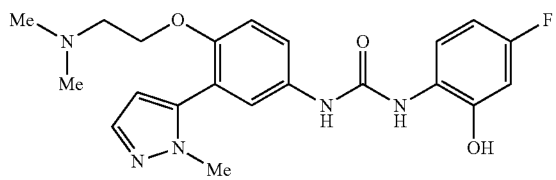 [SMILES: CN(C)CCOc1ccc(NC(=O)Nc2ccc(F)cc2O)cc1-c1ccnn1C] | 1-[4-(2-Dimethylamino-ethoxy)-3-(2-methyl-2H-pyrazol-3-yl)-phenyl]-3-(4-fluoro-2-hydroxy-phenyl)-urea |
| 170 | 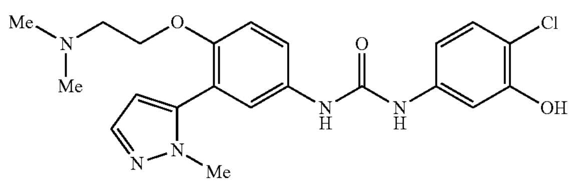 [SMILES: CN(C)CCOc1ccc(NC(=O)Nc2ccc(Cl)c(O)c2)cc1-c1ccnn1C] | 1-(4-Chloro-3-hydroxy-phenyl)-3-[4-(2-dimethylamino-ethoxy)-3-(2-methyl-2H-pyrazol-3-yl)-phenyl]-urea |
| 171 | 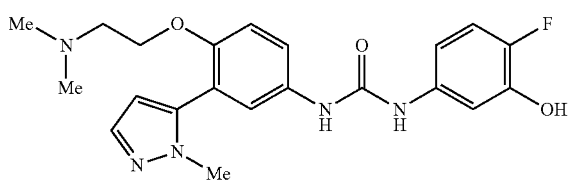 [SMILES: CN(C)CCOc1ccc(NC(=O)Nc2ccc(F)c(O)c2)cc1-c1ccnn1C] | 1-[4-(2-Dimethylamino-ethoxy)-3-(2-methyl-2H-pyrazol-3-yl)-phenyl]-3-(4-fluoro-3-hydroxy-phenyl)-urea |
| 172 | 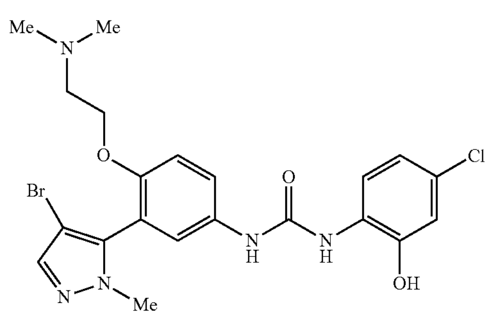 [SMILES: CN(C)CCOc1ccc(NC(=O)Nc2ccc(Cl)cc2O)cc1-c1c(Br)cnn1C] | 1-[3-(4-Bromo-2-methyl-2H-pyrazol-3-yl)-4-(2-dimethylamino-ethoxy)-phenyl]-3-(4-chloro-2-hydroxy-phenyl)-urea |

TABLE A-continued

| Cmpd # | Structure | Chemical |
|---|---|---|
| 173 | 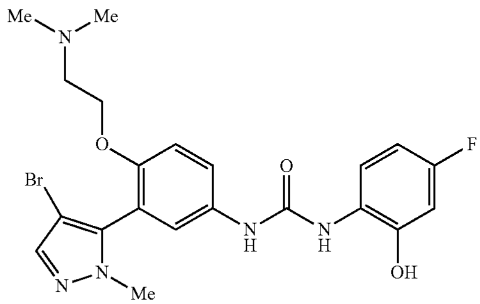 | 1-[3-(4-Bromo-2-methyl-2H-pyrazol-3-yl)-4-(2-dimethylamino-ethoxy)-phenyl]-3-(4-fluoro-2-hydroxy-phenyl)-urea |
| 174 | 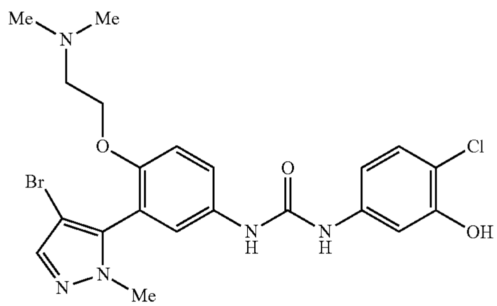 [SMILES: CN(C)CCOc1ccc(NC(=O)Nc2ccc(Cl)c(O)c2)cc1-c1c(Br)cnn1C] | 1-[3-(4-Bromo-2-methyl-2H-pyrazol-3-yl)-4-(2-dimethylamino-ethoxy)-phenyl]-3-(4-chloro-3-hydroxy-phenyl)-urea |
| 175 | 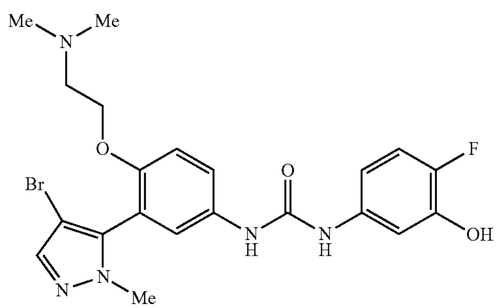 [SMILES: CN(C)CCOc1ccc(NC(=O)Nc2ccc(F)c(O)c2)cc1-c1c(Br)cnn1C] | 1-[3-(4-Bromo-2-methyl-2H-pyrazol-3-yl)-4-(2-dimethylamino-ethoxy)-phenyl]-3-(4-fluoro-3-hydroxy-phenyl)-urea |
| 176 | 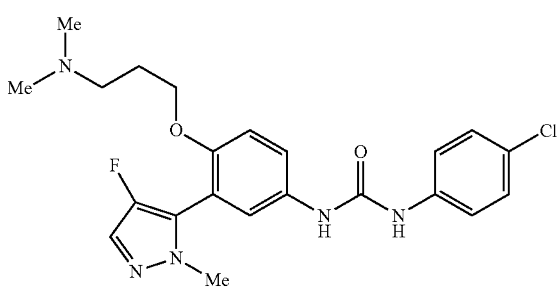 [SMILES: CN(C)CCCOc1ccc(NC(=O)Nc2ccc(Cl)cc2)cc1-c1c(F)cnn1C] | 1-(4-Chloro-phenyl)-3-[4-(3-dimethylamino-propoxy)-3-(4-fluoro-2-methyl-2H-pyrazol-3-yl)-phenyl]-urea |
| 177 | 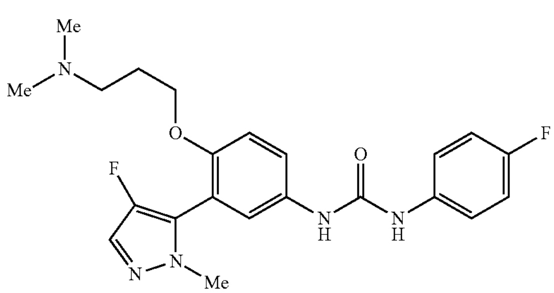 [SMILES: CN(C)CCCOc1ccc(NC(=O)Nc2ccc(F)cc2)cc1-c1c(F)cnn1C] | 1-[4-(3-Dimethylamino-propoxy)-3-(4-fluoro-2-methyl-2H-pyrazol-3-yl)-phenyl]-3-(4-fluoro-phenyl)-urea |

TABLE A-continued

| Cmpd # | Structure | Chemical |
|---|---|---|
| 178 | 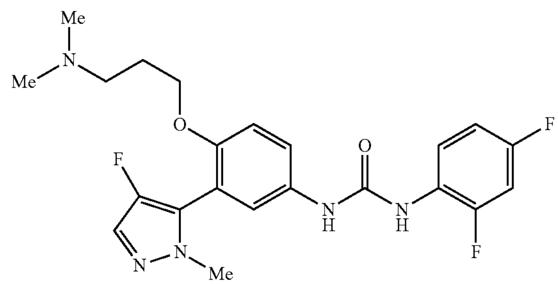 [SMILES: CN(C)CCCOc1ccc(NC(=O)Nc2ccc(F)cc2F)cc1-c1c(F)cnn1C] | 1-(2,4-Difluoro-phenyl)-3-[4-(3-dimethylamino-propoxy)-3-(4-fluoro-2-methyl-2H-pyrazol-3-yl)-phenyl]-urea |
| 179 | 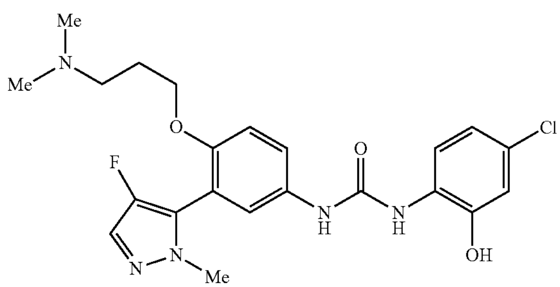 [SMILES: CN(C)CCCOc1ccc(NC(=O)Nc2ccc(Cl)cc2O)cc1-c1c(F)cnn1C] | 1-(4-Chloro-2-hydroxy-phenyl)-3-[4-(3-dimethylamino-propoxy)-3-(4-fluoro-2-methyl-2H-pyrazol-3-yl)-phenyl]-urea |
| 180 | 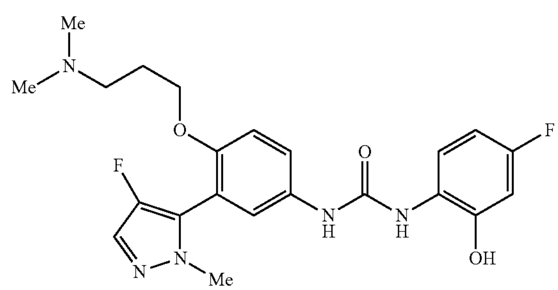 [SMILES: CN(C)CCCOc1ccc(NC(=O)Nc2ccc(F)cc2O)cc1-c1c(F)cnn1C] | 1-[4-(3-Dimethylamino-propoxy)-3-(4-fluoro-2-methyl-2H-pyrazo]-3-yl)-phenyl]-3-(4-fluoro-2-hydroxy-phenyl)-urea |
| 181 | 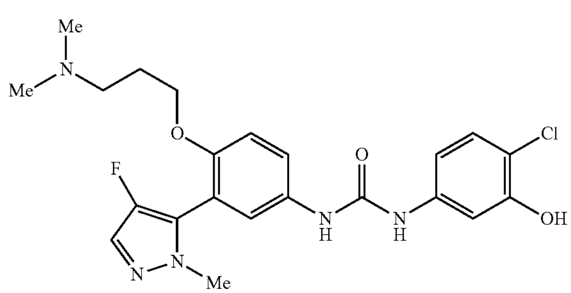 [SMILES: CN(C)CCCOc1ccc(NC(=O)Nc2ccc(Cl)c(O)c2)cc1-c1c(F)cnn1C] | 1-(4-Chloro-3-hydroxy-phenyl)-3-[4-(3-dimethylamino-propoxy)-3-(4-fluoro-2-methyl-2H-pyrazol-3-yl)-phenyl]-urea |
| 182 | 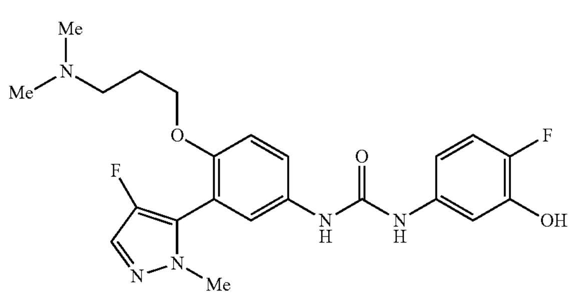 [SMILES: CN(C)CCCOc1ccc(NC(=O)Nc2ccc(F)c(O)c2)cc1-c1c(F)cnn1C] | 1-[4-(3-Dimethylamino-propoxy)-3-(4-fluoro-2-methyl-2H-pyrazol-3-yl)-phenyl]-3-(4-fluoro-3-hydroxy-phenyl)-urea |

TABLE A-continued

| Cmpd # | Structure | Chemical |
|---|---|---|
| 183 | 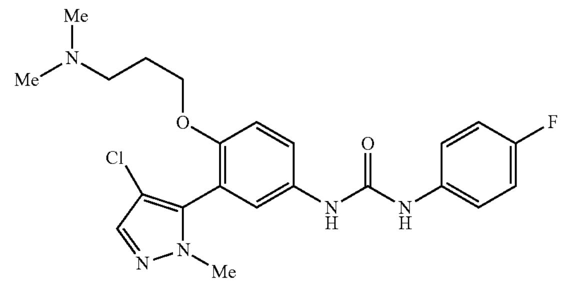 [SMILES: CN(C)CCCOc1ccc(NC(=O)Nc2ccc(F)cc2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-phenyl)-urea |
| 184 | 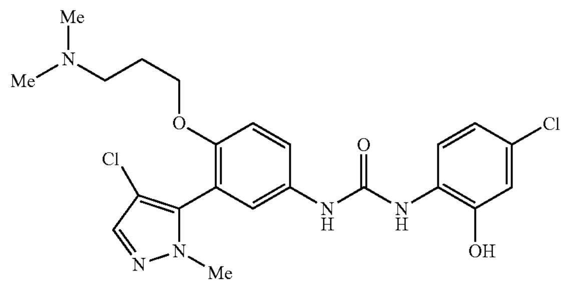 [SMILES: CN(C)CCCOc1ccc(NC(=O)Nc2ccc(Cl)cc2O)cc1-c1c(Cl)cnn1C] | 1-(4-Chloro-2-hydroxy-phenyl)-3-[3-(4-chloro-2-methyl-2H-pyrazol-3-yl)-4-(3-dimethylamino-propoxy)-phenyl]-urea |
| 185 | 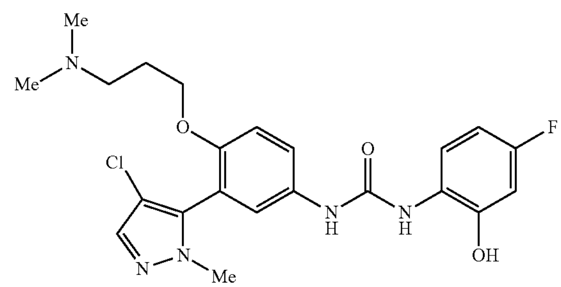 [SMILES: CN(C)CCCOc1ccc(NC(=O)Nc2ccc(F)cc2O)cc1-c1c(Cl)cnn1C] | 1-[3-(4-Chloro-2-methyl-2H-pyrazol-3-yl)-4-(3-dimethylamino-propoxy)-phenyl]-3-(4-fluoro-2-hydroxy-phenyl)-urea |
| 186 | 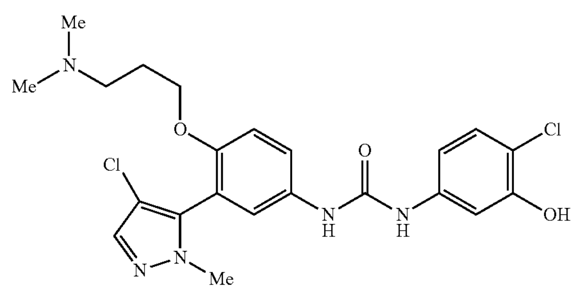 [SMILES: CN(C)CCCOc1ccc(NC(=O)Nc2ccc(Cl)c(O)c2)cc1-c1c(Cl)cnn1C] | 1-(4-Chloro-3-hydroxy-phenyl)-3-[3-(4-chloro-2-methyl-2H-pyrazol-3-yl)-4-(3-dimethylamino-propoxy)-phenyl]-urea |
| 187 | 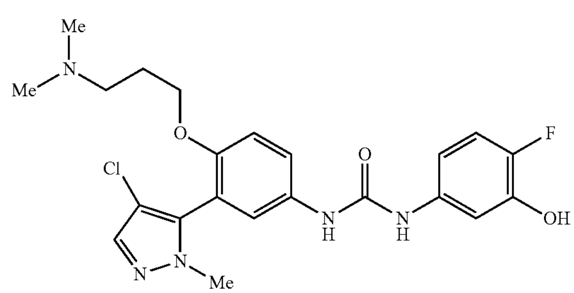 [SMILES: CN(C)CCCOc1ccc(NC(=O)Nc2ccc(F)c(O)c2)cc1-c1c(Cl)cnn1C] | 1-[3-(4-Chloro-2-methyl-2H-pyrazol-3-yl)-4-(3-dimethylamino-propoxy)-phenyl]-3-(4-fluoro-3-hydroxy-phenyl)-urea |

| Cmpd # | Structure | Chemical |
|---|---|---|
| 188 | 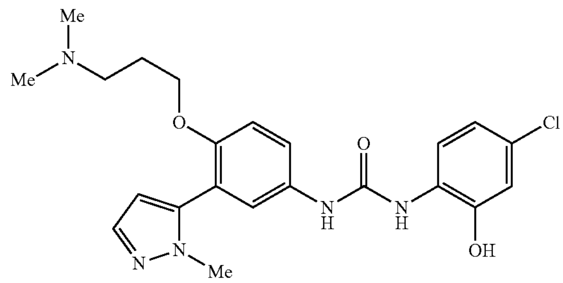 [SMILES: CN(C)CCCOc1ccc(NC(=O)Nc2ccc(Cl)cc2O)cc1-c1ccnn1C] | 1-(4-Chloro-2-hydroxy-phenyl)-3-[4-(3-dimethylamino-propoxy)-3-(2-methyl-2H-pyrazol-3-yl)-phenyl]-urea |
| 189 | 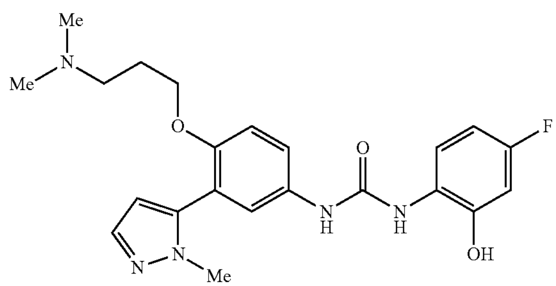 [SMILES: CN(C)CCCOc1ccc(NC(=O)Nc2ccc(F)cc2O)cc1-c1ccnn1C] | 1-[4-(3-Dimethylamino-propoxy)-3-(2-methyl-2H-pyrazol-3-yl)-phenyl]-3-(4-fluoro-2-hydroxy-phenyl)-urea |
| 190 | 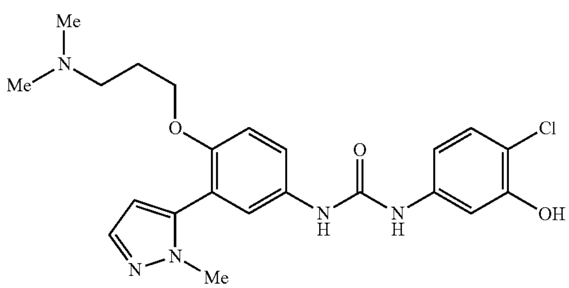 [SMILES: CN(C)CCCOc1ccc(NC(=O)Nc2ccc(Cl)c(O)c2)cc1-c1ccnn1C] | 1-(4-Chloro-3-hydroxy-phenyl)-3-[4-(3-dimethylamino-propoxy)-3-(2-methyl-2H-pyrazol-3-yl)-phenyl]-urea |
| 191 | 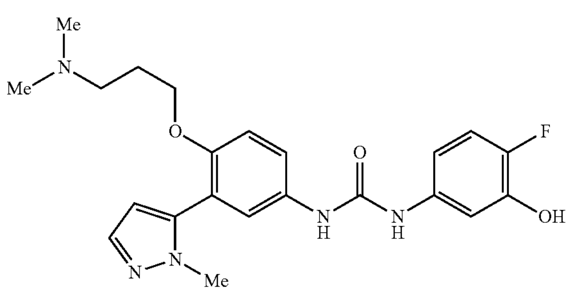 [SMILES: CN(C)CCCOc1ccc(NC(=O)Nc2ccc(F)c(O)c2)cc1-c1ccnn1C] | 1-[4-(3-Dimethylamino-propoxy)-3-(2-methyl-2H-pyrazol-3-yl)-phenyl]-3-(4-fluoro-3-hydroxy-phenyl)-urea |
| 192 | 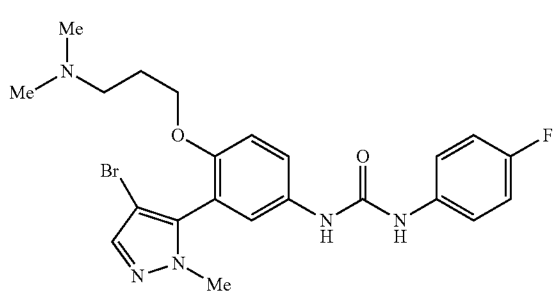 [SMILES: CN(C)CCCOc1ccc(NC(=O)Nc2ccc(F)cc2)cc1-c1c(Br)cnn1C] | 1-[3-(4-Bromo-2-methyl-2H-pyrazol-3-yl)-4-(3-dimethylamino-propoxy)-phenyl]-3-(4-fluoro-phenyl)-urea |

TABLE A-continued

| Cmpd # | Structure | Chemical |
|---|---|---|
| 193 | 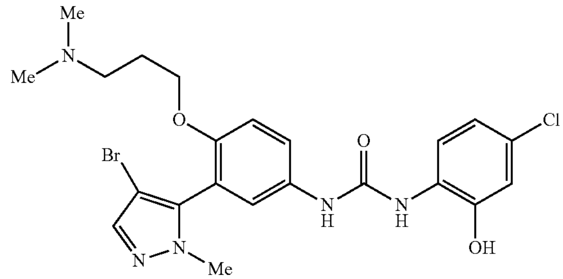 | 1-[3-(4-Bromo-2-methyl-2H-pyrazol-3-yl)-4-(3-dimethylamino-propoxy)-phenyl]-3-(4-chloro-2-hydroxy-phenyl)-urea |
| 194 | 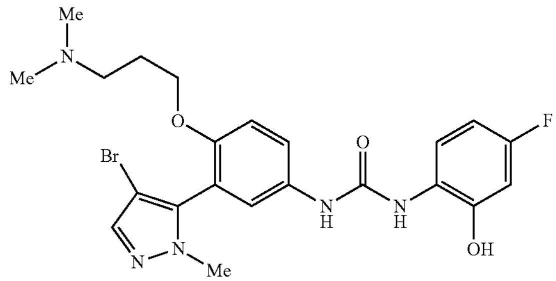 [SMILES: CN(C)CCCOc1ccc(NC(=O)Nc2ccc(F)cc2O)cc1-c1c(Br)cnn1C] | 1-[3-(4-Bromo-2-methyl-2H-pyrazol-3-yl)-4-(3-dimethylamino-propoxy)-phenyl]-3-(4-fluoro-2-hydroxy-phenyl)-urea |
| 195 | 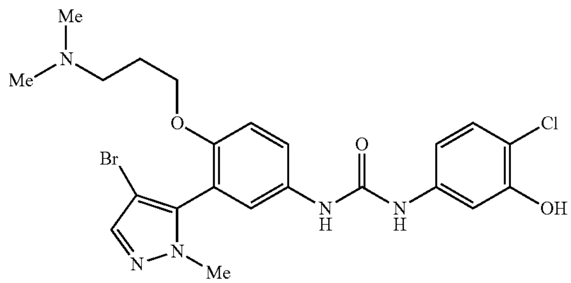 | 1-[3-(4-Bromo-2-methyl]-2H-pyrazol-3-yl)-4-(3-dimethylamino-propoxy)-phenyl]-3-(4-chloro-3-hydroxy-phenyl)-urea |
| 196 | 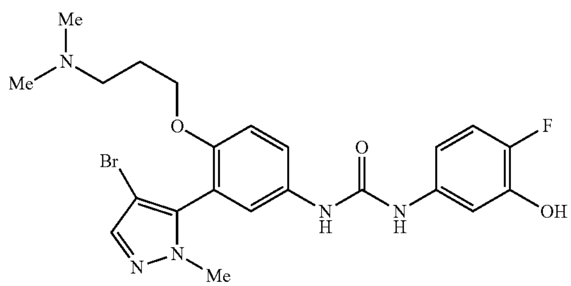 [SMILES: CN(C)CCCOc1ccc(NC(=O)Nc2ccc(F)c(O)c2)cc1-c1c(Br)cnn1C] | 1-[3-(4-Bromo-2-methyl-2H-pyrazol-3-yl)-4-(3-dimethylamino-propoxy)-phenyl]-3-(4-fluoro-3-hydroxy-phenyl)-urea |

Additionally, compounds of the present invention, such as Formula (I) and related Formulae, encompass all pharmaceutically acceptable salts, solvates, and particularly hydrates, thereof.

The compounds of the Formula (I) of the present invention may be prepared according to the general synthetic schemes in FIGS. 17 through 21 and FIGS. 29 through 33 as well as relevant published literature procedures that are used by one skilled in the art, Exemplary reagents and procedures for these reactions appear hereinafter in the working Examples. Protection and deprotection may be carried out by procedures generally known in the art. (see, for example, Greene, W. and Wuts, P. G. M. Protecting Groups in Organic Synthesis, 3$^{rd}$ Edition, 1999 [Wiley]; incorporated herein by reference in its entirety).

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Constitutively Active Human 5HT$_{2A}$

For convenience, the sequence information regarding the non-endogenous, constitutively active human 5-HT2A and identifiers are set forth in TABLE 4:

TABLE 4

| IDENTIFIER | RECEPTOR | SEQ. ID. NO: | FIG. |
|---|---|---|---|
| AP-3 cDNA | 5-HT$_{2A}$ | 27 | 6a |
| AP-3 | 5-HT$_{2A}$ | 28 | 6b |

TABLE 4-continued

| IDENTIFIER | RECEPTOR | SEQ. ID. NO: | FIG. |
|---|---|---|---|
| AP-4 cDNA | 5-HT$_{2A}$ | 29 | 7a |
| AP-4 | 5-HT$_{2A}$ | 30 | 7b |

Indications and Methods of Prophylaxis and/or Treatment

In addition to the foregoing beneficial uses for the modulators of 5-HT$_{2A}$ receptor activity disclosed herein, the compounds disclosed herein are believed to be useful in the treatment of several additional diseases and disorders, and in the amelioration of symptoms thereof. Without limitation, these include the following:

1. Antiplatelet Therapies (5-HT$_{2A}$ Mediated Platelet Aggregation):

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood as a result of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-HT$_{2A}$ receptors are expressed on smooth muscle of blood vessels and 5-HT secreted by activated platelets causes vasoconstriction as well as activation of additional platelets during clotting. There is evidence that a 5-HT$_{2A}$ inverse agonist will inhibit platelet aggregation and thus be a potential treatment as an antiplatelet therapy (see Satimura, K, et al., Clin Cardiol 2002 Jan. 25 (1):28-32; and Wilson, H. C et al., Thromb Haemost 1991 Sep. 2;66(3):355-60).

The 5-HT$_{2A}$ inverse agonists disclosed herein provide beneficial improvement in microcirculation to patients in need of antiplatelet therapy by antagonizing the vasoconstrictive products of the aggregating platelets in, for example and not limitation, the indications described above. Accordingly, in some embodiments, the present invention provides methods for reducing platelet aggregation in a patient in need thereof comprising administering to said patient a composition comprising a 5-HT$_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of said treatment, comprising administering to said patient a composition comprising a 5-HT$_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to a said patient a composition comprising a 5-HT$_{2A}$ inverse agonist disclosed herein at a time where such risk exists.

2. Asthma

It has been suggested that 5-HT (5-hydroxytryptamine) plays a role in the pathophysiology of acute asthma (see Cazzola, M. and Matera, M. G., TIPS, 2000, 21, 13; and De Bie, J. J. et al., British J. Pharm., 1998, 124, 857-864). The compounds of the present invention disclosed herein are useful in the treatment of asthma, and the treatment of the symptoms thereof. Accordingly, in some embodiments, the present invention provides methods for treating asthma in a patient in need of said treatment, comprising administering to said patient a composition comprising a 5-HT$_{2A}$ inverse agonist disclosed herein. In further embodiments, methods are provided for treating a symptom of asthma in a patient in need of said treatment, comprising administering to said patient a composition comprising a 5-HT$_{2A}$ inverse agonist disclosed herein.

3. Agitation

Agitation is a well-recognized behavioral syndrome with a range of symptoms, including hostility, extreme excitement, poor impulse control, tension and uncooperativeness (See Cohen-Mansfield J, and Billig, N., (1986), Agitated Behaviors in the Elderly. I. A Conceptual Review. J Am Geriatr Soc 34(10): 711-721).

Agitation is a common occurrence in the elderly and often associated with dementia such as those caused by Alzheimer's disease, Lewy Body, Parkinson's, and Huntington's, which are degenerative diseases of the nervous system and by diseases that affect blood vessels, such as stroke, or multi-infarct dementia, which is caused by multiple strokes in the brain can also induce dementia. Alzheimer's disease accounts for approximately 50 to 70% of all dementias (See Koss E, et al., (1997), Assessing patterns of agitation in Alzheimer's disease patients with the Cohen-Mansfield Agitation Inventory. The Alzheimer's Disease Cooperative Study. Alzheimer Dis Assoc Disord 11(suppl 2):S45-S50).

An estimated five percent of people aged 65 and older and up to 20 percent of those aged 80 and older are affected by dementia; of these sufferers, nearly half exhibit behavioral disturbances, such as agitation, wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the 5-$HT_{2A}$ receptors in the brain have the effects of reducing agitation in patients, including Alzheimer's dementia (See Katz, I. R., et al., J Clin Psychiatry 1999 February, 60(2): 107-115; and Street, J. S., et al., Arch Gen Psychiatry 2000 October, 57(10):968-976).

The compounds of the invention disclosed herein are useful for treating agitation and symptoms thereof. Thus, in some embodiments, the present invention provides methods for treating agitation in a patient in need of such treatment comprising administering to said patient a composition comprising a 5-$HT_{2A}$ inverse agonist disclosed herein. In some embodiments, the agitation is due to a psychiatric disorder other than dementia. In some embodiments, the present invention provides methods for treatment of agitation or a symptom thereof in a patient suffering from dementia comprising administering to said patient a composition comprising a 5-$HT_{2A}$ inverse agonist disclosed herein. In some embodiments of such methods, the dementia is due to a degenerative disease of the nervous system, for example and without limitation, Alzheimers disease, Lewy Body, Parkinson's disease, and Huntington's disease, or dementia due to diseases that affect blood vessels, including, without limitation, stroke and multi-infarct dementia. In some embodiments, methods are provided for treating agitation or a symptom thereof in a patient in need of such treatment, where the patient is a cognitively intact elderly patient, comprising administering to said patient a composition comprising a 5-$HT_{2A}$ inverse agonist disclosed herein.

4. Add-on Therapy to Haloperidol in the Treatment of Schizophrenia and Other Disorders:

Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of interhuman relationships, and finally psychomotoric disorders (such as catatonia). Other symptoms are also associated with this disorder. (See, American Statistical and Diagnostic Handbook).

Haloperidol (Haldol) is a potent dopamine D2 receptor antagonist. It is widely prescribed for acute schizophrenic symptoms, and is very effective for the positive symptoms of schizophrenia. However, Haldol is not effective for the negative symptoms of schizophrenia and may actually induce negative symptoms as well as cognitive dysfunction. In accordance with some methods of the invention, adding a 5-$HT_{2A}$ inverse agonist concomitantly with Haldol will provide benefits including the ability to use a lower dose of Haldol without losing its effects on positive symptoms, while reducing or eliminating its inductive effects on negative symptoms, and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, huntington's chorea, and nausea and vomiting from chemotherapy and chemotherapeutic antibodies. Administration of 5-$HT_{2A}$ inverse agonists disclosed herein with haloperidol also will provide benefits in these indications.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to said patient a dopamine D2 receptor antagonist and a 5-$HT_{2A}$ inverse agonist disclosed herein.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to said patient haloperidol and a 5-$HT_{2A}$ inverse agonist disclosed herein.

In some embodiments, the present invention provides methods for treating infantile autism, huntington's chorea, or nausea and vomiting from chemotherapy or chemotherapeutic antibodies comprising administering to said patient a dopamine D2 receptor antagonist and a 5-$HT_{2A}$ inverse agonist disclosed herein.

In some embodiments, the present invention provides methods for treating infantile autism, huntington's chorea, or nausea and vomiting from chemotherapy or chemotherapeutic antibodies comprising administering to said patient haloperidol and a 5-$HT_{2A}$ inverse agonist disclosed herein.

In further embodiments, the present invention provides methods for treating schizophrenia in a patient in need of said treatment comprising administering to said patient a dopamine D2 receptor antagonist and a 5-$HT_{2A}$ inverse agonist disclosed herein. Preferably, the dopamine D2 receptor antagonist is haloperidol.

The administration of the dopamine D2 receptor antagonist can be concomitant with administration of the 5-$HT_{2A}$ inverse agonist, or they can be administered at different times. Those of skill in the art will easily be able to determine appropriate dosing regimes for the most efficacious reduction or elimination of deleterions haloperidol effects. In some embodiments, haloperidol and the 5-$HT_{2A}$ inverse agonist are administered in a single dosage form, and in other embodiments, they are administered in separate dosage forms.

The present invention further provides methods of alleviating negative symptoms of schizophrenia induced by the administration of haloperidol to a patient suffering from said schizophrenia, comprising administering to said patient a 5-$HT_{2A}$ inverse agonist as disclosed herein.

5. Sleep Disorders

It is reported in the National Sleep Foundation's 2002 Sleep In America Poll, more than one-half of the adults surveyed (58%) report having experienced one or more symptoms of insomnia at least a few nights a week in the past year. Additionally, about three in ten (35%) say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, compounds of the present invention are effective, for example, in any one or more of the following sleep disorders (ICSD—International Classification of Sleep Disorders: Diagnostic and Coding Manual. *Diagnostic Classification Steering Committee*, American Sleep Disorders Association, 1990):

A. Dyssomnias a. Intrinsic Sleep Disorders:

Psychophysiological insomnia, Sleep state misperception, Idiopathic insomnia, Obstructive sleep apnea syndrome, Central sleep apnea syndrome, Central alveolar hypoventilation syndrome, Periodic limb movement disorder, Restless leg syndrome and Intrinsic sleep disorder NOS.

b. Extrinsic Sleep Disorders:

Inadequate sleep hygiene, Environmental sleep disorder, Altitude insomnia, Adjustment sleep disorder, Insufficient sleep syndrome, Limit-setting sleep disorder, SleepOnset association disorder, Nocturnal eating (drinking) syndrome, Hypnotic dependent sleep disorder, Stimulant-dependent sleep disorder, Alcohol-dependent sleep disorder, Toxin-induced sleep disorder and Extrinsic sleep disorder NOS.

c. Circadian Rhythm Sleep Disorders:

Time zone change (jet lag) syndrome, Shift work sleep disorder, Irregular sleep-wake pattern, Delayed sleep phase syndrome, Advanced sleep phase syndrome, Non-24-hour sleep-wake disorder and Circadian rhythm sleep disorder NOS.

B. Parasomnias a. Arousal Disorders:

Confusional arousals, Sleepwalking and Sleep terrors.

b. Sleep-Wake Transition Disorders:

Rhythmic movement disorder, Sleep starts, Sleep talking and Nocturnal leg cramps.

C. Sleep Disorders Associated with Medical/Psychiatric Disorders a. Associated with Mental Disorders:

Psychoses, Mood disorders, Anxiety disorders, Panic disorders and Alcoholism.

b. Associated with Neurological Disorders:

Cerebral degenerative disorders, Dementia, Parkinsonism, Fatal familial insomnia, Sleep-related epilepsy, Electrical status epilepticus of sleep and Sleep-related headaches. P c. Associated with Other Medical Disorders:

Sleeping sickness, Nocturnal cardiac ischemia, Chronic obstructive pulmonary disease, Sleep-related asthma, Sleep-related gastroesophageal reflux, Peptic ulcer disease, Fibrositis syndrome, Osteoarthritis, Rheumatoid arthritis, Fibromyalgia and Post-surgical.

The effects of sleep deprivation are more than excessive daytime sleepiness. Chronic insomniacs report elevated levels of stress, anxiety, depression and medical illnesses (National Institutes of Health, National Heart, Lung, and Blood Institute, Insomnia Facts Sheet, October 1995). Preliminary evidence suggests that having a sleep disorder that causes significant loss of sleep may contribute to increased susceptibility to infections due to immunosuppression, cardiovascular complications such as hypertension, cardiac arrhythmias, stroke, and myocardial infarction, compromised glucose tolerance, increased obesity and metabolic syndrome. Compounds of the present invention are useful to prevent or alleviate these complications by improving sleep quality.

The most common class of medications for the majority of sleep disorders are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as are compounds of the present invention have demonstrated significant improvements on objective and subjective sleep parameters in normal, healthy volunteers as well as patients with sleep disorders and mood disorders [Sharpley A L, et al. Slow Wave Sleep in Humans: Role of $5HT_{2A}$ and $5HT_{2C}$ Receptors. *Neuropharmacology*, 1994, Vol. 33(3/4):467-71; Winokur A, et al. Acute Effects of Mirtazapine on Sleep Continuity and Sleep Architecture in Depressed Patients: A Pilot Study. *Soc of Biol Psych*, 2000, Vol. 48:75-78; and Landolt H P, et al. Serotonin-2 Receptors and Human Sleep: Effect of Selective Antagonist on EEG Power Spectra. *Neuropsychopharmacology*, 1999, Vol. 21(3):455-66].

Some sleep disorders are sometimes found in conjunction with other conditions and accordingly those conditions are treatable by compounds of Formula (I). For example but not limiting, patients suffering from mood disorders typically suffer from a sleep disorder that can be treatable by compounds of Formula (I). Having one pharmacological agent which treats two or more existing or potential conditions, as does the present invention, is more cost effective, leads to better compliance and has fewer side effects than taking two or more agents.

It is an object of the present invention to provide a therapeutic agent for the use in treating Sleep Disorders. It is another object of the present invention to provide one pharmaceutical agent, which may be useful in treating two or more conditions wherein one of the conditions is a sleep disorder. Compounds of the present invention described herein may be used alone or in combination with a mild sleep inducer (i.e. antihistamine).

Sleep Architecture:

Sleep comprises two physiological states: Non rapid eye movement (NREM) and rapid eye movement (REM) sleep. NREM sleep consists of four stages, each of which is characterized by progressively slower brain wave patterns, with the slower patterns indicating deeper sleep. So called delta sleep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning the patient spends a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a Waking state by limited external stimuli. As a result, the individual cycles through frequent bouts of light sleep interrupted by frequent awakenings throughout the sleep period. Many sleep disorders are characterized by a fragmented sleep architecture. For example, many elderly patients with sleep complaints have difficulty achieving long bouts of deep refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly Stages 3 and 4, and the length of those sleep bouts are increased, while the number and length of waking bouts are decreased. In essence, the architecture of the sleep disorder patient is consolidated to a sleeping state with increased periods of sleep and fewer awakenings during the night and more time is spent in slow wave sleep (Stages 3 and 4) with fewer oscillation Stage 1 and 2 sleep. Compounds of the present invention as described are effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall, and muscles relax. In normal sleep architecture, NREM sleep makes up about 75% of total sleep time; stage 1 accounting for 5-10% of total sleep time, stage 2 for about 45-50%, stage 3 approximately 12%, and stage 4 13-15%. About 90 minutes after sleep onset, NREM sleep gives way to the first REM sleep episode of the night. REM makes up approximately 25% of total sleep time. In contrast to NREM sleep, REM sleep is characterized by high pulse, respiration, and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable; a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

Figure 28:
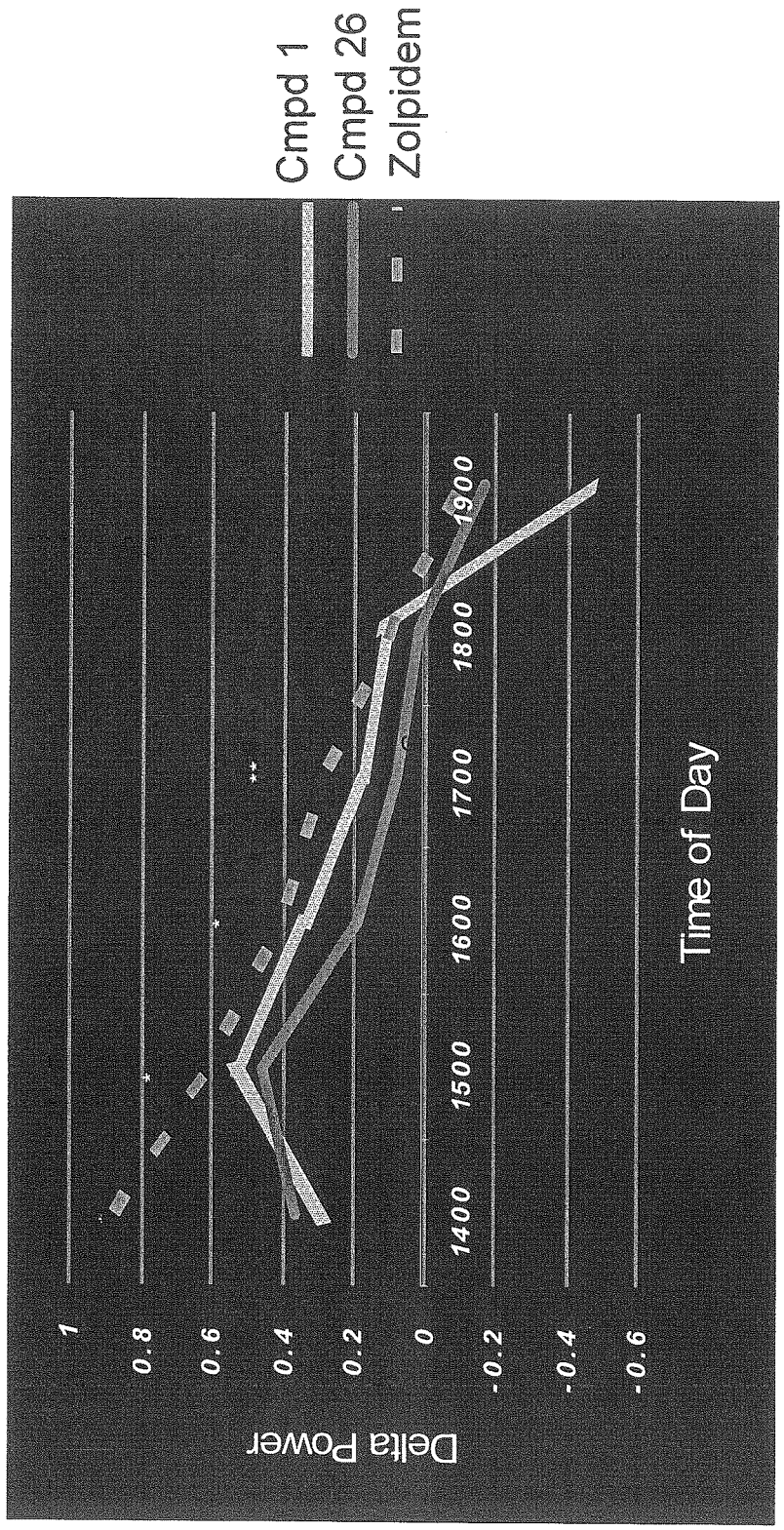
FIG. 28 shows the effect in rats of Compound 1 and Compound 26 on sleep and wakefulness, as measured by delta power, compared to zolpidem.
Figure 29:
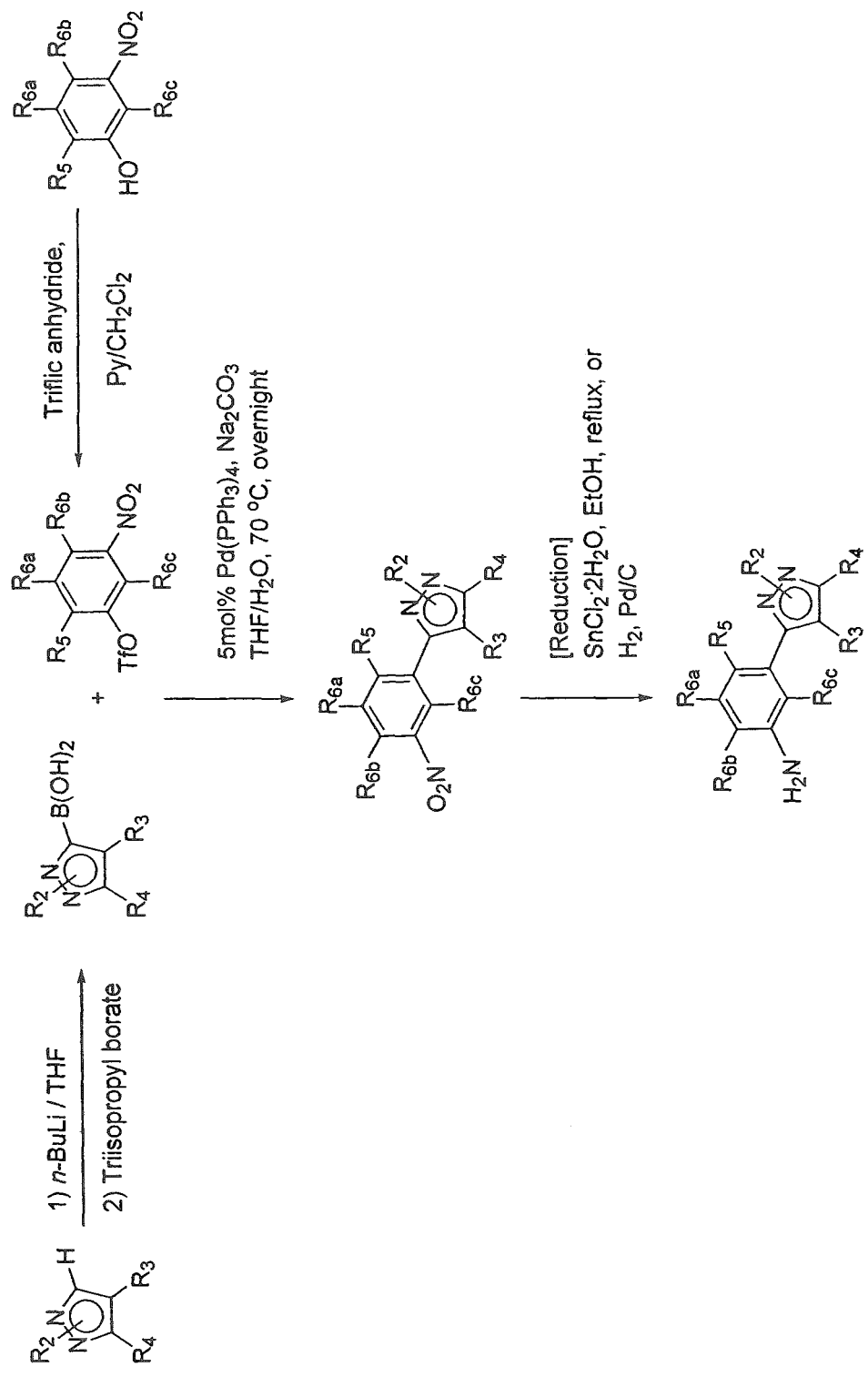
FIG. 29 shows the general synthetic scheme for the preparation of intermediate compounds of the present invention.
Figure 30:
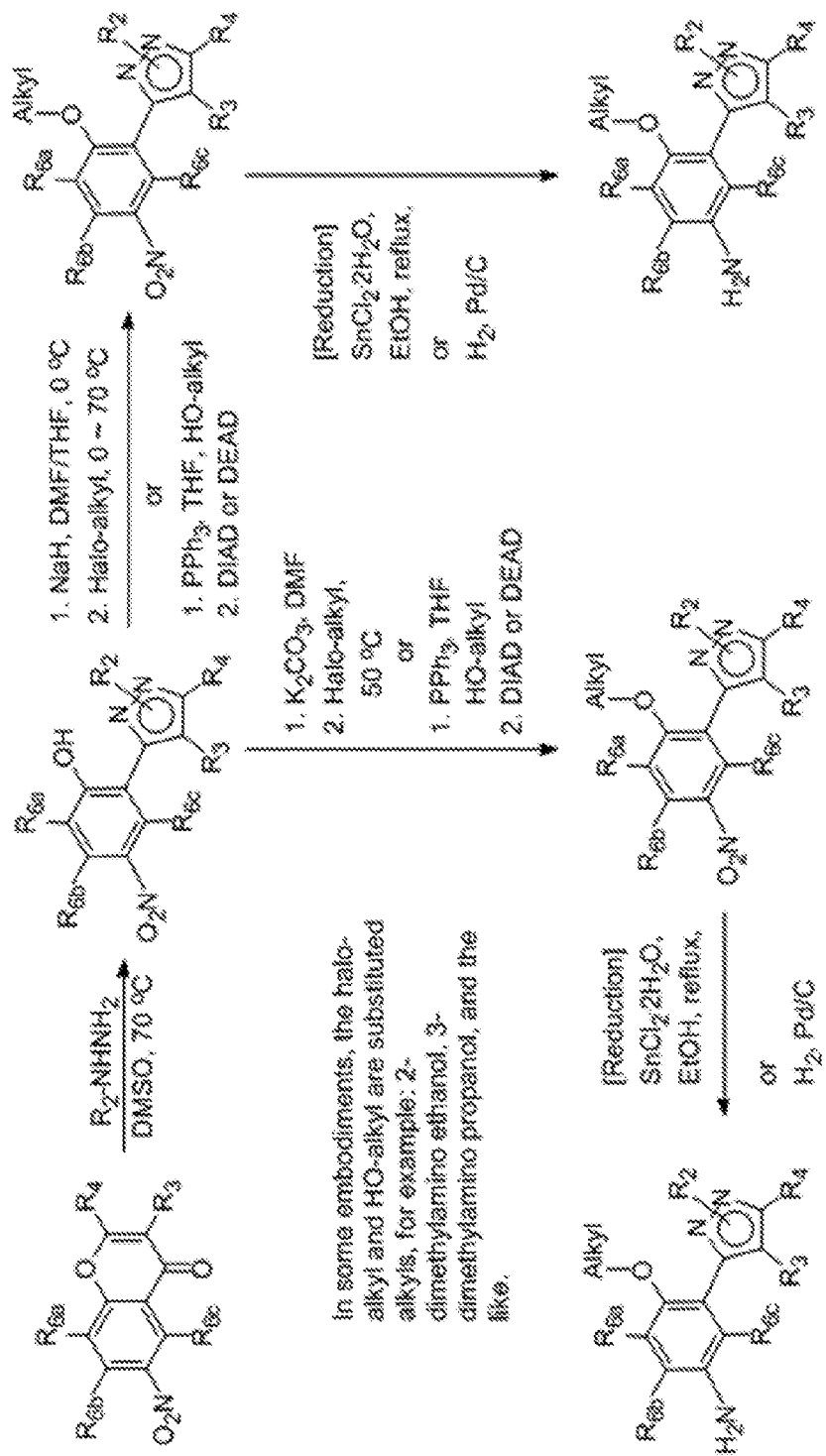
FIG. 30 shows the general synthetic scheme for the preparation of intermediate compounds of the present invention.
Figure 31:
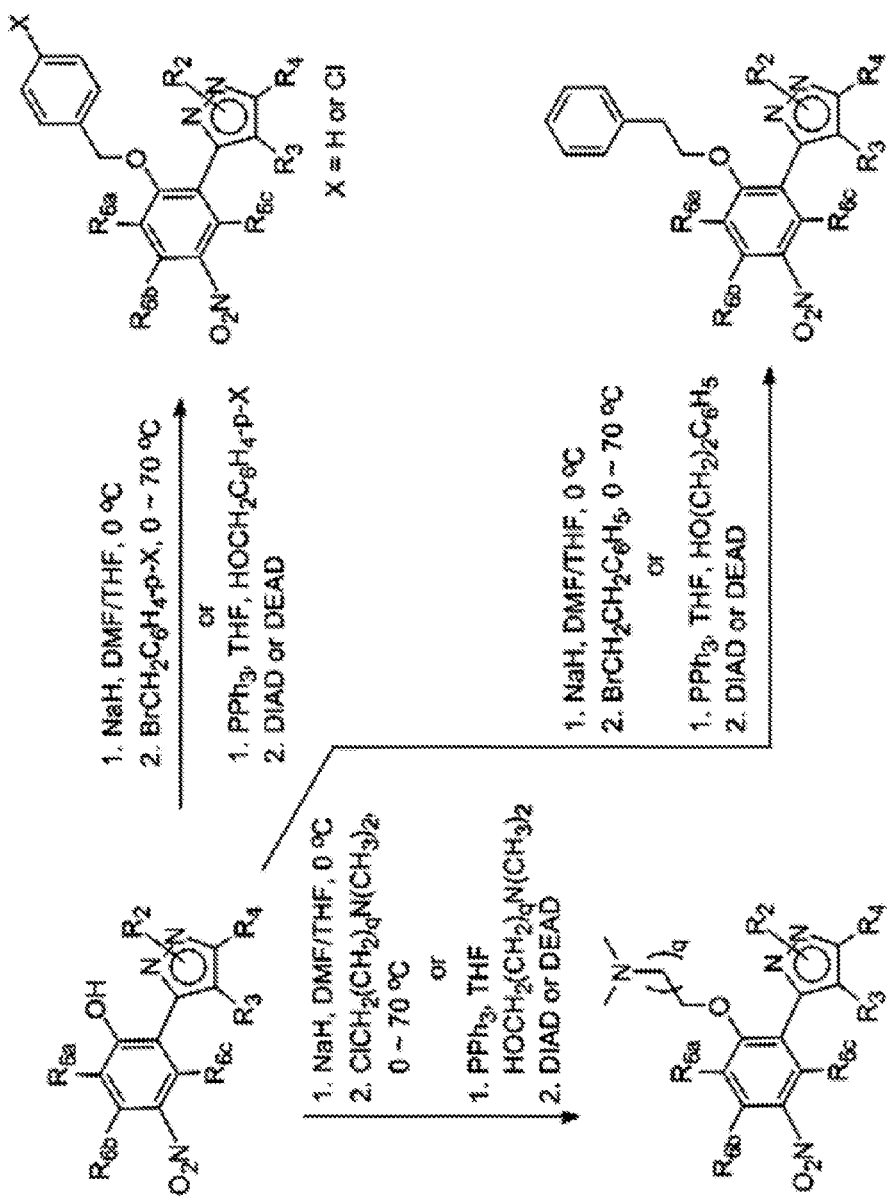
FIG. 31 shows the general synthetic scheme for the preparation of intermediate compounds useful in the preparation of compounds of the present invention.
Figure 32:
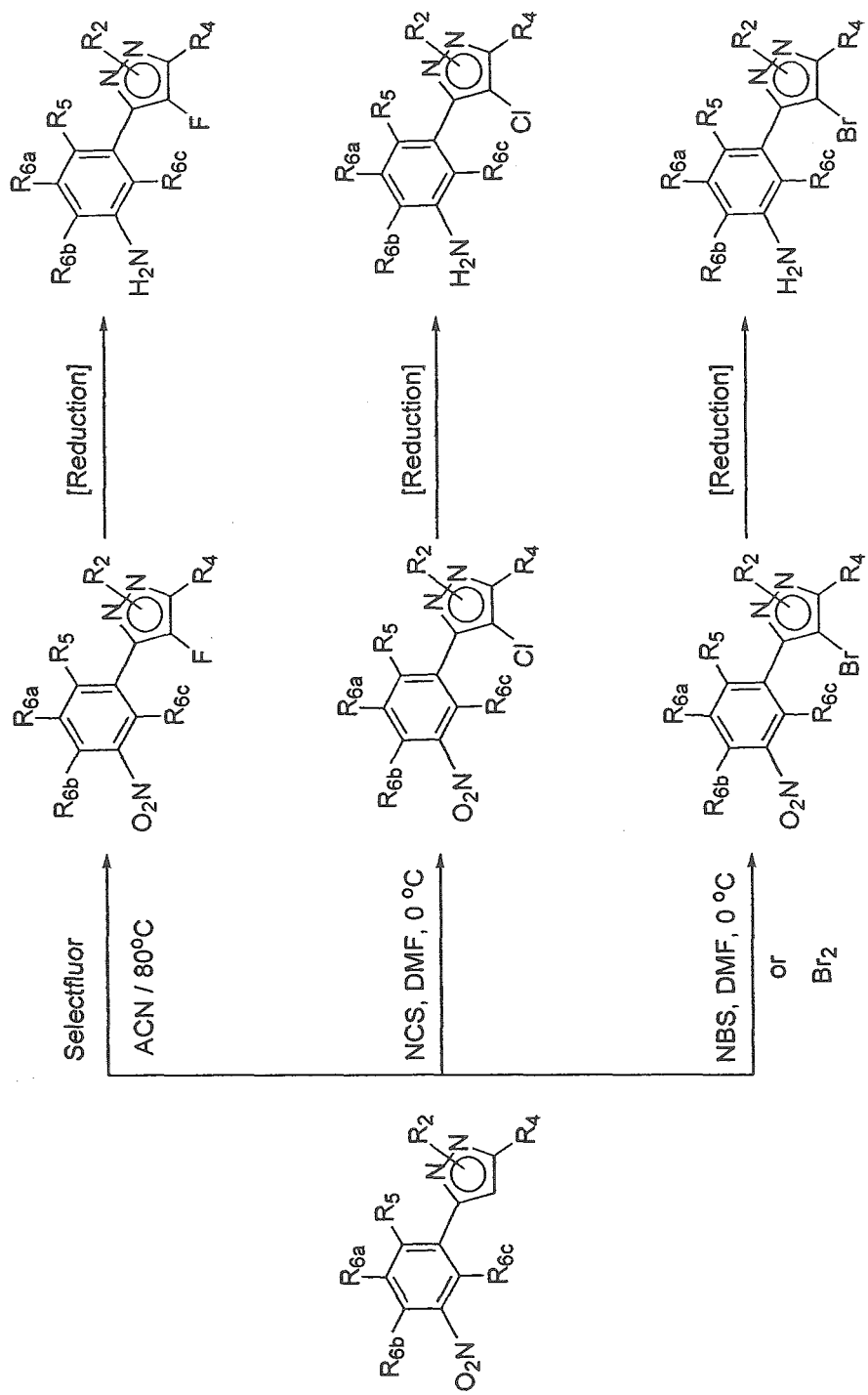
FIG. 32 shows the general synthetic scheme for the preparation of intermediate compounds useful in the preparation of compounds of the present invention.
Figure 33:
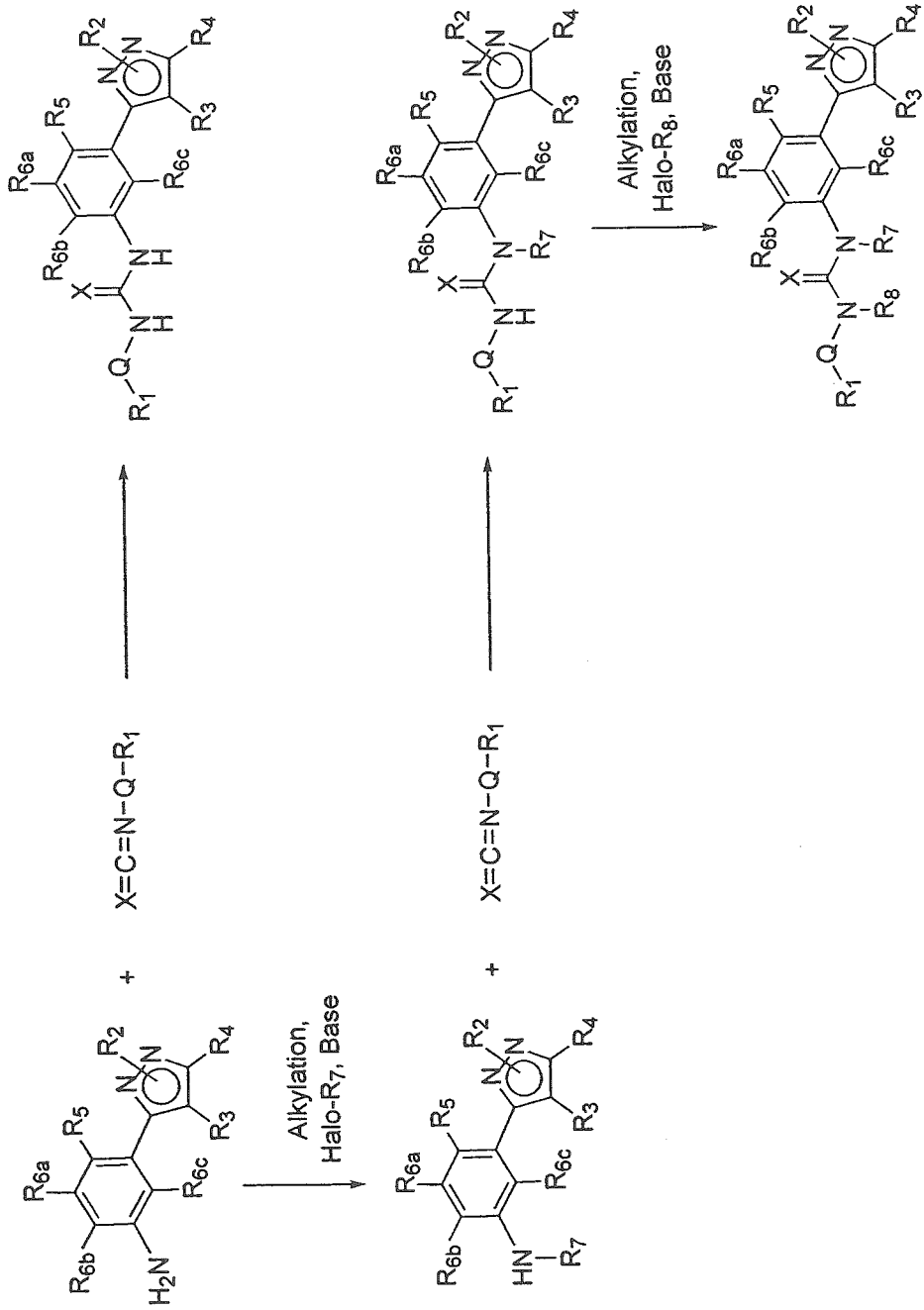
FIG. 33 shows the general synthetic scheme for the preparation of compounds of the present invention.
Figure 34:
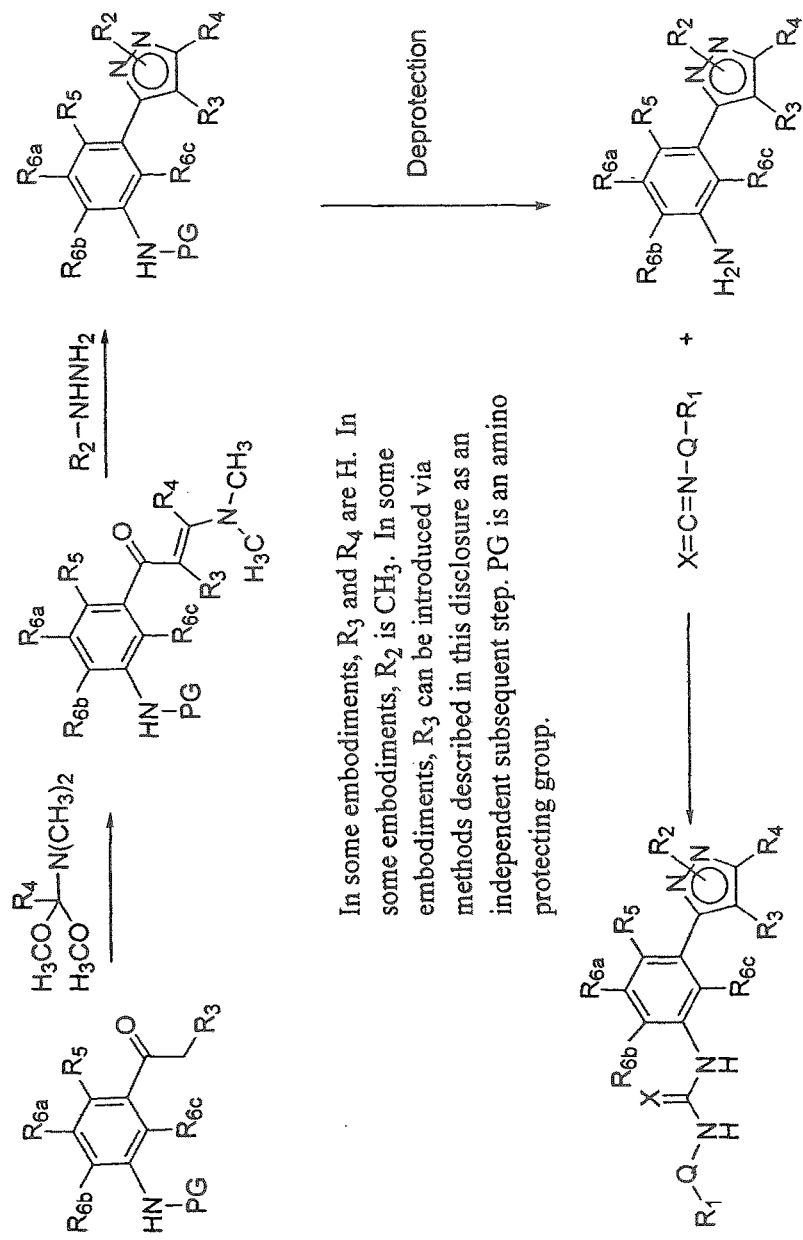
FIG. 34 shows an alternate general synthetic scheme for the preparation of compounds of the present invention.

As disclosed herein, compounds of the present invention also have the ability to increase delta power (see FIG. 28). As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep, and thus have a large build-up of Process S with limited ability to discharge this buildup during sleep. 5-HT2$_A$ inverse agonists tested preclinically and clinically mimic the effect of sleep deprivation on delta power, suggesting that subjects with sleep disorders treated with a 5-HT2$_A$ inverse agonist will be able to achieve deeper more refreshing sleep. These same effects have not been observed with currently marketed pharmacotherapies. In addition, currently marketed pharmacotherapies for sleep have side effects such as hangover effects or addiction that are associated with the GABA receptor. 5-HT2$_A$ inverse agonist do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the compounds of the invention can be useful for the treatment of the sleep disorders characterized by excessive daytime sleepiness such as narcolepsy. Inverse agonists at the serotonin 5HT$_{2A}$ receptor improve the quality of sleep at nighttime which can decrease excessive daytime sleepiness.

Accordingly, another aspect of the present invention relates to the therapeutic use of compounds of the present invention for the treatment of Sleep Disorders. Compounds of the present invention are potent inverse agonists at the serotonin $5HT_{2A}$ receptor and are effective in the treatment of Sleep Disorders by promoting one or more of the following: reducing the sleep onset latency period (measure of sleep induction), reducing the number of nighttime awakenings, and prolonging the amount of time in delta-wave sleep (measure of sleep quality enhancement and sleep consolidation) without effecting REM sleep. In addition, compounds of the present invention are effective either as a monotherapy or in combination with sleep inducing agents, for example but not limiting, antihistamines.

6. Diabetic-Related Pathologies:

Although hyperglycemia is the major cause for the pathogenesis of diabetic complications such as diabetic peripheral neuropathy (DPN), diabetic nephropathy (DN) and diabetic retinopathy (DR), increased plasma serotonin concentration in diabetic patients has also been implicated to play a role in disease progression (Pietraszek, M. H., et al. *Thrombosis Res.* 1992, 66(6), 765-74; and Andrzejewska-Buczko J, et al., *Klin Oczna*. 1996; 98(2), 101-4). Serotonin is believed to play a role in vasospasm and increased platelet aggregability. Improving microvascular blood flow is able to benefit diabetic complications.

A recent study by Cameron and Cotter in *Naunyn Schmiedebergs Arch Pharmacol*. 2003 June; 367(6):607-14, used a $5HT_{2A}$ antagonist experimental drug AT-1015, and other non-specific $5HT_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarogrelate was evaluated for the prevention of the development or progression of diabetic nephropathy (Takahashi, T., et al., *Diabetes Res Clin Pract.* 2002 November; 58(2):123-9). In the trial of 24 months of treatment, sarpogrelate significantly reduced urinary albumin excretion level.

7. Glaucoma

Topical ocular administration of 5-HT2 receptor antagonists result in a decrease in intra ocular pressure (IOP) in monkeys (Chang et al., J. Ocul Pharmacol 1:137-147 (1985)) and humans (Mastropasqua et al., Acta Ophthalmol Scand Suppl 224:24-25 (1997)) indicating utility for similar compounds such as $5\text{-}HT2_A$ inverse agonists in the treatment of ocular hypertensin associated with glaucoma. The 5-HT2 receptor antagonist ketanserin (Mastropasqua supra) and sarpogrelate (Takenaka et al., Investig Ophthalmol Vis Sci 36:S734 (1995)) have been shown to significantly lower IOP in glaucoma patients.

Representative Methods of the Invention:

One aspect of the present invention encompasses methods for modulating the activity of a $5HT_{2A}$ serotonin receptor by contacting the receptor with a compound according to any of the embodiments described herein or a pharmaceutical composition.

One aspect of the present invention encompasses methods for prophylaxis or treatment of platelet aggregation in an individual comprising administering to said individual in need thereof a therapeutically effective amount of a compound according to any of the embodiments described herein or a pharmaceutical composition.

One aspect of the present invention encompasses methods for prophylaxis or treatment of an indication selected from the group consisting of coronary artery disease, myocardial infarction, transient ischemic attack, angina, stroke, and atrial fibrillation in an individual comprising administering to said individual in need thereof a therapeutically effective amount of a compound according to any of the embodiments described herein or a pharmaceutical composition.

One aspect of the present invention encompasses methods for prophylaxis or treatment of reducing the risk of blood clot formation in an angioplasty or coronary bypass surgery individual comprising administering to said individual in need thereof a therapeutically effective amount of a compound according to any of the embodiments described herein or a pharmaceutical composition.

One aspect of the present invention encompasses methods for prophylaxis or treatment of reducing the risk of blood clot formation in an individual suffering from atrial fibrillation, comprising administering to said individual in need thereof a therapeutically effective amount of a compound according to any of the embodiments described herein or a pharmaceutical composition.

One aspect of the present invention encompasses methods for prophylaxis or treatment of asthma in an individual comprising administering to said individual in need thereof a therapeutically effective amount of a compound according to any of the embodiments described herein or a pharmaceutical composition.

One aspect of the present invention encompasses methods for prophylaxis or treatment of a symptom of asthma in an individual comprising administering to said individual in need thereof a therapeutically effective amount of a compound according to any of the embodiments described herein or a pharmaceutical composition.

One aspect of the present invention encompasses methods for prophylaxis or treatment of agitation or a symptom thereof in an individual comprising administering to said individual in need thereof a therapeutically effective amount of a compound according to any of the embodiments described herein or a pharmaceutical composition. In some embodiments, the individual is a cognitively intact elderly individual.

One aspect of the present invention encompasses methods for prophylaxis or treatment of agitation or a symptom thereof in an individual suffering from dementia comprising administering to said individual in need thereof a therapeutically effective amount of a compound according to any of the embodiments described herein or a pharmaceutical composition. In some embodiments, the dementia is due to a degenerative disease of the nervous system. In some embodiments, the dementia is Alzheimers disease, Lewy Body, Parkinson's disease or Huntington's disease. In some embodiments, the dementia is due to diseases that affect blood vessels. In some embodiments, the dementia is due to stroke or multi-infarct dementia.

One aspect of the present invention encompasses methods for prophylaxis or treatment of an individual suffering from at least one of the indications selected from the group consisting of behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of an individual with infantile autism, Huntington's chorea, or nausea and vomiting from chemotherapy or chemotherapeutic antibodies comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of schizophrenia in an individual comprising administering to said individual in need thereof a therapeutically effective amount of a dopamine D2 receptor antagonist and a compound according to any of the embodiments described herein or a pharmaceutical composition. In some embodiments, the dopamine D2 receptor antagonist is haloperidol.

One aspect of the present invention encompasses methods for prophylaxis or treatment of alleviating negative symptoms of schizophrenia induced by the administration of haloperidol to an individual suffering from said schizophrenia, comprising administering to said individual in need thereof a therapeutically effective amount of a compound according to any of the embodiments described herein or a pharmaceutical composition. In some embodiments, the haloperidol and the compound or pharmaceutical composition are administered in separate dosage forms. In some embodiments, the haloperidol and the compound or pharmaceutical composition are administered in a single dosage form.

One aspect of the present invention encompasses methods for prophylaxis or treatment of a sleep disorder in an individual comprising administering to said individual in need thereof a therapeutically effective amount of a compound according to any of the embodiments described herein or a pharmaceutical composition.

In some embodiments, the sleep disorder is a dyssomnia. In some embodiments, the dyssomnia is selected from the group consisting of psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome, and non-24-hour sleep-wake disorder.

In some embodiments, the sleep disorder is a parasomnia. In some embodiments, the parasomnia is selected from the group consisting of confusional arousals, sleepwalking and sleep terrors, rhythmic movement disorder, sleep starts, sleep talking and nocturnal leg cramps. In some embodiments, the sleep disorder is characterized by excessive daytime sleepiness such as narcolepsy.

In some embodiments, the sleep disorder is associated with a medical or psychiatric disorder. In some embodiments, the medical or psychiatric disorder is selected from the group consisting of psychoses, mood disorders, anxiety disorders, panic disorders, alcoholism, cerebral degenerative disorders, dementia, parkinsonism, fatal familial insomnia, sleep-related epilepsy, electrical status epilepticus of sleep, sleep-related headaches, sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical sleep disorder.

One aspect of the present invention encompasses methods for prophylaxis or treatment of a diabetic-related disorder in an individual comprising administering to said individual in need thereof a therapeutically effective amount of a compound according to any of the embodiments described herein or a pharmaceutical composition.

In some embodiments, the diabetic-related disorder is diabetic peripheral neuropathy.

In some embodiments, the diabetic-related disorder is diabetic nephropathy.

In some embodiments, the diabetic-related disorder is diabetic retinopathy.

One aspect of the present invention encompasses methods for prophylaxis or treatment of glaucoma or other diseases of the eye with abnormal intraocular pressure.

One aspect of the present invention encompasses processes for preparing a composition comprising admixing a compound according any embodiments described herein and pharmaceutically acceptable carrier.

One aspect of the present invention is the use of a compound for the production of a medicament for use in the prophylaxis or treatment of a $5HT_{2A}$ mediated disorder.

One embodiment of the present invention is the use of a compound for the production of a medicament for use in the prophylaxis or treatment of a $5HT_{2A}$ mediated disorder wherein the disorder is platelet aggregation.

One embodiment of the present invention is the use of a compound for the production of a medicament for use in the prophylaxis or treatment of a $5HT_{2A}$ mediated disorder wherein the disorder is selected from the group consisting of coronary artery disease, myocardial infarction, transient ischemic attack, angina, stroke, and atrial fibrillation.

One embodiment of the present invention is the use of a compound for the production of a medicament for use in the prophylaxis or treatment of a $5HT_{2A}$ mediated disorder wherein the disorder is a blood clot formation in an angioplasty or coronary bypass surgery individual.

One embodiment of the present invention is the use of a compound for the production of a medicament for use in the prophylaxis or treatment of a $5HT_{2A}$ mediated disorder wherein the disorder is a blood clot formation in an individual suffering from atrial fibrillation.

One embodiment of the present invention is the use of a compound for the production of a medicament for use in the prophylaxis or treatment of a $5HT_{2A}$ mediated disorder wherein the disorder is asthma.

One embodiment of the present invention is the use of a compound for the production of a medicament for use in the prophylaxis or treatment of a $5HT_{2A}$ mediated disorder wherein the disorder is a symptom of asthma.

One embodiment of the present invention is the use of a compound for the production of a medicament for use in the prophylaxis or treatment of a $5HT_{2A}$ mediated disorder wherein the disorder is agitation or a symptom thereof in an individual. In some embodiments the individual is a cognitively intact elderly individual.

One embodiment of the present invention is the use of a compound for the production of a medicament for use in the prophylaxis or treatment of a $5HT_{2A}$ mediated disorder wherein the disorder is agitation or a symptom thereof in an individual suffering from dementia. In some embodiments the dementia is due to a degenerative disease of the nervous system. In some embodiment the dementia is Alzheimers disease, Lewy Body, Parkinson's disease, or Huntington's disease. In some embodiments the dementia is due to diseases that affect blood vessels. In some embodiments the dementia is due to stroke or multi-infract dementia.

One embodiment of the present invention is the use of a compound for the production of a medicament for use in the prophylaxis or treatment of a $5HT_{2A}$ mediated disorder further comprising a dopamine D2 receptor antagonist wherein the disorder is selected from the group consisting of a behavioral disorder, drug induced psychosis, excitative psychosis, Gilles de la Tourette's syndrome, manic disorder, organic or NOS psychosis, psychotic disorder, psychosis, acute schizophrenia, chronic schizophrenia and NOS schizophrenia. In some embodiments the dopamine D2 receptor antagonist is haloperidol.

One embodiment of the present invention is the use of a compound for the production of a medicament for use in the prophylaxis or treatment of a $5HT_{2A}$ mediated disorder further comprising a dopamine D2 receptor antagonist wherein the disorder is infantile autism, Huntington's chorea, or nausea and vomiting from chemotherapy or chemotherapeutic antibodies. In some embodiments the dopamine D2 receptor antagonist is haloperidol.

One embodiment of the present invention is the use of a compound for the production of a medicament for use in the prophylaxis or treatment of a $5HT_{2A}$ mediated disorder further comprising a dopamine D2 receptor antagonist wherein the disorder is schizophrenia. In some embodiments the dopamine D2 receptor antagonist is haloperidol.

One embodiment of the present invention is the use of a compound for the production of a medicament for use in the prophylaxis or treatment of a $5HT_{2A}$ mediated disorder wherein the disorder is a negative symptom or symptoms of schizophrenia induced by the administration of haloperidol.

One embodiment of the present invention is the use of a compound for the production of a medicament for use in the prophylaxis or treatment of a $5HT_{2A}$ mediated disorder wherein the haloperidol and the compound or pharmaceutical composition are administered in separate dosage forms.

One embodiment of the present invention is the use of a compound for the production of a medicament for use in the prophylaxis or treatment of a $5HT_{2A}$ mediated disorder wherein the haloperidol and the compound or pharmaceutical composition are administered in a single dosage form.

One aspect of the present invention are compounds according to any of the embodiments described herein for use in a method of treatment of the human or animal body by therapy.

One aspect of the present invention are compounds according to any of the embodiments described herein for use in a method for the prophylaxis or treatment of a $5HT_{2A}$ mediated disorder, as described herein, in the human or animal body by therapy.

One aspect of the present invention are compounds according to any of the embodiments described herein for use in a method for the prophylaxis or treatment of a sleep disorder, as described herein, in the human or animal body by therapy.

One aspect of the present invention are compounds according to any of the embodiments described herein for use in a method for the prophylaxis or treatment of platelet aggregation in the human or animal body by therapy.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as $5\text{-HT}_{2A}$ receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary.

Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well-known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component.

The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2A}$ receptor modulators, for the treatment of a 5-$HT_{2A}$ mediated disease or disorder in domestic animals (e.g., cats and dogs) and in other domestic animals (e.g., such as cows, chickens, fish, etc.). Those of ordinary skill in the art are readily credited with understanding the utility of such compounds in such settings.

Other Utilities

Another object of the present invention relates to radio-labeled compounds of the present invention that would be useful not only in radio-imaging but also in assays, both in vitro and in vivo, for localizing and quantitating the 5-$HT_{2A}$ receptor in tissue samples, including human, and for identifying 5-$HT_{2A}$ receptor ligands by inhibition binding of a radio-labeled compound. It is a further object of this invention to develop novel 5-$HT_{2A}$ receptor assays of which comprise such radio-labeled compounds.

The present invention embraces isotopically-labeled compounds of the present invention. An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro 5-$HT_{2A}$ receptor labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (I) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3H$]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G, and co-workers in J. Org. Chem. 2002, 67, 943-948.

B. Ortho $^{125}$Iodination of phenols—This procedure allows for the incorporation of $^{125}$I at the ortho position of a phenol as reported by Collier, T. L. and co-workers in J. Labeled Compd Radiopharm. 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)4] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D, and co-workers in J. Labeled Compd Radiopharm. 2001, 44, S280-S282.

A radio-labeled 5-HT$_{2A}$ receptor compound of Formula (I) can be used in a screening assay to identify/evaluate compounds. In general terms, a newly synthesized or identified compound (i.e., test compound) can be evaluated for its ability to reduce binding of the "radio-labeled compound of Formula (I)" to the 5-HT$_{2A}$ receptor. Accordingly, the ability of a test compound to compete with the "radio-labeled compound of Formula (I)" for the binding to the 5-HT$_{2A}$ receptor directly correlates to its binding affinity.

The labeled compounds of the present invention bind to the 5-HT$_{2A}$ receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM, and in still yet another embodiment the labeled inhibitor has an IC$_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1

Syntheses of Compounds of the Present Invention

Illustrated syntheses for compounds of the present invention are shown in FIGS. 17 through 21 and FIGS. 29 through 34 where the symbols have the same definitions as used throughout this disclosure.

The compounds of the invention and their synthesis are further illustrated by the following examples. The following examples are provided to further define the invention without, however, limiting the invention to the particulars of these examples. The compounds described herein, supra and infra, are named according to the CS Chem Draw Ultra Version 7.0.1, AutoNom version 2.2. In certain instances common names are used and it is understood that these common names would be recognized by those skilled in the art.

Chemistry: Proton nuclear magnetic resonance ($^1$H NMR) spectra were recorded on a Varian Mercury Vx-400 equipped with a 4 nucleus auto switchable probe and z-gradient or a Bruker Avance-400equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, t=triplet, q=quartet, m=multiplet, br=broad. Microwave irradiations were carried out using the Emyrs Synthesizer (Personal Chemistry). Thin-layer chromatography (TLC) was performed on silica gel 60 F$_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545 ® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. 2) Mac: HPLC-pumps: LC-8A VP, Shimadzu Inc; HPLC system controller: SCL-10A VP, Shimadzu Inc.

UV-Detector: SPD-10A VP, Shimadzu Inc; Autosampler: 215 Liquid Handler, Gilson Inc; Mass spectrometer: API 150EX with Turbo Ion Spray source, AB/MDS Sciex Software: Masschrom 1.5.2.

Example 1.1:

Preparation of intermediate 3-(4-Bromo-2-methyl-2H-pyrazol-3-yl)-4-methoxy-phenylamine.

To a stirred solution of 4-bromo-5-(2-methoxy-5-nitrophenyl)-1-methyl-1H-pyrazole (1.799 g, 5.76 mmol) in EtOH (20 mL) was added SnCl$_2$.2H$_2$O (5.306 g, 23.05 mmol, 4.0 eq.), the mixture was stirred at reflux for 2 hrs and EtOH was removed under vacuum. The resulting solid was dissolved in EtOAc, 1N NaOH (30 mL) was added, and the mixture was stirred overnight. The white precipitate was filtered off through celite, and the aqueous phase was extracted with EtOAc (3×80 mL). The combined organic phase was dried over anhydrous MgSO$_4$, filtered and evaporated. The crude reaction mixture was purified by SiO$_2$ column chromatography (Eluent: EtOAc/Hexane=1/3 then 1/1) to give 3-(4-bromo-2-methyl-2H-pyrazol-3-yl)-4-methoxy-phenylamine (1.430 g, 5.07 mmol, 88%) as a white solid: LCMS m/z (%)=282 (M+H$^{79}$Br, 98), 284 (M+H$^{81}$Br, 100). $^1$H NMR (400 MHz, CDCl$_3$) δ: 7.52 (s, 1H), 6.86 (d, J=8.8 Hz, 1H), 6.80 (dd, J=2.8, 8.8 Hz, 1H), 6.22 (d, J=2.4 Hz, 1H), 4.25 (broad s, 2H), 3.72 (s, 3H), 3.71 (s, 3H).

The intermediate 4-bromo-5-(2-methoxy-5-nitro-phenyl)-1-methyl-1H-pyrazole was prepared in the following manner:

A. 2-Methyl-2H-pyrazole-3-boronic acid: N-methyl pyrazole (25 mL, 0.3 mol) was dissolved in 500 mL of THF. The solution was then cooled to −78° C in a dry ice/isopropanol bath.

Once the solution reached −78° C, n-BuLi (140 mL, 0.40 mol) was added dropwise by canula. The reaction mixture was stirred at −78° C for 1.5 hours. Then, triisopropyl borate (280 mL, 1.2 mol) was added to the above mixture via canula. While stirring overnight, the reaction temperature was gradually increased from −78° C to 0° C. The pH of the mixture was adjusted to 6 with 1N HCl. THF was removed under reduced pressure, and the aqueous residue was extracted with EtOAc (2×100 mL). The solid was then filtered to yield 108 g (100%) of 2-methyl-2H-pyrazole-3-boronic acid as a yellow solid. (Final product contains about 60% inorganic salt).

B. Trifluoro-methanesulfonic acid 2-methoxy-5-nitro-phenyl ester: To a stirred solution of 2-methoxy-5-nitrophenol (5.092 g, 30 mmol) in a mixture of CH$_2$Cl$_2$ (3 mL) and pyridine (20 mL) was added triflic anhydride (16.478 g, 9.8 mL, 2.0 eq.) dropwise at 0° C The mixture was warmed to room temperature and stirred for 2 hrs. Most of the pyridine was removed under vacuum. The residue was diluted with EtOAc, washed with 1N HCl and water, the aqueous phase was then extracted with EtOAc (3×100 mL). The combined organic phase was washed with brine, dried over anhydrous MgSO$_4$, filtered and evaporated. The crude reaction mixture was purified by SiO$_2$ column chromatography (Eluent: EtOAc/Hexane=1/3 then 1/2) to give the triflated compound trifluoro-methanesulfonic acid 2-methoxy-5-nitro-phenyl ester (8.943 g, 30 mmol, 100%) as a yellow solid: LCMS m/z (%)=302 (M+H, 100). $^1$H NMR (400 MHz, CDCl$_3$) δ: 8.30 (dd, J=4.0, 8.0 Hz, 1H), 8.16 (d, J=4.0 Hz, 1H), 7.15 (d, J=8.0 Hz, 1H), 4.06 (s, 3H).

C. 5-(2-Methoxy-5-nitro-phenyl)-1-methyl-1H-pyrazole: Trifluoro-methanesulfonic acid 2-methoxy-5-nitro-phenyl ester from Step B. (2.561 g, 8.50 mmol), 2-methyl-2H-pyrazole-3-boronic acid from Step A. (4.283 g, 34.01 mmol, 4.0 eq.) and Na$_2$CO$_3$ (10.816 g, 102.04 mmol, 12.0 eq.) were dissolved in a mixture of THF (200 mL) and H$_2$O (100 mL). The resulting mixture was degassed with N$_2$ for 5 mins, followed by the addition of Pd(PPh$_3$)$_4$ (0.486 g, 0.42 mmol, 0.05 eq.). After degassing for another 5 mins it was stirred under Ar at 70° C overnight. Once the reaction was complete, THF was removed under reduced pressure and the aqueous phase was extracted with EtOAc (4×100 mL). The combined organic phase was dried over anhydrous MgSO$_4$, filtered and evaporated. The crude reaction mixture was purified by SiO$_2$ column chromatography (Eluent: EtOAc/Hexane=1/1) to afford compound 5-(2-methoxy-5-nitro-phenyl)-1-methyl-1H-pyrazole (1.799 g, 7.71 mmol, 91%) as a white solid: LCMS m/z (%)=234 (M+H, 100). $^1$H NMR (400 MHz, CDCl$_3$) δ: 8.34 (dd, J=2.8, 9.2 Hz, 1H), 8.19 (d, J=2.8 Hz, 1H), 7.56 (d, J=2.0 Hz, 1H), 7.08 (d, J=9.2 Hz, 1H), 6.31 (d, J=1.6 Hz, 1H), 3.96 (s, 3H), 3.74 (s, 3H).

D. 4-Bromo-5-(2-methoxy-5-nitro-phenyl)-1-methyl-1H-pyrazole: To a stirred solution of 5-(2-methoxy-5-nitro-phenyl)-1-methyl-1H-pyrazole (1.787 g, 7.66 mmol) in DMF (20 mL) was added NBS (1.515 g, 8.43 mmol, 1.1 eq.) in DMF (5 mL) dropwise at 0° C. After stirring at 0° C for 3 hrs, TLC showed completion of the reaction. The mixture was diluted with EtOAc (300 mL), washed with water (3×10 mL) and brine. The EtOAc phase was dried over anhydrous MgSO$_4$, filtered and evaporated. The crude reaction mixture was purified by SiO$_2$ column chromatography (Eluent: EtOAc/Hexane=1/3 then 1/1) to give the product 4-bromo-5-(2-methoxy-5-nitro-phenyl)-1-methyl-1H-pyrazole (2.214 g, 7.09 mmol, 93%) as light yellow solid: LCMS m/z (%)=312 (M+H$^{79}$Br, 100), 314 (M+H$^{81}$Br, 100). $^1$H NMR (400 MHz, CDCl$_3$) δ: 8.40 (dd, J=2.4, 6.9 Hz, 1H), 8.22 (m, 1H), 7.57 (s, 1H), 7.14 (d, J=9.2 Hz, 1H), 3.98 (s, 3H), 3.74 (s, 3H).

Example 1.2:

Preparation of 1-[3-(4-Bromo-2-methyl-2H-pyrazol-3-yl)-4-methoxy-phenyl]-3-(4-chloro-2-trifluoromethyl-phenyl)-urea (Compound 9).

Urea Synthesis (General Procedure): To a stirred solution of 3-(4-bromo-2-methyl-2H-pyrazol-3-yl)-4-methoxy-phenylamine (0.034 g, 0.12 mol, Example 1.1) in CH$_2$Cl$_2$ (1 mL) was added 4-chloro-2-(trifluoromethyl)phenyl isocyanate (0.029 g, 20.0 µL, 0.13 mmol, 1.05 equiv.) at room temperature. White solid precipitated and was filtered and washed with cold CH$_2$Cl$_2$ to afford Compound 9 (0.037 g, 0.074 mmol, 60%) as a white solid. LCMS m/z (%)=503 (M+H$^{79}$Br, 77), 439 (M+H$^{81}$Br, 100). $^1$H NMR (400 MHz, acetone-d$_6$) δ: 8.82 (s, 1H), 8.22 (d, J=9.6 Hz, 1H), 7.62-7.72 (m, 4H), 7.49 (s, 1H), 7.43 (d, J=2.6 Hz, 1H), 7.15 (d, J=9.0 Hz, 1H), 3.83 (s, 3H), 3.68 (s, 3H).

Example 1.3:

Preparation of 1-[3-(4-Bromo-2-methyl-2H-pyrazol-3-yl)-4-methoxy-phenyl]-3-(4-fluoro-phenyl)-urea (Compound 2).

3-(4-Bromo-2-methyl-2H-pyrazol-3-yl)-4-methoxy-phenylamine (2.965 g, 10.5 mmol) was treated with 4-fluoro-phenyl isocyanate (1.601 g, 1.31 mL, 11.6 mmol, 1.1 equiv.) in CH$_2$Cl$_2$ (20 mL), in a similar manner as described in Example 1.2 to afford Compound 2 (3.755 g, 8.94 mmol, 85%) as a white solid. LCMS m/z (%)=419 (M+H$^{79}$Br, 99), 421 (M+H$^{81}$Br, 100). $^1$H NMR (400 MHz, acetone-d$_6$) δ: 8.49 (broad s, 2H), 7.77 (d, J=9.0 Hz, 1H), 7.50-7.58 (m, 2H), 7.50 (s, 1H), 7.43 (s, 1H), 7.12 (d, J=8.9 Hz, 1H), 6.98-7.06 (m, 2H), 3.81 (s, 3H), 3.68 (s, 3H).

Example 1.4:

Preparation of 1-[3-(4-Bromo-2-methyl-2H-pyrazol-3-yl)-4-methoxy-phenyl]-3-(2,4-dichloro-phenyl)-urea (Compound 3).

3-(4-Bromo-2-methyl-2H-pyrazol-3-yl)-4-methoxy-phenylamine (0.031 g, 0.11 mmol) was treated with 2,4-dichlorophenyl isocyanate (0.021 g, 0.11 mmol, 1.0 equiv.) in CH$_2$Cl$_2$ (2 mL), in a similar manner as described in Example 1.2 to afford Compound 3 (0.036 g, 0.076 mmol, 69%) as a white solid. LCMS m/z (%)=469 (M+H$^{79}$Br$^{35}$Cl$^{35}$Cl, 60), 471 (M+H$^{79}$Br$^{35}$Cl$^{37}$Cl&$^{81}$Br$^{35}$Cl$^{35}$Cl, 100), 473

(M+H⁸¹Br³⁵Cl³⁷Cl⁷⁹Br³⁷Cl³⁷Cl, 54), 475 (M+H⁸¹Br³⁷Cl³⁷Cl, 4). ¹H NMR (400 MHz, acetone-d₆) δ: 8.81 (s, 1H), 8.36 (d, J=9.0 Hz, 1H), 7.91 (s, 1H), 7.69 (dd, J=2.7, 9.0 Hz, 1H), 7.50 (s, 1H), 7.48 (d, J=2.4 Hz, 1H), 7.45 (d, J=2.7 Hz, 1H), 7.34 (dd, J=2.4, 9.0 Hz, 1H), 7.15 (d, J=9.0 Hz, 1H), 3.83 (s, 3H), 3.69 (s, 3H).

Example 1.5:

Preparation of 1-[3-(4-Bromo-2-methyl-2H-pyrazol-3-yl)-4-methoxy-phenyl]-3-(4-methoxy-phenyl)-urea (Compound 4).

3-(4-Bromo-2-methyl-2H-pyrazol-3-yl)-4-methoxy-phenylamine (0.031 g, 0.11 mmol) was treated with 4-methoxyphenyl isocyanate (0.016 g, 14.2 μL, 0.11 mmol, 1.0 equiv.) in CH₂Cl₂ (2 mL), in a similar manner as described in Example 1.2 to afford Compound 4 (0.037 g, 0.086 mmol, 78%) as a white solid. LCMS m/z (%)=431 (M+H⁷⁹Br, 89), 433 (M+H⁸¹Br, 100). ¹H NMR (400 MHz, acetone-d₆) δ: 8.02 (s, 1H), 7.89 (s, 1H), 7.67 (dd, J=2.7, 9.0 Hz, 1H), 7.49 (s, 1H), 7.43 (s, 1H), 7.42 (d, J=9.0 Hz, 2H), 7.12 (d, J=9.0 Hz, 1H), 6.85 (d, J=9.0 Hz, 2H), 3.81 (s, 3H), 3.75 (s, 3H), 3.68 (s, 3H).

Example 1.6:

Preparation of 1-[3-(4-Bromo-2-methyl-2H-pyrazol-3-yl)-4-methoxy-phenyl]-3-(4-bromo-phenyl)-urea (Compound 5).

3-(4-Bromo-2-methyl-2H-pyrazol-3-yl)-4-methoxy-phenylamine (0.032 g, 0.11 mmol) was treated with 4-bromophenyl isocyanate (0.022 g, 0.11 mmol, 1.0 equiv.) in CH₂Cl₂ (2 mL), in a similar manner as described in Example 1.2 to afford Compound 5 (0.040 g, 0.08 mmol, 75%) as a white solid. LCMS m/z (%)=479 (M+H⁷⁹Br⁷⁹Br, 51), 481 (M+H⁷⁹Br⁸¹Br, 100), 483 (M+H⁸¹Br⁸¹Br, 50). ¹H NMR (400 MHz, acetone-d₆) δ: 8.22 (s, 1H), 8.14 (s, 1H), 7.68 (dd, J=2.7, 9.0 Hz, 1H), 7.48-7.54 (m, 3H), 7.39-7.46 (m, 3H), 7.14 (d, J=9.0 Hz, 1H), 3.82 (s, 3H), 3.68 (s, 3H).

Example 1.7:

Preparation of 1-[3-(4-Bromo-2-methyl-2H-pyrazol-3-yl)-4-methoxy-phenyl]-3-(4Chloro-3-trifluoromethyl-phenyl)-urea (Compound 6).

3-(4-Bromo-2-methyl-2H-pyrazol-3-yl)-4-methoxy-phenylamine (0.035 g, 0.12 mmol) was treated with 4-chloro-3-(trifluoromethyl)phenyl isocyanate (0.027 g, 0.12 mmol, 1.0 equiv.) in CH₂Cl₂ (2 mL), in a similar manner as described in Example 1.2 to afford Compound 6 (0.051 g, 0.10 mmol, 81%) as a white solid. LCMS m/z (%)=503 (M+H⁷⁹Br³⁵Cl, 78), 505 (M+H⁸¹Br³⁵Cl, 100), 507 (M+H⁸¹Br³⁷Cl, 28). ¹H NMR (400 MHz, acetone-d₆) δ: 8.52 (s, 1H), 8.27 (s, 1H), 8.13 (s, 1H), 7.74 (d, J=8.7 Hz, 1H), 7.68 (d, J=9.0 Hz, 1H), 7.53 (d, J=8.7 Hz, 1H), 7.49 (s, 1H), 7.43 (s, 1H), 7.14 (d, J=9.0 Hz, 1H), 3.82 (s, 3H), 3.68 (s, 3H).

Example 1.8:

Preparation of 1-[3-(4-Bromo-2-methyl-2H-pyrazol-3-yl)-4-methoxy-phenyl]-3-(3,5-difluoro-phenyl)-urea (Compound 7).

3-(4-Bromo-2-methyl-2H-pyrazol-3-yl)-4-methoxy-phenylamine (0.032 g, 0.11 mmol) was treated with 3,5-difluorophenyl isocyanate (0.018 g, 14 μL, 0.11 mmol, 1.0 equiv.) in CH₂Cl₂ (2 mL), in a similar manner as described in Example 1.2 to afford Compound 7 (0.038 g, 0.09 mmol, 77%) as a white solid. LCMS m/z (%)=437 (M+H⁷⁹Br, 100), 439 (M+H⁸¹Br, 100). ¹H NMR (400 MHz, acetone-d₆) δ: 8.47 (s, 1H), 8.23 (s, 1H), 7.68 (dd, J=2.7, 9.0 Hz, 1H), 7.50 (s, 1H), 7.42 (d, J=2.7 Hz, 1H), 7.18-7.27 (m, 2H), 7.15 (d, J=9.0 Hz, 1H), 6.59 (ttt, J=2.3, 9.1, 9.1 Hz, 1H), 3.82 (s, 3H), 3.68 (s, 3H).

Example 1.9:

Preparation of 1-[3-(4-Bromo-2-methyl-2H-pyrazol-3-yl)-4-methoxy-phenyl]-3-(2,4-difluoro-phenyl)-urea (Compound 8).

3-(4-Bromo-2-methyl-2H-pyrazol-3-yl)-4-methoxy-phenylamine (0.027 g, 0.095 mmol) was treated with 2,4-difluorophenyl isocyanate (0.015 g, 11.5 μL, 0.095 mmol, 1.0 equiv.) in CH₂Cl₂ (2 mL), in a similar manner as described in Example 1.2 to afford Compound 8 (0.030 g, 0.069 mmol, 71%) as a white solid. LCMS m/z (%)=437 (M+H⁷⁹Br, 100), 439 (M+H⁸¹Br, 91). ¹H NMR (400 MHz, acetone-d₆) δ: 8.45 (s, 1H), 8.23 (dt, J=6.1, 9.2 Hz, 1H), 7.93 (s, 1H), 7.68 (dd, J=2.6, 9.0 Hz, 1H), 7.49 (s, 1H), 7.44 (d, J=2.6 Hz, 1H), 7.14 (d, J=9.0 Hz, 1H), 7.07 (ddd, J=2.7, 8.7, 11.3 Hz, 1H), 6.93-7.02 (m, 1H), 3.82 (s, 3H), 3.69 (s, 3H).

Example 1.10:

Preparation of 1-[3-(4-Bromo-2-methyl-2H-pyrazol-3-yl)-4-methoxy-phenyl]-3-(3Chloro-phenyl)-urea (Compound 20).

To a stirred solution of 3-(4-Bromo-2-methyl-2H-pyrazol-3-yl)-4-methoxy-phenylamine (0.015 g, 0.051 mmol) in CH₂Cl₂ (1 mL) was added 3-chlorophenyl isocyanate (0.008 g, 7 μL, 0.054 mol, 1.05 equiv.). After the TLC showed the consumption of the starting material, it was isolated by preparative thin layer chromatography (TLC) (Eluent: EtOAc/Hexane=1/1) and Compound 20 (0.020 g, 0.047 mmol, 92%) was obtained as a solid film. LCMS m/z (%)=435 (M+H⁷⁹Br, 68), 437 (M+H⁸¹Br, 100). ¹H NMR (400 MHz, acetone-d₆) δ: 8.29 (s, 1H), 8.19 (s, 1H), 7.80 (t, J=1.9 Hz, 1H), 7.29 (dd, J=2.7, 9.0 Hz, 1H), 7.49 (s, 1H), 7.43 (d, J=2.7 Hz, 1H), 7.34 (d, J=8.4 Hz, 1H), 7.26 (t, J=8.0 Hz, 1H), 7.14 (d, J=9.0 Hz, 1H), 7.00 (d, J=7.8 Hz, 1H), 3.82 (s, 3H), 3.68 (s, 3H).

Example 1.11:

Preparation of 1-[3-(4-Bromo-2-methyl-2H-pyrazol-3-yl)-4-methoxy-phenyl]-3-(3-cyano-phenyl)-urea (Compound 21).

3-(4-Bromo-2-methyl-2H-pyrazol-3-yl)-4-methoxy-phenylamine (0.037 g, 0.13 mmol) was treated with 3-cyanophenyl isocyanate (0.020 g, 0.14 mol, 1.05 equiv.) in CH₂Cl₂ (1 mL), in a similar manner as described in Example 1.10 to afford Compound 21 (0.032 g, 0.08 mmol, 58%) as a white powder. LCMS m/z (%)=426 (M+H⁷⁹Br, 99), 428 (M+H⁸¹Br, 100). ¹H NMR (400 MHz, acetone-d₆) δ: 8.45 (s, 1H), 8.26 (d, J=9.6 Hz, 1H), 8.05 (t, J=1.7 Hz, 1H), 7.74 (dd, J=1.5, 8.2 Hz, 1H), 7.70 (dd, J=2.7, 9.0 Hz, 1H), 7.50 (s, 1H), 7.48 (t, J=8.1 Hz, 1H), 7.43 (d, J=2.7 Hz, 1H), 7.36 (d, J=7.6 Hz, 1H), 7.15 (d, J=9.0 Hz, 1H), 3.83 (s, 3H), 3.69 (s, 3H).

Example 1.12:

Preparation of 1-[3-(4-Bromo-2-methyl-2H-pyrazol-3-yl)-4-methoxy-phenyl]-3-(3,4-difluoro-phenyl)-urea (Compound 10).

3-(4-Bromo-2-methyl-2H-pyrazol-3-yl)-4-methoxy-phenylamine (0.035 g, 0.12 mmol) was treated with 3,4-difluorophenyl isocyanate (0.021 g, 16.0 µL, 0.13 mmol, 1.05 equiv.) in $CH_2Cl_2$ (1 mL), in a similar manner as described in Example 1.2 to afford Compound 10 (0.021 g, 0.047 mmol, 38%) as a white solid. LCMS m/z (%)=437 ($M+H^{79}Br$, 100), 439 ($M+H^{81}Br$, 99). $^1H$ NMR (400 MHz, acetone-$d_6$) δ: 8.29 (s, 1H), 8.16 (s, 1H), 7.74 (dddd, J=2.5, 7.4, 13.4 Hz, 1H), 7.68 (dd, J=2.7, 9.0 Hz, 1H), 7.49 (s, 1H), 7.42 (d, J=2.7 Hz, 1H), 7.11-7.26 (m, 2H), 7.13 (d, J=9.0 Hz, 1H), 3.82 (s, 3H), 3.69 (s, 3H).

Example 1.13:

Preparation of 1-Biphenyl-2-yl-3-[3-(4-bromo-2-methyl-2H-pyrazol-3-yl)-4-methoxy-phenyl]-urea (Compound 22).

3-(4-Bromo-2-methyl-2H-pyrazol-3-yl)-4-methoxy-phenylamine (0.036 g, 0.13 mmol) was treated with 2-biphenylyl isocyanate (0.027 g, 24.0 µL, 0.14 mmol, 1.05 equiv.) in $CH_2Cl_2$ (1 mL), in a similar manner as described in Example 1.10 to afford Compound 22 (0.031 g, 0.06 mmol, 51%) as a white powder. LCMS m/z (%)=477 ($M+H^{79}Br$, 100), 479 ($M+H^{81}Br$, 100). $^1H$ NMR (400 MHz, acetone-$d_6$) δ: 8.41 (s, 1H), 8.17 (d, J=8.3 Hz, 1H), 7.60 (d, J=2.7, 9.0 Hz, 1H), 7.43-7.51 (m, 3H), 7.37-7.43 (m, 3H), 7.29-7.37 (m, 2H), 7.24 (s, 1H), 7.20 (dd, J=1.6, 7.6 Hz, 1H), 7.11 (dd, J=1.0, 7.4 Hz, 1H), 7.08 (d, J=9.0 Hz, 1H), 3.80 (s, 3H), 3.66 (s, 3H).

Example 1.14:

Preparation of 1-[3-(4-Bromo-2-methyl-2H-pyrazol-3-yl)-4-methoxy-phenyl]-3-(3-trifluoromethyl-phenyl)-urea (Compound 11)

3-(4-Bromo-2-methyl-2H-pyrazol-3-yl)-4-methoxy-phenylamine (0.035 g, 0.12 mmol) was treated with α,α,α-trifluoro-m-tolyl isocyanate (0.025 g, 18.0 µL, 0.13 mmol, 1.05 equiv.) in $CH_2Cl_2$ (1 mL), in a similar manner as described in Example 1.2 to afford Compound 11 (0.038 g, 0.080 mmol, 65%) as a white solid. LCMS m/z (%)=469 ($M+H^{79}Br$, 91), 471 ($M+H^{81}Br$, 100). $^1H$ NMR (400 MHz, acetone-$d_6$) δ: 8.42 (s, 1H), 8.23 (s, 1H), 8.07 (s, 1H), 7.64-7.73 (m, 2H), 7.45-7.53 (m, 2H), 7.44 (s, 1H), 7.30 (d, J=7.6 Hz, 1H), 7.15 (d, J=8.9 Hz, 1H), 3.82 (s, 3H), 3.69 (s, 3H).

Example 1.15:

Preparation of 1-[3-(4-Bromo-2-methyl-2H-pyrazol-3-yl)-4-methoxy-phenyl]-3-(4-trifluoromethyl-phenyl)-urea (Compound 12).

3-(4-Bromo-2-methyl-2H-pyrazol-3-yl)-4-methoxy-phenylamine (0.035 g, 0.12 mmol) was treated with α,α,α-trifluoro-p-tolyl isocyanate (0.024 g, 19.0 µL, 0.13 mmol, 1.05 equiv.) in $CH_2Cl_2$ (1 mL), in a similar manner as described in Example 1.2 to afford Compound 12 (0.048 g, 0.102 mmol, 83%) as a white solid. LCMS m/z (%)=469 ($M+H^{79}Br$, 92), 471 ($M+H^{81}Br$, 100). $^1H$ NMR (400 MHz, acetone-$d_6$) δ: 8.51 (s, 1H), 8.27 (s, 1H), 7.76 (d, J=8.3 Hz, 2H), 7.71 (dd, J=2.3, 9.0 Hz, 1H), 7.62 (d, J=8.4 Hz, 2H), 7.52 (s, 1H), 7.46 (d, J=2.3 Hz, 1H), 7.16 (d, J=8.9 Hz, 1H), 3.84 (s, 3H), 3.70 (s, 3H).

Example 1.16:

Preparation of 1-[3-(4-Bromo-2-methyl-2H-pyrazol-3-yl)-4-methoxy-phenyl]-3-(4-Chloro-phenyl)-urea (Compound 1).

3-(4-Bromo-2-methyl-2H-pyrazol-3-yl)-4-methoxy-phenylamine (0.260 g, 0.92 mmol) was treated with 4-chlorophenyl isocyanate (0.144 g, 0.92 mmol, 1.0 equiv.) in $CH_2Cl_2$ (5 mL), in a similar manner as described in Example 1.2 to afford Compound 1 (0.340 g, 0.78 mmol, 84%) as a white solid. LCMS m/z (%)=435 ($M+H^{79}Br^{35}Cl$, 77), 437 ($M+H^{81}Br^{35}Cl$, 100), 439 ($M+H^{81}Br^{37}Cl$, 25). $^1H$ NMR (400 MHz, $CDCl_3$) δ: 7.56 (s, 1H), 7.44 (dd, J=2.7, 8.9 Hz, 1H), 7.34 (d, J=9.0 Hz, 1H), 7.29 (d, J=9.0 Hz, 1H), 7.19 (d, J=2.7 Hz, 1H), 6.59 (s, 1H), 6.47 (s, 1H), 3.84 (s, 3H), 3.74 (s, 3H).

Example 1.17:

Preparation of 1-(3,5-Bis-trifluoromethyl-phenyl)-3-[3-(4-bromo-2-methyl-2H-pyrazol-3-yl)-4-methoxy-phenyl]-urea (Compound 13).

3-(4-Bromo-2-methyl-2H-pyrazol-3-yl)-4-methoxy-phenylamine (0.037 g, 0.13 mmol) was treated with 3,5-bis(trifluoromethyl)phenyl isocyanate (0.036 g, 24.0 µL, 0.14 mmol, 1.05 equiv.) in $CH_2Cl_2$ (1 mL), in a similar manner as described in Example 1.2 to afford Compound 13 (0.030 g, 0.06 mmol, 43%) as a white solid. LCMS m/z (%)=537 ($M+H^{79}Br$, 99), 539 ($M+H^{81}Br$, 100). $^1H$ NMR (400 MHz, acetone-$d_6$) δ: 8.77 (s, 1H), 8.42 (s, 1H), 8.22 (s, 2H), 7.73 (dd, J=2.5, 9.0 Hz, 1H), 7.51 (s, 1H), 7.46 (d, J=2.5 Hz, 1H), 7.18 (d, J=9.0 Hz, 1H), 3.85 (s, 3H), 3.71 (s, 3H).

Example 1.18:

Preparation of 1-[3-(4-Bromo-2-methyl-2H-pyrazol-3-yl)-4-methoxy-phenyl]-3-(4-isopropyl-phenyl)-urea (Compound 23).

3-(4-Bromo-2-methyl-2H-pyrazol-3-yl)-4-methoxy-phenylamine (0.035 g, 0.12 mmol) was treated with 4-isopropylphenyl isocyanate (0.022 g, 21.0 µL, 0.13 mmol, 1.05 equiv.) in $CH_2Cl_2$ (1 mL), in a similar manner as described in Example 1.10 to afford Compound 23 (0.028 g, 0.06 mmol, 50%) as a solid film. LCMS m/z (%)=443 ($M+H^{79}Br$, 100), 445 ($M+H^{81}Br$, 99). $^1H$ NMR (400 MHz, acetone-$d_6$) δ: 8.08 (s, 1H), 8.00 (s, 1H), 7.68 (dd, J=2.6, 8.9 Hz, 1H), 7.49 (s, 1H), 7.40-7.46 (m, 3H), 7.09-7.17 (m, 3H), 3.81 (s, 3H), 3.68 (s, 3H), 2.78-2.92 (m, 1H), 1.21 (s, 3H), 1.20 (s, 3H).

Example 1.19:

Preparation of 1-[3-(4-Bromo-2-methyl-2H-pyrazol-3-yl)-4-methoxy-phenyl]-3-naphthalen-2-yl-urea (Compound 14).

3-(4-Bromo-2-methyl-2H-pyrazol-3-yl)-4-methoxy-phenylamine (0.035 g, 0.12 mmol) was treated with 2-naphthyl isocyanate (0.023 g, 0.13 mmol, 1.05 equiv.) in CH$_2$Cl$_2$ (1 mL), in a similar manner as described in Example 1.2 to afford Compound 14 (0.040 g, 0.09 mmol, 70%) as a white solid. LCMS m/z (%)=451 (M+H$^{79}$Br, 95), 453 (M+H$^{81}$Br, 100). $^1$H NMR (400 MHz, acetone-d$_6$) δ: 8.30 (s, 1H), 8.20 (s, 1H), 8.19 (d, J=1.8 Hz, 1H), 7.56-7.84 (m, 3H), 7.72 (dd, J=2.7, 9.0 Hz, 1H), 7.56 (dd, J=2.1, 8.8 Hz, 1H), 7.50 (s, 1H), 7.48 (d, J=2.7 Hz, 1H), 7.44 (t, J=8.0 Hz, 1H), 7.14 (t, J=8.0 Hz, 1H), 3.83 (s, 3H), 3.70 (s, 3H).

Example 1.20:

Preparation of 1-[3-(4-Bromo-2-methyl-2H-pyrazol-3-yl)-4-methoxy-phenyl]-3-naphthalen-1-yl-urea (Compound 24).

3-(4-Bromo-2-methyl-2H-pyrazol-3-yl)-4-methoxy-phenylamine (0.036 g, 0.13 mmol) was treated with 1-naphthyl isocyanate (0.023 g, 0.14 mmol, 1.05 equiv.) in CH$_2$Cl$_2$ (1 mL), in a similar manner as described in Example 1.10 to afford Compound 24 (0.039 g, 0.09 mmol, 68%) as a white powder. LCMS m/z (%)=451 (M+H$^{79}$Br, 95), 453 (M+H$^{81}$Br, 100). $^1$H NMR (400 MHz, acetone-d$_6$) δ: 8.58 (s, 1H), 8.32 (s, 1H), 8.16 (d, J=7.0 Hz, 1H), 8.10 (d, J=7.3 Hz, 1H), 7.91 (d, J=9.4 Hz, 1H), 7.75 (dd, J=2.7, 9.0 Hz, 1H), 7.65 (d, J=8.2 Hz, 1H), 7.44-7.57 (m, 5H), 7.14 (d, J=9.0 Hz, 1H), 3.83 (s, 3H), 3.69 (s, 3H).

Example 1.21:

Preparation of 1-[3-(4-Bromo-2-methyl-2H-pyrazol-3-yl)-4-methoxy-phenyl]-3-(4-chloro-phenyl)-thiourea (Compound 71).

3-(4-Bromo-2-methyl-2H-pyrazol-3-yl)-4-methoxy-phenylamine (0.037 g, 0.13 mmol) was treated with 4-chlorophenyl isothiocyanate (0.024 g, 0.14 mmol, 1.05 equiv.) in CH$_2$Cl$_2$ (1 mL), in a similar manner as described in Example 1.10 to afford Compound 71 (0.048 g, 0.10 mmol, 80%) as a solid film. LCMS m/z (%)=451 (M+H$^{79}$Br$^{35}$Cl, 85), 453 (M+H$^{81}$Br$^{35}$Cl, 100), 455 (M+H$^{81}$Br$^{37}$Cl, 35). $^1$H NMR (400 MHz, CDCl$_3$) δ: 8.00 (s, 1H), 7.85 (s, 1H), 7.53 (s, 1H), 7.48 (dd, J=2.7, 8.8 Hz, 1H), 7.37 (s, 4H), 7.30 (d, J=2.7 Hz, 1H), 7.08 (d, J=8.8 Hz, 1H), 3.87 (s, 3H), 3.75 (s, 3H).

Example 1.22:

1-[3-(4-Bromo-2-methyl-2H-pyrazol-3-yl)-4-methoxy-phenyl]-3-(3-nitro-phenyl)-urea (Compound 15).

3-(4-Bromo-2-methyl-2H-pyrazol-3-yl)-4-methoxy-phenylamine (0.036 g, 0.13 mmol) was treated with 3-nitrophenyl isocyanate (0.023 g, 0.13 mmol, 1.05 equiv.) in CH$_2$Cl$_2$ (1 mL), in a similar manner as described in Example 1.2 to afford Compound 15 (0.040 g, 0.09 mmol, 70%) as a yellow solid. LCMS m/z (%)=446 (M+H$^{79}$Br, 100), 448 (M+H$^{81}$Br, 89). $^1$H NMR (400 MHz, acetone-d$_6$) δ: 8.63 (s, 1H), 8.58 (s, 1H), 8.28 (s, 1H), 7.80-7.86 (m, 2H), 7.72 (dd, J=2.7, 9.0 Hz, 1H), 7.55 (t, J=8.2 Hz, 1H), 7.50 (s, 1H), 7.45 (d, J=2.7 Hz, 1H), 7.16 (d, J=9.0 Hz, 1H), 3.83 (s, 3H), 3.69 (s, 3H).

Example 1.23:

Preparation of 1-[3-(4-Bromo-2-methyl-2H-pyrazol-3-yl)-4-methoxy-phenyl]-3-(4-fluoro-3-nitro-phenyl)-urea (Compound 16).

3-(4-Bromo-2-methyl-2H-pyrazol-3-yl)-4-methoxy-phenylamine (0.037 g, 0.13 mmol) was treated with 4-fluoro-3-nitrophenyl isocyanate (0.025 g, 0.14 mmol, 1.05 equiv.) in CH$_2$Cl$_2$ (1 mL), in a similar manner as described in Example 1.2 to afford Compound 16 (0.042 g, 0.09 mmol, 69%) as a yellow solid. LCMS m/z (%)=464 (M+H$^{79}$Br, 100), 466 (M+H$^{81}$Br, 96). $^1$H NMR (400 MHz, acetone-d$_6$) δ: 8.55 (s, 1H), 8.44-8.50 (m, 1H), 8.29 (s, 1H), 7.77-7.83 (s, 1H), 7.70 (dd, J=2.7, 9.0 Hz, 1H), 7.49 (s, 1H), 7.37-7.46 (m, 2H), 7.16 (d, J=8.9 Hz, 1H), 3.83 (s, 3H), 3.69 (s, 3H).

Example 1.24:

Preparation of 1-(3-Acetyl-phenyl)-3-[3-(4-bromo-2-methyl-2H-pyrazol-3-yl)-4-methoxy-phenyl]-urea (Compound 17).

3-(4-Bromo-2-methyl-2H-pyrazol-3-yl)-4-methoxy-phenylamine (0.031 g, 0.11 mmol) was treated with 3-acetyl-phenyl isocyanate (0.019 g, 15.8 μL, 0.11 mmol, 1.05 equiv.) in CH$_2$Cl$_2$ (1 mL), in a similar manner as described in Example 1.2 to afford Compound 17 (0.038 g, 0.09 mmol, 79%) as a white solid. LCMS m/z (%)=443 (M+H$^{79}$Br, 99), 466 (M+H$^{81}$Br, 100). $^1$H NMR (400 MHz, acetone-d$_6$) δ: 8.30 (s, 1H), 8.19 (s, 1H), 8.13 (t, J=1.8 Hz, 1H), 7.80 (dd, J=1.4, 8.1 Hz, 1H), 7.70 (dd, J=2.7, 9.0 Hz, 1H), 7.62 (d, J=7.7 Hz, 1H), 7.49 (s, 1H), 7.44 (d, J=2.7 Hz, 1H), 7.41 (t, J=7.9 Hz, 1H), 7.15 (d, J=9.0 Hz, 1H).

Example 1.25:

Preparation of 1-[3-(4-Bromo-2-methyl-2H-pyrazol-3-yl)-4-methoxy-phenyl]-3-(3-methoxy-phenyl)-urea (Compound 72).

3-(4-Bromo-2-methyl-2H-pyrazol-3-yl)-4-methoxy-phenylamine (0.032 g, 0.12 mmol) was treated with 3-methoxy-phenyl isocyanate (0.018 g, 16.0 μL, 0.14 mmol, 1.05 equiv.) in CH$_2$Cl$_2$ (1 mL), in a similar manner as described in Example 1.10 to afford Compound 72 (0.047 g, 0.11 mmol, 94%) as a solid film. LCMS m/z (%)=431 (M+H$^{79}$Br, 100), 433 (M+H$^{81}$Br, 93). $^1$H NMR (400 MHz, acetone-d$_6$) δ: 8.13 (s, 2H), 7.68 (d, J=8.9 Hz, 1H), 7.49 (s, 1H), 7.43 (s, 1H), 7.30 (s, 1H), 7.16 (d, J=8.1 Hz, 1H), 7.12 (d, J=7.3 Hz, 1H), 6.98 (d, J=8.0 Hz, 1H), 3.81 (s, 3H), 3.76 (s, 3H). 3.68 (s, 3H).

Example 1.26:

Preparation of 1-[3-(4-Bromo-2-methyl-2H-pyrazol-3-yl)-4-methoxy-phenyl]-3-(3-fluoro-phenyl)-urea (Compound 18).

3-(4-Bromo-2-methyl-2H-pyrazol-3-yl)-4-methoxy-phenylamine (0.033 g, 0.12 mmol) was treated with 3-fluoro-phenyl isocyanate (0.017 g, 14.3 μL, 0.12 mmol, 1.05 equiv.) in CH$_2$Cl$_2$ (1 mL), in a similar manner as described in Example 1.2 to afford Compound 18 (0.040 g, 0.09 mmol, 82%) as a white solid. LCMS m/z (%)=419 (M+H$^{79}$Br, 100), 421 (M+H$^{81}$Br, 91). $^1$H NMR (400 MHz, acetone-d$_6$) δ: 8.31 (s, 1H), 8.17 (s, 1H), 7.69 (dd, J=2.7, 9.0 Hz, 1H), 7.59 (dt, J=2.2, 12.0 Hz, 1H), 7.50 (s, 1H), 7.43 (d, J=2.6 Hz, 1H), 7.27 (dd, J=8.1, 15.0 Hz, 1H), 7.11-7.19 (m, 2H), 6.73 (ddd, J=2.4, 8.4 Hz, 1H), 3.82 (s, 1H), 3.69 (s, 1H).

Example 1.27:

Preparation of 1-[3-(4-Bromo-2-methyl-2H-pyrazol-3-yl)-4-methoxy-phenyl]-3-(2-fluoro-phenyl)-urea (Compound 25).

3-(4-Bromo-2-methyl-2H-pyrazol-3-yl)-4-methoxy-phenylamine (0.034 g, 0.12 mmol) was treated with 2-fluoro-phenyl isocyanate (0.018 g, 14.4 µL, 0.12 mmol, 1.05 equiv.) in $CH_2Cl_2$ (1 mL), in a similar manner as described in Example 1.10 to afford Compound 25 (0.045 g, 0.11 mmol, 91%) as a solid film. LCMS m/z (%)=419 (M+H$^{79}$Br, 99), 421 (M+H$^{81}$Br, 100). $^1$H NMR (400 MHz, CDCl$_3$) δ: 8.08 (t, J=8.1 Hz, 1H), 7.59 (s, 1H), 7.54 (s, 1H), 7.53-7.59 (m, 1H), 7.40 (s, 1H), 7.12 (d, J=1.5 Hz, 1H), 6.95-7.12 (m, 3H), 6.94 (d, J=5.7 Hz, 1H), 3.77 (s, 3H), 3.70 (s, 3H).

Example 1.28:

Preparation of 1-[3-(4-Bromo-2-methyl-2H-pyrazol-3-yl)-4-methoxy-phenyl]-3-(4-trifluoromethoxy-phenyl)-urea (Compound 19).

3-(4-Bromo-2-methyl-2H-pyrazol-3-yl)-4-methoxy-phenylamine (0.032 g, 0.11 mmol) was treated with 4-(trifluoromethoxy)phenyl isocyanate (0.025 g, 18.4 µL, 0.12 mmol, 1.05 equiv.) in $CH_2Cl_2$ (1 mL), in a similar manner as described in Example 1.2 to afford Compound 19 (0.032 g, 0.07 mmol, 58%) as a white solid. LCMS m/z (%)=485 (M+H$^{79}$Br, 92), 487 (M+H$^{81}$Br, 100). $^1$H NMR (400 MHz, acetone-d$_6$) δ: 8.31 (s, 1H), 8.19 (s, 1H), 7.70 (d, J=9.0 Hz, 1H), 7.66 (d, J=8.4 Hz, 2H), 7.51 (s, 1H), 7.45 (s, 1H), 7.25 (d, J=8.4 Hz, 2H), 7.15 (d, J=8.9 Hz, 1H), 3.83 (s, 3H), 3.70 (s, 3H).

Example 1.29:

Preparation of 1-Benzoyl-3-[3-(4-bromo-2-methyl-2H-pyrazol-3-yl)-4-methoxy-phenyl]-urea (Compound 73).

3-(4-Bromo-2-methyl-2H-pyrazol-3-yl)-4-methoxy-phenylamine (0.033 g, 0.12 mmol) was treated with benzoyl isocyanate (0.020 g, 0.12 mmol, 1.05 equiv.) in $CH_2Cl_2$ (1 mL), in a similar manner as described in Example 1.2 to afford Compound 73 (0.036 g, 0.08 mmol, 72%) as a white solid. LCMS m/z (%)=429 (M+H$^{79}$Br, 99), 431 (M+H$^{81}$Br, 100). $^1$H NMR (400 MHz, acetone-d$_6$) δ: 10.92 (s, 1H), 9.85 (s, 1H), 8.12 (d, J=7.4 Hz, 2H), 7.76 (dd, J=2.6, 9.0 Hz, 1H), 7.68 (t, J=7.3 Hz, 1H), 7.62 (d, J=2.6 Hz, 1H), 7.57 (t, J=7.8 Hz, 2H), 7.51 (s, 1H), 7.21 (d, J=9.0 Hz, 1H), 3.86 (s, 3H), 3.71 (s, 3H).

Example 1.30:

Preparation of 1-Benzyl-3-[3-(4-bromo-2-methyl-2H-pyrazol-3-yl)-4-methoxy-phenyl]-urea (Compound 74).

3-(4-Bromo-2-methyl-2H-pyrazol-3-yl)-4-methoxy-phenylamine (0.034 g, 0.12 mmol) was treated with benzyl isocyanate (0.017 g, 16.0 µL, 0.13 mmol, 1.05 equiv.) in $CH_2Cl_2$ (1 mL), in a similar manner as described in Example 1.10 to afford Compound 74 (0.031 g, 0.08 mmol, 62%) as a solid film. LCMS m/z (%)=415 (M+H$^{79}$Br, 86), 417 (M+H$^{81}$Br, 100). $^1$H NMR (400 MHz, acetone-d$_6$) δ: 8.05 (s, 1H), 7.64 (dd, J=2.7, 9.0 Hz, 1H), 7.47 (s, 1H), 7.40 (d, J=2.7 Hz, 1H), 7.27-7.37 (m, 4H), 7.22 (t, J=7.0 Hz, 1H), 7.07 (d, J=9.0 Hz, 1H), 6.21 (s, 1H), 4.41 (d, J=4.0 Hz, 2H), 3.79 (s, 3H), 3.66 (s, 3H).

Example 1.31:

Preparation of intermediate 3-(4-Bromo-2-methyl-2H-pyrazol-3-yl)-4-ethoxy-phenylamine.

3-(4-Bromo-2-methyl-2H-pyrazol-3-yl)-4-ethoxy-phenylamine was prepared in a similar manner as described in Example 1.1 using 4-bromo-5-(2-ethoxy-5-nitro-phenyl)-1-methyl-1H-pyrazole, SnCl$_2$.2H$_2$O in EtOH [0.225 g, 0.76 mmol, 81% for three steps from 2-(2-methyl-2H-pyrazol-3-yl)-4-nitro-phenol]. LCMS m/z (%)=296 (M+H$^{79}$Br, 100), 298 (M+H$^{81}$Br, 98). $^1$H NMR (400 MHz, CDCl$_3$) δ: 7.52 (s, 1H), 6.86 (d, J=8.7 Hz, 1H), 6.77 (dd, J=2.2, 8.5 Hz, 1H), 6.62 (d, J=2.3 Hz, 1H), 3.82-4.00 (m, 2H), 3.73 (s, 3H), 3.24-3.58 (broad s, 2H), 1.24 (t, J=6.8 Hz, 3H).

The intermediate 4-bromo-5-(2-ethoxy-5-nitro-phenyl)-1-methyl-1H-pyrazole was prepared in the following manner:

A. 2-(2-Methyl-2H-pyrazol-3-yl)-4-nitro-phenol: To methyl hydrazine (1.106 g, 1.3 mL, 23.5 mmol, 4.0 equiv.) was added 4-nitrochromone in DMSO (1.159 g/40 mL, 5.88 mmol, 1.0 equiv.) dropwise via syringe pump at 70° C, the crude reaction mixture was isolated by HPLC to afford 2-(2-methyl-2H-pyrazol-3-yl)-4-nitro-phenol (0.567 g, 2.59 mmol, 44%) as a white solid. LCMS m/z=220 (M+H). $^1$H NMR (400 MHz, acetone-d$_6$) δ: 8.24 (dd, J=2.9, 9.0 Hz, 1H), 8.13 (d, J=2.8 Hz, 1H), 7.46 (d, J=1.8 Hz, 1H), 7.26 (d, J=9.0 Hz, 1H), 6.36 (d, J=1.8 Hz, 1H), 3.77 (s, 3H).

B. 5-(2-Ethoxy-5-nitro-phenyl)-1-methyl-1H-pyrazole (General Alklyation Procedure): To a stirred solution of 2-(2-methyl-2H-pyrazol-3-yl)-4-nitro-phenol (0.206 g, 0.94 mmol) in a mixture of DMF/THF (1 mL/5 mL) was added NaH (60%, 0.082 g, 1.88 mmol, 2.0 equiv.) at 0° C. It was stirred for 30 mins, iodoethane (0.444 g, 0.23 mL, 3.0 equiv.) was then added, the mixture was warmed up to 70° C and stirred until the consumption of the starting material. It was quenched with saturated NH$_4$Cl, diluted with EtOAc, washed with water and the aqueous phase was extracted with EtOAc (3×50 mL). The combined organic phase was washed with brine, dried over MgSO$_4$, filtered and evaporated. The crude reaction mixture was subjected to the bromination without any purification. LCMS m/z=248 (M+H). $^1$H NMR (400 MHz, CDCl$_3$) δ: 8.33 (dd, J=2.5, 9.1 Hz, 1H), 8.21 (d, J=2.5 Hz, 1H), 7.57 (d, J=1.3 Hz, 1H), 7.07 (d, J=9.1 Hz, 1H), 6.34 (s, 1H), 4.22 (dd, J=7.0, 13.9 Hz, 2H), 3.78 (s, 3H), 1.44 (t, J=6.8 Hz, 3H).

C. 4-Bromo-5-(2-ethoxy-5-nitro-phenyl)-1-methyl-1H-pyrazole: The crude reaction mixture of 5-(2-ethoxy-5-nitro-phenyl)-1-methyl-1H-pyrazole was treated with NBS in DMF, in a similar manner as described in Example 1.1, Step D, provided brominated compound 4-bromo-5-(2-ethoxy-5-nitro-phenyl)-1-methyl-1H-pyrazole. It was reduced directly to the aniline as described in this example above. LCMS m/z (%)=326 (M+H$^{79}$Br, 88), 328 (M+H$^{81}$Br, 100). $^1$H NMR (400 MHz, CDCl$_3$) δ: 8.38 (dd, J=2.7, 9.2 Hz, 1H), 8.22 (d, J=2.7 Hz, 1H), 7.59 (s, 1H), 7.11 (d, J=9.2 Hz, 1H), 4.14-4.32 (m, 2H), 3.76 (s, 3H), 1.43 (t, J=6.8 Hz, 3H).

Example 1.32:

Preparation of 1-[3-(4-Bromo-2-methyl-2H-pyrazol-3-yl)-4-ethoxy-phenyl]-3-(4Chloro-phenyl)-urea (Compound 67)

3-(4-Bromo-2-methyl-2H-pyrazol-3-yl)-4-ethoxy-phenylamine (0.040 g, 0.13 mmol) was treated with 4-chlorophenyl isocyanate (0.023 g, 0.15 mmol, 1.1 equiv.) in $CH_2Cl_2$ (1 mL), in a similar manner as described in Example 1.2 to afford Compound 67 (0.034 g, 0.08 mmol, 56%) as a white solid. LCMS m/z (%)=449 (M+H$^{79}$Br$^{35}$Cl, 72), 451 (M+H$^{81}$Br$^{35}$Cl, 100), 453 (M+H$^{81}$Br$^{37}$Cl, 26). $^1$H NMR (400 MHz, acetone-d$_6$) δ: 8.22 (s, 1H), 8.14 (s, 1H), 7.66 (dd, J=2.7, 9.0 Hz, 1H), 7.56 (d, J=8.8 Hz, 2H), 7.49 (s, 1H), 7.43 (d, J=2.7 Hz, 1H), 7.28 (d, J=8.8 Hz, 2H), 7.12 (d, J=9.0 Hz, 1H), 3.98-4.18 (m, 2H), 3.71 (s, 3H), 1.28 (t, J=7.1 Hz, 3H).

Example 1.33:

Preparation of 1-[3-(4-Bromo-2-methyl-2H-pyrazol-3-yl)-4-ethoxy-phenyl]-3-(4-fluoro-phenyl)-urea (Compound 68)

3-(4-Bromo-2-methyl-2H-pyrazol-3-yl)-4-ethoxy-phenylamine (0.039 g, 0.13 mmol) was treated with 4-fluorophenyl isocyanate (0.020 g, 16.6 μL, 0.14 mmol, 1.1 equiv.) in $CH_2Cl_2$ (1 mL), in a similar manner as described in Example 1.2 to afford Compound 68 (0.034 g, 0.08 mmol, 59%) as a white solid. LCMS m/z (%)=433 (M+H$^{79}$Br, 100), 435 (M+H$^{81}$Br, 99). $^1$H NMR (400 MHz, acetone-d$_6$) δ: 8.13 (s, 1H), 8.11 (s, 1H), 7.66 (dd, J=2.7, 8.9 Hz, 1H), 7.50-7.57 (m, 2H), 7.49 (s, 1H), 7.42 (d, J=2.7 Hz, 1H), 7.11 (d, J=8.9 Hz, 1H), 7.04 (t, J=8.8 Hz, 2H), 3.96-4.18 (m, 2H), 3.71 (s, 3H), 1.28 (t, J=7.1 Hz, 3H).

Example 1.34:

Preparation of intermediate 3-(4-Bromo-2-methyl-2H-pyrazol-3-yl)-4-isopropoxy-phenylamine.

The crude reaction mixture of 4-bromo-5-(2-isopropoxy-5-nitro-phenyl)-1-methyl-1H-pyrazole (as described below) was reduced in the presence of SnCl$_2$.2H$_2$O, in a similar manner as described in Example 1.1, providing 3-(4-bromo-2-methyl-2H-pyrazol-3-yl)-4-isopropoxy-phenylamine (0.043 g, 0.14 mmol, 50% for three steps). LCMS m/z (%)=310 (M+H$^{79}$Br, 99), 312 (M+H$^{81}$Br, 100). $^1$H NMR (400 MHz, CDCl$_3$) δ: 7.51 (s, 1H), 6.89 (d, J=8.8 Hz, 1H), 6.76 (dd, J=2.7, 8.6 Hz, 1H), 6.62 (d, J=2.7 Hz, 1H), 4.08 (ddd, J=6.1, 6.1, 12.2 Hz, 1H), 3.74 (s, 3H), 1.21 (d, J=6.1 Hz, 3H), 1.01 (d, J=6.1 Hz, 3H).

Intermediate 4-bromo-5-(2-isopropoxy-5-nitro-phenyl)-1-methyl-1H-pyrazole was prepared in the following manner:

A. 5-(2-Isopropoxy-5-nitro-phenyl)-1-methyl-1H-pyrazole: To a stirred solution of 2-(2-methyl-2H-pyrazol-3-yl)-4-nitro-phenol (0.061 g, 0.28 mmol) in DMF (3 mL) was added K$_2$CO$_3$ (0.077 g, 0.56 mmol, 2.0 equiv.) at r.t., it was stirred for 30 mins and isopropyl bromide (110 μL, 0.146 g, 1.16 mmol, 4.0 equiv.) was added. The mixture was stirred at 50° C until the consumption of starting material was complete. The reaction mixture was diluted with EtOAc, washed with water and the aqueous phase was extracted with EtOAc. The combined organic phase was washed with brine, dried over MgSO$_4$, filtered and evaporated. LCMS m/z=262 (M+H). $^1$H NMR (400 MHz, CDCl$_3$) δ: 8.31 (dd, J=2.8, 9.2 Hz, 1H), 8.20 (d, J=2.8 Hz, 1H), 7.56 (s, 1H), 7.06 (d, J=9.2 Hz, 1H), 6.3 (s, 1H), 4.74 (ddd, J=6.1, 6.1, 12.1 Hz, 1H), 1.37 (s, 3H), 1.36 (s, 3H).

B. 4-Bromo-5-(2-isopropoxy-5-nitro-phenyl)-1-methyl-1H-pyrazole: The crude reaction mixture of 5-(2-isopropoxy-5-nitro-phenyl)-1-methyl-1H-pyrazole was brominated, in a similar manner as described in Example 1.1, Step D, providing 4-bromo-5-(2-isopropoxy-5-nitro-phenyl)-1-methyl-1H-pyrazole. LCMS m/z (%)=340 (M+H$^{79}$Br, 85), 342 (M+H$^{81}$Br, 100). $^1$H NMR (400 MHz, CDCl$_3$) δ: 8.36 (dd, J=2.8, 9.2 Hz, 1H), 8.20 (d, J=2.8 Hz, 1H), 7.57 (s, 1H), 7.10 (d, J=9.2 Hz, 1H), 4.73 (ddd, J=6.1, 6.1, 12.1 Hz, 1H), 1.39 (d, J=6.1 Hz, 3H), 1.32 (d, J=6.0 Hz, 3H).

Example 1.35:

Preparation of 1-[3-(4-Bromo-2-methyl-2H-pyrazol-3-yl)-4-isopropoxy-phenyl]-3-(4-Chloro-phenyl)-urea (Compound 59).

3-(4-Bromo-2-methyl-2H-pyrazol-3-yl)-4-isopropoxy-phenylamine (0.024 g, 0.08 mmol) was treated with 4-chlorophenyl isocyanate (0.014 g, 0.09 mmol, 1.1 equiv.) in $CH_2Cl_2$ (1 mL), in a similar manner as described in Example 1.10 to afford Compound 59 (0.034 g, 0.07 mmol, 91%) as a white solid. LCMS m/z (%)=463 (M+H$^{79}$Br$^{35}$Cl, 82), 465 (M+H$^{81}$Br$^{35}$Cl, 100), 467 (M+H$^{81}$Br$^{37}$Cl, 29). $^1$H NMR (400 MHz, acetone-d$_6$) δ: 8.24 (s, 1H), 8.17 (s, 1H), 7.65 (dd, J=2.5, 8.9 Hz, 1H), 7.55 (d, J=8.6 Hz, 2H), 7.49 (s, 1H), 7.42 (d, J=2.5 Hz, 1H), 7.28 (d, J=8.6 Hz, 2H), 4.42-4.52 (m, 1H), 3.70 (s, 3H), 1.26 (d, J=6.0 Hz, 3H), 1.11 (d, J=6.0 Hz, 3H).

Example 1.36:

Preparation of 1-[3-(4-Bromo-2-methyl-2H-pyrazol-3-yl)-4-isopropoxy-phenyl]-3-(4-fluoro-phenyl)-urea (Compound 60).

3-(4-Bromo-2-methyl-2H-pyrazol-3-yl)-4-isopropoxy-phenylamine (0.027 g, 0.09 mmol) was treated with 4-fluorophenyl isocyanate (0.013 g, 11.0 μL, 0.10 mmol, 1.1 equiv.) in $CH_2Cl_2$ (1 mL), in a similar manner as described in Example 1.2 to afford Compound 60 (0.015 g, 0.03 mmol, 38%) as a white solid. LCMS m/z (%)=447 (M+H$^{79}$Br, 98), 449 (M+H$^{81}$Br, 100). $^1$H NMR (400 MHz, acetone-d$_6$) δ: 8.11 (s, 2H), 7.65 (dd, J=2.4, 8.9 Hz, 1H), 7.54 (dd, J=4.9, 8.7 Hz, 2H), 7.49 (s, 1H), 7.41 (d, J=2.6 Hz, 1H), 7.12 (d, J=8.9 Hz, 1H), 7.04 (t, J=8.8 Hz, 2H), 4.40-4.52 (m, 1H), 3.70 (s, 3H), 1.26 (d, J=6.0 Hz, 3H), 1.11 (d, J=6.0 Hz, 3H).

Example 1.37:

Preparation of 4-Benzyloxy-3-(4-bromo-2-methyl-2H-pyrazol-3-yl)-phenylamine.

The reaction mixture of 5-(2-benzyloxy-5-nitro-phenyl)-4-bromo-1-methyl-1H-pyrazole was reduced in the presence of SnCl$_2$.2H$_2$O, in a similar manner as described in Example 1.1, providing 4-benzyloxy-3-(4-bromo-2-methyl-2H-pyrazol-3-yl)-phenylamine (0.079 g, 0.22 mmol, 39% for three steps). LCMS m/z (%)=358 (M+H$^{79}$Br, 98), 360 (M+H$^{81}$Br, 100). $^1$H NMR (400 MHz, CDCl$_3$) δ: 7.45 (s, 1H), 7.15-7.26 (m, 3H), 7.10 (d, J=6.6 Hz, 2H), 6.83 (d, J=8.7 Hz, 1H), 6.66 (dd, J=2.8, 8.6 Hz, 1H), 6.55 (d, J=2.8 Hz, 1H), 4.83 (AB quartet, J=12.0, 17.2 Hz, 2H), 3.62 (s, 3H).

The intermediate 5-(2-benzyloxy-5-nitro-phenyl)-4-bromo-1-methyl-1H-pyrazole was prepared in the following manner:

A. 5-(2-Benzyloxy-5-nitro-phenyl)-1-methyl-1H-pyrazole: 2-(2-Methyl-2H-pyrazol-3-yl)-4-nitro-phenol (0.124 g, 0.57 mmol) was treated with NaH (0.049 g, 1.13 mmol, 2.0 equiv.) and benzyl bromide (0.297 g, 0.21 mL, 1.70 mmol, 3.0 equiv.) in a mixture of DMF/THF (2 mL/4 mL), in a similar manner as described in Example 1.31, Step B, providing 5-(2-benzyloxy-5-nitro-phenyl)-1-methyl-1H-pyrazole. LCMS m/z=310 (M+H). $^1$H NMR (400 MHz, CDCl$_3$) δ: 8.32 (dd, J=2.8, 9.1 Hz, 1H), 8.24 (d, J=2.8 Hz, 1H), 7.59 (d, J=1.7 Hz, 1H), 7.22-7.45 (m, 5H), 7.16 (d, J=9.1 Hz, 1H), 6.37 (d, J=1.7 Hz, 1H), 5.25 (s, 2H), 3.77 (s, 3H).

B. 5-(2-Benzyloxy-5-nitro-phenyl)-4-bromo-1-methyl-1H-pyrazole: The crude reaction mixture of 5-(2-benzyloxy-5-nitro-phenyl)-1-methyl-1H-pyrazole was treated with NBS (0.113 g, 0.63 mmol, 1.1 equiv.), in a similar manner as described in Example 1.1, Step D, providing to 5-(2-Benzyloxy-5-nitro-phenyl)-4-bromo-1-methyl-1H-pyrazole. LCMS m/z (%)=388 (M+H$^{79}$Br, 100), 390 (M+H$^{81}$Br, 94). $^1$H NMR (400 MHz, CDCl$_3$) δ: 8.36 (dd, J=2.8, 9.2 Hz, 1H), 8.23 (d, J=2.8 Hz, 1H), 7.59 (s, 1H), 7.25-7.42 (m, 5H), 7.19 (d, J=9.2 Hz, 1H), 5.24 (s, 2H), 3.73 (s, 3H).

Example 1.38:

Preparation of 1-[4-Benzyloxy-3-(4-bromo-2-methyl-2H-pyrazol-3-yl)-phenyl]-3-(4-Chloro-phenyl)-urea (Compound 61).

4-Benzyloxy-3-(4-bromo-2-methyl-2H-pyrazol-3-yl)-phenylamine (0.023 g, 0.09 mmol) was treated with 4-chlorophenyl isocyanate (0.016 g, 0.10 mmol, 1.1 equiv.) in CH$_2$Cl$_2$ (1 mL), in a similar manner as described in Example 1.2 to afford Compound 61 (0.019 g, 0.04 mmol, 42%) as a white solid. LCMS m/z (%)=511 (M+H$^{79}$Br$^{35}$Cl, 82), 513 (M+H$^{81}$Br$^{35}$Cl, 100), 515 (M+H$^{81}$Br$^{37}$Cl, 33). $^1$H NMR (400 MHz, acetone-d$_6$) δ: 8.22 (s, 1H), 8.16 (s, 1H), 7.66 (dd, J=2.4, 8.9 Hz, 1H), 7.55 (d, J=8.7 Hz, 2H), 7.50 (s, 1H), 7.46 (d, J=2.5 Hz, 1H), 7.28-7.35 (m, 5H), 7.28 (d, J=8.7 Hz, 2H), 7.22 (d, J=8.9 Hz, 1H), 5.13 (AB quartet, J=12.0, 24.3 Hz, 2H), 3.69 (s, 3H).

Example 1.39:

Preparation of 1-[4-Benzyloxy-3-(4-bromo-2-methyl-2H-pyrazol-3-yl)-phenyl]-3-(4-fluoro-phenyl)-urea (Compound 62).

4-Benzyloxy-3-(4-bromo-2-methyl-2H-pyrazol-3-yl)-phenylamine (0.031 g, 0.09 mmol) was treated with 4-fluorophenyl isocyanate (0.013 g, 11.0 μL, 0.10 mmol, 1.1 equiv.) in CH$_2$Cl$_2$ (1 mL), in a similar manner as described in Example 1.2 to afford Compound 62 (0.011 g, 0.02 mmol, 26%) as a white solid. LCMS m/z (%)=511 (M+H$^{79}$Br, 82), 513 (M+H$^{81}$Br, 100). $^1$H NMR (400 MHz, acetone-d$_6$) δ: 8.12 (s, 2H), 7.66 (dd, J=2.6, 8.9 Hz, 1H), 7.54 (dd, J=4.8, 9.0 Hz, 2H), 7.50 (s, 1H), 7.47 (d, J=2.6 Hz, 1H), 7.25-7.36 (m, 5H), 7.22 (d, J=8.9 Hz, 1H), 7.04 (t, J=8.8 Hz, 2H), 5.13 (AB quartet, J=12.0, 24.4 Hz, 2H), 3.69 (s, 3H).

Example 1.40:

Preparation of intermediate 3-(4-Bromo-2-methyl-2H-pyrazol-3-yl)-4-(4-chloro-benzyloxy)-phenylamine.

The crude reaction mixture of 4-bromo-5-[2-(4-chloro-benzyloxy)-5-nitro-phenyl]-1-methyl-1H-pyrazole (as described below) was treated with SnCl$_2$.2H$_2$O (0.378 g, 1.64 mmol, 4.0 equiv.) in EtOH (5 mL), in a similar manner as described in Example 1.1, providing aniline 3-(4-bromo-2-methyl-2H-pyrazol-3-yl)-4-(4-chloro-benzyloxy)-phenylamine (0.114 g, 0.29 mmol, 71% for two steps). LCMS m/z (%)=392 (M+H$^{79}$Br$^{35}$Cl, 70), 394 (M+H$^{81}$Br$^{35}$Cl, 100), 396 (M+H$^{81}$Br$^{37}$Cl, 23). $^1$H NMR (400 MHz, CDCl$_3$) δ: 7.54 (s, 1H), 7.28 (d, J=8.2 Hz, 2H), 7.11 (d, J=8.2 Hz, 2H), 6.90 (d, J=8.7 Hz, 1H), 6.76 (dd, J=2.7, 8.7 Hz, 1H), 6.63 (d, J=2.7 Hz, 1H), 4.86 (AB quartet, J=12.1, 20.9 Hz, 2H), 3.71 (s, 3H).

The intermediate 4-bromo-5-[2-(4-chloro-benzyloxy)-5-nitro-phenyl]-1-methyl-1H-pyrazole was prepared in the following manner:

A. 5-[2-(4-Chloro-benzyloxy)-5-nitro-phenyl]-1-methyl-1H-pyrazole: 2-(2-Methyl-2H-pyrazol-3-yl)-4-nitro-phenol (0.143 g, 0.65 mmol) was treated with NaH (0.057 g, 1.30 mmol, 2.0 equiv.) and 4-chlorobenzyl bromide (0.332 g, 1.96 mmol, 3.0 equiv.) in a mixture of DMF/THF (0.9 mL/2.5 mL), in a similar manner as described in Example 1.31, Step B, providing 5-[2-(4-chloro-benzyloxy)-5-nitro-phenyl]-1-methyl-1H-pyrazole (0.142 g, 0.41 mmol, 63%) as an oil. LCMS m/z (%)=344 (M+H$^{35}$Cl, 100), 346 (M+H$^{37}$Cl, 39). $^1$H NMR (400 MHz, CDCl$_3$) δ: 8.33 (d, J=2.8, 9.1 Hz, 1H), 8.23 (d, J=9.1 Hz, 1H), 7.58 (d, J=1.7 Hz, 1H), 7.36 (d, J=8.3 Hz, 2H), 7.21 (d, J=8.3 Hz, 1H), 7.13 (d, J=9.1 Hz, 1H), 6.36 (d, J=1.7 Hz, 1H), 5.20 (s, 2H), 3.75 (s, 3H).

B. 4-Bromo-5-[2-(4-chloro-benzyloxy)-5-nitro-phenyl]-1-methyl-1H-pyrazole: 5-[2-(4-Chloro-benzyloxy)-5-nitro-phenyl]-1-methyl-1H-pyrazole was treated with NBS (0.082 g, 0.45 mmol, 1.05 equiv.), in a similar manner as described in Example 1.1, Step D, providing 4-bromo-5-[2-(4-chloro-benzyloxy)-5-nitro-phenyl]-1-methyl-1H-pyrazole. LCMS m/z (%)=422 (M+H$^{79}$Br$^{35}$Cl, 85), 424 (M+H$^{81}$Br$^{35}$Cl, 100), 426 (M+H$^{81}$Br$^{37}$Cl, 26). $^1$H NMR (400 MHz, CDCl$_3$) δ: 8.37 (dd, J=2.7, 9.2 Hz, 1H), 8.22 (d, J=2.7 Hz, 1H), 7.59 (s, 1H), 7.34 (d, J=8.3 Hz, 2H), 7.21 (d, J=8.3 Hz, 2H), 7.16 (d, J=9.2 Hz, 1H), 5.20 (AB quartet, J=12.1, 15.2 Hz, 2H), 3.72 (s, 3H).

Example 1.41:

Preparation of 1-[3-(4-Bromo-2-methyl-2H-pyrazol-3-yl)-4-(4-Chloro-benzyloxy)-phenyl]-3-(4-Chloro-phenyl)-urea (Compound 63).

3-(4-Bromo-2-methyl-2H-pyrazol-3-yl)-4-(4-chloro-benzyloxy)-phenylamine (0.029 g, 0.08 mmol) was treated with 4-chlorophenyl isocyanate (0.014 g, 0.09 mmol, 1.2 equiv.) in CH$_2$Cl$_2$ (1 mL), in a similar manner as described in Example 1.2 to afford Compound 63 (0.027 g, 0.05 mmol, 65%) as a white solid. LCMS m/z (%)=545 (M+H$^{79}$Br$^{35}$Cl$^{35}$Cl, 65), 547 (M+H$^{79}$Br$^{35}$Cl$^{37}$Cl$^{81}$Br$^{35}$Cl$^{35}$Cl, 100), 549 (M+H$^{81}$Br$^{35}$Cl$^{37}$Cl$^{79}$Br$^{37}$Cl$^{37}$C, 45), 551 (M+H$^{81}$Br$^{37}$Cl$^{37}$Cl, 6). $^1$H NMR (400 MHz, acetone-d$_6$) δ: 8.23 (s, 1H), 8.17 (s, 1H), 7.66 (dd, J=2.7, 9.0 Hz, 1H), 7.56 (d, J=8.9 Hz, 2H), 7.50 (s, 1H), 7.46 (d, J=2.7 Hz, 1H), 7.37 (d, J=8.7 Hz, 2H), 7.33 (d, J=8.7 Hz, 2H), 7.28 (d, J=8.9 Hz, 2H), 7.22 (d, J=9.0 Hz, 1H), 5.14 (AB quartet, J=12.3, 24.8 Hz, 2H), 3.69 (s, 3H).

Example 1.42:

Preparation of 1-[3-(4-Bromo-2-methyl-2H-pyrazol-3-yl)-4-(4-Chloro-benzyloxy)-phenyl]-3-(4-fluoro-phenyl)-urea (Compound 64).

3-(4-Bromo-2-methyl-2H-pyrazol-3-yl)-4-(4-chloro-benzyloxy)-phenylamine (0.032 g, 0.08 mmol) was treated with 4-fluorophenyl isocyanate (0.014 g, 11.1 μL, 0.10 mmol, 1.2 equiv.) in CH$_2$Cl$_2$ (1 mL), in a similar manner as described in Example 1.2 to afford Compound 64 (0.023 g, 0.04 mmol, 54%) as a white solid. LCMS m/z (%)=545 (M+H$^{79}$Br$^{35}$Cl, 65), 547 (M+H$^{81}$Br$^{35}$Cl, 100), 549 (M+H$^{81}$Br$^{37}$Cl, 25). $^1$H NMR (400 MHz, acetone-d$_6$) δ: 8.13 (s, 2H), 7.66 (dd, J=2.7, 9.0 Hz, 1H), 7.51-7.56 (m, 3H), 7.50 (s, 1H), 7.46 (d, J=2.7 Hz, 1H), 7.37 (d, J=8.7 Hz, 2H), 7.33 (d, J=8.7 Hz, 2H), 7.21 (d, J=9.0 Hz, 1H), 7.05-7.75 (m, 2H), 5.14 (AB quartet, J=12.3, 24.8 Hz, 2H), 3.69 (s, 3H).

Example 1.43:

Preparation of intermediate 3-(4-Bromo-2-methyl-2H-pyrazol-3-yl)-4-phenethyloxy-phenylamine.

The crude reaction mixture of 4-bromo-1-methyl-5-(5-nitro-2-phenethyloxy-phenyl)-1H-pyrazole (as described below) was reduced with SnCl$_2$.2H$_2$O (0.387 g, 1.68 mmol, 4.0 equiv.) in EtOH, in a similar manner as described in Example 1.1, providing aniline 3-(4-Bromo-2-methyl-2H-pyrazol-3-yl)-4-phenethyloxy-phenylamine (0.124 g, 0.33 mmol, 80% for two steps) as an oil. LCMS m/z (%)=372 (M+H$^{79}$Br, 94), 394 (M+H$^{81}$Br, 100). $^1$H NMR (400 MHz, CDCl$_3$) δ: 7.54 (s, 1H), 7.18-7.33 (m, 3H), 7.08 (d, J=7.7 Hz, 2H), 6.85 (d, J=8.7 Hz, 1H), 6.77 (dd, J=2.7, 8.7 Hz, 1H), 6.61 (d, J=2.6 Hz, 1H), 3.99-4.15 (m, 2H), 3.53 (s, 3H), 3.10-3.40 (broad s, 2H), 2.83-3.00 (m, 2H).

The intermediate 4-bromo-1-methyl-5-(5-nitro-2-phenethyloxy-phenyl)-1H-pyrazole was prepared in the following manner:

A. 1-Methyl-5-(5-nitro-2-phenethyloxy-phenyl)-1H-pyrazole: 2-(2-Methyl-2H-pyrazol-3-yl)-4-nitro-phenol (0.125 g, 0.57 mmol) was treated with NaH (0.049 g, 1.14 mmol, 2.0 equiv.) and (2-bromoethyl)benzene (0.323 g, 0.24 mL, 1.71 mmol, 3.0 equiv.) in a mixture of DMF/THF (0.9 mL/2.5 mL), in a similar manner as described in Example 1.31, Step B, providing 1-methyl-5-(5-nitro-2-phenethyloxy-phenyl)-1H-pyrazole (0.137 g, 0.42 mmol, 74%) as an oil. LCMS m/z (%)=324 (M+H). $^1$H NMR (400 MHz, CDCl$_3$) δ: 8.31 (dd, J=2.8, 9.1 Hz, 1H), 8.17 (d, J=2.8 Hz, 1H), 7.59 (s, 1H), 7.20-7.36 (m, 3H), 7.09 (d, J=7.1 Hz, 2H), 7.05 (d, J=9.2 Hz, 1H), 6.26 (s, 1H), 4.33 (t, J=6.6 Hz, 2H), 3.55 (s, 3H), 3.05 (t, J=6.6 Hz, 2H).

B. 4-Bromo-1-methyl-5-(5-nitro-2-phenethyloxy-phenyl)-1H-pyrazole: 1-Methyl-5-(5-nitro-2-phenethyloxy-phenyl)-1H-pyrazole (0.137 g, 0.42 mmol) was treated with NBS (0.084 g, 0.46 mmol, 1.05 equiv.) in DMF (5 mL), in a similar manner as described in Example 1.1, Step D, providing 4-bromo-1-methyl-5-(5-nitro-2-phenethyloxy-phenyl)-1H-pyrazole. LCMS m/z (%)=402 (M+H$^{79}$Br, 100), 404 (M+H$^{81}$Br, 97). $^1$H NMR (400 MHz, CDCl$_3$) δ: 8.27 (dd, J=2.8, 9.2 Hz, 1H), 8.10 (d, J=2.8 Hz, 1H), 7.52 (s, 1H), 7.16-7.24 (m, 3H), 6.94-7.03 (m, 3H), 4.18-4.28 (m, 2H), 3.37 (s, 3H), 2.88-3.02(m, 2H).

Example 1.44:

Preparation of 1-[3-(4-Bromo-2-methyl-2H-pyrazol-3-yl)-4-phenethyloxy-phenyl]-3-(4-Chloro-phenyl)-urea (Compound 66).

3-(4-Bromo-2-methyl-2H-pyrazol-3-yl)-4-phenethyloxy-phenylamine (0.028 g, 0.07 mmol) was treated with 4-chlorophenyl isocyanate (0.014 g, 0.09 mmol, 1.2 equiv.) in CH$_2$Cl$_2$ (1 mL), in a similar manner as described in Example 1.10 to afford Compound 66 (0.025 g, 0.05 mmol, 66%) as a solid film. LCMS m/z (%)=525 (M+H$^{79}$Br$^{35}$Cl, 85), 527 (M+H$^{81}$Br$^{35}$Cl, 100), 529 (M+H$^{81}$Br$^{37}$Cl, 31). $^1$H NMR (400 MHz, acetone-d$_6$) δ: 8.34 (s, 1H), 8.26 (s, 1H), 7.65 (dd, J=2.7, 8.9 Hz, 1H), 7.56 (d, J=8.9 Hz, 2H), 7.53 (s, 1H), 7.43 (d, J=2.7 Hz, 1H), 7.16-7.31 (m, 5H), 7.09-7.16 (m, 3H), 4.11-4.30 (m, 2H), 3.51 (s, 3H), 2.86-3.06 (m, 2H).

Example 1.45:

Preparation of 1-[3-(4-Bromo-2-methyl-2H-pyrazol-3-yl)-4-phenethyloxy-phenyl]-3-(4-fluoro-phenyl)-urea (Compound 65).

3-(4-Bromo-2-methyl-2H-pyrazol-3-yl)-4-phenethyloxy-phenylamine (0.029 g, 0.08 mmol) was treated with 4-fluorophenyl isocyanate (0.013 g, 11.0 μL, 0.09 mmol, 1.2 equiv.) in CH$_2$Cl$_2$ (1 mL), in a similar manner as described in Example 1.10 to afford Compound 65 (0.030 g, 0.06 mmol, 74%) as a solid film. LCMS m/z (%)=509 (M+H$^{79}$Br, 100), 511 (M+H$^{81}$Br, 97). $^1$H NMR (400 MHz, acetone-d$_6$) δ: 8.22 (s, 2H), 7.63 (d, J=8.9 Hz, 1H), 7.48-7.56 (m, 3H), 7.41 (s, 1H), 7.15-7.28 (m, 3H), 7.08-7.16 (m, 3H), 7.03 (t, J=8.7 Hz, 2H), 4.08-4.30 (m, 2H), 3.50 (s, 3H), 2.86-3.06 (m, 2H).

Example 1.46:

Preparation of intermediate 3-(4-Bromo-2-methyl-2H-pyrazol-3-yl)-4-(2-dimethylamino-ethoxy)-phenylamine.

{2-[2-(4-Bromo-2-methyl-2H-pyrazol-3-yl)-4-nitro-phenoxy]-ethyl}-dimethyl-amine (0.128 g, 0.35 mmol) was treated with SnCl$_2$.2H$_2$O (0.319 g, 1.39 mmol, 4.0 equiv.) in EtOH (20 mL), in a similar manner as described in Example 1.1, providing 3-(4-bromo-2-methyl-2H-pyrazol-3-yl)-4-(2-dimethylamino-ethoxy)-phenylamine (0.067 g, 0.20 mmol, 56%) as an oil. LCMS m/z (%)=339 (M+H$^{79}$Br, 78), 341 (M+H$^{81}$Br, 100). $^1$H NMR (400 MHz, acetone-d$_6$) δ: 7.68 (dd, J=2.5, 8.9 Hz, 1H), 7.55 (s, 1H), 7.45-7.51 (m, 2H), 4.62-4.82 (m, 2H), 3.76 (s, 3H), 3.65-3.76 (m, 2H), 2.87 (s, 6H).

The intermediate {2-[2-(4-bromo-2-methyl-2H-pyrazol-3-yl)-4-nitro-phenoxy]-ethyl}-dimethyl-amine was prepared in the following manner:

A. Dimethyl-{2-[2-(2-methyl-2H-pyrazol-3-yl)-4-nitro-phenoxy]-ethyl}-amine: 2-(2-Methyl-2H-pyrazol-3-yl)-4-nitro-phenol (0.344 g, 1.57 mmol) was treated with NaH (0.252 g, 6.29 mmol, 4.0 equiv.) and 2-(dimethylamino) ethyl chloride hydrochloride (0.458 g, 3.14 mmol, 2.0 equiv.) in a mixture of DMF/THF (2 mL/10 mL), in a similar manner as described in Example 1.31, Step B, providing dimethyl-{2-[2-(2-methyl-2H-pyrazol-3-yl)-4-nitro-phenoxy]-ethyl}-amine (0.280 g, 0.96 mmol, 62%) as a yellow solid. LCMS m/z (%)=291 (M+H). $^1$H NMR (400 MHz, CDCl$_3$) δ: 8.31 (dd, J=2.8, 9.1 Hz, 1H), 8.18 (d, J=2.8 Hz, 1H), 7.52 (d, J=1.9 Hz, 1H), 7.08 (d, J=9.1 Hz, 1H), 6.30 (d, J=1.9 Hz, 1H), 4.20 (t, J=5.7 Hz, 2H), 3.76 (s, 3H), 2.69 (t, J=5.7 Hz, 2H), 2.22 (s, 6H).

B. {2-[2-(4-Bromo-2-methyl-2H-pyrazol-3-yl)-4-nitro-phenoxy]-ethyl}-dimethyl-amine: Dimethyl-{2-[2-(2-methyl-2H-pyrazol-3-yl)-4-nitro-phenoxy]-ethyl}-amine (0.239 g, 0.82 mmol) in CH$_2$Cl$_2$ (10 mL) was added Br$_2$ (47 μL, 0.145 g, 0.91 mmol, 1.1 equiv.) in CH$_2$Cl$_2$ (3.5 mL) dropwise at 0° C, the mixture was stirred at this temperature for 3 hrs. More Br$_2$ (40 μL) was added and the mixture was stirred for another 2 hrs in order to consume the rest of the starting material. It was quenched by saturated $Na_2S_2O_3$, washed with saturated $NaHCO_3$ and the aqueous phase was extracted with EtOAc. The combined organic phase was washed with brine, dried over $MgSO_4$, filtered and evaporated. The crude reaction mixture was purified by HPLC to provide {2-[2-(4-bromo-2-methyl-2H-pyrazol-3-yl)-4-nitrophenoxy]-ethyl}-dimethyl-amine (0.128 g, 0.35 mmol, 42%). LCMS m/z (%)=369 (M+H$^{79}$Br, 100), 371 (M+H$^{81}$Br, 97). $^1$H NMR (400 MHz, CDCl$_3$) δ: 8.45 (dd, J=2.6, 9.2 Hz, 1H), 8.21 (d, J=2.6 Hz, 1H), 7.59 (s, 1H), 7.19 (d, J=9.2 Hz, 1H), 4.34-4.56 (m, 2H), 3.60 (s, 3H), 3.23-3.50 (m, 2H), 2.59 (s, 6H).

Example 1.47:

Preparation of 1-[3-(4-Bromo-2-methyl-2H-pyrazol-3-yl)-4-(2-dimethylamino-ethoxy)-phenyl]-3-(4-Chloro-phenyl)-urea (Compound 69).

To a stirred solution of 3-(4-bromo-2-methyl-2H-pyrazol-3-yl)-4-(2-dimethylamino-ethoxy)-phenylamine (0.033 g, 0.10 mmol) in $CH_2Cl_2$ (2.0 mL) was added 4-chlorophenyl isocyanate (0.017 g, 0.11 mmol, 1.1 equiv.). The solvent was removed after the completion of the reaction and it was purified by the HPLC. The pure fractions were collected and $CH_3CN$ was evaporated under vacuum. The residue was diluted with EtOAc and neutralized with saturated $NaHCO_3$, the EtOAc phase was washed with brine, dried over $MgSO_4$, filtered and evaporated. Compound 69 was obtained in 85% yield. LCMS m/z (%)=492 (M+H$^{79}$Br$^{35}$Cl, 78), 494 (M+H$^{81}$Br$^{35}$Cl, 100), 496 (M+H$^{81}$Br$^{37}$Cl, 28). $^1$H NMR (400 MHz, acetone-d$_6$) δ: 8.27 (s, 1H), 8.20 (1H), 7.66 (dd, J=2.7, 9.0 Hz, 1H), 7.56 (d, J=8.9 Hz, 2H), 7.48 (s, 1H), 7.43 (d, J=2.7 Hz, 1H), 7.29 (d, J=8.9 Hz, 2H), 7.14 (d, J=9.0 Hz, 1H), 3.98-4.20 (m, 2H), 3.73 (s, 1H), 2.48-2.68 (m, 2H), 2.16 (s, 6H).

Example 1.48:

Preparation of 1-[3-(4-Bromo-2-methyl-2H-pyrazol-3-yl)-4-(2-dimethylamino-ethoxy)-phenyl]-3-(4-fluoro-phenyl)-urea (Compound 70).

3-(4-Bromo-2-methyl-2H-pyrazol-3-yl)-4-(2-dimethyl-amino-ethoxy)-phenylamine (0.034 g, 0.10 mmol) was treated with 4-fluorophenyl isocyanate (0.015 g, 12.5 μL, 0.11 mmol, 1.1 equiv.) in $CH_2Cl_2$ (2 mL) in a similar manner as described in Example 1.47 to afford Compound 70 (0.020 g, 0.04 mmol, 42%). LCMS m/z (%)=476 (M+H$^{79}$Br, 100), 478 (M+H$^{81}$Br, 87). $^1$H NMR (400 MHz, acetone-d$_6$) δ: 8.17 (s, 2H), 7.66 (dd, J=2.7, 9.0 Hz, 1H), 7.50-7.58 (m, 2H), 7.48 (s, 1H), 7.43 (d, J=2.7 Hz, 1H), 7.13 (d, J=9.0 Hz, 1H), 7.04 (t, J=8.8 Hz, 2H), 3.98-4.20 (m, 2H), 3.73 (s, 3H), 2.49-2.66 (m, 2H), 2.16 (s, 6H).

Example 1.49:

Preparation of 1-[3-(4-Bromo-2-methyl-2H-pyrazol-3-yl)-4-hydroxy-phenyl]-3-(4-chloro-phenyl)-urea (Compound 58).

To Compound 1 (see Example 1.16) in $CH_2Cl_2$ (1.170 g, 2.68 mmol) was added anhydrous $AlCl_3$ (1.432 g, 10.74 mmol, 4.0 equiv.) slowly at 0° C, it was stirred under reflux overnight and then quenched with saturated $NaHCO_3$. The mixture was extracted with EtOAc, the combined organic phase was washed with water and brine, dried over $MgSO_4$, filtered and evaporated. It was first purified with $SiO_2$ column chromatography (Eluent: EtOAc/Hexane=1/3 to 1/1) and the major fractions containing Compound 58 were then purified by HPLC. The pure fractions were neutralized with saturated $NaHCO_3$, extracted with EtOAc and dried with anhydrous $MgSO_4$. $MgSO_4$ was filtered and the solvent was removed under vacuum to provide Compound 58 as a white solid. LCMS m/z (%)=421 (M+H$^{79}$Br$^{35}$Cl, 69), 423 (M+H$^{81}$Br$^{35}$Cl, 100), 425 (M+H$^{81}$Br$^{37}$Cl, 21). $^1$H NMR (400 MHz, acetone-d$_6$) δ: 8.47 (s, 1H), 8.16 (s, 1H), 8.04 (s, 1H), 7.44 (d, J=8.9 Hz, 2H), 7.38-7.43 (m, 1H), 7.35 (s, 1H), 7.26 (d, J=2.6 Hz, 1H), 7.15 (d, J=8.9 Hz, 2H), 6.87 (d, J=8.8 Hz, 1H), 3.62 (s, 3H).

Example 1.50:

Preparation of Intermediate 4-Methoxy-3-(2-methyl-2H-pyrazol-3-yl)-phenylamine.

5-(2-Methoxy-5-nitro-phenyl)-1-methyl-1H-pyrazole (2.11 g, 9.06 mmol) was treated with $SnCl_2.2H_2O$ (8.341 g, 36.22 mmol, 4.0 equiv.) in EtOH (50 mL), in a similar manner as described in Example 1.1, providing 4-methoxy-3-(2-methyl-2H-pyrazol-3-yl)-phenylamine (1.592 g, 7.8 3 mmol, 87%) as an oil. LCMS m/z (%)=204 (M+H). $^1$H NMR (400 MHz, CDCl$_3$) δ: 7.51 (d, J=1.8 Hz, 1H), 6.83 (d, J=8.7 Hz, 1H), 6.76 (dd, J=2.8, 8.7 Hz, 1H), 6.62 (d, J=2.8 Hz, 1H), 6.22 (d, J=1.8 Hz, 1H), 3.74 (s, 3H), 3.73 (s, 3H), 3.24-3.55 (broad s, 2H).

Example 1.51:

Preparation of 1-(4-Chloro-phenyl)-3-[4-methoxy-3-(2-methyl-2H-pyrazol-3-yl)-phenyl]-urea (Compound 75).

4-Methoxy-3-(2-methyl-2H-pyrazol-3-yl)-phenylamine (0.291 g, 1.43 mmol) was treated with 4-chlorophenyl isocyanate (0.247 g, 1.57 mmol, 1.1 equiv.) in $CH_2Cl_2$ (5 mL), in a similar manner as described in Example 1.2 to afford Compound 75 (0.415 g, 1.16 mmol, 81%) as a white solid. LCMS m/z (%)=357 (M+H). $^1$H NMR (400 MHz, acetone-d$_6$) δ: 8.21 (s, 1H), 8.07 (s, 1H), 7.58 (dd, J=2.8, 8.9 Hz, 1H), 7.56 (d, J=8.8 Hz, 2H), 7.44 (d, J=2.7 Hz, 1H), 7.39 (d, J=1.8 Hz, 1H), 7.28 (d, J=8.8 Hz, 2H), 7.08 (d, J=8.9 Hz, 1H), 6.20 (d, J=1.8 Hz, 1H), 3.81 (s, 3H), 3.68 (s, 3H).

Example 1.52:

Preparation of Intermediate 3-(4-Chloro-2-methyl-2H-pyrazol-3-yl)-4-methoxy-phenylamine.

4-Chloro-5-(2-methoxy-5-nitro-phenyl)-1-methyl-1H-pyrazole (2.27 g, 8.5 mmol) was dissolved in dry EtOH (150 mL) and heated to 75° C. The heated solution was then treated with Sn(II) chloride dihydrate (9.6 g, 42.5 mmol) and stirred at 75° C After three hours, the reaction was found to be complete by TLC and LCMS. The solvent was removed under reduced pressure. The residue was subsequently diluted with EtOAc (100 mL) and 1N NaOH, neutralizing the reaction to a pH of approximately 6 or 7. The mix was then filtered through celite. The organic layer was separated, and the aqueous layer was extracted with EtOAc (2×50 mL). The organic layers were combined, dried over $Na_2SO_4$, filtered, and the solvent removed under reduced pressure. The residue was then purified by flash chromatography (Biotage, $SiO_2$, Hexanes/EtOAc gradient elution) to afford 1.73 g (86%) of 3-(4-chloro-2-methyl-2H-pyrazol-3-yl)-4-methoxy-phenylamine as a light brown solid. LCMS m/z (%)=240 (M+H$^{37}$Cl, 37), 238 (M+H$^{35}$Cl, 100). $^1$H NMR (400 MHz, CDCl$_3$) δ: 7.48 (s, 1H), 6.87 (d, J=8, 1H), 6.81 (dd, J$_1$=8, J$_2$=4, 1H), 6.63 (d, J=4, 1H), 3.72 (s, 3H), 3.70 (s, 3H).

The intermediate 4-chloro-5-(2-methoxy-5-nitro-phenyl)-1-methyl-1H-pyrazole was prepared in the following manner:

5-(2-Methoxy-5-nitro-phenyl)-1-methyl-1H-pyrazole (2.37 g, 10.17 mmol) was dissolved in DMF (100 mL). The solution was then heated to 80° C N-Chlorosuccinimide (1.49 g, 11.1 mmol) was added at 80° C under Argon gas. After two hours of continuous stirring, the reaction was checked by TLC and LCMS, and found to be incomplete. An additional aliquot of NCS (0.5 g, 3.7 mmol) was added, bringing the reaction to completion after 1.5 hours. While stirring, a portion of water (200 mL) was added to force the product to precipitate out of solution. After the precipitation was complete, the flask containing the solid was cooled in an ice water bath for 10 minutes. The solid was then filtered under vacuum and rinsed with water, yielding 2.4 g (89%) of 4-chloro-5-(2-methoxy-5-nitro-phenyl)-1-methyl-1H-pyrazole. This material was used in the next step without purification. LCMS m/z (%)=267 (M+H, 100). $^1$H NMR (400 MHz, CDCl$_3$) δ: 8.41 (dd, J$_1$=8 Hz, J$_2$=4 Hz, 1H), 8.22 (d, J=4 Hz, 1H), 7.53 (s, 1H), 7.14 (d, J=12 Hz, 1H), 3.97 (s, 3H), 3.72 (s, 3H).

Example 1.53:

Preparation of 1-[3-(4-Chloro-2-methyl-2H-pyrazol-3-yl)-4-methoxy-phenyl]-3-(4-fluoro-phenyl)-urea (Compound 28).

3-(4-Chloro-2-methyl-2H-pyrazol-3-yl)-4-methoxy-phenylamine (20 mg, 0.08 mmol) was dissolved in anhydrous CH$_2$Cl$_2$ (150 mL) and treated with 4-Fluorophenyl isocyanate, Compound 28 began to precipitate out immediately as a white solid. The reaction was stirred at room temperature for three hours. Then, the flask containing the solid was cooled in an ice water bath for 20 minutes. The solid was then filtered under vacuum and rinsed with CH$_2$Cl$_2$, yielding 17.7 mg (26%) of Compound 28. LCMS m/z (%)=377 (M+H$^{37}$Cl, 39), 375 (M+H$^{35}$Cl, 100). $^1$H NMR (400 MHz, DMSO-d$_6$) δ: 8.95 (s, 1H), 8.93 (s, 1H), 7.86 (s, 1H), 7.81 (dd, J$_1$=8 Hz, J$_2$=4 Hz, 1H), 7.71 (dd, J$_1$=8 Hz, J$_2$=4 Hz, 2H), 7.62 (d, J=2, 1H), 7.41 (d, J=12 Hz, 1H), 7.38 (t, J=12 Hz, 2H), 4.01 (s, 3H), 3.86 (s, 3H).

Example 1.54:

Preparation of 1-[3-(4-Chloro-2-methyl-2H-pyrazol-3-yl)-4-methoxy-phenyl]-3-(3-fluoro-phenyl)-urea (Compound 36).

3-(4-Chloro-2-methyl-2H-pyrazol-3-yl)-4-methoxy-phenylamine was treated with 3-Fluorophenyl isocyanate in a similar manner to as described in Example 1.53, providing 0.5 mg (1%) of Compound 36: LCMS m/z (%)=377 (M+H$^{37}$Cl, 40), 375 (M+H$^{35}$Cl, 100). $^1$H NMR (400 MHz, acetone-d$_6$) δ: 8.23 (s, 1H), 7.45 (dt, J$_1$=12, J$_2$=4, J$_3$=2 Hz, 1H), 7.37 (s, 1H), 7.32 (s, 1H), 7.17 (d, J=24 Hz, 1H), 7.15 (dd, J$_1$=8 Hz, J$_2$=2 Hz, 1H), 7.03 (dd, J$_1$=8 Hz, J$_2$=4 Hz, 1H), 6.77 (d, J=2 Hz, 1H), 6.63 (td, J$_1$=8 Hz, J$_2$=4 Hz, 1H), 3.68 (s, 3H), 3.52 (s, 3H).

Example 1.55:

Preparation of 1-[3-(4-Chloro-2-methyl-2H-pyrazol-3-yl)-4-methoxy-phenyl]-3-(2,4-difluoro-phenyl)-urea (Compound 29).

3-(4-Chloro-2-methyl-2H-pyrazol-3-yl)-4-methoxy-phenylamine was treated with 2,4-difluorophenyl isocyanate in a similar manner as described in Example 1.53, providing 26.7 mg (36%) of Compound 29: LCMS m/z (%)=395 (M+H$^{37}$Cl, 35), 393 (M+H$^{35}$Cl, 100). $^1$H NMR (400 MHz, DMSO-d$_6$) δ: 9.00 (s, 1H), 8.43 (s, 1H), 8.03 (m, J$_1$=12 Hz, J$_2$=4 Hz, 1H), 7.56 (s, 1H), 7.50 (dd, J$_1$=8 Hz, J$_2$=4 Hz, 1H), 7.34 (d, J=4 Hz, 1H), 7.28 (m, J$_1$=12 Hz, J$_2$=4 Hz, 1H), 7.12 (d, J=8 Hz, 1H), 7.01 (m, J$_1$=8 Hz, J$_2$=2 Hz, 1H), 3.72 (s, 3H), 3.56 (s, 3H).

Example 1.56:

Preparation of 1-[3-(4-Chloro-2-methyl-2H-pyrazol-3-yl)-4-methoxy-phenyl]-3-(3-methoxy-phenyl)-urea (Compound 30).

3-(4-Chloro-2-methyl-2H-pyrazol-3-yl)-4-methoxy-phenylamine was treated with 3-Methoxyphenyl isocyanate in a similar manner as described in Example 1.53, providing 7.5 mg (27%) of Compound 30 (Note: Compound 30 did not precipitate out. Therefore, the CH$_2$Cl$_2$ was removed under reduced pressure, the residue was dissolved in 5 mL DMSO, and purified by preparative HPLC): LCMS m/z (%)=389 (M+H$^{37}$Cl, 39), 387 (M+H$^{35}$Cl, 100). $^1$H NMR (400 MHz, acetone-d$_6$) δ: 7.99 (s, 1H), 7.49 (dd, J$_1$=8 Hz, J$_2$=2 Hz, 1H), 7.29 (d, J=8 Hz, 1H), 7.28 (s, 1H), 7.12 (t, J=2 Hz, 1H), 6.95 (d, J=2 Hz, 1H), 6.93 (d, J=4 Hz, 1H), 6.81 (dd, J$_1$=8 Hz, J$_2$=4 Hz, 1H), 6.37 (dd, J$_1$=8 Hz, J$_2$=4 Hz, 1H), 3.63 (s, 3H), 3.57 (s, 3H), 3.47 (s, 3H).

Example 1.57:

Preparation of 1-[3-(4-Chloro-2-methyl-2H-pyrazol-3-yl)-4-methoxy-phenyl]-3-(2-trifluoromethoxy-phenyl)-urea (Compound 34).

3-(4-Chloro-2-methyl-2H-pyrazol-3-yl)-4-methoxy-phenylamine was treated with 2-trifluoromethoxyphenyl isocyanate in a similar manner as described in Example 1.53, providing 1.5 mg (3%) of Compound 34: LCMS m/z (%)=440 (M+H$^{37}$Cl, 14), 438 (M+H$^{35}$Cl, 14). $^1$H NMR (400 MHz, acetone-d$_6$) δ: 8.19 (s, 1H), 7.90 (s, 1H), 7.43 (d, J=4 Hz, 1H), 7.25 (s, 1H), 7.04 (t, J=12 Hz, 2H), 6.99 (dd, J$_1$=8 Hz, J$_2$=2 Hz, 1H), 6.75 (d, J=4 Hz, 1H), 6.72 (d, J=4 Hz, 1H), 6.66 (d, J=2 Hz, 1H), 3.63 (s, 3H), 3.45 (s, 3H).

Example 1.58:

Preparation of 1-(3-Acetyl-phenyl)-3-[3-(4-Chloro-2-methyl-2H-pyrazol-3-yl)-4-methoxy-phenyl]-urea (Compound 35).

3-(4-Chloro-2-methyl-2H-pyrazol-3-yl)-4-methoxy-phenylamine was treated with 3-Acetylphenyl isocyanate in a similar manner as described in Example 1.53, providing 3.7 mg (6%) of Compound 35 (Note: Compound 35 did not precipitate out. Therefore, the CH$_2$Cl$_2$ was removed under reduced pressure, the residue was dissolved in 5 mL DMSO, and purified by preparative HPLC): LCMS m/z (%)=401 (M+H$^{37}$Cl, 27), 399 (M+H$^{35}$Cl, 100). $^1$H NMR (400 MHz, acetone-$d_6$) δ: 8.91 (s, 1H), 8.80 (s, 1H), 8.23 (s, 1H), 7.84 (d, J=8 Hz, 1H), 7.75 (dd, $J_1$=12 Hz, $J_2$=3 Hz, 1H), 7.62 (d, J=8 Hz, 1H), 7.56 (d, J=4 Hz, 1H), 7.49 (s, 1H), 7.43 (t, J=8 Hz, 1H), 7.16 (d, J=8 Hz, 1H), 3.84 (s, 3H), 3.69 (s, 3H), 3.42 (s, 3H).

Example 1.59:

Preparation of 1-[3-(4-Chloro-2-methyl-2H-pyrazol-3-yl)-4-methoxy-phenyl]-3-(4-Chloro-phenyl)-urea (Compound 26).

3-(4-Chloro-2-methyl-2H-pyrazol-3-yl)-4-methoxy-phenylamine was treated with 4-chlorophenyl isocyanate in a similar manner as described in Example 1.53, providing 12 mg (30%) of Compound 26: LCMS m/z (%)=393 (M+H$^{37}$Cl, 60), 391 (M+H$^{35}$Cl, 100). $^1$H NMR (400 MHz, DMSO-$d_6$) δ: 8.80 (s, 1H), 8.71 (s, 1H), 7.62 (s, 1H), 7.57 (dd, $J_1$=8 Hz, $J_2$=4 Hz, 1H), 7.49 (dd, $J_1$=8 Hz, $J_2$=2 Hz, 2H), 7.39 (d, J=4 Hz, 1H), 7.33 (dd, $J_1$=8 Hz, $J_2$=2 Hz, 2H), 7.17 (d, J=8 Hz, 1H), 3.77 (s, 3H), 3.62 (s, 3H).

Example 1.60:

Preparation of 1-[3-(4-Chloro-2-methyl-2H-pyrazol-3-yl)-4-methoxy-phenyl]-3-(4-isopropyl-phenyl)-urea (Compound 76).

3-(4-Chloro-2-methyl-2H-pyrazol-3-yl)-4-methoxy-phenylamine was treated with 4-isopropylphenyl isocyanate in a similar manner as described in Example 1.53, providing 1.3 mg (2%) of Compound 76 (Note: Compound 76 did not precipitate out. Therefore, the CH$_2$Cl$_2$ was removed under reduced pressure, the residue was dissolved in 5 mL DMSO, and purified by preparative HPLC): LCMS m/z (%)=401 (M+H$^{37}$Cl, 31), 399 (M+H$^{35}$Cl, 100). $^1$H NMR (400 MHz, acetone-$d_6$) δ: 8.63 (s, 1H), 8.52 (s, 1H), 7.59 (dd, $J_1$=8 Hz, $J_2$=4 Hz, 1H), 7.41 (d, J=2 Hz, 1H), 7.37 (dd, $J_1$=12 Hz, $J_2$=2 Hz, 2H), 7.33 (s, 1H), 7.17 (dd, $J_1$=8 Hz, $J_2$=2 Hz, 2H), 7.00 (d, J=12 Hz, 1H), 3.68 (s, 3H), 3.54 (s, 3H).

Example 1.61:

Preparation of 1-[3-(4-Chloro-2-methyl-2H-pyrazol-3-yl)-4-methoxy-phenyl]-3-(2,4-dichloro-phenyl)-urea (Compound 77).

3-(4-Chloro-2-methyl-2H-pyrazol-3-yl)-4-methoxy-phenylamine was treated with 2,4-dichlorophenyl isocyanate in a similar manner as described in Example 1.53, providing 16.4 mg (24%) of Compound 77 (Note: Compound 77 did not precipitate out. Therefore, the CH$_2$Cl$_2$ was removed under reduced pressure, the residue was dissolved in 5 mL DMSO, and purified by preparative HPLC): LCMS m/z (%)=427 (M+H$^{37}$Cl, 72), 425 (M+H$^{35}$Cl, 100). $^1$H NMR (400 MHz, acetone-$d_6$) δ: 8.85 (s, 1H), 8.26 (dd, $J_1$=12 Hz, $J_2$=4 Hz, 1H) 7.90 (s, 1H), 7.59 (dd, $J_1$=8 Hz, $J_2$=4 Hz, 1H), 7.38 (d, J=4 Hz, 1H), 7.36 (s, 1H), 7.36 (s, 1H), 7.24 (dd, $J_1$=12 Hz, $J_2$=4 Hz, 1H), 7.05 (d, J=8 Hz, 1H), 3.72 (s, 3H), 3.56 (s, 3H).

Example 1.62:

Preparation of 1-[3-(4-Chloro-2-methyl-2H-pyrazol-3-yl)-4-methoxy-phenyl]-3-naphthalen-1-yl-urea (Compound 78).

3-(4-Chloro-2-methyl-2H-pyrazol-3-yl)-4-methoxy-phenylamine was treated with 1-naphthyl isocyanate in a similar manner as described in Example 1.53, providing 21.1 mg (60%) of Compound 78: LCMS m/z (%)=409 (M+H$^{37}$Cl, 38), 407 (M+H$^{35}$Cl, 100). $^1$H NMR (400 MHz, DMSO-$d_6$) δ: 9.02 (s, 1H), 8.71 (s, 1H), 8.10 (d, J=8 Hz, 1H), 7.96 (d, J=8 Hz, 1H), 7.91 (d, J=8 Hz, 1H), 7.61 (s, 1H), 7.59 (t, J=4 Hz, 1H), 7.58 (s, 1H), 7.56 (t, J=2 Hz, 1H), 7.54 (dd, $J_1$=4 Hz, $J_2$=2 Hz, 1H), 7.45 (d, J=8 Hz, 1H), 7.41 (d, J=4 Hz, 1H), 7.16 (d, J=8 Hz, 1H), 3.75 (s, 3H), 3.60 (s, 3H).

Example 1.63:

Preparation of 1-[3-(4-Chloro-2-methyl-2H-pyrazol-3-yl)-4-methoxy-phenyl]-3-(4-chloro-2-trifluoromethyl-phenyl)-urea (Compound 79).

3-(4-Chloro-2-methyl-2H-pyrazol-3-yl)-4-methoxy-phenylamine was treated with 4-chloro-2-trifluoromethylphenyl isocyanate in a similar manner as described in Example 1.53, providing 4.4 mg (8%) of Compound 79 (Note: Compound 79 did not precipitate out. Therefore, the CH$_2$Cl$_2$ was removed under reduced pressure, the residue was dissolved in 5 mL DMSO, and purified by preparative HPLC): LCMS m/z (%)=461 (M+H$^{37}$Cl, 60), 459 (M+H$^{35}$Cl, 100). $^1$H NMR (400 MHz, acetone-$d_6$) δ: 8.99 (s, 1H), 8.30 (s, 1H), 8.16 (dd, $J_1$=8 Hz, $J_2$=2 Hz, 1H), 8.01 (d, J=8 Hz, 1H), 7.66 (s, 1H), 7.64 (d, J=4 Hz, 1H), 7.45 (d, J=4 Hz, 1H), 7.43 (s, 1H), 7.12 (d, J=8 Hz, 1H), 3.79 (s, 3H), 3.63 (s, 3H).

Example 1.64:

Preparation of 1-[3-(4-Chloro-2-methyl-2H-pyrazol-3-yl)-4-methoxy-phenyl]-3-(4-trifluoromethyl-phenyl)-urea (Compound 80).

3-(4-Chloro-2-methyl-2H-pyrazol-3-yl)-4-methoxy-phenylamine was treated with 4-trifluoromethylphenyl isocyanate in a similar manner as described in Example 1.53, providing 8 mg (15%) of Compound 80 (Note: Compound 80 did not precipitate out. Therefore, the CH$_2$Cl$_2$ was removed under reduced pressure, the residue was dissolved in 5 mL DMSO, and purified by preparative HPLC): LCMS m/z (%)=427 (M+H$^{37}$Cl, 22), 425 (M+H$^{35}$Cl, 100). $^1$H NMR (400 MHz, acetone-$d_6$) δ: 8.48 (s, 1H), 8.24 (s, 1H), 7.56 (d, J=8 Hz, 2H), 7.50 (dd, $J_1$=8 Hz, $J_2$=2 Hz, 1H), 7.40 (d, J=8 Hz, 1H), 7.28 (d, J=4 Hz, 1H), 7.27 (s, 1H), 6.96 (d, J=12 Hz, 1H), 3.62 (s, 3H), 3.46 (s, 3H).

Example 1.65:

Preparation of 1-(4-Bromo-phenyl)-3-[3-(4-chloro-2-methyl-2H-pyrazol-3-yl)-4-methoxy-phenyl]-urea (Compound 81).

3-(4-Chloro-2-methyl-2H-pyrazol-3-yl)-4-methoxy-phenylamine was treated with 4-bromophenyl isocyanate in a similar manner as described in Example 1.53, providing 2.3 mg (6%) of Compound 81: LCMS m/z (%)=437 (M+H$^{37}$Cl, 100), 435 (M+H$^{35}$Cl, 82). $^1$H NMR (400 MHz, DMSO-$d_6$) δ: 8.97 (d, J=2 Hz, 2H), 8.80 (s, 1H), 8.70 (s, 1H), 7.61 (s, 1H), 7.53 (dd, $J_1$=12 Hz, $J_2$=8 Hz, 1H), 7.44 (t, J=4 Hz, 2H), 7.35 (d, J=4 Hz, 1H), 7.13 (d, J=8 Hz, 1H), 3.74 (s, 3H), 3.58 (s, 3H).

Example 1.66:

Preparation of 1-(3,5-Bis-trifluoromethyl-phenyl)-3-[3-(4-chloro-2-methyl-2H-pyrazol-3-yl)-4-methoxy-phenyl]-urea (Compound 82).

3-(4-Chloro-2-methyl-2H-pyrazol-3-yl)-4-methoxy-phenylamine was treated with 3,5-Bis(trifluoromethyl)phenyl isocyanate in a similar manner as described in Example 1.53, providing 21.5 mg (32%) of Compound 82: LCMS m/z (%)=495 (M+H$^{37}$Cl, 41), 493 (M+H$^{35}$Cl, 100). $^1$H NMR (400 MHz, DMSO-d$_6$) δ: 9.58 (s, 1H), 9.18 (s, 1H), 8.31 (s, 2H), 7.80 (s, 1H), 7.79 (s, 1H), 7.79 (dd, J$_1$=8 Hz, J$_2$=4 Hz, 1H), 7.59 (d, J=2 Hz, 1H), 7.36 (d, J=8 Hz, 1H), 3.96 (s, 3H), 3.80 (s, 3H).

Example 1.67:

Preparation of Intermediate 3-(4-Fluoro-2-methyl-2H-pyrazol-3-yl)-4-methoxy-phenylamine.

Two reduction methods were utilized in the preparation of the 3-(4-Fluoro-2-methyl-2H-pyrazol-3-yl)-4-methoxy-phenylamine as shown below:

Reduction Method A: 4-Fluoro-5-(2-methoxy-5-nitro-phenyl)-1-methyl-1H-pyrazole (205 mg, 0.817 mmol) in EtOH (25 mL) was treated with Sn(II) chloride dihydrate (626.3 mg, 2.45 mmol) and heated to 50° C for 12 hours. The reaction was allowed to cool to room temperature and 10% NaOH (100 ml) was added. EtOAc (50 ml) was added and the organic layer was separated. The aqueous layer was extracted with EtOAc (2×50 mL) and the organics combined, dried over Na$_2$SO$_4$, filtered, and the solvent removed under reduced pressure. The residue was dissolved in DMSO (5 ml), and purified by preparative HPLC to afford 85 mg (47%) of 3-(4-fluoro-2-methyl-2H-pyrazol-3-yl)-4-methoxy-phenylamine as a light brown oil. LCMS m/z (%)=222 (M+H, 100). $^1$H NMR (400 MHz, CDCl$_3$) δ: 7.38 (d, J$_{H,F}$=4.8 Hz, 1H), 6.86 (d, J=8.8 Hz, 1H), 6.79 (dd, J$_1$=8.8 Hz, J$_2$=2.8 Hz, 1H), 6.64 (d, J=2.8 Hz, 1H), 3.75 (s, 3H), 3.69 (s, 3H), 3.21 (s, 2H). $^{19}$F NMR (376 MHz, CDCl$_3$) δ: −175.50 (d, J$_{H,F}$=5.3 Hz, 1F).

Reduction Method B: 4-Fluoro-5-(2-methoxy-5-nitro-phenyl)-1-methyl-1H-pyrazole (109 mg, 0.434 mmol) in EtOH (10 mL) was treated with Pd—C(10 wt. %, Degussa) and a balloon of H$_2$ was allowed to bubble through the slurry. The reaction mixture was filtered through celite and the solvent was removed under reduced pressure to afford 93 mg (97%) of 3-(4-fluoro-2-methyl-2H-pyrazol-3-yl)-4-methoxy-phenylamine as a light brown oil. LCMS m/z (%)=222 (M+H, 100). $^1$H NMR (400 MHz, CDCl$_3$) δ: 7.38 (d, J$_{H,F}$=4.4 Hz, 1H), 6.86 (d, J=8.8 Hz, 1H), 6.78 (dd, J$_1$=8.8 Hz, J$_2$=2.8 Hz, 1H), 6.63 (d, J=2.8 Hz, 1H), 3.74 (s, 3H), 3.68 (s, 3H), 3.53 (s, 2H). $^{19}$F NMR (376 MHz, CDCl$_3$) δ: −175.50 (d, J$_{H\ F}$=5.3 Hz, 1F).

The intermediate 4-fluoro-5-(2-methoxy-5-nitro-phenyl)-1-methyl-1H-pyrazole used in Reduction Methods A and B was prepared in the following manner:

5-(2-Methoxy-5-nitro-phenyl)-1-methyl-1H-pyrazole (300.0 mg, 1.29 mmol) was dissolved in ACN (15 ml) in a polypropylene 20 mL scintillation vial. To this solution, Selectfluor (913.9 mg, 2.58 mmol) was added and the mixture was degassed with argon and heated to 80° C for 6 hours. The solvent was removed under reduced pressure and the residue was dissolved in 50 mL EtOAc and 30 mL 3N HCl. The organic layer was separated and the aqueous layer was extracted with EtOAc (2×50 ml). The organic layers were combined, dried over Na$_2$SO$_4$, filtered, and the solvent removed under reduced pressure. The residue was then purified by flash chromatography (Biotage SiO$_2$, Hexanes (0.01% TEA)/EtOAc gradient elution) to afford 108 mg (33%) of 4-fluoro-5-(2-methoxy-5-nitro-phenyl)-1-methyl-1H-pyrazole as a white solid. LCMS m/z (%)=252 (M+H, 100). $^1$H NMR (400 MHz, CDCl$_3$) δ: 8.39 (d, J=9.2 Hz, 1H), 8.22 (s, 1H), 7.44 (d, J$_{H,F}$=4.4 Hz, 1H), 7.12 (d, J=9.2 Hz, 1H) 3.98 (s, 3H), 3.77 (s, 3H). $^{19}$F NMR (376 MHz, CDCl$_3$) δ: −175.50 (d, J$_{H\ F}$=5.3 Hz, 1F).

Example 1.68:

Preparation of 1-(4-Chloro-phenyl)-3-[3-(4-fluoro-2-methyl-2H-pyrazol-3-yl)-4-methoxy-phenyl]-urea (Compound 27).

3-(4-Fluoro-2-methyl-2H-pyrazol-3-yl)-4-methoxy-phenylamine (49 mg, 0.22 mmol) was dissolved in 3 mL of CH$_2$Cl$_2$, treated with 4-chlorophenylisocyanate (40 mg, 0.27 mmol), and stirred at room temperature overnight. The solvent was removed under reduced pressure, dissolved in DMSO (5 ml), and purified by preparative HPLC to afford Compound 27 as a white solid, 41 mg, 49% yield: LCMS m/z (%)=377 (M+H$^{37}$Cl, 31), 375 (M+H$^{35}$Cl, 100). $^1$H NMR (400 MHz, acetone-d$_6$) δ: 8.77 (s, 1H), 8.67 (s, 1H), 7.66 (ddd, J$_1$=9.0 Hz, J$_2$=2.6 Hz, 1H), 7.60 (d, J=9.2 Hz, 2H), 7.54 (d, J=2.8 Hz, 1H), 7.38 (d, J$_{H,F}$=4.4 Hz, 1H), 7.27 (d, J=8.8 Hz, 2H), 7.12 (d, J=8.8 Hz, 1H), 3.83 (s, 3H), 3.65 (s, 3H). $^{19}$F NMR (376 MHz, acetone-d$_6$) δ: −177.39 (d, J$_{H,F}$=5.3 Hz, 1F).

Example 1.69:

Preparation of 1-[3-(4-Fluoro-2-methyl-2H-pyrazol-3-yl)-4-methoxy-phenyl]-3-(4-fluoro-phenyl)-urea (Compound 31).

3-(4-Fluoro-2-methyl-2H-pyrazol-3-yl)-4-methoxy-phenylamine (45 mg, 0.20 mmol) was dissolved in 3 mL of CH$_2$Cl$_2$, treated with 4-fluorophenylisocyanate (28 uL, 0.24 mmol), and stirred at room temperature overnight. The compound of interest precipitated out of solution and was filtered and washed with CH$_2$Cl$_2$ to afford Compound 31 as a white solid, 56 mg, 77% yield: LCMS m/z (%)=359 (M+H, 100). $^1$H NMR (400 MHz, acetone-d$_6$) δ: 8.12 (s, 1H), 8.08 (s, 1H), 7.63 (ddd, J$_1$=9.0 Hz, J$_2$=2.6 Hz, 1H), 7.54 (m, 2H), 7.48 (d, J=2.8 Hz, 1H), 7.38 (d, J$_{H,F}$=4.8 Hz, 1H), 7.13 (d, J=8.8 Hz, 1H), 7.05 (dd, J$_1$=9.0 Hz, J$_2$=9.0 Hz, 2H), 3.83 (s, 3H), 3.65 (s, 3H). $^{19}$F NMR (376 MHz, acetone-d$_6$) δ: −123.08 (m, 1F), −177.41 (d, J$_{H,F}$=5.3 Hz, 1F).

Example 1.70:

Preparation of 1-(3,4-Difluoro-phenyl)-3-[3-(4-fluoro-2-methyl-2H-pyrazol-3-yl)-4-methoxy-phenyl]-urea (Compound 32).

3-(4-Fluoro-2-methyl-2H-pyrazol-3-yl)-4-methoxy-phenylamine was treated with 3,4-difluorophenylisocyanate, in a similar manner as described in Example 1.69, providing 27 mg (63% yield) of Compound 32: LCMS m/z (%)=377 (M+H, 100). $^1$H NMR (400 MHz, acetone-d$_6$) δ: 8.28 (s, 1H), 8.12 (s, 1H), 7.74 (ddd, J$_1$=13.5 Hz, J$_2$=7.3 Hz, J$_3$=2.5 Hz, 1H), 7.63 (ddd, J$_1$=8.8 Hz, J$_2$=2.8 Hz, 1H), 7.47 (d, J=2.8 Hz, 1H), 7.38 (d, J$_{H,F}$=4.4 Hz, 1H), 7.16 (m, 3H), 3.84 (s, 3H), 3.65 (s, 3H). $^{19}$F NMR (376 MHz, acetone-d$_6$) δ: −138.89 (m, 1F), −148.38 (m, 1F), −177.40 (d, J$_{H,F}$=5.3 Hz, 1F).

Example 1.71:

Preparation of 1-[3-(4-Fluoro-2-methyl-2H-pyrazol-3-yl)-4-methoxy-phenyl]-3-(3-fluoro-phenyl)-urea (Compound 33).

3-(4-Fluoro-2-methyl-2H-pyrazol-3-yl)-4-methoxy-phenylamine was treated with 3-fluorophenylisocyanate, in a similar manner as described in Example 1.68, providing 15 mg (55% yield) of Compound 33: LCMS m/z (%)=359 (M+H, 100). $^1$H NMR (400 MHz, J acetone-$d_6$) δ: 8.38 (s, 1H), 8.21 (s, 1H), 7.64 (dd, $J_1$=9.0 Hz, $J_2$=2.6 Hz, 1H), 7.59 (d, J=12.0 Hz, 1H), 7.48 (d, J=2.8 Hz, 1H), 7.39 (d, $J_{H,F}$=4.8 Hz, 1H), 7.27 (dd, $J_1$=14.8 Hz, $J_2$=8.0 Hz, 1H), 7.15 (d, J=9.6 Hz, 1H), 7.12 (s, 1H), 6.72 (dd, $J_1$=9.6 Hz, $J_2$=7.2 Hz, 1H), 3.83 (s, 3H), 3.65 (s, 3H). $^{19}$F NMR (376 MHz, acetone-$d_6$) δ: −114.00 (m, 1F), −177.35 (d, $J_{H,F}$=3.8 Hz, 1F).

Example 1.72:

Preparation of 1-(2,4-Difluoro-phenyl)-3-[3-(4-fluoro-2-methyl-2H-pyrazol-3-yl)-4-methoxy-phenyl]-urea (Compound 37).

3-(4-Fluoro-2-methyl-2H-pyrazol-3-yl)-4-methoxy-phenylamine was treated with 2,4-difluorophenylisocyanate, in a similar manner as described in Example 1.68, providing 21 mg (58% yield) of Compound 37: LCMS m/z (%)=377 (M+H, 100). $^1$H NMR (400 MHz, acetone-$d_6$) δ: 8.50 (s, 1H), 8.24 (m, 1H), 7.98 (s, 1H), 7.64 (dd, $J_1$=9.0 Hz, $J_2$=2.6 Hz, 1H), 7.51 (d, J=2.4 Hz, 1H), 7.38 (d, $J_{H\,F}$=4.8 Hz, 1H), 7.14 (d, J=8.8 Hz, 1H), 7.06 (ddd, $J_1$=11.4 Hz, $J_2$=8.6 Hz, $J_3$=2.8 Hz, 1H), 6.99 (dd, $J_1$=9.6 Hz, $J_2$=9.6 Hz, 1H), 3.83 (s, 3H), 3.65 (s, 3H). $^{19}$F NMR (376 MHz, acetone-$d_6$) δ: −119.93 (m, 1F), −127.63 (m, 1F)−177.41 (d, $J_{H\,F}$=4.1 Hz, 1F).

Example 1.73:

Preparation of 1-(3-Chloro-phenyl)-3-[3-(4-fluoro-2-methyl-2H-pyrazol-3-yl)-4-methoxy-phenyl]-urea (Compound 83).

3-(4-Fluoro-2-methyl-2H-pyrazol-3-yl)-4-methoxy-phenylamine was treated with 3-chlorophenylisocyanate, in a similar manner as described in Example 1.68. An additional purification by flash chromatography ($SiO_2$, Hexanes/EtOAc gradient elution) was necessary, providing a 10 mg (27% yield) of Compound 83: LCMS m/z (%)=377 (M+H$^{37}$Cl, 25), 375 (M+H$^{35}$Cl, 100). $^1$H NMR (400 MHz, acetone-$d_6$) δ: 8.28 (s, 1H), 8.16 (s, 1H), 7.80 (s, 1H), 7.64 (dd, $J_1$=8.8 Hz, $J_2$=2.8 Hz 1H), 7.48 (d, J=2.8 Hz, 1H), 7.38 (d, $J_{H\,F}$=4.8 Hz, 1H), 7.34 (dd, $J_1$=9.2 Hz, $J_2$=0.8 Hz, 1H), 7.26 (dd, $J_1$=8.2, $J_2$=8.2 Hz, 1H), 7.13 (d, J=8.8 Hz, 1H), 7.00 (dd, $J_1$=8.8 Hz, $J_2$=0.8 Hz, 1H), 3.83 (s, 3H), 3.65 (s, 3H). $^{19}$F NMR (376 MHz, acetone-$d_6$) δ: −177.35 (d, $J_{H\,F}$=4.1 Hz, 1F).

Example 1.74:

Preparation of 1-(4-Bromo-phenyl)-3-[3-(4-fluoro-2-methyl-2H-pyrazol-3-yl)-4-methoxy-phenyl]-urea (Compound 85).

3-(4-Fluoro-2-methyl-2H-pyrazol-3-yl)-4-methoxy-phenylamine was treated with 4-bromophenylisocyanate, in a similar manner as described in Example 1.68, providing 27 mg (60% yield) of Compound 85: LCMS m/z (%)=421 (M+H$^{81}$Br, 100), 419 (M+H$^{79}$Br, 100). $^1$H NMR (400 MHz, acetone-$d_6$) δ: 8.24 (s, 1H), 8.13 (s, 1H), 7.63 (dd, $J_1$=9.0 Hz, $J_2$=2.6 Hz, 1H), 7.51 (d, J=8.8 Hz, 2H), 7.48 (d, J=2.8 Hz, 1H), 7.42 (d, J=8.8 Hz, 2H), 7.38 (d, $J_{H,F}$=4.4 Hz, 1H), 7.13 (d, J=9.2 Hz, 1H), 3.83 (s, 3H), 3.65 (s, 3H). $^{19}$F NMR (376 MHz, acetone-$d_6$) δ: −177.39 (d, $J_{H\,F}$=5.3 Hz, 1F).

Example 1.75:

Preparation of 1-[3-(4-Fluoro-2-methyl-2H-pyrazol-3-yl)-4-methoxy-phenyl]-3-(4-trifluoromethyl-phenyl)-thiourea (Compound 86).

3-(4-Fluoro-2-methyl-2H-pyrazol-3-yl)-4-methoxy-phenylamine was treated with 4-trifluoromethylphenylthioisocyanate, in a similar manner as described in Example 1.69. An additional purification by flash chromatography (Biotage $SiO_2$, Hexanes/EtOAc gradient elution) was necessary, providing 38 mg (68% yield) of Compound 86: LCMS m/z (%)=425 (M+H, 100). $^1$H NMR (400 MHz, acetone-$d_6$) δ: 9.32 (d, J=20.0 Hz, 2H), 7.83 (d, J=8.4 Hz, 2H), 7.67 (d, J=8.8 Hz, 2H), 7.61 (dd, $J_1$=8.8 Hz, $J_2$=2.8 Hz, 1H), 7.45 (d, J=2.4 Hz, 1H), 7.38 (d, $J_{H,F}$=4.8 Hz, 1H), 7.20 (d, J=8.8 Hz, 1H), 3.88 (s, 3H), 3.67 (s, 3H). $^{19}$F NMR (376 MHz, acetone-$d_6$) δ: −63.10 (s, 3F), −176.49 (d, $J_{H,F}$=4.1 Hz, 1F).

Example 1.76:

Preparation of 1-(4-Chloro-3-trifluoromethyl-phenyl)-3-[3-(4-fluoro-2-methyl-2H-pyrazol-3-yl)-4-methoxy-phenyl]-urea (Compound 84).

3-(4-Fluoro-2-methyl-2H-pyrazol-3-yl)-4-methoxy-phenylamine was treated with 4-chloro-3-trifluoromethylphenylisocyanate, in a similar manner as described in Example 1.68, providing 15 mg (29% yield) of Compound 84: LCMS m/z (%)=445 (M+H$^{37}$Cl, 34), 443 (M+H$^{35}$Cl, 100). $^1$H NMR (400 MHz, acetone-$d_6$) δ: 8.69 (s, 1H), 8.39 (s, 1H), 8.15 (d, J=2.4 Hz, 1H), 7.74 (dd, $J_1$=8.6 Hz, $J_2$=2.2 Hz 1H), 7.65 (dd, $J_1$=9.0 Hz, $J_2$=2.6 Hz, 1H), 7.53 (d, J=8.8 Hz, 1H), 7.49 (d, J=2.4 Hz, 1H), 7.38 (d, $J_{H\,F}$=4.4 Hz, 1H), 7.14 (d, J=9.2 Hz, 1H) 3.83 (s, 3H), 3.65 (s, 3H). $^{19}$F NMR (376 MHz, acetone-$d_6$) δ: −63.75 (s, 3F), −177.40 (d, $J_{H,F}$=5.3 Hz, 1F).

Example 1.77:

Preparation of 1-[3-(4-Fluoro-2-methyl-2H-pyrazol-3-yl)-4-methoxy-phenyl]-3-(4-methoxy-phenyl)-urea (Compound 87).

3-(4-Fluoro-2-methyl-2H-pyrazol-3-yl)-4-methoxy-phenylamine was treated with 4-methoxyphenylisocyanate, in a similar manner as described in Example 1.68. Additionally the residue was washed with $CH_2Cl_2$, providing 18 mg (29% yield) of Compound 87: LCMS m/z (%)=371 (M+H, 100). $^1$H NMR (400 MHz, acetone-$d_6$) δ: 8.06 (s, 1H), 7.95 (s, 1H), 7.63 (dd, $J_1$=8.8 Hz, $J_2$=2.8 Hz, 1H), 7.49 (d, J=2.8 Hz, 1H), 7.42 (d, J=8.4 Hz, 2H), 7.37 (d, $J_{H\,F}$=4.4 Hz, 1H), 7.11 (d, J=9.2 Hz, 1H), 6.85 (d, J=9.2 Hz, 2H), 3.82 (s, 3H), 3.75 (s, 3H), 3.65 (s, 3H). $^{19}$F NMR (376 MHz, acetone-$d_6$) δ: −177.41 (d, $J_{H,F}$=4.1 Hz, 1F).

Example 1.78:

Preparation of 1−(3-Acetyl-phenyl)-3-[3-(4-fluoro-2-methyl-2H-pyrazol-3-yl)-4-methoxy-phenyl]-urea (Compound 88).

3-(4-Fluoro-2-methyl-2H-pyrazol-3-yl)-4-methoxy-phenylamine was treated with 3-acetylphenylisocyanate, in a similar manner as described in Example 1.68. An additional purification by flash chromatography (SiO$_2$, Hexanes/EtOAc gradient elution) was necessary, providing 36 mg (53% yield) of Compound 88: LCMS m/z (%)=383 (M+H, 100). $^1$H NMR (400 MHz, acetone-d$_6$) δ: 8.31 (s, 1H), 8.17 (s, 1H), 8.13 (s, 1H), 7.79 (dd, J$_1$=9.0 Hz, J$_2$=2.2 Hz, 1H), 7.63 (d, J$_1$=15.5 Hz, J$_2$=8.3 Hz, J$_3$=2.7 Hz, 1H), 7.50 (d, J=2.4 Hz, 1H), 7.41 (m, 3H), 7.14 (d, J=9.2 Hz, 1H), 3.84 (s, 3H), 3.65 (s, 3H), 2.56 (s, 3H). $^{19}$F NMR (376 MHz, acetone-d$_6$) δ: −177.39 (d, J$_{H,F}$=4.1 Hz, 1F).

Example 1.79:

Preparation of 1-[3-(4-Fluoro-2-methyl-2H-pyrazol-3-yl)-4-methoxy-phenyl]-3-(4-trifluoromethyl-phenyl)-urea (Compound 89).

3-(4-Fluoro-2-methyl-2H-pyrazol-3-yl)-4-methoxy-phenylamine was treated with 4-trifluoromethylphenylisocyanate, in a similar manner as described in Example 1.69, providing 24 mg (49% yield) of Compound 89: LCMS m/z (%)=409 (M+H, 100). $^1$H NMR (400 MHz, acetone-d$_6$) δ: 8.56 (s, 1H), 8.29 (s, 1H), 7.75 (d, J=8.8 Hz, 2H), 7.65 (dd, J$_1$=9.0 Hz, J$_2$=2.6 Hz, 1H), 7.60 (d, J=8.4 Hz, 2H), 7.50 (d, J=2.4 Hz, 1H), 7.38 (d, J$_{H,F}$=4.4 Hz, 1H), 7.14 (d, J=8.8 Hz, 1H), 3.84 (s, 3H), 3.65 (s, 3H). $^{19}$F NMR (376 MHz, acetone-d$_6$) δ: −62.80 (s, 3F), −177.39 (d, J$_{H,F}$=4.1 Hz, 1F).

Example 1.80

Preparation of 1-[3-(4-Fluoro-2-methyl-2H-pyrazol-3-yl)-4-methoxy-phenyl]-3-(3-trifluoromethyl-phenyl)-urea (Compound 90).

3-(4-Fluoro-2-methyl-2H-pyrazol-3-yl)-4-methoxy-phenylamine was treated with 3-trifluoromethylphenylisocyanate, in a similar manner as described in Example 1.69, providing 37 mg (48% yield) of Compound 90: LCMS m/z (%)=409 (M+H, 100). $^1$H NMR (400 MHz, acetone-d$_6$) δ: 8.50 (s, 1H), 8.27 (s, 1H), 8.07 (s, 1H), 7.67 (d, J=8.8 Hz, 1H), 7.64 (d, J=2.4 Hz, 1H), 7.49 (m, 2H), 7.38 (d, J$_{H,F}$=4.8 Hz, 1H), 7.30 (d, J=8.0 Hz, 1H), 7.14 (d, J=8.8 Hz, 1H), 3.84 (s, 3H), 3.65 (s, 3H). $^{19}$F NMR (376 MHz, acetone-d$_6$) δ: −63.85 (s, 3F), −177.42 (d, J$_{H,F}$=4.1 Hz, 1F).

Example 1.81:

Preparation of Intermediate 3-(4-Bromo-2-isopropyl-2H-pyrazol-3-yl)-4-methoxy-phenylamine.

To a solution of 4-bromo-1-isopropyl-5-(2-methoxy-5-nitro-phenyl)-1H-pyrazole (0.50 g, 1.47 mmol) in ethanol (5.0 mL), was added SnCl$_2$.2H$_2$O (1.3 g, 5.88 mmol) and the mixture was heated at 55° C overnight. The ethanol was evaporated and the residue was taken up in ethyl acetate (50 mL) and washed with 10% NaOH (10 mL). The organic layer was dried over MgSO$_4$ and evaporated to yield a light yellow solid. The crude material was purified via Biotage silica chromatography (hexane/EtOAc, 3/1) to yield a pale yellow solid of 3-(4-bromo-2-isopropyl-2H-pyrazol-3-yl)-4-methoxy-phenylamine (0.38 g, 85%). LCMS m/z (%)=311 M+H$^+$, ($^{79}$Br, 100), ($^{81}$Br, 96.5), $^1$H NMR (400 MHz, CDCl$_3$) δ: 7.47 (s, 1H), 6.78 (d, J=8.08 Hz, 1H), 6.72 (dd, J$_1$=8.01 Hz, J$_2$=2.78 Hz, 1H), 6.54 (d, J=2.78 Hz, 1H), 4.14 (m, 1H), 3.63 (s, 3H), 1.4 (d, J=6.57 Hz, 3H), 1.23 (d, J=6.57 Hz, 3H).

The intermediate 4-Bromo-1-isopropyl-5-(2-methoxy-5-nitro-phenyl)-1H-pyrazole was prepared in the following manner:

A. 1-Isopropyl-1H-pyrazole: To a solution of pyrazole (50.0 g, 735.3 mmol) in aqueous sodium hydroxide (123.5 g NaOH/200 mL of water), was added isopropyl bromide (180.0 g, 1470.1 mmol) and the mixture was then heated to reflux for 6-7 days. The reaction mixture was cooled and extracted with ethyl acetate (3×300 ml). The combined organic layers were dried over MgSO$_4$. Removal of the volatiles in vacuo provided a light yellow oil, which was distilled via Kugelrohr at 140° C and 10 Torr, to provide 1-isopropyl-1H-pyrazole as a colorless oil (43 g, 53%). LCMS m/z (%) =111 M+H$^+$, (100). $^1$H NMR (400 MHz, DMSO-d$_6$) δ: 7.72 (d, J=2.3 Hz, 1H), 7.41 (t, 1H), 6.21 (t, 1H), 4.5 (q, 1H), 1.41-1.37 (d, J=11.1 Hz).

B. 2-Isopropyl-2H-pyrazole-3-boronic acid: n-BuLi (17.46 g, 110 mL, 273 mM, in hexanes) was slowly added over 30 minutes at −78° C to a THF solution of 1-isopropyl-1H-pyrazole (25.0 g, 227 mmol). The reaction mixture was stirred at −78° C for 2 hours. A solution of cooled triisopropoxy boronate (170.0 g, 909 mmol) was added slowly via canula over 45 minutes. The reaction mixture was allowed to warm to room temperature and stirred overnight. The reaction mixture was adjusted to pH 6-7 with HCl (1M, 170 mL). The solvent was evaporated to dryness and the resulting residue was triturated with 1:1 ethylacetate:dichloromethane, the suspension filtered and the solvent was evaporated in vacuo to yield 2-isopropyl-2H-pyrazole-3-boronic acid as a colorless solid (20.0 g, 58%). LCMS m/z (%)=154 M+H$^+$, (100). $^1$H NMR (400 MHz, DMSO-d$_6$) δ: 8.14 (s, 2H), 7.2 (s, 1H), 6.5 (s, 1H), 5.05 (m, 1H), 1.2 (d, J=9.0 Hz, 6H).

C. 1-Isopropyl-5-(2-methoxy-5-nitro-phenyl)-1H-pyrazole: To a mixture of trifluoro-methanesulfonic acid 2-methoxy-5-nitro-phenyl ester, (4.1 g, 13.6 mmol; see Example 1.1, Step B for preparation), 2-isopropyl-2H-pyrazole-3-boronic acid (5.2 g, 34.1 mmol), and anhydrous Cs$_2$CO$_3$ (17.7 g, 54.4 mmol) in DME under argon was added Pd (PPh$_3$)$_4$ (0.79 g, 0.68 mmol) and the mixture was heated at 80° C for 16 h. The reaction mixture was cooled, filtered through Celite and evaporated to dryness. The residue was taken up in ethyl acetate and the solution was washed with water. The organic layer was dried over MgSO$_4$ and evaporated to afford a crude product as a brown solid. The crude material was purified via Biotage silica chromatography (hexane/EtOAc, 3/1) to yield a colorless solid, 1-isopropyl-5-(2-methoxy-5-nitro-phenyl)-1H-pyrazole (1.88 g, 52%). LCMS m/z (%)=261 M+H$^+$ (100), $^1$H NMR (400 MHz, CDCl$_3$) δ: 8.36 (dd, J$_1$=9.09 Hz, J$_2$=2.5 Hz, 1H), 8.18 (d, J=8.18 Hz, 1H), 7.65 (s, 1H), 7.09 (d, J=8.08 Hz, 1H), 6.25 (s, 1H), 4.16 (dd, J$_1$=13.14 Hz, J$_2$=6.57 Hz, 1H), 3.95 (s, 3H), 1.45 (d, J=6.82 Hz, 6H).

D. 4-Bromo-1-isopropyl-5-(2-methoxy-5-nitro-phenyl)-1H-pyrazole: To a stirred, ice-cooled solution of 1-isopropyl-5-(2-methoxy-5-nitro-phenyl)-1H-pyrazole (1.0 g, 3.83 mmol) in DMF (10 mL) was added NBS (0.75 g, 4.22 mmol) slowly over a period of 10 minutes. The reaction mixture was warmed to ambient temperature and stirred for 2 h. The reaction was poured into an ice-water mixture with vigorous stirring to form a white solid, which was filtered and washed with cold water until free of DMF. The solid was dried in vacuo to give colorless solid 4-bromo-1-isopropyl-5-(2-methoxy-5-nitro-phenyl)-1H-pyrazole (1.25 g, 96%). LCMS m/z (%)=340 M+H$^+$, ($^{79}$Br, 100), 342 ($^{81}$Br, 96.5). $^1$H NMR (400 MHz, CDCl$_3$) δ: 8.4 (dd, J$_1$=9.09 Hz, J$_2$=2.78

Hz, 1H), 8.19 (d, J=2.78), 7.6 (s, 1H), 7.14 (d, J=9.35 Hz, 1H), 4.11 (m, 1H), 3.96 (s, 3H), 1.49 (d, J=6.52 Hz, 3H), 1.36 (d, J=6.52 Hz, 3H).

Example 1.82:

Preparation of Intermediate 3-(4-Chloro-2-isopropyl-2H-pyrazol-3-yl)-4-methoxy-phenylamine.

To a solution of 4-chloro-1-isopropyl-5-(2-methoxy-5-nitro-phenyl)-1H-pyrazole (0.18 g, 0.61 mmol) in ethanol (5.0 mL), was added $SnCl_2.2H_2O$ (0.56 g, 2.44 mmol) and the mixture was heated at 55° C overnight. The ethanol was evaporated and the residue was taken up in ethyl acetate (50 mL) and washed with 10% NaOH (10 mL). The organic layer was dried over $MgSO_4$ and evaporated to yield a light yellow solid. The crude material was purified via Biotage silica chromatography (hexane/EtOAc, 3/1) to yield a pale yellow solid of 3-(4-chloro-2-isopropyl-2H-pyrazol-3-yl)-4-methoxy-phenylamine (0.116 g, 75%). LCMS m/z (%)=267 M+H$^+$, ($^{35}$Cl, 100), 269 ($^{37}$Cl, 28.5)), $^1$H NMR (400 MHz, $CDCl_3$) δ: 7.47 (s, 1H), 6.78 (d, J=8.08 Hz, 1H), 6.72 (dd, $J_1$=8.01 Hz, $J_2$=2.78 Hz, 1H), 6.54 (d, J=2.78 Hz, 1H), 4.14 (m, 1H), 3.63 (s, 3H), 1.4 (d, J=6.57 Hz, 3H), 1.23 (d, J=6.57 Hz, 3H).

The intermediate 4-chloro-1-isopropyl-5-(2-methoxy-5-nitro-phenyl)-1H-pyrazole was prepared in the following manner:

To a stirred, ice-cooled solution of 1-isopropyl-5-(2-methoxy-5-nitro-phenyl)-1H-pyrazole from Example 1.81, Step C (1.0 g, 3.83 mmol) in DMF (10 mL) was added NCS (0.56 g, 4.22 mmol) over a period of 10 minutes. The reaction mixture was warmed to ambient temperature and stirred at 55° C for 6 h. The reaction mixture was cooled and poured into an ice-water mixture with vigorous stirring to form a white solid, which was filtered and washed with cold water until free of DMF. The solid was dried in vacuo to yield 4-chloro-1-isopropyl-5-(2-methoxy-5-nitro-phenyl)-1H-pyrazole (1.1 g, 97%). LCMS m/z (%)=296 M+H$^+$, ($^{35}$Cl, 100), 298 ($^{37}$Cl, 28.5). $^1$H NMR (400 MHz, $CDCl_3$) δ: 8.4 (dd, $J_1$=9.09 Hz, $J_2$=2.78 Hz, 1H), 8.19 (d, J=2.8 Hz), 7.6 (s, 1H), 7.14 (d, J=9.18 Hz, 1H), 4.10 (m, 1H), 3.94 (s, 3H), 1.49 (d, J=6.62 Hz, 3H), 1.36 (d, J=6.62 Hz, 3H).

Example 1.83:

Preparation of Intermediate 3-(2-Isopropyl-2H-pyrazol-3-yl)-4-methoxy-phenylamine.

To a solution of 1-isopropyl-5-(2-methoxy-5-nitro-phenyl)-1H-pyrazole, from Example 1.81, Step C (0.57 g, 2.18 mmol) in ethanol (5.0 mL), was added $SnCl_2.2H_2O$ (1.97 g, 8.74 mmol) and the mixture was heated at 55° C overnight. The ethanol was evaporated and the residue was taken in ethyl acetate (50 mL) and washed with 10% NaOH (10 mL). The organic layer was dried over $MgSO_4$ and evaporated to yield a light yellow solid. The crude material was purified via Biotage silica chromatography (hexane/EtOAc, 3/1) to yield a pale yellow solid of 3-(2-isopropyl-2H-pyrazol-3-yl)-4-methoxy-phenylamine (0.465 g, 94%). LCMS m/z (%)=232 M+H$^+$ (100), $^1$H NMR (400 MHz, $CDCl_3$) δ: 7.47 (s, 1H), 6.78 (d, J=8.08 Hz, 1H), 6.72 (dd, $J_1$=8.01 Hz, $J_2$=2.78 Hz, 1H), 6.54 (d, J=2.78 Hz, 1H), 6.25 (s, 1H), 4.14 (m, 1H), 3.63 (s, 3H), 1.4 (d, J=6.57 Hz, 3H), 1.23 (d, J=6.57 Hz, 3H).

Example 1.84:

Preparation of 1-(4-Chloro-phenyl)-3-[3-(2-isopropyl-2H-pyrazol-3-yl)-4-methoxy-phenyl]-urea (Compound 43).

To a solution of 3-(2-isopropyl-2H-pyrazol-3-yl)-4-methoxy-phenylamine (0.1 g, 0.433 mmol) in $CH_2Cl_2$, was added 4-chlorophenyl isocyanate (0.0733 g, 0.476 mmol) and stirred overnight. The resulting precipitate was filtered and washed with methylene chloride/hexane (1:1), and dried in vacuo to yield Compound 43 as a colorless solid (0.050 g, 30%). LCMS m/z (%)=386 M+H$^+$ ($^{37}$Cl, 26), 385 M+H$^+$ ($^{35}$Cl, 94), $^1$H NMR (400 MHz, DMSO-$d_6$) δ: 8.84 (bs, 1H), 8.77 (bs, 1H), 7.48 (d, J=1.91 Hz, 1H), 7.46 (d, J=1.84 Hz, 1H), 7.44 (d, J=3.65 Hz, 1H), 7.33 (t, 1H), 7.3 (s, 1H), 7.29 (d, J=7.68 Hz, 2H), 7.07 (d, J=8.9 Hz, 2H), 6.13 (d, J=1.83 Hz, 1H), 4.25 (m, 1H), 3.7 (s, 3H), 1.3 (d, J=6.76 Hz, 6H).

Example 1.85:

Preparation of 1-(4-Fluoro-phenyl)-3-[3-(2-isopropyl-2H-pyrazol-3-yl)-4-methoxy-phenyl]-urea (Compound 44).

To a solution of 3-(2-isopropyl-2H-pyrazol-3-yl)-4-methoxy-phenylamine (0.1 g, 0.433 mmol) in $CH_2Cl_2$, was added 4-fluoro phenyl isocyanate (0.0652 g, 0.476 mmol) and stirred overnight. The resulting precipitate was filtered and washed with methylene chloride/hexane (1:1), and dried in vacuo to yield Compound 44 as a colorless solid (0.050 g, 30%). LCMS m/z (%)=369 M+H$^+$, (100), $^1$H NMR (400 MHz, DMSO-$d_6$) δ: 8.59 (bs, 1H), 8.52 (bs, 1H), 7.42-7.35 (m, 4H), 7.28-7.27 (d, J=2.7 Hz, 1H), 7.057 (m, 3H), 6.07 (d, J=1.76 Hz, 1H), 4.10 (m, 1H), 3.66 (s, 3H), 1.24 (d, J=6.56 Hz, 6H).

Example 1.86:

Preparation of 1-(3,4-Difluoro-phenyl)-3-[3-(2-isopropyl-2H-pyrazol-3-yl)-4-methoxy-phenyl]-urea (Compound 46).

To a solution of 3-(2-isopropyl-2H-pyrazol-3-yl)-4-methoxy-phenylamine (0.1 g, 0.433 mmol) in $CH_2Cl_2$, was added 3,4-difluoro phenyl isocyanate (0.067 g, 0.476 mmol) and stirred overnight. The resulting precipitate was filtered and washed with methylene chloride/hexane (1:1), and dried in vacuo to yield Compound 46 as a colorless solid (0.078 g, 42%). LCMS m/z (%)=387 M+H$^+$, (100), $^1$H NMR (400 MHz, acetone-$d_6$) δ: 8.45 (bs, 1H), 8.27 (bs, 1H), 7.65-7.59 (m, 3H), 7.485 (d, J=2.56 Hz, 1H), 7.228-7.009 (m, 4H), 6.245 (d, J=1.73 Hz, 1H), 4.36 (m, 1H), 3.82 (s, 3H), 1.418 (d, J=6.61 Hz, 6H).

Example 1.87:

Preparation of 1-(3-Chloro-4-fluoro-phenyl)-3-[3-(2-isopropyl-2H-pyrazol-3-yl)-4-methoxy-phenyl]-urea (Compound 47).

To a solution of 3-(2-isopropyl-2H-pyrazol-3-yl)-4-methoxy-phenylamine (0.1 g, 0.433 mmol) in CH2Cl2, was added 3-chloro-4-fluoro phenyl isocyanate (0.075 g, 0.476 mmol) and stirred overnight. The resulting precipitate was filtered and washed with methylene chloride/hexane (1:1), and dried in vacuo to yield Compound 47 as a colorless solid (0.090 g, 52%). LCMS m/z (%)=405 M+H+($^{37}$Cl, 23) 403 M+H+($^{35}$Cl, 60), $^1$H NMR (400 MHz, acetone-d$_6$) δ: 8.3 (bs, 1H), 8.1 (bs, 1H), 7.82-7.796 (dd, J$_1$=6.75 Hz, J$_2$=2.58 Hz, 1H), 7.536 (d, J=2.67 Hz, 2H), 7.514 (d, J=2.67 Hz, 2H), 7.43 (d, J=1.57 Hz, 1H), 7.368 (d, J=2.65 Hz, 1H), 7.299 (d, J=1.23 Hz, 1H), 7.136 (t, 1H), 6.079 (d, J=1.69 Hz, 1H), 4.224 (m, 1H), 3.73 (s, 3H), 1.308 (d, J=6.61 Hz, 6H).

Example 1.88:

Preparation of 1-(2-Chloro-4-trifluoromethyl-phenyl)-3-[3-(2-isopropyl-2H-pyrazol-3-yl)-4-methoxy-phenyl]-urea (Compound 48).

To a solution of 3-(2-isopropyl-2H-pyrazol-3-yl)-4-methoxy-phenylamine (0.1 g, 0.433 mmol) in CH$_2$Cl$_2$, was added 2-Chloro-4-trifluoromethylphenyl isocyanate (0.106 g, 0.476 mmol) and stirred overnight. The resulting precipitate was filtered and washed with methylene chloride/hexane (1:1), and dried in vacuo to yield Compound 48 as a colorless solid (0.109 g, 56%). LCMS m/z (%)=455 M+H+ ($^{37}$Cl, 35), 453 M+H+($^{35}$Cl, 100), $^1$H NMR (400 MHz, acetone-d$_6$) δ: 8.78 (bs, 1H), 8.48 (d, J=8.97 Hz, 1H), 7.99 (bs, 1H), 7.615 (s, 1H), 7.52-7.46 (m, 1H), 7.375 (d, J=1.41 Hz, 1H), 7.337 (d, J=2.64 Hz, 1H), 6.973 (d, J=8.92 Hz, 1H), 6.027 (d, J=1.63 Hz, 1H), 4.151 (m, 1H), 3.676 (s, 3H), 1.244 (d, J=6.61 Hz, 6H).

Example 1.89:

Preparation of 1-[3-(4-Bromo-2-isopropyl-2H-pyrazol-3-yl)-4-methoxy-phenyl]-3-(4Chloro-phenyl)-urea (Compound 49).

To a solution of 3-(4-bromo-2-isopropyl-2H-pyrazol-3-yl)-4-methoxy-phenylamine (0.08 g, 0.258 mmol) in CH$_2$Cl$_2$, was added 4-chloro phenyl isocyanate (0.041 g, 0.263 mmol) and stirred overnight. The resulting precipitate was filtered and washed with methylene chloride/hexane (1:1), and dried in vacuo to yield Compound 49 as a colorless solid (0.052 g, 42%). LCMS m/z (%)=463 (M+H+ $^{79}$Br, 35Cl, 41), 465 M+H+($^{81}$Br$^{35}$Cl 88), 467 H+(81 Br 37Cl, 21), $^1$H NMR (400 MHz, acetone-d$_6$) δ: 8.30 (bs, 1H), 8.24 (bs, 1H), 7.685 (d, J=2.66 Hz, 1H), 7.577 (d, J=1.92 Hz, 2H), 7.74 (d, J=2.65, 1H), 7.292 (d, J=1.9 Hz, 2H), 7.280 (d, J=1.6 Hz, 1H), 7.135 (d, J=9.01 Hz, 1H), 4.256 (m, 1H), 3.811 (s, 3H), 1.447 (d, J=6.61 Hz, 3H), 1.288 (d, J=6.61 Hz, 3H).

Example 1.90:

Preparation of 1-[3-(4-Bromo-2-isopropyl-2H-pyrazol-3-yl)-4-methoxy-phenyl]-3-(4-fluoro-phenyl)-urea (Compound 50).

To a solution of 3-(4-bromo-2-isopropyl-2H-pyrazol-3-yl)-4-methoxy-phenylamine (0.08 g, 0.258 mmol) in CH$_2$Cl$_2$, was added 4-fluoro phenyl isocyanate (0.036 g, 0.263 mmol) and stirred overnight. The resulting precipitate was filtered and washed with methylene chloride/hexane (1:1), and dried in vacuo to yield Compound 50 as a colorless solid (0.037 g, 32%). LCMS m/z (%)=449 M+H+ ($^{81}$Br, 58), 447 M+H+(79 Br, 63), $^1$H NMR (400 MHz, CDCl$_3$) δ: 7.5 (s, 1H), 7.346 (d, J=1.95 Hz, 2H), 7.326 9bs, 1H), 7.151 (d, J=4.77 Hz, 1H), 7.124 (t, 1H), 6.995 (d, J=1.87 Hz, 2H), 6.869 (d, J=5.42 Hz, 1H), 6.847 (d, J=4.71 Hz, 1H), 4.045 (m, 1H), 3.651 (s, 3H), 1.333 (d, J=6.61 Hz, 3H), 1.160 (d, J=6.61 Hz, 3H).

Example 1.91:

Preparation of 1-[3-(4-Bromo-2-isopropyl-2H-pyrazol-3-yl)-4-methoxy-phenyl]-3-(3,4-difluoro-phenyl)-urea (Compound 51).

To a solution of 3-(4-bromo-2-isopropyl-2H-pyrazol-3-yl)-4-methoxy-phenylamine (0.08 g, 0.258 mmol) in CH$_2$Cl$_2$, was added 3,4-difluoro phenyl isocyanate (0.041 g, 0.263 mmol) and stirred overnight. The resulting precipitate was filtered and washed with methylene chloride/hexane (1:1), and dried in vacuo to yield Compound 51 as a colorless solid (0.096 g, 80%). LCMS m/z (%)=467 M+H+ ($^{81}$Br, 88), 465, M+H+($^{79}$Br, 95), $^1$H NMR (400 MHz, DMSO-d$_6$) δ: 8.816 (bs, 1H), 8.681 (bs, 1H), 7.5 (s, 1H), 7.412 (d, J=2.51 Hz, 2H), 7.389 (d, J=2.51 Hz, 2H), 7.199 (t, 1H), 7.167 (s, 1H), 6.983 (t, 1H), 3.989 (m, 1H), 3.596 (s, 3H), 1.225 (d, J=6.61 Hz, 3H), 1.078 (d, J=6.61 Hz, 3H).

Example 1.92:

Preparation of 1-[3-(4-Bromo-2-isopropyl-2H-pyrazol-3-yl)-4-methoxy-phenyl]-3-(3-Chloro-4-fluoro-phenyl)-urea (Compound 52).

To a solution of 3-(4-bromo-2-isopropyl-2H-pyrazol-3-yl)-4-methoxy-phenylamine (0.08 g, 0.258 mmol) in CH$_2$Cl$_2$, was added 3-chloro-4-fluoro phenyl isocyanate (0.045 g, 0.263 mmol) and stirred overnight. The resulting precipitate was filtered and washed with methylene chloride/hexane (1:1), and dried in vacuo to yield Compound 52 as a colorless solid (0.067 g, 54%). LCMS m/z (%)=485 M+H+ (81Br $^{37}$Cl, 30), 483 M+H+ ($^{81}$Br $^{35}$Cl, 100), 481 M+H+ ($^{79}$Br $^{35}$Cl, 72), $^1$H NMR (400 MHz, CDCl$_3$) δ: 7.7 (s, 1H), 7.4 (d, J=1.8 Hz, 1H), 7.3 (d, J=1.8 Hz, 1H), 7.25 (s, 1H), 7.1-6.8 (m, 3H), 4.2 (m, 1H), 3.8 (s, 3H), 1.5 (d, J=6.61 Hz, 3H), 1.3 (d, J=6.61 Hz, 3H).

Example 1.93:

Preparation of 1-[3-(4-Bromo-2-isopropyl-2H-pyrazol-3-yl)-4-methoxy-phenyl]-3-(2Chloro-4-trifluoromethyl-phenyl)-urea (Compound 53).

To a solution of 3-(4-bromo-2-isopropyl-2H-pyrazol-3-yl)-4-methoxy-phenylamine (0.08 g, 0.258 mmol) in CH$_2$Cl$_2$, was added 3-chloro-4-trifluoromethyl-phenyl isocyanate (0.059 g, 0.263 mmol) and stirred overnight at ambient temperature. The resulting precipitate was filtered and washed with methylene chloride/hexane (1:1), and dried in vacuo to yield Compound 53 as a colorless solid (0.1 g, 73%). LCMS m/z (%)=535 M+H+ ($^{81}$Br 37 Cl, 39), 533 M+H+ ($^{81}$Br 35Cl, 100), 531 M+H+ ($^{79}$Br $^{35}$Cl, 63), $^1$H NMR (400 MHz, DMSO-d$_6$) δ: 8.582 (bs, 1H), 8.456 (bs, 1H), 7.864 (s, 1H), 7.654 (d, J=8.28 Hz, 1H), 7.557 (d, J=2.76 Hz, 1H), 7.536 (d, J=2.76 Hz, 1H), 7.369 (d, J=9.13 Hz, 1H), 4.133 (m, 1H), 3.752 (s, 3H), 1.375 (d, J=6.61 Hz, 3H), 1.217 (d, J=6.61 Hz, 3H).

Example 1.94:

Preparation of 1-[3-(4-Chloro-2-isopropyl-2H-pyrazol-3-yl)-4-methoxy-phenyl]-3-(4-Chloro-phenyl)-urea (Compound 45).

To a solution of 3-(4-chloro-2-isopropyl-2H-pyrazol-3-yl)-4-methoxy-phenylamine (0, g, 0.433 mmol) in CH$_2$Cl$_2$, was added 4-chloro-phenyl isocyanate (0.073 g, 0.476 mmol) and stirred overnight. The resulting precipitate was filtered and washed with methylene chloride/hexane (1:1), and dried in vacuo to yield Compound 45 as a colorless solid (0.097 g, 54%). LCMS m/z (%)=421 M+H+ ($^{37}$Cl, 53), 419 M+H+ ($^{35}$Cl, 77) $^1$H NMR (400 MHz, CDCl$_3$) δ: 7.689 (bs, 2H), 7.617 (s, 1H), 7.460 (d, J=2.62 Hz, 1H), 7.438 (d, J=2.52 Hz, 1H), 7.22-7.28 (m, 3H), 6.947 (d, J=8.93 Hz, 1H) 4.245 (m, 1H), 3.808 (s, 3H), 1.575 (d, J=6.35 Hz, 3H), 1.381 (d, J=6.35 Hz, 3H).

Example 1.95:

Preparation of 1-[3-(4-Chloro-2-isopropyl-2H-pyrazol-3-yl)-4-methoxy-phenyl]-3-(4-fluoro-phenyl)-urea (Compound 54).

To a solution of 3-(4-chloro-2-isopropyl-2H-pyrazol-3-yl)-4-methoxy-phenylamine (0.1 g, 0.433 mmol) in CH$_2$Cl$_2$, was added 4-fluoro-phenyl isocyanate (0.065 g, 0.476 mmol) and stirred overnight. The resulting precipitate was filtered and washed with methylene chloride/hexane (1:1), and dried in vacuo to yield Compound 54 as a colorless solid (0.055 g, 33%). LCMS m/z (%)=405 M+H+($^{37}$Cl, 20), 404 M+H+($^{35}$Cl, 50), $^1$H NMR (400 MHz, acetone-d$_6$) δ: 8.62 (bs, 1H), 8.101 (s, 1H), 8.081 (d, J=2.3 Hz, 2H), 7.967 (t, 1H), 7.885 (d, J=2.21 Hz, 2H), 7.558 (d, J=8.91 Hz, 1H), 7.473 (t, 1H), 4.67 (m, 1H), 4.238 (s, 3H), 1.873 (d, J=6.61 Hz, 3H), 1.713 (d, J=6.61 Hz, 3H).

Example 1.96:

Preparation of 1-[3-(4-Chloro-2-isopropyl-2H-pyrazol-3-yl)-4-methoxy-phenyl]-3-(3,4-difluoro-phenyl)-urea (Compound 55).

To a solution of 3-(4-chloro-2-isopropyl-2H-pyrazol-3-yl)-4-methoxy-phenylamine (0, g, 0.433 mmol) in CH$_2$Cl$_2$, was added 3,4-difluoro-phenyl isocyanate (0.075 g, 0.476 mmol) and stirred overnight. The resulting precipitate was filtered and washed with methylene chloride/hexane (1:1), and dried in vacuo to yield Compound 55 as a colorless solid (0.062 g, 35%). LCMS m/z (%)=423 M+H+($^{37}$Cl, 23), 421 M+H+($^{35}$Cl, 67), $^1$H NMR (400 MHz, acetone-d$_6$) δ: 8.199 (d, J=2.44 Hz, 1H), 8.181 (d, J=2.42 Hz, 1H), 8.166 (d, J=2.37 Hz, 1H), 8.147 (d, J=2.08 Hz, 1H), 8.106 (d, J=2.65 Hz, 1H), 8.085 (d, J=2.68 Hz, 1H), 7.967 (s, 1H), 7.880 (d, J=2.61 Hz, 1H), 7.627 (t, 1H), 7.594 (d, J=3.86 Hz, 1H) 7.563 (d, J=8.96 Hz, 1H), 4.669 (m, 1H), 4.242 (s, 3H), 1.874 (d, J=6.61 Hz, 3H), 1.713 (d, J=6.61 Hz, 3H).

Example 1.97:

Preparation of 1-(3-Chloro-4-fluoro-phenyl)-3-[3-(4-Chloro-2-isopropyl-2H-pyrazol-3-yl)-4-methoxy-phenyl]-urea (Compound 56).

To a solution of 3-(4-chloro-2-isopropyl-2H-pyrazol-3-yl)-4-methoxy-phenylamine (0.1 g, 0.433 mmol) in CH$_2$Cl$_2$, was added 3-chloro-4-fluoro-phenyl isocyanate (0.082 g, 0.476 mmol) and stirred overnight. The resulting precipitate was filtered and washed with methylene chloride/hexane (1:1), and dried in vacuo to yield Compound 56 as a colorless solid (0.052 g, 28%). LCMS m/z (%)=439 M+H+ ($^{37}$Cl, 29), 437 M+H+($^{35}$Cl, 46), $^1$H NMR (400 MHz, acetone-d$_6$) δ: 8.764 (bs, 1H), 8.673 (bs, 1H), 8.31-8.28 (m, 1H), 8.110 (d, J=2.72 Hz, 1H), 8.088 (d, J=2.71 Hz, 1H), 7.974 (s, 1H), 7.878 (d, J=2.68 Hz, 1H), 7.828-7.788 (m, 1H), 7.68-7.64 (m, 1H), 7.635-7.563 (m, 1H), 4.668 (m, 1H), 4.246 (s, 3H), 1.874 (d, J=6.61 Hz, 3H), 1.713 (d, J=6.61 Hz, 3H).

Example 1.98:

Preparation of 1-[3-(4-Chloro-2-isopropyl-2H-pyrazol-3-yl)-4-methoxy-phenyl]-3-(2-Chloro-4-trifluoromethyl-phenyl)-urea (Compound 57).

To a solution of 3-(4-chloro-2-isopropyl-2H-pyrazol-3-yl)-4-methoxy-phenylamine (0, g, 0.433 mmol) in CH$_2$Cl$_2$, was added 2-chloro-4-trifluoromethyl-phenyl isocyanate (0.107 g, 0.476 mmol) and stirred overnight. The resulting precipitate was filtered and washed with methylene chloride/ hexane (1:1), and dried in vacuo to yield Compound 57 as a colorless solid (0.085 g, 40%). LCMS m/z (%)=489 M+H+($^{37}$Cl, 25), 488 M+H+($^{35}$Cl$^{37}$Cl, 25), 487 M+H+ ($^{35}$Cl, 100), $^1$H NMR (400 MHz, acetone-d$_6$) δ: 8.88 (bs, 1H), 8.544 (bs, 1H), 8.063 (s, 1H), 7.669 (d, J=1.54 Hz, 1H), 7.606 (d, J=2.69 Hz, 1H), 7.58 (t, 1H), 7.549 (d, J=1.51 Hz, 1H), 7.385 (d, J=2.68 Hz, 1H), 7.68-7.64 (m, 1H), 7.080 (d, J=8.98 Hz, 1H), 4.145 (m, 1H), 3.742 (s, 3H), 1.345 (d, J=6.61 Hz, 3H), 1.188 (d, J=6.61 Hz, 3H).

Example 1.99:

Preparation of Intermediate 3-(4-Bromo-2-methyl-5-trifluoromethyl-2H-pyrazol-3-yl)-4-methoxy-phenylamine.

To a stirred solution of 4-bromo-5-(2-methoxy-5-nitro-phenyl)-1-methyl-3-trifluoromethyl-1H-pyrazole (0.08 g, 0.20 mmol) in EtOH (0.7 mL) was added SnCl$_2$.2H$_2$O (0.18 g, 0.80 mmol, 4.0 eq.) and the mixture was stirred at reflux for 2 hours followed by the removal of EtOH under vacuum. The resulting solid was dissolved in EtOAc and 1N NaOH was added until the pH was adjusted to 6. The mixture was stirred overnight and filtered through celite. The aqueous phase was extracted with EtOAc (3×50 mL). The combined organic phase was dried over anhydrous MgSO$_4$, filtered and evaporated to give 3-(4-bromo-2-methyl-5-trifluoromethyl-2H-pyrazol-3-yl)-4-methoxy-phenylamine (0.06 g, 0.17 mmol, 99% yield after two steps) as a white solid: LCMS m/z (%)=350 (M+H$^{79}$Br, 95), 352 (M+H$^{81}$Br, 100). $^1$H NMR (400 MHz, CDCl$_3$) δ: 6.78 (dd, J=14.0, 6.0 Hz, 1H), 6.76 (dd, J=8.0, 4.0 Hz, 1H), 6.54 (d, J=4.0 Hz, 1H), 3.67 (s, 3H), 3.66 (s, 3H) 3.36 (broad s, 2H).

The intermediate 4-bromo-5-(2-methoxy-5-nitro-phenyl)-1-methyl-3-trifluoromethyl-1H-pyrazole was prepared in the following manner:

A. 2-Methyl-5-trifluoromethyl-2H-pyrazole-3-boronic acid: 1-methyl-3-trifluromethyl-1H-pyrazole (1.00 g, 6.66 mmol) was dissolved in THF (25 mL) in an oven-dried round bottom flask and cooled to −78° C in an acetone/dry ice bath. 2.5 M n-butyl lithium/hexane (3.196 mL, 7.99 mmol) was added drop wise to the stirred solution followed by drop wise addition of triisopropyl borate (5.01 g, 26.64 mmol). The mixture was warmed to room temperature and stirred for three hours. The reaction mixture was adjusted to pH 6 with 1N HCl solution followed by the removal of THF under vacuum. The aqueous phase was extracted with EtOAc (3×100 mL). The combined organic phase was washed with brine and dried over anhydrous MgSO$_4$, filtered and evaporated to give 2-methyl-5-trifluoromethyl-2H-pyrazole-3-boronic acid (1.12 g, 5.80 mmol, 87% yield)

as a white solid: LCMS m/z (%)=195 (M+H, 100). $^1$H NMR (400 MHz, DMSO-d$_6$) δ: 8.37-8.40 (m, 2H), 7.57 (dd, J=4.0 Hz, 1H), 4.06 (s, 3H).

B. 5-(2-Methoxy-5-nitro-phenyl)-1-methyl-3-trifluoromethyl-1H-pyrazole: Trifluoro-methanesulfonic acid 2-methoxy-5-nitro-phenyl ester (0.10 g, 0.34 mmol), 2-methyl-5-trifluoromethyl-2H-pyrazole-3-boronic acid (0.10 g, 0.52 mmol, 1.5 eq.) and Na$_2$CO$_3$ (0.04 g, 0.41 mmol, 1.2 eq.) were dissolved in a mixture of DME (6 mL) and H$_2$O (0.6 mL) in an argon flushed round bottom flask. The mixture was degassed with argon for 5 minutes, followed by the addition of Pd(PPh$_3$)$_4$ (0.04 g, 0.03 mmol, 0.01 eq.). The reaction mixture was degassed under argon for another 5 minutes and stirred at 70° C overnight. Once the reaction was complete, the DME was removed under vacuum and the crude reaction mixture was purified by SiO$_2$ column chromatography (Eluent: EtOAc/Hexane=5% to 30%). Final purification was achieved via reverse phase C-18 HPLC to afford 5-(2-methoxy-5-nitro-phenyl)-1-methyl-3-trifluoromethyl-1H-pyrazole (0.05 g, 0.17 mmol, 49% yield): LCMS m/z (%)=302 (M+H, 100). $^1$H NMR (400 MHz, CDCl$_3$) δ: 8.38 (dd, J=10.0, 2.0 Hz, 1H), 8.19 (d, J=4.0 Hz, 1H), 7.12 (d, J=8.0 Hz, 1H), 6.57 (s, 1H), 3.98 (s, 3H), 3.78 (s, 3H).

C. 4-Bromo-5-(2-methoxy-5-nitro-phenyl)-1-methyl-3-trifluoromethyl-1H-pyrazole: NBS (0.03 g, 0.18 mmol, 1.1 eq.) in DMF (1/3 mL) was added drop wise to a stirred solution at 0° C of 5-(2-methoxy-5-nitro-phenyl)-1-methyl-3-trifluoromethyl-1H-pyrazole (0.05 g, 0.17 mmol) in DMF (2/3 mL). The reaction mixture was stirred at 0° C for 4 hrs and TLC indicated no product. An additional equivalent of NBS was added and the reaction mixture was stirred at 70° C overnight. A second and third equivalent of NBS was added the following day which resulted in completion of the reaction. The DMF was removed under vacuum and the crude mixture was diluted with EtOAc (50 mL), washed with brine (3×10 mL). The EtOAc phase was dried over anhydrous MgSO$_4$, filtered and evaporated to give the partially purified product 4-bromo-5-(2-methoxy-5-nitro-phenyl)-1-methyl-3-trifluoromethyl-1H-pyrazole (0.08 g) as a light yellow solid: LCMS m/z (%)=380 (M+H$^{79}$Br, 80), 382 (M+H$^{81}$Br, 100). $^1$H NMR (400 MHz, CDCl$_3$) δ: 8.44 (dd, J=8.0, 4.0 Hz, 1H), 8.22 (d, 1H), 7.15 (d, J=8.0 Hz, 1H), 3.98 (s, 3H), 3.78 (s, 3H).

Example 1.100:

Preparation of Intermediate 3-(4-Chloro-2-methyl-5-trifluoromethyl-2H-pyrazol-3-yl)-4-methoxy-phenylamine.

To a stirred solution of 4-chloro-5-(2-methoxy-5-nitro-phenyl)-1-methyl-3-trifluoromethyl-1H-pyrazole (0.11 g, 0.33 mmol) in EtOH (1.0 mL) was added SnCl$_2$.2H$_2$O (0.30 g, 1.31 mmol, 4.0 eq.) and the mixture was stirred at reflux for 2 hours followed by the removal of EtOH under vacuum. The resulting solid was dissolved in EtOAc and 1N NaOH was added until the pH was adjusted to 6. The mixture was stirred overnight and filtered through celite. The aqueous phase was extracted with EtOAc (3×50 mL). The combined organic phase was dried over anhydrous MgSO$_4$, filtered and evaporated to give 3-(4-chloro-2-methyl-5-trifluoromethyl-2H-pyrazol-3-yl)-4-methoxy-phenylamine (0.067 g, 0.22 mmol, 66% yield after two steps) as a white solid: LCMS m/z (%)=306 (M+H$^{35}$Cl, 100), 308 (M+H$^{37}$Cl, 33). $^1$H NMR (400 MHz, CDCl$_3$) δ: 6.86 (dd, J=14.0, 6.0 Hz, 1H), 6.84 (dd, J=8.0, 4.0 Hz, 1H), 6.63 (d, J=4.0 Hz, 1H), 3.74 (s, 3H), 3.72 (s, 3H).

The intermediate 4-chloro-5-(2-methoxy-5-nitro-phenyl)-1-methyl-3-trifluoromethyl-1H-pyrazole was prepared in the following manner:

NCS (0.05 g, 0.37 mmol, 1.1 eq.) dissolved in DMF (2/3 mL) was added drop wise to a stirred solution of 5-(2-methoxy-5-nitro-phenyl)-1-methyl-3-trifluoromethyl-1H-pyrazole, see Example 1.99 (0.1 g, 0.33 mmol) in DMF (1 1/3 mL) at 0° C. The reaction mixture was stirred 0° C and TLC indicated no product. An additional equivalent of NCS was added and the reaction mixture was stirred at 80° C overnight which resulted in completion of the reaction. The DMF was removed under vacuum and the crude mixture was diluted with EtOAc (50 mL) and washed with brine (3×10 mL). The EtOAc phase was dried over anhydrous MgSO$_4$, filtered and evaporated to give the partially purified product 4-chloro-5-(2-methoxy-5-nitro-phenyl)-1-methyl-3-trifluoromethyl-1H-pyrazole (0.13 g) as a light yellow solid: LCMS m/z (%)=336 (M+H$^{35}$Cl, 100), 382 (M+H$^{37}$Cl, 33). $^1$H NMR (400 MHz, CDCl$_3$) δ: 8.37 (dd, J=8.0, 4.0 Hz, 1H), 8.16 (d, J=4.0 Hz 1H), 7.09 (d, J=8.0 Hz, 1H), 3.92 (s, 3H), 3.69 (s, 3H).

Example 1.101:

Preparation of Intermediate 4-Methoxy-3-(2-methyl-5-trifluoromethyl-2H-pyrazol-3-yl)-phenylamine.

SnCl$_2$.2H$_2$O (0.15 g, 0.66 mmol, 4.0 eq.) was added to a stirred solution of 5-(2-methoxy-5-nitro-phenyl)-1-methyl-3-trifluoromethyl-1H-pyrazole, see Example 1.99, (0.05 g, 0.16 mmol) in EtOH (2.0 mL). The mixture was stirred at reflux for 4 hrs and EtOH was removed under vacuum. The resulting solid was dissolved in EtOAc and 1N NaOH was added until the pH was adjusted to 6. The mixture was stirred overnight and filtered through celite. The aqueous phase was extracted with EtOAc (3×50 mL). The combined organic phase was dried over anhydrous MgSO$_4$, filtered and evaporated to give 4-methoxy-3-(2-methyl-5-trifluoromethyl-2H-pyrazol-3-yl)-phenylamine (0.04 g, 0.15 mmol, 97% yield): LCMS m/z (%)=272 (M+H, 100). $^1$H NMR (400 MHz, CDCl$_3$) δ: 6.82 (dd, J=16.0, 4.0 Hz, 1H), 6.79 (dd, J=10.0, 2.0 Hz, 1H), 6.61 (d, 1H), 6.46 (s, 1H), 3.76 (s, 3H), 3.74 (s, 3H).

Example 1.102:

1-[3-(4-Bromo-2-methyl-5-trifluoromethyl-2H-pyrazol-3-yl)-4-methoxy-phenyl]-3-(4-chloro-phenyl)-urea (Compound 38).

Urea synthesis for Compound 38 (general procedure for Examples 1.103-1.106):

To a stirred solution of aniline 3-(4-bromo-2-methyl-5-trifluoromethyl-2H-pyrazol-3-yl)-4-methoxy-phenylamine (0.03 g, 0.08 mmol) in CH$_2$Cl$_2$ (1 mL) was added 4-chlorophenyl isocyanate (0.01 g, 0.08 mmol, 1.0 eq.) at room temperature. White solid precipitated and was filtered and washed with cold CH$_2$Cl$_2$ to afford Compound 38 (0.02 g, 0.04 mmol, 50% yield) as a white solid: LCMS m/z (%)=503 (M+H$^{79}$Br, 67), 505 (M+H$^{81}$Br, 100). $^1$H NMR (400 MHz, MeOH-d$_4$) δ: 7.59 (dd, J=6.0, 2.0 Hz, 1H), 7.42 (d, J=8.0

Hz, 2H), 7.38 (d, J=4.0 Hz, 1H), 7.27 (d, J=8.0 Hz, 2H), 7.16 (d, J=8.0 Hz, 1H), 3.84 (s, 3H), 3.75 (s, 3H).

Example 1.103:

1-[3-(4-Bromo-2-methyl-5-trifluoromethyl-2H-pyrazol-3-yl)-4-methoxy-phenyl]-3-(4-fluoro-phenyl)-urea (Compound 39).

3-(4-Bromo-2-methyl-5-trifluoromethyl-2H-pyrazol-3-yl)-4-methoxy-phenylamine (0.03 g, 0.08 mmol) was treated with 4-fluorophenyl isocyanate (0.01 g, 8.99 µL, 0.08 mmol, 1.1 equiv.) in $CH_2Cl_2$ (2.0 mL), in a similar manner as described in Example 1.102, to afford Compound 39 (0.03 g, 0.05 mmol, 64% yield) as a white solid: LCMS m/z (%)=487 (M+H$^{79}$Br, 100), 489 (M+H$^{81}$Br, 93). $^1$H NMR (400 MHz, MeOH-d$_4$) δ: 7.58 (dd, J=10.0, 2.0 Hz, 1H), 7.42 (dd, J=4.0 Hz, 2H), 7.38 (dd, J=10.0, 2.0 Hz, 1H), 7.16 (d, J=12.0 Hz, 1H), 7.03 (dd, J=12.0, 8.0 Hz, 2H), 3.84 (s, 3H), 3.75 (s, 3H).

Example 1.104:

1-[3-(4-Chloro-2-methyl-5-trifluoromethyl-2H-pyrazol-3-yl)-4-methoxy-phenyl]-3-(4-fluoro-phenyl)-urea (Compound 40).

3-(4-Chloro-2-methyl-5-trifluoromethyl-2H-pyrazol-3-yl)-4-methoxy-phenylamine (0.03 g, 0.11 mmol) was treated with 4-fluorophenyl isocyanate (0.02 g, 14.6 µL, 0.13 mmol, 1.2 equiv.) in $CH_2Cl_2$ (4.0 mL), in a similar manner as described in Example 1.102. The product was further purified via reverse phase C-18 HPLC to afford Compound 40 (0.03 g, 0.07 mmol, 63% yield) as a white solid: LCMS m/z (%)=443 (M+H$^{37}$Cl, 100), 445 (M+H$^{35}$Cl, 36). $^1$H NMR (400 MHz, MeOH-d$_4$) δ: 7.58 (dd, J=10.0, 2.0 Hz, 1H), 7.42 (dd, J=4.0 Hz, 2H), 7.40 (dd, J=8.0, 4.0 Hz, 1H), 7.16 (d, J=8.0 Hz, 1H), 7.03 (dd, J=10.0, 6.0 Hz, 2H), 3.84 (s, 3H), 3.74 (s, 3H).

Example 1.105:

1-[3-(4-Chloro-2-methyl-5-trifluoromethyl-2H-pyrazol-3-yl)-4-methoxy-phenyl]-3-(4-chloro-phenyl)-urea (Compound 41).

3-(4-Chloro-2-methyl-5-trifluoromethyl-2H-pyrazol-3-yl)-4-methoxy-phenylamine (0.03 g, 0.11 mmol) was treated with 4-chlorophenyl isocyanate (0.02 g, 0.13 mmol, 1.2 equiv.) in $CH_2Cl_2$ (4.0 mL), in a similar manner as described in Example 1.102. The product was further purified via reverse phase C-18 HPLC to afford Compound 41 (0.03 g, 0.06 mmol, 56% yield) as a white solid: LCMS m/z (%)=459 (M+H$^{35}$Cl, 100), 461 (M+H$^{35}$Cl$^{37}$Cl, 84), 463 (M+H$^{37}$Cl, 10). $^1$H NMR (400 MHz, MeOH-d$_4$) δ: 7.59 (dd, J=8.0, 4.0 Hz, 1H), 7.41 (dd, J=8.0, 8.0 Hz, 2H), 7.40 (dd, J=8.0, 1H), 7.27 (d, J=8.0 Hz, 2H), 7.17 (d, J=12.0 Hz, 1H), 3.84 (s, 3H), 3.74 (s, 3H).

Example 1.106:

1-(4-Chloro-phenyl)-3-[4-methoxy-3-(2-methyl-5-trifluoromethyl-2H-pyrazol-3-yl)-phenyl]-urea (Compound 42).

4-Methoxy-3-(2-methyl-5-trifluoromethyl-2H-pyrazol-3-yl)-phenylamine (0.02 g, 0.08 mmol) was treated with 4-chlorophenyl isocyanate (0.01 g, 10.45 µL, 0.093 mmol, 1.2 equiv.) in $CH_2Cl_2$ (3.0 mL), in a similar manner as described in Example 1.102. The product was further purified via reverse phase C-18 HPLC to afford Compound 42 (0.03 g, 0.07 mmol, 88% yield) as a white solid: LCMS m/z (%)=425 (M+H$^{37}$Cl, 100), 427 (M+H$^{35}$Cl, 34). $^1$H NMR (400 MHz, MeOH-d$_4$) δ: 7.50 (dd, J=10.0, 2.0 Hz, 1H), 7.42 (dd, J=8.0 Hz, 3H), 7.27 (dd, J=6.0, 2.0 Hz, 2H), 7.12 (d, J=8.0 Hz, 1H), 3.84 (s, 3H), 3.76 (s, 3H).

Example 1.107:

Preparation of intermediate 1-(4-chloro-phenyl)-3-(4-oxo-4H-chromen-6-yl)-urea.

Step 1: Preparation of 6-amino-chromen-4-one.

To a solution of 6-nitrochromone (2.0 g, 10.5 mmol) in Methanol/Ethyl acetate (100 mL/20 mL) purged with argon, was added 5% Pd/C (Degussa-wet, 0.5 g) catalyst. Hydrogen gas was bubbled through the slurry with stirring until (2 hrs.) LCMS and TLC showed no starting material. The spent palladium catalyst was filtered off through a celite, and the solid was washed with methanol. The combined filtrate and washings were evaporated to produce 6-amino-chromen-4-one as a light yellow solid (1.58 g, 94%). LCMS m/z (%)=162 (M+H, 100), $^1$H NMR (400 MHz, CDCl$_3$) δ: 7.79-7.81 (d, J=5.96 Hz, 1H), 7.38 (d, J=2.86 Hz, 1H), 7.29-7.31 (d, J=8.88 Hz, 1H), 7.01-7.04 (dd, J=8.80, 2.8 Hz, 1H), 6.26-6.28 (d, J=5.96 Hz, 1H), 5.299 (s, 2H).

Step 2: Preparation of 1-(4-chloro-phenyl)-3-(4-oxo-4H-chromen-6-yl)-urea.

To the slurry of 6-aminochromone (3.0 g, 18.6 mmol) stirred and heated to 80° C in toluene (200 mL) was added 4-chlorophenyl isocyanate (3.2 g, 20.5 mmol) and the mixture was refluxed for 18 hrs. The reaction mixture was cooled and the precipitate was filtered and washed with methanol. The residue was dried in vacuo to afford a yellow powder (5.8 g, 99%) of 1-(4-chloro-phenyl)-3-(4-oxo-4H-chromen-6-yl)-urea. LCMS m/z (%)=315 (M+H, $^{35}$Cl 100), 317 (M+H, $^{37}$Cl 32.2)$^1$H NMR (400 MHz, DMSO-d$_6$) δ: 9.098 (bs, 1H), 8.94 (bs, 1H), 8.28-8.30 (d, J=5.99 Hz, 1H), 8.20-8.21 (d, J=2.69 Hz, 1H), 7.81-7.84 (dd, J=9.0, 2.75 Hz, 1H), 7.62-7.64 (d, J=9.07 Hz, 1H), 7.52-7.55 (dd, J=6.84, 2.16 Hz, 2H), 7.35-7.37 (dd, J=6.85, 2.11 Hz, 2H), 6.33-6.34 (d, J=5.98 Hz, 1H).

Example 1.108:

Preparation of 1-(4-Chloro-phenyl)-3-[4-hydroxy-3-(2-methyl-2H-pyrazol-3-yl)-phenyl]-urea (Compound 119).

To a cooled and stirred solution of methyl hydrazine (1.46 g, 31.6 mmol) in pyridine was added slurry of 1-(4-Chlorophenyl)-3-(4-oxo-4H-chromen-6-yl)-urea (2.5 g, 7.9 mmol) in pyridine over a period of 10 mins. The reaction mixture was left at this temperature for another 2 hrs and then warmed to room temperature slowly. After 6 hrs the reaction mixture turned clear. The reaction was stirred at this temperature for 18 hrs and pyridine was evaporated. The dark colored residue was dissolved in DMSO and purified using Varian Prep. HPLC system. (The two regioisomers were separated. The fractions containing Compound 119 were dried in vacuo to produce a colorless powder (1.78 g, 47%) 1-(4-Chloro-phenyl)-3-[4-hydroxy-3-(2-methyl-2H-pyrazol-3-yl)-phenyl]-urea. LCMS m/z (%)=343 (M+H, $^{35}$Cl 100), 345 (M+H, $^{37}$Cl, 32.5). $^1$H NMR (400 MHz, DMSO-d$_6$) δ: 9.59 (bs, 1H), 8.72 (bs, 1H), 8.48 (bs, 1H), 7.43-7.46 (dd, J=6.8, 2.07 Hz, 2H), 7.41 (d, J=1.83 Hz, 1H), 7.28-7.30 (dd, J=7.13, 2.09 Hz, 2H), 7.26 (d, J=2.72 Hz, 1H), 6.88-6.90 (d, J=9.36 Hz, 1H), 6.21 (d, J=1.84 Hz, 1H), 3.67 (s, 3H).

Example 1.109:

Preparation of 1-(4-Chloro-phenyl)-3-[4-hydroxy-3-(1-methyl-1H-pyrazol-3-yl)-phenyl]-urea (Compound 154).

To a cooled and stirred solution of methyl hydrazine (1.46 g, 31.6 mmol) in pyridine was added slurry of Compound 119 (2.5 g, 7.9 mmol) in pyridine over a period of 10 mins. The reaction mixture was left at this temperature for another 2 hrs and then warmed to room temperature slowly. After 6 hrs the reaction mixture turned clear. The reaction was stirred at this temperature for 18 hrs. Then pyridine was evaporated. The dark colored residue was dissolved in DMSO and purified using Varian Preparative HPLC system at a flow rate of 60 mL/Min, and 2=240. The regio isomers were separated. The fractions containing Compound 154 were dried in vacuo to produce an off-white solid 1-(4-Chloro-phenyl)-3-[4-hydroxy-3-(1-methyl-1H-pyrazol-3-yl)-phenyl]-urea (0.3 g, 12%). LCMS m/z (%)=343 (M+H, $^{35}$Cl 100), 345 (M+H, $^{37}$Cl, 32.5). $^1$H NMR (400 MHz, DMSO-d$_6$) δ:10.26 (bs, 1H), 8.73 (bs, 1H), 8.46 (bs, 1H), 7.82 (d, J=2.32 Hz, 1H), 7.77 (d, J=3.62 Hz, 1H), 7.44-7.49 (m, 2H), 7.16-7.19 (dd, J=8.74, 2.62 Hz, 1H), 6.83-6.85 (d, J=8.72 Hz, 1H), 6.71-6.72 (d, J=2.36 Hz, 1H), 3.91 (s, 3H).

Example 1.110:

Preparation of 1-[3-(4-Chloro-2-methyl-2H-pyrazol-3-yl)-4-hydroxy-phenyl]-3-(4-chloro-phenyl)-urea (Compound 121).

To a stirred and cooled solution of Compound 119 (0.22 g, 0.63 mmol), in DMF (2.0 mL) was added N-chlorosuccinimide (0.168, 1.26 mmol). The reaction was stirred until the LCMS showed no starting material (2.5 hrs). The reaction mixture was poured into ice cooled water containing Na$_2$S$_2$O$_3$ and NaHCO$_3$ and the resulting solid was filtered, washed with ice-cooled water and dried in vacuo to afford a off-white solid 1-[3-(4-Chloro-2-methyl-2H-pyrazol-3-yl)-4-hydroxy-phenyl]-3-(4-chloro-phenyl)-urea (0.14 g, 58%). LCMS m/z (%)=377 (M+H, $^{35}$Cl, $^{35}$Cl, 100), 379 (M+H, $^{35}$Cl, $^{37}$Cl, 59.4), 381 (M+H, $^{37}$Cl, $^{37}$Cl, 10.0). $^1$H NMR (400 MHz, DMSO-d$_6$) δ: 9.76 (bs, 1H), 8.73 (bs, 1H), 8.56 (bs, 1H), 7.58 (s, 1H), 7.44-7.46 (dd, J=8.6, 2.03 Hz, 2H), 7.34-7.37 (dd, J=8.79, 2.7 Hz, 1H), 7.29 (dd, J=8.85, 2.07 Hz, 3H), 6.92-6.94 (d, J=6.78 Hz, 1H), 3.64 (s, 3H).

Example 1.111:

Preparation of 1-[3-(4-Chloro-2-methyl-2H-pyrazol-3-yl)-4-(3-dimethylamino-propoxy)-phenyl]-3-(4-chloro-phenyl)-urea (Compound 128).

To a stirred and cooled solution of Compound 119, 1-(4-Chloro-phenyl)-3-[4-hydroxy-3-(2-methyl-2H-pyrazol-3-yl)-phenyl]-urea, (0.1 g, 0.2923 mmol), triphenyl phosphine (0.291 g, 1.1078 mmol) and 3-dimethyl amino propanol (0.114 g, 1.099 mmol) in THF (25 mL) was added diisopropyl azodicarboxylate (0.224 g, 1.104 mmol) slowly over 10 minutes. The reaction mixture was allowed to warm to room temperature and stirred for 4 hrs at this temperature. The THF was evaporated and the syrup was dissolved in DMSO and purified using preperative HPLC at 60 mL/min flow and λ=240. The fractions containing the product were evaporated. The pink colored residue was subjected to 2$^{nd}$ purification using SiO$_2$ flash chromatography (eluant: 1% methanol in DCM to 15% methanol in DCM). The fractions containing the product were evaporated to afford a colorless solid. To a cooled solution of the solid in methanol was added a solution of N-chlorosuccinimide (0.044 g, 0.3215 mmol) in methanol. The reaction mixture was stirred for 60 minutes. Next, the methanol was evaporated and the residue was purified using silica and 15% methanol in DCM as eluant. The fractions containing the product were evaporated and dried in vacuo to produce a off-white solid of 1-[3-(4-Chloro-2-methyl-2H-pyrazol-3-yl)-4-(3-dimethylamino-propoxy)-phenyl]-3-(4-chloro-phenyl)-urea (0.015 g, 12%). LCMS m/z (%)=462 (M+H $^{35}$Cl, $^{35}$Cl 100), 464 (M+H, $^{35}$Cl, $^{37}$Cl, 70.2), 466 (M+H, $^{37}$Cl, $^{37}$Cl, 11.2) $^1$H NMR (400 MHz, acetone-d$_6$) δ: 8.29 (bs, 1H), 8.21 (bs, 1H), 7.61-7.64 (dd, J=8.94, 2.73 Hz, 1H), 7.53-7.56 (dd, J=7.09, 2.09 Hz, 2H), 7.46 (s, 1H), 7.43-7.46 (d, J=2.7 Hz, 1H), 7.26-7.28 (dd, J=7.09, 2.07 Hz, 2H), 7.11-7.13 (d, J=8.98 Hz, 1H), 3.98-4.1 (m, 2H), 3.67 (s, 3H), 2.21-2.25 (m, 2H), 2.09 (s, 6H), 1.75-1.79 (m, 2H).

Example 1.112:

Preparation of 1-[3-(4-Bromo-2-methyl-2H-pyrazol-3-yl)-4-(3-dimethylamino-propoxy)-phenyl]-3-(3,4-difluoro-phenyl)-urea (Compound 148).

To a cooled and stirred solution of Compound 136 (0.03 g, 0.0698 mmol), in methanol, was added N-bromosuccinimide (0.014 g, 0.077 mmol). The reaction mixture was stirred at this temperature for 10 minutes and warmed to ambient temperature. Methanol was evaporated and the residue was purified on silica using 1% MeOH/DCM to 15% MeOH/DCM as eluent. The fractions containing the product were evaporated in vacuo to produce 1-[3-(4-bromo-2-methyl-2H-pyrazol-3-yl)-4-(3-dimethylamino-propoxy)-phenyl]-3-(3,4-difluoro-phenyl)-urea as an off-white solid (0.014 g, 40%). LCMS m/z (%)=508 (M+H, $^{79}$Br, 100), 510 (M+H, $^{81}$Br, 82.6), $^1$H NMR (400 MHz, acetone-d$_6$) δ: 8.69 (bs, 1H), 8.53 (bs, 1H), 7.70-7.76 (m, 1H), 7.59-7.62 (dd, J=8.95, 2.74 Hz, 1H), 7.46 (s, 1H), 7.44 (d, J=2.7 Hz, 1H), 7.08-7.16 (m, 3H), 3.98-4.1 (m, 2H), 3.67 (s, 3H), 2.43-2.47 (m, 2H), 2.25 (s, 6H), 1.85-1.91 (m, 2H).

Example 1.113:

Preparation of 1-[3-(4-Bromo-2-methyl-2H-pyrazol-3-yl)-4-(3-dimethylamino-propoxy)-phenyl]-3-(2-chloro-phenyl)-urea (Compound 149).

To a cooled and stirred solution of Compound 140 (0.04 g, 0.0936 mmol), in methanol, was added N-bromosuccinimide (0.018 g, 0.102 mmol). The reaction mixture was stirred at this temperature for 10 minutes and warmed to ambient temperature. Methanol was evaporated and the residue was purified on silica using 1% MeOH/DCM to 15% MeOH/DCM as eluent. The fractions containing the product were evaporated in vacuo to produce 1-[3-(4-bromo-2-methyl-2H-pyrazol-3-yl)-4-(3-dimethylamino-propoxy)-phenyl]-3-(2-chloro-phenyl)-urea as an off-white solid (0.02 g, 42%). LCMS m/z (%)=506 (M+H $^{79}$Br, $^{35}$Cl, 83.9), 508 (M+H, 81Br, $^{35}$Cl, 100), 510 (M+H, 81Br, $^{37}$Cl, 30)$^1$H NMR (400 MHz, acetone-d$_6$) δ: 8.59 (bs, 1H), 8.09-9.12 (dd, J=9.3, 1.51 Hz, 1H) 7.63 (bs, 1H), 7.43-7.46 (dd, J$_1$=8.95 Hz, J$_2$=2.75 Hz, 1H), 7.27 (s, 1H), 7.22-7.29 (d, J=2.72 Hz, 1H), 7.16-7.18 (dd, J=8.63, 1.4 Hz, 1H), 7.05-7.08 (m, 1H), 6.91-6.93 (d, J=8.98 Hz, 1H), 6.77-6.81 (m, 1H), 3.48-3.91 (m, 2H), 3.48 (s, 3H), 2.01-2.05 (m, 2H), 1.89 (s, 6H), 1.56-1.61 (m, 2H).

Example 1.114:

Preparation of 1-[3-(4-Bromo-2-methyl-2H-pyrazol-3-yl)-4-(3-dimethylamino-propoxy)-phenyl]-3-(2-fluoro-phenyl)-urea (Compound 150).

To a cooled and stirred solution of Compound 138 (0.04 g, 0.0972 mmol), in methanol, was added N-bromosuccinimide (0.019 g, 0.107 mmol). The reaction mixture was stirred at this temperature for 10 minutes and warmed to ambient temperature. Methanol was evaporated and the residue was purified on silica using 1% MeOH/DCM to 15% MeOH/DCM as eluant. The fractions containing the product were evaporated in vacuo to produce 1-[3-(4-bromo-2-methyl-2H-pyrazol-3-yl)-4-(3-dimethylamino-propoxy)-phenyl]-3-(2-fluoro-phenyl)-urea as a off-white solid (0.02 g, 42%). LCMS m/z (%)=490 (M+H $^{79}$Br, 100), 492 (M+H, $^{81}$Br, 99.9). $^1$H NMR (400 MHz, acetone-d$_6$) δ: 8.59 (bs, 1H), 8.37 (d, J=1.57 Hz, 1H) 8.1 (bs, 1H), 7.72-7.75 (dd, J=8.95, 2.75, 1H), 7.57 (s, 1H), 7.52-7.53 (d, J=2.72 Hz, 1H), 7.18-7.22 (m, 3H), 7.07 (m, 1H) 4.07-4.19 (m, 2H), 3.78 (s, 3H), 2.3-2.35 (m, 2H), 2.19 (s, 6H), 1.85-1.88 (m, 2H).

Example 1.115:

Preparation of 1-[3-(4-Bromo-2-methyl-2H-pyrazol-3-yl)-4-hydroxy-phenyl]-3-(2,4-difluoro-phenyl)-urea (Compound 103).

1-[3-(4-Bromo-2-methyl-2H-pyrazol-3-yl)-4-methoxy-phenyl]-3-(2,4-difluoro-phenyl)-urea (Compound 8, 1.44 g, 3.30 mmol) was dissolved in anhydrous CH$_2$Cl$_2$ (30 mL). The solution was stirred while cooling the temperature to 0° C in an ice water bath. After allowing it to stir for another 10 minutes, AlCl$_3$ (1.76 g, 13.20 mmol) was added slowly. This was followed by stirring the reaction for an additional 20 minutes, and subsequently increasing the temperature to 80° C. After one hour, the reaction was shown to be complete by TLC and LC/MS. It was worked up with EtOAc (2×50 mL) and 10% Potassium Sodium Tartrate (2×50 mL). Upon being treated to this work up, the aluminum was removed from the solution. The organic layer was then dried with Na$_2$SO$_4$, filtered, and the solvent was removed under reduced pressure. The residue was then purified by HPLC, yielding 1.43 g (100%) of Compound 103 LCMS m/z (%)=425 (M+H$^{81}$Br, 100), 423 (M+H$^{79}$Br, 88). $^1$H NMR (400 MHz, DMSO-d$_6$) δ 9.74 (s, 1H), 8.87 (s, 1H), 8.40 (s, 1H), 8.08-8.03 (m, 1H), 7.58 (s, 1H), 7.36 (dd, J$_1$=8 Hz, J$_2$=4 Hz, 1H), 7.33-7.27 (m, 1H), 7.28 (d, J=2 Hz, 1H), 7.04-7.01 (m, 1H), 6.95 (d, J=8 Hz, 1H), 3.67 (s, 3H).

Example 1.116:

Preparation of 1-[3-(4-Bromo-2-methyl-2H-pyrazol-3-yl)-4-(2-dimethylamino-ethoxy)-phenyl]-3-(2,4-difluoro-phenyl)-urea (Compound 123).

Compound 103 (73.7 mg, 0.17 mmol) was dissolved in anhydrous THF (5 mL). PPh$_3$ (173 mg, 0.64 mmol) and 2-Dimethylamino ethanol (65.5 μL, 0.63 mmol) were then added to the solution, and the reaction was stirred at room temperature. After stirring for five minutes, DIAD (127 μL, 0.64 mmol) was added to the reaction dropwise. The reaction was found to be complete by TLC and LC/MS after 30 minutes. The solvent was then removed under reduced pressure. The residue was purified twice by flash chromatography (Biotage, SiO$_2$, Dichloromethane/Methanol gradient elution) and twice by HPLC to afford 26.4 mg (31%) of Compound 123 as a light brown oil: LCMS m/z (%)=496 (M+H$^{81}$Br, 100), 494 (M+H$^{79}$Br, 94). $^1$H NMR (400 MHz, DMSO-d$_6$) δ 8.99 (s, 1H), 8.44 (s, 1H), 8.07-8.01 (m, 1H), 7.59 (s, 1H), 7.52 (dd, J$_1$=8 Hz, J$_2$=4 Hz, 1H), 7.35 (d, J=4, 1H), 7.32-7.26 (m, 1H), 7.17 (d, J=12 Hz, 1H), 7.05-7.00 (m, 1H), 4.11 (dm, 2H), 3.65 (s, 3H), 2.58 (dm, 2H), 2.11 (s, 6H).

Example 1.117:

Preparation of (2-{2-(4-Bromo-2-methyl-2H-pyrazol-3-yl)-4-[3-(2,4-difluoro-phenyl)-ureido]-phenoxy}-ethyl)-carbamic acid tert-butyl ester (Compound 147)

Compound 147 was prepared in a similar manner as described in Example 1.116 using N-Boc-aminoethanol and DEAD, providing 25 mg (39%) of Compound 147. LCMS m/z (%)=566 (M+H$^{79}$Br, 21), 568 (M+H$^{81}$Br, 12). $^1$H NMR (400 MHz, DMSO-d$_6$) δ 9.00 (s, 1H), 8.45 (s, 1H), 8.07-8.00 (m, 1H), 7.59 (s, 1H), 7.51 (dd, J$_1$=8 Hz, J$_2$=2 Hz, 1H), 7.35 (d, J=4, 1H), 7.32 (m, 1H), 7.16 (d, J=8 Hz, 1H), 7.05-7.00 (m, 1H), 6.89-6.87 (m, 1H), 4.03-3.98 (m, 1H), 3.98-3.92 (m, 1H), 3.64 (s, 3H), 3.34-3.29 (m, 1H), 3.22-3.17 (m, 1H), 1.36 (s, 9H).

Example 1.118:

Preparation of 1-[3-(4-bromo-2-methyl-2H-pyrazol-3-yl)-4-hydroxy-phenyl]-3-(4-chloro-phenyl)-urea (Compound 58).

Compound 1, (1.56 g, 3.58 mmol) was dissolved in anhydrous CH$_2$Cl$_2$ (50 mL). The solution was stirred while cooling the temperature to 0° C in an ice water bath. After allowing it to stir for another 10 minutes, AlCl$_3$ (1.91 g, 14.32 mmol) was added slowly. This was followed by stirring the reaction for an additional 20 minutes, and subsequently increasing the temperature to 80° C. After one hour, the reaction was shown to be complete by TLC and LC/MS. It was worked up with EtOAc (2×50 mL) and 10% Potassium Sodium Tartrate (2×50 mL). Upon being treated to this work up, the aluminum was removed from the solution. The organic layer was then dried with Na$_2$SO$_4$, filtered, and the solvent was removed under reduced pressure. The residue was purified by HPLC to afford Compound 58 (402 mg, 27%): LCMS m/z (%)=423 (M+H$^{37}$Cl, 100), 421 (M+H$^{35}$Cl, 98). $^1$H NMR (400 MHz, DMSO-d$_6$) δ 9.74 (s, 1H), 8.76 (s, 1H), 8.59 (s, 1H), 7.60 (s, 1H), 7.48 (d, J=8 Hz, 2H), 7.39 (dd, J$_1$=8 Hz, J$_2$=4 Hz, 1H), 7.32 (d, J=8 Hz, 2H), 7.28 (d, J=2 Hz, 1H), 6.96 (d, J=12 Hz, 1H), 3.67 (s, 3H).

Example 1.119:

Preparation of 1-[3-(4-Chloro-2-methyl-2H-pyrazol-3-yl)-4-methoxy-phenyl]-3-(3-chloro-phenyl)-urea (Compound 91).

3-(4-Chloro-2-methyl-2H-pyrazol-3-yl)-4-methoxy-phenylamine (30 mg, 0.13 mmol) was treated with 3-Chlorophenyl isocyanate (17 µL, 0.14 mmol) in a similar manner to Example 1.53, providing 25 mg (46%) of Compound 91: LCMS m/z (%)=391 (M+H$^{35}$Cl, 100), 393 (M+H$^{37}$Cl, 70). $^1$H NMR (400 MHz, acetone-d$_6$) δ: 8.51 (s, 1H), 8.41 (s, 1H), 7.84 (t, 1H), 7.71 (dd, J$_1$=8 Hz, J$_2$=4 Hz, 1H), 7.49 (s, 1H), 7.49 (d, J=2 Hz, 1H), 7.38 (d, J=8 Hz, 1H), 7.29 (t, 1H), 7.16 (d, J=8 Hz, 1H), 7.01 (d, J=8 Hz, 1H), 3.84 (s, 3H), 3.68 (s, 3H).

Example 1.120:

Preparation of 1-[3-(4-Chloro-2-methyl-2H-pyrazol-3-yl)-4-methoxy-phenyl]-3-(3,4-difluoro-phenyl)-urea (Compound 92).

3-(4-Chloro-2-methyl-2H-pyrazol-3-yl)-4-methoxy-phenylamine (30 mg, 0.13 mmol) was treated with 3,4-Difluorophenyl isocyanate (17 µL, 0.14 mmol) in a similar manner to Example 1.53, providing 18.6 mg (34%) of Compound 92: LCMS m/z (%)=393 (M+H$^{35}$Cl, 100), 395 (M+H$^{37}$Cl, 38). $^1$H NMR (400 MHz, acetone-d$_6$) δ: 8.18 (s, 1H), 8.05 (s, 1H), 7.65 (m, 1H), 7.57 (dd, J$_1$=8 Hz, J$_2$=4 Hz, 1H), 7.36 (s, 1H), 7.33 (d, J=2 Hz, 1H), 7.09 (d, J=4 Hz, 1H), 7.06 (d, J=2 Hz, 1H), 7.04 (d, J=8 Hz, 1H), 3.72 (s, 3H), 3.55 (s, 3H).

Example 1.121:

Preparation of 1-[3-(4-Chloro-2-methyl-2H-pyrazol-3-yl)-4-methoxy-phenyl]-3-(3,5-difluoro-phenyl)-urea (Compound 93).

3-(4-Chloro-2-methyl-2H-pyrazol-3-yl)-4-methoxy-phenylamine (30 mg, 0.13 mmol) was treated with 3,4-Difluorophenyl isocyanate (17 µL, 0.14 mmol) in a similar manner to Example 1.53, providing 24.6 mg (44%) of Compound 93: LCMS m/z (%)=393 (M+H$^{35}$Cl, 100), 395 (M+H$^{37}$Cl, 47). $^1$H NMR (400 MHz, acetone-d$_6$) δ: 8.26 (s, 1H), 8.01 (s, 1H), 7.47 (dd, J$_1$=8 Hz, J$_2$=2 Hz, 1H), 7.26 (s, 1H), 7.22 (d, J=2 Hz, 1H), 7.04 (dd, J$_1$=12 Hz, J$_2$=4 Hz, 2H), 6.95 (d, J=8 Hz, 1H), 6.40 (m, 1H), 3.62 (s, 3H), 3.48 (s, 3H).

Example 1.122:

Preparation of 1-Benzoyl-3-[3-(4-chloro-2-methyl-2H-pyrazol-3-yl)-4-methoxy-phenyl]-urea (Compound 95).

3-(4-Chloro-2-methyl-2H-pyrazol-3-yl)-4-methoxy-phenylamine (20 mg, 0.08 mmol) was treated with benzyl isocyanate (14 mg, 0.09 mmol) in a similar manner to Example 1.53, providing 10 mg (31%) of Compound 95: LCMS m/z (%)=385 (M+H$^{35}$Cl, 11), 387 (M+H$^{37}$Cl, 4). $^1$H NMR (400 MHz, CDCl$_3$) δ: 10.85 (s, 1H), 9.15 (s, 1H), 7.88 (d, J=12 Hz, 2H), 7.58 (dd, J$_1$=8 Hz, J$_2$=2 Hz, 1H), 7.54 (d, J=8 Hz, 1H), 7.49 (s, 1H), 7.43 (d, J=4 Hz, 1H), 7.41 (d, J=8 Hz, 2H), 6.95 (d, J=8 Hz, 1H), 3.75 (s, 3H), 3.64 (s, 3H).

Example 1.123:

Preparation of 1-[3-(4-Chloro-2-methyl-2H-pyrazol-3-yl)-4-methoxy-phenyl]-3-(2-fluoro-phenyl)-urea (Compound 97).

3-(4-Chloro-2-methyl-2H-pyrazol-3-yl)-4-methoxy-phenylamine (20 mg, 0.08 mmol) was treated with 2-Fluorophenyl isocyanate (10 µL, 0.09 mmol) in a similar manner to Example 1.53, providing 8.0 mg (26%) of Compound 97: LCMS m/z (%)=375 (M+H$^{35}$Cl, 100), 377 (M+H$^{37}$Cl, 43). $^1$H NMR (400 MHz, CDCl$_3$) δ: 8.26 (t, 1H), 7.73 (dd, J$_1$=8 Hz, J$_2$=4 Hz, 1H), 7.69 (s, 1H), 7.36 (t, 1H), 7.35 (d, J=4 Hz, 1H), 7.29 (t, 1H), 7.24 (d, J=8 Hz, 1H), 7.19 (d, J=8 Hz, 1H), 7.17 (d, J=8 Hz, 1H), 3.97 (s, 3H), 3.86 (s, 3H).

Example 1.124:

Preparation of 1-[3-(4-Chloro-2-methyl-2H-pyrazol-3-yl)-4-methoxy-phenyl]-3-(3-cyano-phenyl)-urea (Compound 109).

3-(4-Chloro-2-methyl-2H-pyrazol-3-yl)-4-methoxy-phenylamine (55 mg, 0.23 mmol) was treated with 3-Cyanophenyl isocyanate (37 mg, 0.26 mmol) in a similar manner to Example 1.53, providing 57 mg (65%) of Compound 109: LCMS m/z (%)=382 (M+H$^{35}$Cl, 100), 384 (M+H$^{37}$Cl, 38). $^1$H NMR (400 MHz, DMSO-d$_6$) δ: 9.02 (s, 1H), 8.85 (s, 1H), 7.98 (t, 1H), 7.68 (d, J=8 Hz, 1H), 7.62 (s, 1H), 7.59 (dd, J$_1$=12 Hz, J$_2$=2 Hz, 1H), 7.50 (t, 1H), 7.42 (t, 1H), 7.42 (d, J=4 Hz, 1H), 7.18 (d, J=8 Hz, 1H), 3.78 (s, 3H), 3.62 (s, 3H).

Example 1.125:

Preparation of 1-Benzyl-3-[3-(4-chloro-2-methyl-2H-pyrazol-3-yl)-4-methoxy-phenyl]-urea (Compound 105):

3-(4-Chloro-2-methyl-2H-pyrazol-3-yl)-4-methoxy-phenylamine (59 mg, 0.25 mmol) was treated with benzyl isocyanate (34 µL, 0.28 mmol) in a similar manner to Example 1.53, providing 42.7 mg (46.1%) of Compound 105: LCMS m/z (%)=371 (M+H$^{35}$Cl, 100), 373 (M+H$^{37}$Cl, 40). $^1$H NMR (400 MHz, DMSO-d$_6$) δ: 8.55 (s, 1H), 7.58 (s, 1H), 7.50 (dd, J$_1$=8 Hz, J$_2$=4 Hz, 1H), 7.33 (m, 5H), 7.30 (d, J=4 Hz, 1H), 7.10 (d, J=12 Hz, 1H), 6.58 (s, 1H), 4.28 (s, 2H), 3.73 (s, 3H), 3.58 (s, 3H).

Example 1.126:

Preparation of 1-[3-(4-Chloro-2-methyl-2H-pyrazol-3-yl)-4-methoxy-phenyl]-3-(3-nitro-phenyl)-urea (Compound 110).

3-(4-Chloro-2-methyl-2H-pyrazol-3-yl)-4-methoxy-phenylamine (36 mg, 0.15 mmol) was treated with 3-Nitrophenyl isocyanate (28 mg, 0.17 mmol) in a similar manner to Example 1.53, providing 8.7 mg (15%) of Compound 110: LCMS m/z (%)=402 (M+H$^{35}$Cl, 100), 404 (M+H$^{37}$Cl, 38). $^1$H NMR (400 MHz, DMSO-d$_6$) δ: 9.22 (s, 1H), 8.84 (s, 1H), 8.55 (s, 1H), 7.83 (dd, J$_1$=8 Hz, J$_2$=4 Hz, 1H), 7.72 (d, J=8 Hz, 1H), 7.62 (s, 1H), 7.61 (d, J=4 Hz, 1H), 7.58 (s, 1H), 7.58 (t, 1H), 7.41 (d, J=4 Hz, 1H), 7.19 (d, J=12 Hz, 1H), 3.78 (s, 3H), 3.62 (s, 3H).

Example 1.127:

Preparation of 1-[3-(4-Bromo-2-methyl-2H-pyrazol-3-yl)-4-methoxy-phenyl]-3-[3-(1-hydroxy-ethyl)-phenyl]-urea (Compound 94).

Compound 17 (30.2 mg, 0.07 mmol, see Example 1.24) was dissolved in ethanol (5 mL). Sodium Borohydride (3.1 mg, 0.08 mmol) was added under Argon gas. The reaction was stirred overnight and found to be complete by TLC and LC/MS. The mixture was worked up with 1N Hydrogen Chloride solution (10 mL) and EtOAc (2×15 mL). The organic layers were combined and washed with water, dried over Na$_2$SO$_4$, filtered, and the solvent removed under reduced pressure. The residue was then purified by HPLC to afford 19.4 mg (63%) of Compound 94: LCMS m/z (%)=445 (M+H$^{79}$Br, 25), 447 (M+H$^{81}$Br, 25). $^1$H NMR (400 MHz, CDCl$_3$) δ: 7.34 (dd, J$_1$=8 Hz, J$_2$=2 Hz, 1H), 7.26 (s, 1H), 7.20 (s, 1H), 7.14 (s, 1H), 7.11 (d, J=8 Hz, 1H), 7.09 (s, 1H), 7.06 (t, 1H), 6.95 (d, J=4 Hz, 1H), 6.85 (d, J=8 Hz, 1H), 6.76 (d, J=8 Hz, 1H), 4.65 (m, 1H), 3.59 (s, 3H), 3.49 (s, 3H), 1.27 (d, J=4 Hz, 3H).

Example 1.128:

Preparation of 1-[3-(4-Bromo-2-methyl-2H-pyrazol-3-yl)-4-methoxy-phenyl]-3-[3-(1-hydroxyimino-ethyl)-phenyl]-urea (Compound 96).

Compound 17 (54 mg, 0.12 mmol, see Example 1.24) was dissolved in ethanol (10 mL). Hydroxylamine hydrochloride (17 mg, 0.24 mmol) was added under Argon gas. The pH of the solution was then adjusted to pH=4 with 1N Hydrogen Chloride solution. The reaction was stirred overnight at room temperature and found to be complete by TLC and LC/MS. The ethanol was removed under reduced pressure. Then, the residue was worked up with EtOAc (2×20 mL) and Brine (20 mL). The organic layers were combined, dried over Na$_2$SO$_4$, filtered, and the solvent removed under reduced pressure. The residue was then purified by HPLC to afford 8.8 mg (16%) of Compound 96: LCMS m/z (%)=458 (M+H$^{79}$Br, 96), 460 (M+H$^{81}$Br, 100). $^1$H NMR (400 MHz, CDCl$_3$) δ: 7.78 (s, 1H), 7.70 (s, 1H), 7.68 (s, 1H), 7.48 (dd, J$_1$=12 Hz, J$_2$=4 Hz, 1H), 7.42 (s, 1H), 7.41 (dd, J$_1$=8 Hz, J$_2$=4 Hz, 1H), 7.39 (d, J=4 Hz, 1H), 7.30 (t, 1H), 7.19 (d, J=8 Hz, 1H), 7.15 (s, 1H), 7.08 (dd, J$_1$=12 Hz, J$_2$=4 Hz, 1H), 6.88 (dd, J$_1$=12 Hz, J$_2$=8 Hz, 1H), 3.66 (s, 3H), 3.58 (s, 3H), 1.99 (s, 3H).

Example 1.129:

Preparation of 1-[3-(4-Bromo-2-methyl-2H-pyrazol-3-yl)-4-methoxy-phenyl]-3-(4-chloro-2-hydroxy-phenyl)-urea (Compound 107).

3-(4-Bromo-2-methyl-2H-pyrazol-3-yl)-4-methoxy-phenylamine (66 mg, 0.23 mmol) was dissolved in Dichloroethane (1.5 mL). In another flask, 4-nitrophenyl chloroformate was dissolved in Dichloroethane (3 mL) and the solution was heated until it fully dissolved using a heat gun. The two solutions were combined with a catalytic amount of pyridine, and stirred at room temperature. Once the carbamate formed in solution, "Stratospheres" scavenger was added. The mixture was stirred rapidly and filtered after two hours. 2-Amino-5-chlorophenol was then dissolved in pyridine (1 mL) and added to the reaction. After 5 hours of stirring, the reaction was found to be complete by TLC and LC/MS. The solvent was removed under reduced pressure and the residue was purified by HPLC providing 36.5 mg (35%) of Compound 107: LCMS m/z (%)=451 (M+H$^{79}$Br, 80), 453 (M+H$^{81}$Br, 100). $^1$H NMR (400 MHz, CDCl$_3$) δ: 7.74 (s, 1H), 7.67 (s, 1H), 7.53 (d, J=8 Hz, 1H), 7.28 (s, 1H), 7.28 (d, J=12 Hz, 1H), 7.12 (d, J=8 Hz, 1H), 6.99 (s, 1H), 6.91 (d, J=8 Hz, 1H), 3.89 (s, 3H), 3.82 (s, 3H).

Example 1.130:

Preparation of 1-[3-(4-Bromo-2-methyl-2H-pyrazol-3-yl)-4-methoxy-phenyl]-3-(2,2-difluoro-benzo[1,3]dioxol-5-yl)-urea (Compound 115):

3-(4-Bromo-2-methyl-2H-pyrazol-3-yl)-4-methoxy-phenylamine (63 mg, 0.22 mmol) was coupled to 5-Amino-2,2-difluoro-1,3-benzodioxole in a similar manner as described in Example 1.129, providing 32 mg (30%) of Compound 115: LCMS m/z (%)=481 (M+H$^{79}$Br, 96), 483 (M+H$^{81}$Br, 100). $^1$H NMR (400 MHz, acetone-d$_6$) δ: 8.42 (s, 1H), 8.28 (s, 1H), 7.76 (d, J=4 Hz, 1H), 7.70 (dd, J$_1$=8 Hz, J$_2$=4 Hz, 1H), 7.52 (s, 1H), 7.45 (d, J=2 Hz, 1H), 7.19 (d, J=12 Hz, 1H), 7.16 (d, J=2 Hz, 1H), 7.14 (d, J=4 Hz, 1H), 3.83 (s, 3H), 3.70 (s, 3H).

Example 1.131:

Preparation of Intermediate 4-(2-Dimethylamino-ethoxy)-3-(2-methyl-2H-pyrazol-3-yl)-phenylamine.

Step 1: Preparation of N-[4-Hydroxy-3-(2-methyl-2H-pyrazol-3-yl)-phenyl]-acetamide.

A mixture of N-[4-methoxy-3-(2-methyl-2H-pyrazol-3-yl)-phenyl]-acetamide (2.0 g, 8.15 mmol) in anhydrous 1,2-dichloroethane (60 mL) was cooled at 0° C on an ice bath and stirred for 10 minutes. Anhydrous aluminium chloride (4.35 g, 32.6 mmol) was added and the reaction mixture stirred at 0° C for 20 minutes, then moved to an oil bath and stirred at 80° C for 1 hour. Ethyl acetate was added and washed with potassium sodium tartrate (10%) twice. Organic layer was separated, dried over anhydrous Na$_2$SO$_4$, filtered and concentrated to give a crude product that was purified via preparative HPLC. The corresponding fractions were collected and lyophilized to afford N-[4-hydroxy-3-(2-methyl-2H-pyrazol-3-yl)-phenyl]-acetamide as a white solid in 70.0% yield. LCMS m/z (%)=232 (M+H, 100). $^1$H NMR (400 MHz, DMSO-d$_6$) δ: 7.39 (s, 1H), 6.86 (d, J=8.74 Hz, 1H), 6.62 (d, J=8.70 Hz, 1H), 6.47 (s, 1H), 6.15 (s, 1H), 4.80 (bs, 2H), 3.87 (t, J=5.80 Hz, 2H), 3.63 (s, 3H), 2.44 (t, J=5.80 Hz, 2H), 2.08 (s, 6H).

Step 2: Preparation of N-[4-(2-dimethylamino-ethoxy)-3-(2-methyl-2H-pyrazol-3-yl)-phenyl]-acetamide.

To a solution of N-[4-hydroxy-3-(2-methyl-2H-pyrazol-3-yl)-phenyl]-acetamide (0.85 g, 3.7 mmol) in THF (40 mL), triphenyl phosphine (2.91 g, 11.1 mmol) and 2-dimethylamino ethanol (1.11 mL, 11.1 mmol) were added followed by dropwise addition of diisopropyl azodicarboxylate (DIAD) (2.15 mL, 11.1 mmol). The reaction mixture was stirred at room temperature for 2 hours, concentrated to give a crude product that was subjected to a purification on preparative HPLC. The corresponding fractions were collected, neutralized with 1N NaOH and extracted with EtOAc four times to afford N-[4-(2-dimethylamino-ethoxy)-3-(2-methyl-2H-pyrazol-3-yl)-phenyl]-acetamide as a colorless waxy solid in 51.2% yield. LCMS m/z (%)=303 (M+H, 100). $^1$H NMR (400 MHz, DMSO-d$_6$) δ: 9.94 (s, 1H), 7.63 (d, J=8.93 Hz, 1H), 7.52 (s, 1H), 7.46 (s, 1H), 7.14 (d, J=8.98 Hz, 1H), 6.25 (s, 1H), 4.07 (t, J=5.82 Hz, 2H), 3.69 (s, 3H), 2.56 (t, J=5.80 Hz, 2H), 2.15 (s, 6H), 2.05 (s, 3H).

Step 3: Preparation of 4-(2-dimethylamino-ethoxy)-3-(2-methyl-2H-pyrazol-3-yl)-phenylamine Compound N-[4-(2-dimethylamino-ethoxy)-3-(2-methyl-2H-pyrazol-3-yl)-phenyl]-acetamide (0.50 g, 1.7 mmol) was dissolved in ethanol (25 mL), sodium hydroxide (1.5 g, pallets) in 8 mL of water was added and reaction mixture stirred at 80° C overnight then concentrated. Water and brine were added then extracted with EtOAc four times. Organic layers were combined, dried over anhydrous Na$_2$SO$_4$ then solvent removed under reduced pressure to afford 4-(2-dimethylamino-ethoxy)-3-(2-methyl-2H-pyrazol-3-yl)-phenylamine as a light brown oil in 87.5% yield. LCMS m/z (%)=261 (M+H, 100). $^1$H NMR (400 MHz, DMSO-d$_6$) δ:

9.82 (s, 1H), 9.71 (bs, 1H), 7.48-7.45 (m, 3H), 6.93 (d, J=8.74 Hz, 1H), 6.23 (s, 1H), 3.7 (s, 3H), 2.0 (s, 3H).

Example 1.132:

Preparation of 1-(4-Chloro-phenyl)-3-[4-(2-dimethylamino-ethoxy)-3-(2-methyl-2H-pyrazol-3-yl)-phenyl]-urea (Compound 127).

A solution of 4-(2-dimethylamino-ethoxy)-3-(2-methyl-2H-pyrazol-3-yl)-phenylamine (26.0 mg, 0.1 mmol) in methylene chloride (1 mL) was treated with 4-chlorophenylisocyanate (13.3 µL, 0.105 mmol) then reaction mixture stirred at room temperature overnight and concentrated to give an oily residue that was subjected to a purification by flash chromatography (SiO$_2$, CH$_2$Cl2/MeOH gradient elution) to afford Compound 127 as a white solid in 69.8% yield. LCMS m/z (%)=414 (M+H $^{35}$Cl, 100), 416 (M+H $^{37}$Cl, 36). $^1$H NMR (400 MHz, acetone-d$_6$) δ: 8.51 (s, 1H), 8.36 (s, 1H), 7.62-7.59 (m, 3H), 7.50 (s, 1H), 7.42 (s, 1H), 7.31 (d, J=8.90 Hz, 2H), 7.12 (d, J=8.92 Hz, 1H), 6.24 (s, 1H), 4.11 (t, J=5.86 Hz, 2H), 3.77 (s, 3H), 2.61 (t, J=5.85 Hz, 2H), 2.20 (s, 6H).

Example 1.133:

Preparation of 1-[4-(2-Dimethylamino-ethoxy)-3-(2-methyl-2H-pyrazol-3-yl)-phenyl]-3-(4-fluoro-phenyl)-urea (Compound 142).

4-(2-Dimethylamino-ethoxy)-3-(2-methyl-2H-pyrazol-3-yl)-phenylamine (26.0 mg, 0.1 mmol) was treated with 4-fluorophenyl isocyanate (11.8 µL, 0.105 mmol) in a similar manner as described in Example 1.2 to afford Compound 142 as a white solid in 66.4% yield. LCMS m/z (%)=398 (M+H, 100). $^1$H NMR (400 MHz, acetone-d$_6$) δ: 8.33 (s, 1H), 8.25 (s, 1H), 7.61-7.56 (m, 3H), 8.49 (s, 1H), 7.42 (s, 1H), 7.11-7.04 (m, 3H), 6.24 (s, 1H), 4.11 (t, J=5.85 Hz, 2H), 3.77 (s, 3H), 2.62 (t, J=5.85 Hz, 2H), 2.20 (s, 6H).

Example 1.134:

Preparation of 1-(2,4-Difluoro-phenyl)-3-[4-(2-dimethylamino-ethoxy)-3-(2-methyl-2H-pyrazol-3-yl)-phenyl]-urea (Compound 141).

4-(2-Dimethylamino-ethoxy)-3-(2-methyl-2H-pyrazol-3-yl)-phenylamine (26.0 mg, 0.1 mmol) was treated with 2,4-difluorophenyl isocyanate (12.4 µL, 0.105 mmol) in a similar manner as described in Example 1.2 to afford Compound 141 as a white solid in 73.3% yield. LCMS m/z (%)=416 (M+H, 100). $^1$H NMR (400 MHz, DMSO-d$_6$) δ: 8.95 (s, 1H), 8.46 (s, 1H), 8.08-8.02 (m, 1H), 7.45-7.42 (m, 2H), 7.37 (d, J=2.7 Hz, 1H), 7.33-7.27 (m, 1H), 7.12 (d, J=8.95 Hz, 1H), 7.05-6.98 (m, 1H), 6.24 (d, J=2.7 Hz, 1H), 4.03 (t, J=5.80 Hz, 2H), 3.67 (s, 3H), 2.54 (t, J=5.73 Hz, 2H), 2.12 (s, 6H).

Example 1.135:

Preparation of 1-(3-Acetyl-phenyl)-3-[4-(2-dimethylamino-ethoxy)-3-(2-methyl-2H-pyrazol-3-yl)-phenyl]-urea (Compound 143).

4-(2-Dimethylamino-ethoxy)-3-(2-methyl-2H-pyrazol-3-yl)-phenylamine (26.0 mg, 0.1 mmol) was treated with 3-acetylphenyl isocyanate (16.9 µL, 0.105 mmol) in a similar manner as described in Example 1.2 to afford Compound 143 as a colorless waxy solid in 64.3% yield. LCMS m/z (%)=422 (M+H, 100). $^1$H NMR (400 MHz, DMSO-d$_6$) δ: 8.98 (s, 1H), 8.73 (s, 1H), 8.10 (s, 1H), 7.52-7.42 (m, 4H), 7.37 (d, J=8.06 Hz, 1H), 7.37 (d, J=6.75 Hz, 1H), 7.33-7.28 (m, 4H), 7.15 (d, J=8.98 Hz, 1H), 6.28 (s, 1H), 4.08 (t, J=5.80 Hz, 2H), 3.71 (s, 3H), 2.54 (m, 6H), 2.12 (s, 6H).

Example 1.136:

Preparation of 1-[4-(2-Dimethylamino-ethoxy)-3-(2-methyl-2H-pyrazol-3-yl)-phenyl]-3-(3-methoxy-phenyl)-urea (Compound 146).

4-(2-Dimethylamino-ethoxy)-3-(2-methyl-2H-pyrazol-3-yl)-phenylamine (26.0 mg, 0.1 mmol) was treated with 3-methoxyphenyl isocyanate (13.8 µL, 0.105 mmol) in a similar manner as described in Example 1.2 to afford Compound 146 as a colorless waxy solid in 71.1% yield. LCMS m/z (%)=410 (M+H, 100). $^1$H NMR (400 MHz, DMSO-d$_6$) δ: 8.70 (s, 1H), 8.63 (s, 1H), 7.45-7.42 (m, 2H), 7.37 (d, J=2.7 Hz, 1H), 7.18-7.10 (m, 3H), 6.91 (dd, J=8.02 Hz, 1.2 Hz, 1H), 6.53 (dd, J=7.71 Hz, 2.05 Hz, 1H), 6.24 (d, J=1.83 Hz, 1H), 4.03 (t, J=5.80 Hz, 2H), 3.72 (s, 3H), 3.67 (s, 3H), 2.52 (t, J=5.80 Hz, 2H), 2.12 (s, 6H).

Example 1.137:

Preparation of 1-(2,2-Difluoro-benzo[1,3]dioxol-5-yl)-3-[4-(2-dimethylamino-ethoxy)-3-(2-methyl-2H-pyrazol-3-yl)-phenyl]-urea (Compound 144).

To a solution of 4-(2-dimethylamino-ethoxy)-3-(2-methyl-2H-pyrazol-3-yl)-phenylamine (26.0 mg, 0.1 mmol) in methylene chloride (1 mL) pyridine (24.3 µL, 0.3 mmol) and 4-nitrophenyl chloroformate (20.2 mg, 0.1 mmol) were added and the mixture was stirred at room temperature for 1 hour. 5-Amino-2,2-difluoro-1,3-benzodioxole (11.6 µL, 0.1 mmol) was added, the reaction mixture stirred at room temperature for 48 hours and concentrated to give an oily residue that was subjected to a purification by flash chromatography (SiO$_2$, CH$_2$Cl$_2$/MeOH gradient elution) to afford Compound 144 as an off-white solid in 14.0% yield. LCMS m/z (%)=460 (M+H, 100). $^1$H NMR (400 MHz, DMSO-d$_6$) δ: 10.30 (s, 1H), 7.64 (d, J=8.96 Hz, 1H), 7.53 (s, 1H), 7.42 (s, 1H), 7.40-7.34 (m, 4H), 7.13 (d, J=8.92 Hz, 1H), 6.22 (s, 1H), 4.10 (t, J=5.56 Hz, 2H), 3.65 (s, 3H), 3.63 (s, 2H), 2.76-2.65 (m, 2H), 2.22 (s, 6H).

Example 1.138:

Preparation of 1-[3-(4-Chloro-2-methyl-2H-pyrazol-3-yl)-4-hydroxy-phenyl]-3-(2,4-difluoro-phenyl)-urea (Compound 120).

A mixture of 1-[3-(4-Chloro-2-methyl-2H-pyrazol-3-yl)-4-methoxy-phenyl]-3-(2,4-difluoro-phenyl)urea (Compound 77, example 1.61) (0.270 g, 0.69 mmol) in anhydrous 1,2-dichloroethane (10 mL) was cooled to 0° C on an ice bath and stirred for 10 minutes. Anhydrous aluminium chloride (0.368 g, 2.76 mmol) was added and the reaction mixture stirred at 0° C for 20 minutes, then moved to an oil bath and stirred at 80° C for 1 hour. Ethyl acetate was added and washed with potasium sodium tartrate (10%) twice. Organic layer was separated, dried over anhydrous Na$_2$SO$_4$, filtered and concentrated to give the crude product that was further purified via HPLC. The corresponding fractions were collected and lyophilized to afford Compound 120 as a white solid in 75.0% yield. LCMS m/z (%)=379 (M+H $^{35}$Cl, 100), 381 (M+H $^{37}$Cl, 40). $^1$H NMR (400 MHz. DMSO-d$_6$) δ: 9.81 (s, 1H), 8.92 (s, 1H), 8.45 (s, 1H), 8.12-8.06 (m, 1H), 7.63 (s, 1H), 7.40-7.31 (m, 3H), 7.09-7.04 (m, 1H), 6.99 (d, J$_1$=8.72 Hz, 1H), 3.69 (s, 3H).

Example 1.139:

Preparation of 1-[3-(4-Chloro-2-methyl-2H-pyrazol-3-yl)-4-(2-dimethylamino-ethoxy)-phenyl]-3-(2,4-difluoro-phenyl)-urea (Compound 132).

To a solution of 1-[3-(4-chloro-2-methyl-2H-pyrazol-3-yl)-4-hydroxy-phenyl]-3-(2,4-difluoro-phenyl)urea (see above) (0.035 g, 0.09 mmol) in THF (3 mL), triphenyl phosphine (0.071 g, 0.27 mmol) and 2-dimethylamino ethanol (27.1 µL, 0.27 mmol) were added followed by dropwise addition of diisopropyl azodicarboxylate (DIAD) (52.3 µL, 0.27 mmol). The reaction mixture was stirred at room temperature for 2 hours, concentrated to give a crude product that was purified via preparative HPLC. The corresponding fractions were collected, neutralized with 1N NaOH and extracted with EtOAc. A second purification by flash chromatography (SiO$_2$, CH$_2$Cl$_2$/MeOH gradient elution) afforded Compound 132 as an off-white solid in 45.9% yield. LCMS m/z (%)=450 (M+H $^{35}$Cl, 100), 452 (M+H $^{37}$Cl, 32). $^1$H NMR (400 MHz. DMSO-d$_6$) δ: 9.11 (s, 1H), 8.56 (s, 1H), 8.06-8.00 (m, 1H), 7.60 (s, 1H), 7.52 (d, J=8.95 Hz, 1H), 7.38 (s, 1H), 7.33-7.27 (m, 1H), 7.17 (d, J=9.04 Hz, 1H), 7.05-6.98 (m, 1H), 4.12-3.95 (m, 2H), 3.65 (s, 3H), 2.55-2.51 (m, 2H), 2.10 (s, 6H).

Example 1.140:

Preparation of 1-[3-(4-Chloro-2-methyl-2H-pyrazol-3-yl)-4-(3-dimethylamino-propoxy)-phenyl]-3-(2,4-difluoro-phenyl)-urea (Compound 133).

To a solution of 1-[3-(4-chloro-2-methyl-2H-pyrazol-3-yl)-4-hydroxy-phenyl]-3-(2,4-difluoro-phenyl)urea (see above) (0.035 g, 0.09 mmol) in THF (3 mL), triphenyl phosphine (0.071 g, 0.27 mmol) and 3-dimethylamino propanol (31.6 µL, 0.27 mmol) were added followed by dropwise addition of diisopropyl azodicarboxylate (DIAD) (52.3 µL, 0.27 mmol). The reaction mixture was stirred at room temperature for 2 hours, concentrated to give a crude product that was purified via preparative HPLC. The corresponding fractions were collected, neutralized with 1N NaOH and extracted with EtOAc four times. A second purification by flash chromatography (SiO$_2$, CH$_2$Cl$_2$/MeOH gradient elution) afforded Compound 133 as an off-white solid in 25.4% yield. LCMS m/z (%)=464 (M+H $^{35}$Cl, 100), 466 (M+H $^{37}$Cl, 39). $^1$H NMR (400 MHz, DMSO-d$_6$) δ: 9.02 (s, 1H), 8.47 (s, 1H), 8.07-8.01 (m, 1H), 7.62 (s, 1H), 7.51 (d, J=8.90 Hz, 1H), 7.38 (s, 1H), 7.33-7.28 (m, 1H), 7.15 (d, J=9.02 Hz, 1H), 7.03-6.97 (m, 1H), 4.11-3.94 (m, 2H), 3.63 (s, 3H), 2.28-2.18 (m, 2H), 2.11 (s, 6H), 1.78-1.69 (m, 2H).

Example 1.141:

Preparation of 1-[3-(4-Bromo-2-methyl-2H-pyrazol-3-yl)-4-trifluoromethoxy-phenyl]-3-(4-chloro-phenyl)-urea (Compound 108).

Step A: Preparation of (3-bromo-4-trifluoromethoxy-phenyl)-carbamic acid tert-butyl ester.

A solution of 3-bromo-4-(trifluoromethoxy)aniline (3.84 g, 15 mmol) in dioxane (15 mL) was treated with di-tert-butyl-dicarbonate (4.91 g, 22.5 mmol) then the reaction mixture heated at 80° C overnight. The solvent was removed under reduced pressure to give an oily residue that was triturated with hexanes. The precipitate was collected by filtration to give (3-bromo-4-trifluoromethoxy-phenyl)-carbamic acid tert-butyl ester as a white solid in 61.0% yield. $^1$H NMR (400 MHz, DMSO-d$_6$) δ: 9.78 (bs, 1H), 7.87 (s, 1H), 7.54-7.43 (m, 2H), 1.51 (s, 9H).

Step B: Preparation of [3-(2-methyl-2H-pyrazol-3-yl)-4-trifluoromethoxy-phenyl]-carbamic acid tert-butyl ester.

A 25-mL round-bottom flask was charged with (3-bromo-4-trifluoromethoxy-phenyl)-carbamic acid tert-butyl ester (230.0 mg, 0.65 mmol), 1-methyl pyrazole-5-boronic acid (392.9 mg, 1.93 mmol), sodium carbonate (137.8 mg, 1.3 mmol), DME (5 mL) and water (0.5 mL) under argon atmosphere. Tetrakis(triphenylphosphine)palladium (75.1 mg, 0.065 mmol) was added and reaction mixture purged with argon again. The reaction mixture was heated at 80° C overnight then cooled to room temperature. Ethyl acetate (10 mL) was added then washed with brine and water. Organic layer was separated, dried over anhydrous sodium sulfate, filtered and concentrated to give a residue that was subjected to a purification by flash chromatography (SiO$_2$, Hexanes/EtOAc gradient elution) to afford [3-(2-methyl-2H-pyrazol-3-yl)-4-trifluoromethoxy-phenyl]-carbamic acid tert-butyl ester as an off-white solid in 36.5% yield. LCMS m/z (%)=358 (M+H, 100). $^1$H NMR (400 MHz, DMSO-d$_6$) δ: 9.83 (bs, 1H), 7.77 (d, J=8.95 Hz, 1H), 7.69 (s, 1H), 7.63 (s, 1H), 7.57 (d, J=8.84 Hz, 1H), 6.45 (s, 1H), 3.78 (s, 3H), 1.60 (s, 9H).

Step C: Preparation of [3-(2-methyl-2H-pyrazol-3-yl)-4-trifluoromethoxy-phenyl]-carbamic acid tert-butyl ester.

To a solution of [3-(2-methyl-2H-pyrazol-3-yl)-4-trifluoromethoxy-phenyl]-carbamic acid tert-butyl ester (65 mg, 0.18 mmol) in DMF (1.5 mL)N-bromosuccinimide (35.6 mg, 0.2 mmol) was added at 0° C then reaction mixture stirred at room temperature overnight. The resulting mixture was diluted with ethyl acetate, washed with brine and water. The organic layer was separated, dried over anhydrous sodium sulfate, filtered and concentrated to give a yellow oily residue that was subjected to a purification by flash chromatography (SiO$_2$, Hexanes/EtOAc gradient elution) to afford [3-(2-methyl-2H-pyrazol-3-yl)-4-trifluoromethoxy-phenyl]-carbamic acid tert-butyl ester as a white solid in 89.2% yield. LCMS m/z (%)=436 (M+H $^{79}$Br, 100), 438 (M+H $^{81}$Br, 98). $^1$H NMR (400 MHz, CD$_3$OD) δ: 7.79 (d, J=8.90 Hz, 1H), 7.61 (s, 1H), 7.55 (s, 1H), 7.43 (d, J=8.94 Hz, 1H), 3.73 (s, 3H), 1.55 (s, 9H).

Step D: Preparation of 1-[3-(4-Bromo-2-methyl-2H-pyrazol-3-yl)-4-trifluoro-methoxy-phenyl]-3-(4-chloro-phenyl)-urea (Compound 108).

To a solution of [3-(2-methyl-2H-pyrazol-3-yl)-4-trifluoromethoxy-phenyl]-carbamic acid tert-butyl ester (21.8 mg, 0.05 mmol) in methylene chloride (0.5 mL), trifluroacetic acid (0.5 mL) was added and reaction mixture stirred at room temperature for 20 minutes. The solvent was removed under reduced pressure to afford 3-(4-bromo-2-methyl-2H-pyrazol-3-yl)-4-trifluoromethoxy-phenylamine trifluoroacetate as a colorless oil in quantitative yield. LCMS m/z (%)=336 (M+H $^{79}$Br, 100), 338 (M+H $^{81}$Br, 95). This compound was dissolved in methylene chloride (0.8 mL) then treated with N,N-diisopropylethylamine until pH=7-8. 4-Chlorophenyl isocyanate (8.5 mg, 0.055 mmol) was added and reaction mixture stirred at room temperature overnight and concentrated to give a residue that was subjected to apurification by flash chromatography (SiO$_2$, Hexanes/EtOAc gradient elution) to afford Compound 108 as a white solid in 62.0% yield. LCMS m/z (%)=489 (M+H $^{79}$Br $^{35}$Cl, 93), 491 (M+H $^{81}$Br $^{35}$Cl, 100), 493 (M+H $^{81}$Br $^{37}$Cl, 34). $^1$H NMR (400 MHz, CD$_3$OD) δ: 7.71 (dd, J=8.98 Hz, 2.72 Hz, 1H), 7.64-7.62 (m, 2H), 7.49-7.45 (m, 3H), 7.33-7.30 (m, 2H), 3.76 (s, 3H).

Example 1.142:

Preparation of 1-[3-(4-Bromo-2-methyl-2H-pyrazol-3-yl)-4-trifluoromethoxy-phenyl]-3-(2,4-difluoro-phenyl)-urea (Compound 113).

To a solution of [3-(2-methyl-2H-pyrazol-3-yl)-4-trifluoromethoxy-phenyl]-carbamic acid tert-butyl ester (21.8 mg, 0.05 mmol) in methylene chloride (0.5 mL), trifluroacetic acid (0.5 mL) was added and reaction mixture stirred at room temperature for 20 minutes. The solvent was removed under reduced pressure to afford 3-(4-bromo-2-methyl-2H-pyrazol-3-yl)-4-trifluoromethoxy-phenylamine trifluoroacetate as a colorless oil in quantitative yield. LCMS m/z (%)=336 (M+H $^{79}$Br, 100), 338 (M+H $^{81}$Br, 95). This compound was dissolved in methylene chloride (0.8 mL) then treated with N,N-diisopropylethylamine until pH=7-8. 2,4-Difluorophenyl isocyanate (8.5 mg, 0.055 mmol) was added and reaction mixture stirred at room temperature overnight and concentrated to give a residue that was subjected to a purification by flash chromatography (SiO$_2$, Hexanes/EtOAc gradient elution) to afford Compound 113 as a white solid in 46.3% yield. LCMS m/z (%)=491 (M+H $^{79}$Br, 100), 493 (M+H $^{81}$Br, 98). $^1$H NMR (400 MHz, CD$_3$OD) δ: 8.06-8.00 (m, 1H), 7.71 (dd, J=9.00 Hz, 2.74 Hz, 1H), 7.65-7.62 (m, 2H), 7.48 (d, J=9.00 Hz, 1H), 7.09-7.00 (m, 1H), 6.99-6.94 (m, 1H), 3.76 (s, 3H).

Example 1.143:

Preparation of 1-(2,4-Difluoro-phenyl)-3-[4-(3-dimethylamino-propoxy)-3-(2-methyl-2H-pyrazol-3-yl)-phenyl]-urea (Compound 124).

To a solution of 4-(3-dimethylamino-propoxy)-3-(2-methyl-2H-pyrazol-3-yl)-phenylamine (21.4 mg, 0.078 mmol) in CH$_2$Cl$_2$ (2 mL) was added 2,4-difluorophenyl isocyanate (0.10 µL, 0.084 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 124 as a colorless solid (30.2 mg, 73%). LCMS m/z (%)=430 (MH$^+$) (100), $^1$H NMR (400 MHz, DMSO-d$_6$) δ: 8.94 (bs, 1H), 8.46 (bs, 1H), 8.09-8.00 (m, 1H), 7.45 (d, J=1.80 Hz, 1H), 7.42 (dd, J=8.89, 2.72 Hz, 1H), 7.34-7.26 (m, 1H), 7.09 (d, J=8.94 Hz, 1H), 7.06-6.99 (m, 1H), 6.24 (d, J=1.83 Hz, 1), 3.97 (t, J=6.32 Hz, 2H), 3.65 (s, 3H), 2.23 (t, J=7.07 Hz, 2H), 2.10 (s, 6H), 1.78-1.69 (m, 2H).

Example 1.144:

Preparation of 1-[4-(3-Dimethylamino-propoxy)-3-(2-methyl-2H-pyrazol-3-yl)-phenyl]-3-(2-fluoro-phenyl)-urea (Compound 138).

To a solution of 4-(3-dimethylamino-propoxy)-3-(2-methyl-2H-pyrazol-3-yl)-phenylamine (60.6 mg, 0.221 mmol) in CH$_2$Cl$_2$ (2 mL) was added 2-fluorophenyl isocyanate (0.27 µL, 0.240 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 138 as a colorless solid (85.5 mg, 91%). LCMS m/z (%)=412 (MH$^+$) (100), $^1$H NMR (400 MHz, DMSO-d$_6$) δ: 9.36 (bs, 1H), 8.25 (bs, 1H), 8.15 (dd, J=8.34, 1.52 Hz, 1H), 7.47-7.42 (m, 3H), 7.40 (d, J=2.78 Hz, 1H), 7.31-7.26 (m, 1H), 7.11 (d, J=9.09 Hz, 1H), 7.05-6.99 (m, 1H), 6.25 (d, J=2.02 Hz, 1H), 3.98 (t, J=6.32 Hz, 2H), 3.66 (s, 3H), 2.19 (t, J=7.07 Hz, 2H), 2.07 (s, 6H), 1.77-1.69 (m, 2H).

Example 1.145:

Preparation of 1-[4-(3-Dimethylamino-propoxy)-3-(2-methyl-2H-pyrazol-3-yl)-phenyl]-3-(4-trifluoromethyl-phenyl)-urea (Compound 137).

To a solution of 4-(3-dimethylamino-propoxy)-3-(2-methyl-2H-pyrazol-3-yl)-phenylamine (45.8 mg, 0.167 mmol) in CH$_2$Cl$_2$ (2 mL) was added 4-(trifluoromethyl) phenyl isocyanate (0.28 µL, 0.196 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 137 as a colorless solid (25.1 mg, 33%). LCMS m/z (%)=462 (MH$^+$) (100), $^1$H NMR (400 MHz, DMSO-d$_6$) δ: 9.11 (bs, 1H), 8.75 (bs, 1H), 7.65 (d, J=9.08 Hz, 2H), 7.62 (d, J=9.35 Hz, 2H), 7.47 (dd, J=9.09, 2.78 Hz, 1H), 7.45 (d, J=1.77 Hz, 1H), 7.39 (d, J=2.78 Hz, 1H), 7.10 (d, J=8.84 Hz, 1H), 6.24 (d, J=1.77 Hz, 1H), 3.98 (t, J=6.32 Hz, 2H), 3.66 (s, 3H), 2.19 (t, J=7.07 Hz, 2H), 2.07 (s, 6H), 1.77-1.69 (m, 2H).

Example 1.146:

Preparation of 1-[4-(3-Dimethylamino-propoxy)-3-(2-methyl-2H-pyrazol-3-yl)-phenyl]-3-(2-fluoro-5-methyl-phenyl)-urea (Compound 139).

To a solution of 4-(3-dimethylamino-propoxy)-3-(2-methyl-2H-pyrazol-3-yl)-phenylamine (43.9 mg, 0.160 mmol) in CH$_2$Cl$_2$ (2 mL) was added 2-fluoro-5-methylphenyl isocyanate (0.23 µL, 0.176 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 139 as a colorless solid (53.2 mg, 78%). LCMS m/z (%)=426 (MH$^+$) (100), $^1$H NMR (400 MHz, DMSO-d$_6$) δ: 8.98 (bs, 1H), 8.42 (bs, 1H), 7.96 (dd, J=7.89, 1.96 Hz, 1H), 7.45 (d, J=1.82 Hz, 1H), 7.44-7.38 (m, 2H), 7.13-7.06 (m, 2H), 6.82-6.75 (m, 1H), 6.24 (d, J=1.85 Hz, 1H), 3.98 (t, J=6.35 Hz, 2H), 3.66 (s, 3H), 2.25 (s, 3H), 2.19 (t, J=7.03 Hz, 2H), 2.07 (s, 6H), 1.77-1.68 (m, 2H).

Example 1.147:

Preparation of 1-(2-Chloro-phenyl)-3-[4-(3-dimethylamino-propoxy)-3-(2-methyl-2H-pyrazol-3-yl)-phenyl]-urea (Compound 140).

To a solution of 4-(3-dimethylamino-propoxy)-3-(2-methyl-2H-pyrazol-3-yl)-phenylamine (51.4 mg, 0.187 mmol) in CH$_2$Cl$_2$ (2 mL) was added 2-chlorophenyl isocyanate (0.25 µL, 0.207 mmol) and stirred for two hours. The resulting material was purified by solid phase extraction (SCX, 1 gram cartridge), eluting with methanol (30 mL)

followed by 2M NH$_3$ in methanol (30 mL). The NH$_3$ containing fractions were dried in vacuo to afford Compound 140 as a colorless solid (76.5 mg, 95%). LCMS m/z (%)=428 (M+H$^{35}$Cl, 100), 430 (M+H$^{37}$Cl, 37) $^1$H NMR (400 MHz, DMSO-d$_6$) δ: 9.36 (bs, 1H), 8.25 (bs, 1H), 8.15 (dd, J=8.33, 1.48 Hz, 1H), 7.48-7.42 (m, 3H), 7.40 (d, J=2.70 Hz, 1H), 7.31-7.26 (m, 1H), 7.11 (d, J=8.92 Hz, 1H), 7.05-6.99 (m, 1H), 6.25 (d, J=1.84 Hz, 1H), 3.98 (t, J=6.36 Hz, 2H), 3.66 (s, 3H), 2.19 (t, J=7.04 Hz, 2H), 2.07 (s, 6H), 1.77-1.69 (m, 2H).

Example 1.148:

Preparation of 1-(3-Chloro-phenyl)-3-[4-(3-dimethylamino-propoxy)-3-(2-methyl-2H-pyrazol-3-yl)-phenyl]-urea (Compound 134).

To a solution of 4-(3-dimethylamino-propoxy)-3-(2-methyl-2H-pyrazol-3-yl)-phenylamine (47.4 mg, 0.173 mmol) in CH$_2$Cl$_2$ (2 mL) was added 3-chlorophenyl isocyanate (0.24 µL, 0.197 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 134 as a colorless solid (31.0 mg, 42%). LCMS m/z (%)=428 (M+H$^{35}$Cl, 100), 430 (M+H$^{37}$Cl, 39), $^1$H NMR (400 MHz, DMSO-d$_6$) δ: 8.64 (bs, 1H), 8.59 (bs, 1H), 7.47-7.41 (m, 3H), 7.45 (d, J=1.79 Hz, 1H), 7.37 (d, J=2.71 Hz, 1H), 7.30-7.23 (m, 2H), 7.09 (d, J=8.97 Hz, 1H), 6.98-6.92 (m, 1H), 6.24 (d, J=1.85 Hz, 1H), 3.97 (t, J=6.36 Hz, 2H), 3.66 (s, 3H), 2.19 (t, J=7.04 Hz, 2H), 2.07 (s, 6H), 1.77-1.69 (m, 2H).

Example 1.149:

Preparation of 1-[4-(3-Dimethylamino-propoxy)-3-(2-methyl-2H-pyrazol-3-yl)-phenyl]-3-(4-methoxyphenyl)-urea (Compound 131).

To a solution of 4-(3-dimethylamino-propoxy)-3-(2-methyl-2H-pyrazol-3-yl)-phenylamine (38.3 mg, 0.140 mmol) in CH$_2$Cl$_2$ (2 mL) was added 4-methoxyphenyl isocyanate (0.21 µL, 0.162 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 131 as a colorless solid (53.1 mg, 90%). LCMS m/z (%)=424 (MH$^+$) (100), $^1$H NMR (400 MHz, DMSO-d$_6$) δ: 8.49 (bs, 1H), 8.43 (bs, 1H), 7.44 (d, J=1.86 Hz, 1H), 7.42 (dd, J=8.92, 2.73 Hz, 1H), 7.36 (d, J=2.71 Hz, 1H), 7.33 (d, J=9.09 Hz, 2H), 7.07 (d, J=8.96 Hz, 1H), 6.85 (d, J=9.09 Hz, 2H), 6.23 (d, J=1.82 Hz, 1H), 3.96 (t, J=6.35 Hz, 2H), 3.71 (s, 3H), 3.65 (s, 3H), 2.18 (t, J=7.05 Hz, 2H), 2.07 (s, 6H), 1.77-1.69 (m, 2H).

Example 1.150:

Preparation of 1-[4-(3-Dimethylamino-propoxy)-3-(2-methyl-2H-pyrazol-3-yl)-phenyl]-3-p-tolyl-urea (Compound 130).

To a solution of 4-(3-dimethylamino-propoxy)-3-(2-methyl-2H-pyrazol-3-yl)-phenylamine (45.9 mg, 0.167 mmol) in CH$_2$Cl$_2$ (2 mL) was added 4-methylphenyl isocyanate (0.24 µL, 0.191 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 130 as a colorless solid (61.8 mg, 91%). LCMS m/z (%)=408 (MH$^+$) (100), $^1$H NMR (400 MHz, DMSO-d$_6$) δ: 8.53 (bs, 1H), 8.52 (bs, 1H), 7.44 (d, J=1.77 Hz, 1H), 7.43 (dd, J=8.91, 2.73 Hz, 1H), 7.36 (d, J=2.70 Hz, 1H), 7.31 (d, J=8.43 Hz, 2H), 7.08 (d, J=8.92 Hz, 1H), 7.06 (d, J=8.32 Hz, 2H), 6.23 (d, J=1.82 Hz, 1H), 3.96 (t, J=6.36 Hz, 2H), 3.65 (s, 3H), 2.23 (s, 3H), 2.19 (t, J=7.05 Hz, 2H), 2.07 (s, 6H), 1.77-1.69 (m, 2H).

Example 1.151:

Preparation of 1-(3-Chloro-4-fluoro-phenyl)-3-[4-(3-dimethylamino-propoxy)-3-(2-methyl-2H-pyrazol-3-yl)-phenyl]-urea (Compound 135).

To a solution of 4-(3-dimethylamino-propoxy)-3-(2-methyl-2H-pyrazol-3-yl)-phenylamine (57.3 mg, 0.209 mmol) in CH$_2$Cl$_2$ (2 mL) was added 3-chloro-4-fluorophenyl isocyanate (0.30 µL, 0.241 mmol) and stirred for two hours. The resulting material was purified by solid phase extraction (SCX, 1 gram cartridge), eluting with methanol (30 mL) followed by 2M NH$_3$ in methanol (30 mL).

The NH$_3$ containing fractions were dried in vacuo to afford Compound 135 as a colorless solid (66.2 mg, 71%). LCMS m/z (%)=446 (M+H$^{35}$Cl, 100), 448 (M+H$^{37}$Cl, 35), $^1$H NMR (400 MHz, DMSO-d$_6$) δ: 8.87 (bs, 1H), 8.69 (bs, 1H), 7.81-7.77 (m, 1H), 7.47-7.42 (m, 2H), 7.37 (d, J=2.71 Hz, 1H), 7.35-7.26 (m, 2H), 7.09 (d, J=8.98 Hz, 1H), 6.24 (d, J=1.83 Hz, 1H), 3.98 (t, J=6.36 Hz, 2H), 3.65 (s, 3H), 2.19 (t, J=7.04 Hz, 2H), 2.07 (s, 6H), 1.77-1.69 (m, 2H).

Example 1.152:

Preparation of 1-(3,4-Difluoro-phenyl)-3-[4-(3-dimethylamino-propoxy)-3-(2-methyl-2H-pyrazol-3-yl)-phenyl]-urea (Compound 136).

To a solution of 4-(3-dimethylamino-propoxy)-3-(2-methyl-2H-pyrazol-3-yl)-phenylamine (61.1 mg, 0.223 mmol) in CH$_2$Cl$_2$ (2 mL) was added 3,4-difluorophenyl isocyanate (0.30 µL, 0.256 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 136 as a colorless solid (53.3 mg, 56%). LCMS m/z (%)=430 (M+H, 100), $^1$H NMR (400 MHz, DMSO-d$_6$) δ: 8.93 (bs, 1H), 8.72 (bs, 1H), 7.71-7.61 (m, 1H), 7.49-7.42 (m, 2H), 7.37 (d, J=2.68 Hz, 1H), 7.35-7.28 (m, 1H), 7.14-7.06 (m, 1H), 7.09 (d, J=8.96 Hz, 1H), 6.23 (d, J=1.82 Hz, 1H), 3.97 (t, J=6.37 Hz, 2H), 3.65 (s, 3H), 2.19 (t, J=7.05 Hz, 2H), 2.07 (s, 6H), 1.77-1.68 (m, 2H).

Example 1.153:

Preparation of 1-[4-(3-Dimethylamino-propoxy)-3-(2-methyl-2H-pyrazol-3-yl)-phenyl]-3-phenyl-urea (Compound 145).

To a solution of 4-(3-dimethylamino-propoxy)-3-(2-methyl-2H-pyrazol-3-yl)-phenylamine (45.6 mg, 0.166 mmol) in CH$_2$Cl$_2$ (2 mL) was added phenyl isocyanate (0.20 µL, 0.184 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 145 as a colorless solid (45.3 mg, 69%). LCMS m/z (%)=394 (M+H, 100), $^1$H NMR (400 MHz, DMSO-d$_6$) δ: 8.64 (bs, 1H), 8.59 (bs, 1H), 7.48-7.41 (m, 4H), 7.37 (d, J=2.71 Hz, 1H), 7.29-7.23 (m, 2H), 7.09 (d, J=8.97 Hz, 1H), 6.98-6.92 (m, 1H), 6.24 (d, J=1.85 Hz, 1H), 3.97 (t, J=6.36 Hz, 2H), 3.66 (s, 3H), 2.19 (t, J=7.04 Hz, 2H), 2.07 (s, 6H), 1.77-1.68 (m, 2H).

Example 1.154:

Preparation of 1-[4-(3-Dimethylamino-propoxy)-3-(2-methyl-2H-pyrazol-3-yl)-phenyl]-3-(4-fluoro-phenyl)-urea (Compound 125).

To a solution of 4-(3-dimethylamino-propoxy)-3-(2-methyl-2H-pyrazol-3-yl)-phenylamine (24.6 mg, 0.090 mmol) in CH$_2$Cl$_2$ (2 mL) was added 4-fluorophenyl isocyanate (0.12 µL, 0.107 mmol) and stirred for two hours. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 125 as a colorless solid (27.0 mg, 73%). LCMS m/z (%)=412 (M+H, 100), $^1$H NMR (400 MHz, DMSO-d$_6$) δ: 8.67 (bs, 1H), 8.58 (bs, 1H), 7.48-7.41 (m, 4H), 7.36 (d, J=2.70 Hz, 1H), 7.14-7.06 (m, 3H), 6.23 (d, J=1.82 Hz, 1H), 3.97 (t, J=6.34 Hz, 2H), 3.65 (s, 3H), 2.18 (t, J=7.05 Hz, 2H), 2.07 (s, 6H), 1.77-1.68 (m, 2H).

Example 1.155:

Preparation of 1-(4-Chloro-benzyl)-3-[4-(3-dimethylamino-propoxy)-3-(2-methyl-2H-pyrazol-3-yl)-phenyl]-urea (Compound 126).

To a solution of 4-(3-dimethylamino-propoxy)-3-(2-methyl-2H-pyrazol-3-yl)-phenylamine (20.5 mg, 0.075 mmol) in CH$_2$Cl$_2$ (2 mL) was added 4-chlorobenzyl isocyanate (0.17 µL, 0.128 mmol) and stirred overnight. The resulting material was purified by solid phase extraction (SCX, 1 gram cartridge), eluting with methanol (30 mL) followed by 2M NH$_3$ in methanol (30 mL). The NH$_3$ containing fractions were dried in vacuo to afford Compound 126 as a slightly yellow oil (29.8 mg, 90%). LCMS m/z (%)=442 (M+H$^{35}$Cl, 100), 444 (M+H$^{37}$Cl, 40)$^1$H NMR (400 MHz, DMSO-d$_6$) δ: 8.53 (bs, 1H), 7.43 (d, J=1.81 Hz, 1H), 7.41-7.36 (m, 4H), 7.34-7.28 (m, 3H), 7.03 (d, J=8.94 Hz, 1H), 6.63 (d, J=6.00 Hz, 1H), 6.20 (d, J=1.83 Hz, 1H), 4.26 (d, J=5.96 Hz, 2H), 3.94 (t, J=6.36 Hz, 2H), 3.63 (s, 3H), 2.18 (t, J=7.05 Hz, 2H), 2.06 (s, 6H), 1.77-1.69 (m, 2H).

Example 1.156:

Preparation of 1-(2,2-Difluoro-benzo[1,3]dioxol-5-yl)-3-[4-(3-dimethylamino-propoxy)-3-(2-methyl-2H-pyrazol-3-yl)-phenyl]-urea (Compound 129).

To a solution of 4-nitrophenyl chloroformate (55.1 mg, 0.273 mmol) in 1,2-dichloroethane (7 mL) and pyridine (22 µL, 0.272 mmol) was added 5-amino-2,2-difluoro-1,3-benzodioxole (28 µL, 0.241 mmol) and stirred for one hour. A spatula of StratoSpheres PL-DETA resin was added and stirring continued for an additional hour. The resulting mix was filtered (washing with 3 mL 1,2-dichloroethane) into a flask containing 4-(3-dimethylamino-propoxy)-3-(2-methyl-2H-pyrazol-3-yl)-phenylamine (49.7 mg, 0.181 mmol) and stirring continued overnight. The resulting material was purified by HPLC. The product was dried in vacuo to afford Compound 129 as a white solid (29.0 mg, 34%). LCMS m/z (%)=474 (M+H, 100), $^1$H NMR (400 MHz, DMSO-d$_6$) δ: 8.91 (bs, 1H), 8.61 (bs, 1H), 7.65 (d, J=2.09 Hz, 1H), 7.44 (d, J=1.86 Hz, 1H), 7.44 (dd, J=8.88, 2.82 Hz, 1H), 7.37 (d, J=2.71 Hz, 1H), 7.29 (d, J=8.75 Hz, 1H), 7.09 (d, J=8.95 Hz, 1H), 7.07 (dd, J=8.78, 2.18 Hz, 1H), 6.23 (d, J=1.81 Hz, 1H), 3.97 (t, J=6.35 Hz, 2H), 3.65 (s, 3H), 2.19 (t, J=7.03 Hz, 2H), 2.07 (s, 6H), 1.77-1.67 (m, 2H).

Example 1.157:

Preparation of Dimethyl-{3-[2-(2-methyl-2H-pyrazol-3-yl)-4-nitro-phenoxy]-propyl}-amine.

Dimethyl-{3-[2-(2-methyl-2H-pyrazol-3-yl)-4-nitro-phenoxy]-propyl}-amine was synthesized from 2-(2-methyl-2H-pyrazol-3-yl)-4-nitro-phenol (4.064 g) using a similar manner as described in Example 1.139. Yellow oil (3.147 g, 56%). LCMS m/z (%)=305 (M+H, 100), $^1$H NMR (400 MHz, DMSO-d$_6$) δ: 8.35 (dd, J=9.19, 2.90 Hz, 1H), 8.10 (d, J=2.88 Hz, 1H), 7.50 (d, J=1.86 Hz, 1H), 7.39 (d, J=9.26 Hz, 1H), 6.37 (d, J=1.86 Hz, 1H), 4.21 (t, J=6.40 Hz, 2H), 3.67 (s, 3H), 2.21 (t, J=6.98 Hz, 2H), 2.08 (s, 6H), 1.85-1.76 (m, 2H).

Example 1.158:

Preparation of N-[4-Hydroxy-3-(2-methyl-2H-pyrazol-3-yl)-phenyl]-acetamide.

To a suspension of N-[4-methoxy-3-(2-methyl-2H-pyrazol-3-yl)-phenyl]-acetamide (2.57 g, 10.48 mmol) in 1,2-dichloroethane (75 mL) was added BBr$_3$ (10 mL, 106 mmol) and stirred for three hours. The nonhomogeneous suspension was heated to reflux for 15 minutes and then cooled to room temperature. The reaction was quenched by slow addition of methanol. The resulting material was purified by HPLC. The product was dried in vacuo to afford N-[4-hydroxy-3-(2-methyl-2H-pyrazol-3-yl)-phenyl]-acetamide as a white solid (508 mg, 21%). LCMS m/z (%)=232 (M+H, 100), $^1$H NMR (400 MHz, DMSO-d$_6$) δ: 9.77 (bs, 1H), 9.66 (bs, 1H), 7.44-7.40 (m, 3H), 6.89 (d, J=8.85 Hz, 1H), 6.37 (d, J=1.81 Hz, 1H), 3.66 (s, 3H), 1.99 (s, 3H).

Example 1.159:

Preparation of N-[4-(3-Dimethylamino-propoxy)-3-(2-methyl-2H-pyrazol-3-yl)-phenyl]-acetamide.

N-[4-(3-Dimethylamino-propoxy)-3-(2-methyl-2H-pyrazol-3-yl)-phenyl]-acetamide was synthesized from N-[4-hydroxy-3-(2-methyl-2H-pyrazol-3-yl)-phenyl]-acetamide (489 mg) using a similar manner as described in Example 1.139. Colorless oil (375.1 mg, 56%). LCMS m/z (%)=317 (M+H, 100), $^1$H NMR (400 MHz, DMSO-d$_6$) δ: 9.89 (bs, 1H), 7.58 (dd, J=8.92, 2.66 Hz, 1H), 7.48 (d, J=2.65 Hz, 1H), 7.44 (d, J=1.84 Hz, 1H), 7.08 (d, J=8.98 Hz, 1H), 6.21 (d, J=1.85 Hz, 1H), 3.97 (t, J=6.37 Hz, 2H), 3.63 (s, 3H), 2.19 (t, J=7.03 Hz, 2H), 2.07 (s, 6H), 2.01 (s, 3H), 1.77-1.68 (m, 2H).

Example 1.160:

Preparation of 4-(3-dimethylamino-propoxy)-3-(2-methyl-2H-pyrazol-3-yl)-phenylamine.

Method 1: Dimethyl-{3-[2-(2-methyl-2H-pyrazol-3-yl)-4-nitro-phenoxy]-propyl}-amine (1.4047 g, 4.62 mmol) and 5% Pd/C (114 mg) were stirred in methanol (50 mL) under 1 atm of hydrogen for 75 minutes. The suspension was filtered through celite and dried in vacuo to afford 4-(3-dimethylamino-propoxy)-3-(2-methyl-2H-pyrazol-3-yl)-phenylamine as an orange oil (1.27 g, 100%).

Method 2. 4-(3-dimethylamino-propoxy)-3-(2-methyl-2H-pyrazol-3-yl)-phenylamine (375 mg, 1.18 mmol) and 50% NaOH in $H_2O$ (2.5 mL) were refluxed overnight in methanol (20 mL). The resulting material was purified by HPLC to give an orange oil (230.2 mg, 71%).

LCMS m/z (%)=275 (M+H, 100), $^1$H NMR (400 MHz, DMSO-$d_6$) δ: 7.40 (d, J=1.81 Hz, 1H), 6.85 (d, J=8.73 Hz, 1H), 6.62 (dd, J=8.68, 2.82 Hz, 1H), 6.47 (d, J=2.80 Hz, 1H), 6.15 (d, J=1.83 Hz, 1H), 4.80 (bs, 2H), 3.81 (t, J=6.35 Hz, 2H), 3.62 (s, 3H), 2.13 (t, J=7.04 Hz, 2H), 2.05 (s, 6H), 1.69-1.59 (m, 2H).

Example 1.161:

Preparation of 1-[3-(4-Bromo-2-methyl-2H-pyrazol-3-yl)-4-methoxy-phenyl]-3-(4-dimethylamino-phenyl)-urea (Compound 116).

To 3-(4-bromo-2-methyl-2H-pyrazol-3-yl)-4-methoxy-phenylamine (34.9 mg, 0.124 mmol) in $CH_2Cl_2$ (3 mL) was added 4-(dimethylamino)phenyl isocyanate (21 mg, 0.129 mmol) and stirred for two days. The resulting material was purified by HPLC. The product was dried in vacuo to afford Compound 116 as a waxy solid (13.5 mg, 25%). LCMS m/z (%)=444 (M+H$^{79}$Br, 100), 446 (M+H$^{81}$Br, 95), $^1$H NMR (400 MHz, DMSO-$d_6$) δ: 8.51 (bs, 1H), 8.26 (bs, 1H), 7.61 (s, 1H), 7.53 (dd, J=8.97, 2.71 Hz, 1H), 7.34 (d, J=2.70 Hz, 1H), 7.24 (d, J=9.03 Hz, 2H), 7.12 (d, J=9.05 Hz, 1H), 6.68 (d, J=9.07 Hz, 2H), 3.75 (s, 3H), 3.63 (s, 3H), 2.82 (s, 6H).

Example 1.162:

Preparation of 1-(4-Chloro-phenyl)-3-[4-(3-dimethylamino-propoxy)-3-(2-methyl-2H-pyrazol-3-yl)-phenyl]-urea (Compound 122).

Compound 122 was synthesized from Compound 119 (79.2 mg, 0.231 mmol) using a similar manner as described in Example 1.139. White solid (19.6 mg, 20%). LCMS m/z (%)=428 (M+H$^{35}$Cl, 100), 430 (M+H$^{37}$Cl, 39), $^1$H NMR (400 MHz, DMSO-$d_6$) δ: 8.80 (bs, 1H), 8.63 (bs, 1H), 7.50-7.42 (m, 4H), 7.36 (d, J=2.71 Hz, 1H), 7.31 (d, J=8.90 Hz, 2H), 7.09 (d, J=8.96 Hz, 1H), 6.23 (d, J=1.81 Hz, 1H), 3.97 (t, J=6.35 Hz, 2H), 3.65 (s, 3H), 2.19 (t, J=7.05 Hz, 2H), 2.07 (s, 6H), 1.77-1.68 (m, 2H).

Example 1.163:

Preparation of 1-[3-(4-Bromo-2-methyl-2H-pyrazol-3-yl)-4-(3-dimethylamino-propoxy)-phenyl]-3-(4-chloro-phenyl)-urea (Compound 117).

Compound 117 was synthesized from Compound 58 (65.1 mg, 0.154 mmol) using a similar manner as described in Example 1.139. White solid (41.8 mg, 53%). LCMS m/z (%)=506 (M+H$^{79}$Br, 100), 508 (M+H$^{81}$Br, 81), $^1$H NMR (400 MHz, DMSO-$d_6$) δ: 8.81 (bs, 1H), 8.71 (bs, 1H), 7.62 (s, 1H), 7.53 (dd, J=8.96, 2.71 Hz, 1H), 7.47 (d, J=8.92 Hz, 2H), 7.35 (d, J=2.70 Hz, 1H), 7.31 (d, J=8.88 Hz, 2H), 7.14 (d, J=9.03 Hz, 1H), 4.07-3.99 (m, 1H), 3.98-3.89 (m, 1H), 3.64 (s, 3H), 2.18 (t, J=6.58 Hz, 2H), 2.07 (s, 6H), 1.77-1.66 (m, 2H).

Example 1.164:

Preparation of {2-(4-Bromo-2-methyl-2H-pyrazol-3-yl)-4-[3-(4-chloro-phenyl)-ureido]-phenoxy}-acetic acid (Compound 118).

{2-(4-Bromo-2-methyl-2H-pyrazol-3-yl)-4-[3-(4-chloro-phenyl)-ureido]-phenoxy}-acetic acid ethyl ester was synthesized from Compound 58 (125.5 mg, 0.298 mmol) using a similar manner as described in Example 1.139. The resulting material was purified by HPLC. The product was dried in vacuo to afford the ethyl ester as an impure brown solid (99.9 mg).

To a solution of the ethyl ester in methanol (1 mL) and THF (5 mL) was added 1M LiOH in $H_2O$ (1 mL). After 30 minutes the resulting material was purified by HPLC. The product was dried in vacuo to afford Compound 118 as a white solid (54.0 mg, 38% over two steps). LCMS m/z (%)=479 (M+H$^{79}$Br, 71), 481 (M+H$^{81}$Br, 100), $^1$H NMR (400 MHz, DMSO-$d_6$) δ: 13.06 (bs, 1H), 8.80 (bs, 1H), 8.73 (bs, 1H), 7.61 (s, 1H), 7.51 (dd, J=9.02, 2.61 Hz, 1H), 7.47 (d, J=8.87 Hz, 2H), 7.38 (d, J=2.67 Hz, 1H), 7.31 (d, J=8.85 Hz, 2H), 7.00 (d, J=9.08 Hz, 1H), 4.75 (d, J=16.65 Hz, 1H), 4.68 (d, J=16.61 Hz, 1H), 3.72 (s, 3H).

Example 1.165:

Preparation of 1-[3-(4-Bromo-2H-pyrazol-3-yl)-4-methoxy-phenyl]-3-(2,4-difluoro-phenyl)-urea (Compound 152).

Step 1: Preparation of 3-Diethylamino-1-(2-hydroxy-5-nitro-phenyl)-propenone.

6-Nitrochromone (6.64 g, 34.78 mmol) was dissolved in pyridine (55 mL) by warming at 55° C. Diethylamine (3.05 g, 41.73 mmol) was added in drops under nitrogen at 55° C with stirring, and the mixture was stirred for 40 minutes [LCMS showed complete conversion to product, peak at 265 (M+H)]. The resulting mixture was cooled to room temperature and solvent removed under vacuum to afford the product as a yellow solid (8.94 g, 97%). LCMS m/z (%)=265 (M+H, 100), $^1$H NMR (Bruker, 400 MHz, CDCl$_3$) δ: 15.3 (s, 1H), 8.61 (s, 1H), 8.22 (dd, J=12.4 Hz, 1H), 8.01 (d, J=12 Hz, 1H), 6.98 (d, J=8 Hz, 1H), 5.85 (d, J=16 Hz, 1H), 3.45 (q, J=8 Hz, 4H), 1.31 (t, J=8 Hz, 6H).

Step 2: Preparation of 3-Diethylamino-1-(2-methoxy-5-nitro-phenyl)-propenone.

To a stirred solution of 3-Diethylamino-1-(2-hydroxy-5-nitro-phenyl)-propenone (6.5 g, 24.6 mmole) in acetone (200 mL) was added potassium carbonate (6.8 g, 49.2 mmole). After 30 minutes dimethyl sulfate (3.73 g, 29.5 mmole) was added to the reaction mixture and stirred at ambient temperature for 20 hrs. The slurry was filtered off and the filtrate was evaporated to furnish a yellow solid. The crude was purified on silica (Biotage) using hexane to 30% ethyl acetate in hexane as eluant. The fractions containing the product were evaporated in vacuo to afford a light yellow solid (5.2 g, 76%). LCMS m/z (%)=279 (M+H, 100), $^1$H NMR (Bruker, 400 MHz, CDCl$_3$) δ: 8.5 (bs, 1H), 8.23-8.26

(dd, J=9.1, 2.1 Hz, 1H), 7.6 (bs, 1H), 6.98-7.01 (d, J=9.0 Hz, 1H), 5.51-5.54 (d, J=12.84 Hz, 1H), 3.98 (s, 3H), 3.28-3.31 (q, J=6.95 Hz, 4H), 1.31 (t, J=6.68 Hz, 6H).

Step 3: Preparation of 1-(5-Amino-2-methoxy-phenyl)-3-diethylamino-propenone.

To a solution of 3-Diethylamino-1-(2-methoxy-5-nitrophenyl)-propenone (0.6 g, 2.16 mmole) in methanol (30 mL) purged with argon was added 5% Pd—C(Degussa, 0.25 g). Then hydrogen gas was bubbled (30 minutes) through the mixture until LCMS and TLC showed complete conversion to product. The slurry was filtered off through a celite and the filtrate was evaporated in vacuo to furnish a yellow solid (0.45 g, 84%). LCMS m/z (%)=249 (M+H, 100), $^1$H NMR (Bruker, 400 MHz, CDCl$_3$) δ: 6.9 (bs, 1H), 6.76-6.78 (d, J=8.6 Hz, 1H), 6.67-6.71 (dd, J=8.58, 2.61 Hz, 2H), 5.64 (bs, 1H), 3.78 (s, 3H), 3.5 (bs, 1H), 3.28-3.31 (q, J=6.95 Hz, 4H), 1.22-1.24 (t, J=6.68 Hz, 6H).

Step 4: Preparation of 1-[3-(3-Diethylamino-acryloyl)-4-methoxy-phenyl]-3-(2,4-difluoro-phenyl)-urea.

To a solution of 1-(5-Amino-2-methoxy-phenyl)-3-diethylamino-propenone (1.78 g, 7.18 mmole) in methylene chloride (60 mL) was added a solution of 2,4-difluorophenyl isocyanate (1.34 g, 8.62 mmole) in methylene chloride (10 mL) over a period of 10 minutes. The reaction mixture was stirred at ambient temperature for 18 hrs. The solvent was evaporated and the resulting solid was purified on silica (Biotage) using DCM to 30% ethyl acetate in DCM as eluant. The fractions containing the product were evaporated in vacuo to furnish a yellow solid (2.7 g, 96%). LCMS m/z (%)=404 (M+H, 100), $^1$H NMR (Bruker, 400 MHz, DMSO-d$_6$) δ: 8.91 (bs, 1H), 8.41 (bs, 1H), 8.06-8.12 (m, 1H), 7.46-7.48 (d, J=8.68 Hz 1H), 7.42 (bs, 1H), 7.29-7.35 (m, 1H), 7.01-7.08 (m, 2H), 5.5 (bs, 1H), 3.78 (s, 3H), 3.27 (bs, 4H), 1.13-1.2 (t, J=7.01 Hz, 6H).

Step 5: Preparation of 1-(2,4-Difluoro-phenyl)-3-[4-methoxy-3-(2H-pyrazol-3-yl)-phenyl]-urea To a solution of 1-[3-(3-Diethylamino-acryloyl)-4-methoxy-phenyl]-3-(2,4-difluoro-phenyl)-urea (1.5 g, 3.72 mmole) in methanol/acetic acid (50 mL/2.0 mL) mixture was added hydrazine (0.82 g, 37.22 mmole). The reaction mixture was refluxed at 55 C for 20 hrs. The methanol/acetic acid was evaporated from the reaction mixture and the solid was triturated with ether/methanol. The solid was filtered and washed with ether. Next, the solid was dried in vacuo to furnish a colorless solid (1.0 g, 76%). LCMS m/z (%)=345 (M+H, 100), $^1$H NMR (Bruker, 400 MHz, DMSO-d$_6$) δ:13.0 (bs, 1H), 8.89 (bs, 1H), 8.37 (bs, 1H), 8.09-810 (d, J=6.05 Hz, 1H), 7.74-7.97 (bs, 1H), 7.52-7.64 (bs, 1H), 7.39-7.40 (d, J=5.94 Hz, 1H), 7.27-7.32 (m, 2H), 7.01-7.09 (m, 2H), 6.73 (s, 1H), 3.82 (s, 3H) (major tautomer).

Step 6: Preparation of 1-[3-(4-Bromo-2H-pyrazol-3-yl)-4-methoxy-phenyl]-3-(2,4-difluoro-phenyl)-urea.

To a cooled and stirred solution of 1-(2,4-Difluoro-phenyl)-3-[4-methoxy-3-(2H-pyrazol-3-yl)-phenyl]-urea (0.6 g, 1.74 mmole) in DMF (15 mL) was added N-bromosuccinimide (0.37 g, 2.09 mmole) over a period of 15 minutes. The reaction mixture was warmed slowly to ambient temperature and stirred for another 2 hrs. The reaction mixture was poured into well-stirred ice water containing NaHCO$_3$/Na$_2$S$_2$O$_3$. The resulting solid was filtered and washed with ice water (50 mL). The solid was dried in vacuo to afford off-white solid (0.68 g, 92%). LCMS m/z (%)=425 (M+H, $^{79}$Br, 100), 427 (M+H, $^{81}$ Br, 99). $^1$H NMR (Bruker, 400 MHz, DMSO-d$_6$) δ: 8.96 (bs, 1H), 8.44 (bs, 1H), 8.02-8.08 (m, 1H), 7.48 (bs, 2H), 7.27-7.32 (m, 1 h), 6.99-7.08 (m, 2H), 3.73 (s, 3H) (major tautomer).

Example 2

A. Construction of Constitutively Active 5-HT$_{2C}$ Receptor cDNA

1. Endogenous Human 5-HT$_{2C}$

The cDNA encoding endogenous human 5-HT$_{2C}$ receptor was obtained from human brain poly-A$^+$ RNA by RT-PCR. The 5' and 3' primers were derived from the 5' and 3' untranslated regions and contained the following sequences:

```
                                          (SEQ.ID.NO.: 1)
    5'-GACCTCGAGGTTGCTTAAGACTGAAGCA-3'

(SEQ.ID.NO.: 2)
    5'-ATTTCTAGACATATGTAGCTTGTACCGT-3'
```

PCR was performed using either TaqPlus™ precision polymerase (Stratagene) or rTth™ polymerase (Perkin Elmer) with the buffer systems provided by the manufacturers, 0.25 μM of each primer, and 0.2 mM of each of the four (4) nucleotides. The cycle condition was 30 cycles of 94° C for 1 minute, 57° C for 1 minute and 72° C for 2 minutes. The 1.5 kb PCR fragment was digested with Xho I and Xba I and subcloned into the Sal I-Xba I site of pBluescript.

The derived cDNA clones were fully sequenced and found to correspond to published sequences.

2. AP-1 cDNA

The cDNA containing a S310K mutation (AP-1 cDNA) in the third intracellular loop of the human 5-HT$_{2C}$ receptor was constructed by replacing the Sty I restriction fragment containing amino acid 310 with synthetic double stranded oligonucleotides encoding the desired mutation. The sense strand sequence utilized had the following sequence:

```
                                          (SEQ.ID.NO: 3)
    5'-CTAGGGGCACCATGCAGGCTATCAACAATGAAAGAAAAGCTA
    AGAAAGTC-3'
``` and the antisense strand sequence utilized had the following sequence:

```
                                          (SEQ.ID.NO: 4)
    5'-CAAGGACTTTCTTAGCTTTTCTTTCATTGTTGATAGCCTGCA
    TGGTGCCC-3'.
```

B. Construction of Constitutively Active 5-HT$_{2A}$ Receptor cDNA

1. Human 5-HT$_{2A}$ (C322K; AP-2)

The cDNA containing the point mutation C322K in the third intracellular loop was constructed by using the Sph I restriction enzyme site, which encompasses amino acid 322. For the PCR procedure, a primer containing the C322K mutation:

```
                                          (SEQ.ID.NO: 5)
    5'-CAAAGAAAGTACTGGGCATCGTCTTCTTCCT-3'
``` was used along with the primer from the 3' untranslated region SEQ. ID. NO:6.

```
                                          (SEQ.ID.NO: 6)
    5'-TGCTCTAGATTCCAGATAGGTGAAAACTTG-3'
```

The resulting PCR fragment was then used to replace the 3' end of the wild type 5-HT$_{2A}$ by the T4 polymerase blunted Sph I site. PCR was performed using pfu polymerase (Stratagene) with the buffer system provided by the manufacturer and 10% DMSO, 0.25 mM of each primer, 0.5 mM of each of the 4 nucleotides. The cycle conditions were 25 cycles of 94° C for 1 minute, 60° C for 1 minute, and 72° C for 1 minute.

2. AP-3 cDNA

The human 5-$HT_{2A}$ cDNA with intracellular loop 3 (IC3) or IC3 and cytoplasmic tail replaced by the corresponding human 5-$HT_{2C}$ cDNA was constructed using PCR-based mutagenesis.

(a) Replacement of IC3 Loo

The IC3 loop of human 5-$HT_{2A}$ cDNA was first replaced with the corresponding human 5-$HT_{2C}$ cDNA. Two separate PCR procedures were performed to generate the two fragments, Fragment A and Fragment B, that fuse the 5-$HT_{2C}$ IC3 loop to the transmembrane 6 (TM6) of 5-$HT_{2A}$. The 237 bp PCR fragment, Fragment A, containing 5-$HT_{2C}$ IC3 and the initial 13 bp of 5-$HT_{2A}$ TM6 was amplified by using the following primers:

```
                                       (SEQ.ID.NO: 7)
5'-CCGCTCGAGTACTGCGCCGACAAGCTTTGAT-3'

(SEQ.ID.NO: 8)
5'-CGATGCCCAGCACTTTCGAAGCTTTTCTTTCATTGTTG-3'
```

The template used was human 5-$HT_{2C}$ cDNA.

The 529 bp PCR fragment, Fragment B, containing the C-terminal 13 bp of IC3 from 5-$HT_{2C}$ and the C-terminal of 5-$HT_{2A}$ starting at beginning of TM6, was amplified by using the following primers:

```
                                       (SEQ.ID.NO: 9)
5'-AAAAGCTTCGAAAGTGCTGGGCATCGTCTTCTTCCT-3'

(SEQ.ID.NO: 10)
5'-TGCTCTAGATTCCAGATAGGTGAAAACTTG-3'
```

The template used was human 5-$HT_{2A}$ cDNA.

Second round PCR was performed using Fragment A and Fragment B as co-templates with SEQ. ID. NO:7 and SEQ. ID. NO:10 (it is noted that the sequences for SEQ. ID. NOS.: 6 and 10 are the same) as primers. The resulting 740 bp PCR fragment, Fragment C, contained the IC3 loop of human 5-$HT_{2C}$ fused to TM6 through the end of the cytoplasmic tail of human 5-$HT_{2A}$. PCR was performed using pfu™ polymerase (Stratagene) with the buffer system provided by the manufacturer, and 10% DMSO, 0.25 mM of each primer, and 0.5 mM of each of the four (4) nucleotides. The cycle conditions were 25 cycles of 94° C for 1 minute, 57° C (1st round PCR) or 60° C (2nd round PCR) for 1 minute, and 72° C for 1 minute (1st round PCR) or 90 seconds (2nd round PCR).

To generate a PCR fragment containing a fusion junction between the human 5-$HT_{2A}$ TM5 and the IC3 loop of 5-$HT_{2C}$, four (4) primers were used. The two external primers, derived from human 5-$HT_{2A}$, had the following sequences:

```
                                       (SEQ.ID.NO.: 11)
5'-CGTGTCTCTCCTTACTTCA-3'
```

The other primer used was SEQ. ID. NO.: 6 (see note above regarding SEQ. ID. NOS. 6 and 11). The first internal primer utilized was an antisense strand containing the initial 13 bp of IC3 of 5-$HT_{2C}$ followed by the terminal 23 bp derived from TM5 of 5-$HT_{2A}$:

```
                                       (SEQ.ID.NO.: 12)
5'-TCGGCGCAGTACTTTGATAGTTAGAAAGTAGGTGAT-3'
```

The second internal primer was a sense strand containing the terminal 14 bp derived from TM5 of 5-$HT_{2A}$ followed by the initial 24 bp derived from IC3 of 5-$HT_{2C}$:

```
                                       (SEQ.ID.NO.: 13)
5'-TTCTAACTATCAAAGTACTGCGCCGACAAGCTTTGATG-3'.
```

PCR was performed using endogenous human 5-$HT_{2A}$ and a co-template, Fragment C, in a 50 mL reaction volume containing 1×pfu buffer, 10% DMSO, 0.5 mM of each of the four (4) nucleotides, 0.25 mM of each external primer (SEQ. ID. NOS. 10 and 11), 0.06 mM of each internal primer (SEQ. ID. NOS. 12 and 13) and 1.9 units of pfu polymerase (Stratagene). The cycle conditions were 25 cycles of 94° C for 1 minute, 52° C for 1 minute, and 72° C for 2 minutes and 10 seconds. The 1.3 kb PCR product was then gel purified and digested with Pst I and EcoR I. The resulting 1 kb Pst I-EcoR I fragment was used to replace the corresponding fragment in the endogenous human 5-$HT_{2A}$ sequence to generate the mutant 5-$HT_{2A}$ sequence encoding the IC3 loop of 5-HT2C.

(b) Replacement of the Cytoplasmic Tail

To replace the cytoplasmic tail of 5-$HT_{2A}$ with that of 5-$HT_{2C}$, PCR was performed using a sense primer containing the C-terminal 22 bp of TM7 of endogenous human 5-$HT_{2A}$ followed by the initial 21 bp of the cytoplasmic tail of endogenous human 5-$HT_{2C}$:

```
                                       (SEQ.ID.NO: 14)
5'-TTCAGCAGTCAACCCACTAGTCTATACTCTGTTCAACAAAATT-3'
```

The antisense primer was derived from the 3' untranslated region of endogenous human 5-$HT_{2C}$:

```
                                       (SEQ.ID.NO: 15)
5'-ATTTCTAGACATATGTAGCTTGTACCGT-3'.
```

The resulting PCR fragment, Fragment D, contained the last 22 bp of endogenous human 5-$HT_{2A}$ TM7 fused to the cytoplasmic tail of endogenous human 5-$HT_{2C}$. Second round PCR was performed using Fragment D and the co-template was endogenous human 5-$HT_{2A}$ that was previously digested with Acc I to avoid undesired amplification. The antisense primer used was SEQ. ID. NO:15 (the sequences for SEQ. ID. NOS. 15 and 2 are the same) and the sense primer used was derived from endogenous human 5-$HT_{2A}$: 5'-ATCACCTACTTTCTAACTA-3' (SEQ. ID. NO:16).

PCR conditions were as set forth in Example 2 section B2(a) for the first round PCR, except that the annealing temperature was 48° C and the extension time was 90 seconds. The resulting 710 b PCR product was digested with Apa I and Xba I and used to replace the corresponding Apa I-Xba I fragment of either (a) endogenous human 5-$HT_{2A}$, or (b) 5-$HT_{2A}$ with 2C $IC_3$ to generate (a) endogenous human 5-$HT_{2A}$ with endogenous human 5-$HT_{2C}$ cytoplasmic tail and (b) AP-3, respectively.

4. AP-4 cDNA

This mutant was created by replacement of the region of endogenous human 5-$HT_{2A}$ from amino acid 247, the middle of TM5 right after $Pro^{246}$, to amino acid 337, the middle of TM6 just before $Pro^{338}$, by the corresponding region of AP-1 cDNA. For convenience, the junction in TM5 is referred to as the "2A-2C junction," and the junction in TM6 is referred to as the "2C-2A junction."

Three PCR fragments containing the desired hybrid junctions were generated. The 5' fragment of 561 bp containing the 2A-2C junction in TM5 was generated by PCR using endogenous human 5-HT$_{2A}$ as template, SEQ. ID. NO.:11 as the sense primer, and the antisense primer was derived from 13 b of 5-HT$_{2C}$ followed by 20 bp of 5-HT$_{2A}$ sequence:

```
                                            (SEQ.ID.NO: 17)
5'-CCATAATCGTCAGGGGAATGAAAAATGACACAA-3'
```

The middle fragment of the 323 bp contains endogenous human 5-HT$_{2C}$ sequence derived from the middle of TM5 to the middle of TM6, flanked by 13 bp of 5-HT$_{2A}$ sequences from the 2A-2C junction and the 2C-2A junction. This middle fragment was generated by using AP-1 cDNA as a template, a sense primer containing 13 bp of 5-HT$_{2A}$ followed by 20 bp of 5-HT$_{2C}$ sequences across the 2A-2C junction and having the sequence:

```
                                            (SEQ.ID.NO: 18)
5'-ATTTTTCATTCCCCTGACGATTATGGTGATTAC-3';
``` and an antisense primer containing 13 bp of 5-HT$_{2A}$ followed by 20 bp of 5-HT$_{2C}$ sequences across the

```
                                            (SEQ.ID.NO: 19)
5'-TGATGAAGAAAGGGCACCACATGATCAGAAACA-3'.
```

The 3' fragment of 487 bp containing the 2C-2A junction was generated by PCR using endogenous human 5-HT$_{2A}$ as a template and a sense primer having the following sequence from the 2C-2A junction:

```
                                            (SEQ.ID.NO: 20)
5'-GATCATGTGGTGCCCTTTCTTCATCACAAACAT-3'
``` and the antisense primer was SEQ. ID. NO:6 (see note above regarding SEQ. ID. NOS. 6 and 10).

Two second round PCR reactions were performed separately to link the 5' and middle fragment (5'M PCR) and the middle and 3' fragment (M3' PCR). The 5'M PCR co-template used was the 5' and middle PCR fragment as described above, the sense primer was SEQ. ID. NO:11 and the antisense primer was SEQ. ID. NO.:19. The 5'M PCR procedure resulted in an 857 bp PCR fragment.

The M3' PCR used the middle and M3' PCR fragment described above as the co-template, SEQ. ID. NO.: 18 as the sense primer and SEQ. ID. NO.:6 (see note above regarding SEQ. ID. NOS. 6 and 10) as the antisense primer, and generated a 784 bp amplification product. The final round of PCR was performed using the 857 bp and 784 bp fragments from the second round PCR as the co-template, and SEQ. ID. NO:11 and SEQ. ID. NO: 6 (see note above regarding SEQ. ID. NOS. 6 and 10) as the sense and the antisense primer, respectively. The 1.32 kb amplification product from the final round of PCR was digested with Pst I and Eco RI. Then resulting 1 kb Pst I-Eco RI fragment was used to replace the corresponding fragment of the endogenous human 5-HT$_{2A}$ to generate mutant 5-HT$_{2A}$ with 5-HT$_{2C}$: S310K/IC3. The Apa I-Xba fragment of AP3 was used to replace the corresponding fragment in mutant 5-HT$_2$A with 5-HT2c: S310K/IC3 to generate AP4.

Example 3

Receptor Expression

A. pCMV

Figure 8:
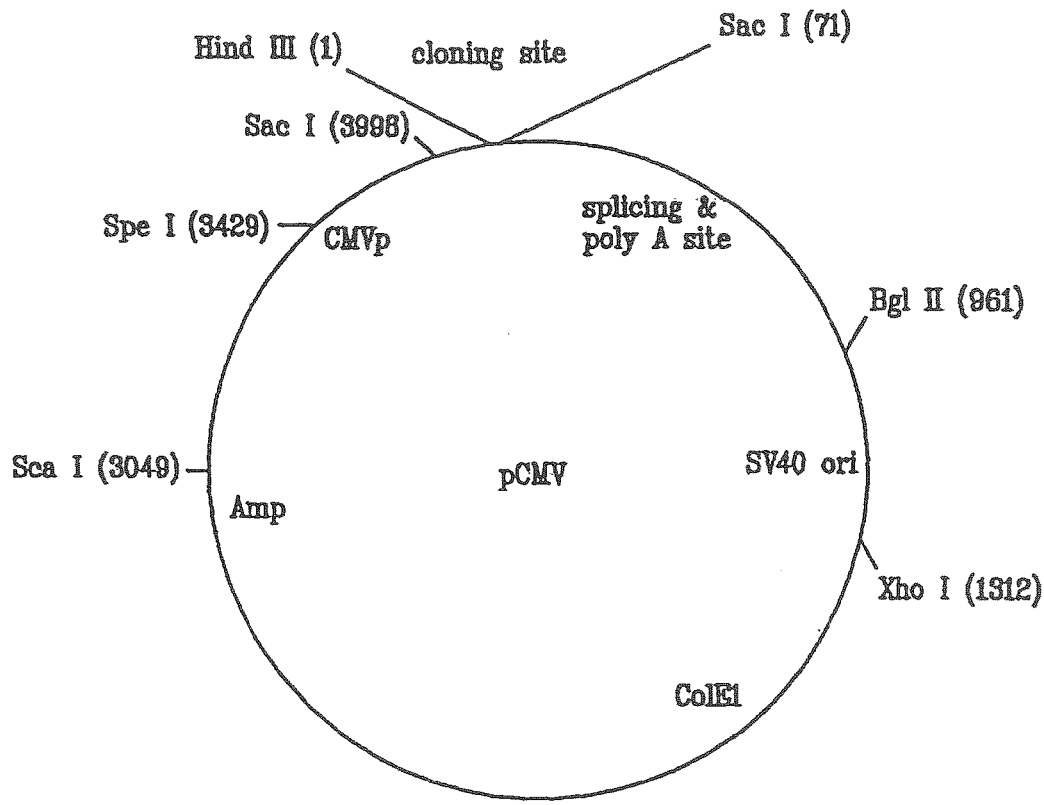
FIG. 8 is a representation of the preferred vector, pCMV, used herein.

Although a variety of expression vectors are available to those in the art, for purposes of utilization for both the endogenous and non-endogenous receptors discussed herein, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. See FIG. 8.

B. Transfection Procedure

For the generic assay ([$^{35}$S]GTPγS; Example 4) and the antagonist binding assay (mesulergine; Example 15), transfection of COS-7 or 293T cells was accomplished using the following protocol.

On day one, 5×10$^6$ COS-7 cells or 1×10$^7$ 293T cells per 150 mm plate were plated out. On day two, two reaction tubes were prepared (the proportions to follow for each tube are per plate): tube A was prepared by mixing 20 µg DNA (e.g., pCMV vector; pCMV vector AP-1 cDNA, etc.) in 1.2 ml serum free DMEM (Irvine Scientific, Irvine, Calif.); tube B was prepared by mixing 120 µl lipofectamine (Gibco BRL) in 1.2 ml serum free DMEM. Tubes A and B were then admixed by inversions (several times), followed by incubation at room temperature for 30-45 min. The admixture is referred to as the "transfection mixture". Plated COS-7 cells were washed with 1×PBS, followed by addition of 10 ml serum free DMEM. 2.4 ml of the transfection mixture was then added to the cells, followed by incubation for 4 hrs at 37° C/5% CO$_2$. The transfection mixture was then removed by aspiration, followed by the addition of 25 ml of DMEM/ 10% Fetal Bovine Serum. Cells were then incubated at 37° C/5% CO$_2$. After 72 hr incubation, cells were then harvested and utilized for analysis.

Example 4

GTP Membrane Binding Scintillation Proximity Assay

The advantages of using [$^{35}$S]GTPγS binding to measure constitutive activation are that: (a) [$^{35}$S]GTPγS binding is generically applicable to all G protein-coupled receptors; and (b) [$^{35}$S]GTPγS binding is proximal at the membrane surface, thereby making it less likely to pick-up molecules which affect the intracellular cascade. The assay utilizes the ability of G protein-coupled receptors to stimulate [$^{35}$S] GTPγS binding to membranes expressing the relevant receptors. Therefore, the assay may be used to directly screen compounds at the disclosed serotonin receptors.

Figure 9:
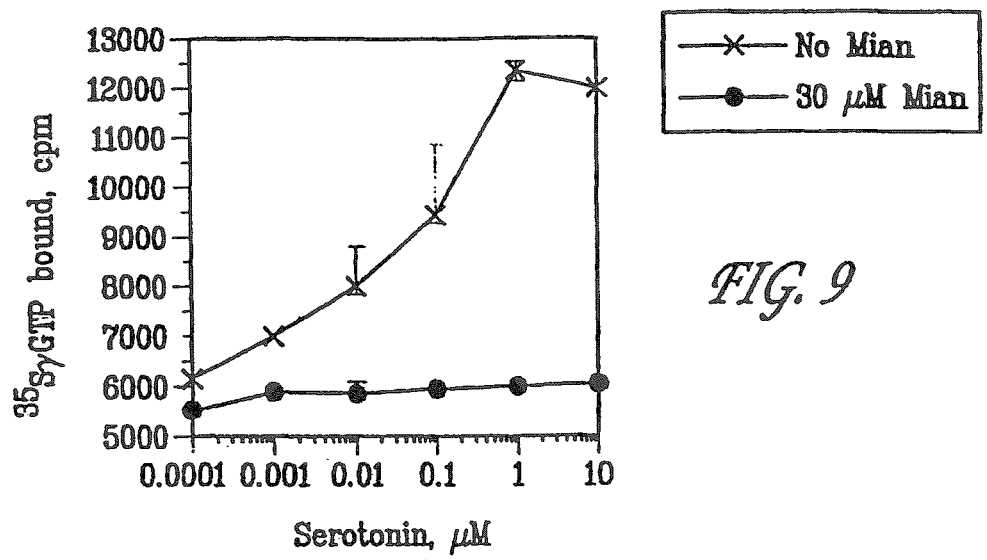
FIG. 9 is a diagram illustrating (1) enhanced ($^{35}$S)GTPγS binding to membranes prepared from COS cells expressing the endogenous human 5-HT$_{2C}$ receptor in response to serotonin, and (2) inhibition by mianserin using wheatgerm agglutinin scintillation proximity beads. The concentration of ($^{35}$S)GTPγS was held constant at 0.3 nM, and the concentration of GDP was held at 1 μM. The concentration of the membrane protein was 12.5 μg.

FIG. 9 demonstrates the utility of a scintillation proximity assay to monitor the binding of [$^{35}$S]GTPγS to membranes expressing, e.g., the endogenous human 5-HT$_{2C}$ receptor expressed in COS cells. In brief, a preferred protocol for the assay is such that the assay was incubated in 20 mM HEPES, pH 7.4, binding buffer with 0.3 nM [$^{35}$S]GTPγS and 12.5 µg membrane protein and 1 µM GDP for 30 minutes. Wheat-germ agglutinin beads (25 µl; Amersham) were then added and the mixture was incubated for another 30 minutes at room temperature. The tubes were then centrifuged at 1500×g for 5 minutes at room temperature and then counted in a scintillation counter. As shown in FIG. 9, serotonin, which as the endogenous ligand activates the 5-HT$_{2C}$ receptor, stimulated [$^{35}$S]GTPγS binding to the membranes in a concentration dependant manner. The stimulated binding was completely inhibited by 30 μM mianserin, a compound considered as a classical 5-HT$_{2C}$ antagonist, but also known as a 5-HT$_{2C}$ inverse agonist.

Although this assay measures agonist-induced binding of [$^{35}$S]GTPγS to membranes and can be routinely used to measure constitutive activity of receptors, the present cost of wheatgerm agglutinin beads may be prohibitive. A less costly but equally applicable alternative also meets the needs of large-scale screening. Flash plates and Wallac™ scintistrips may be used to format a high throughput [$^{35}$S]GTPγS binding assay. This technique allows one to monitor the tritiated ligand binding to the receptor while simultaneously monitoring the efficacy via [$^{35}$S]GTPγS binding. This is possible because the Wallac™ beta counter can switch energy windows to analyze both tritium and $^{35}$S-labeled probes.

Also, this assay may be used for detecting of other types of membrane activation events that result in receptor activation. For example, the assay may be used to monitor $^{32}$P phosphorylation of a variety of receptors (including G protein-coupled and tyrosine kinase receptors). When the membranes are centrifuged to the bottom of the well, the bound [$^{35}$S]GTPγS or the $^{32}$P-phosphorylated receptor will activate the scintillant coated on the wells. Use of Scinti® strips (Wallac™) demonstrate this principle. Additionally, this assay may be used for measuring ligand binding to receptors using radiolabeled ligands. In a similar manner, the radiolabeled bound ligand is centrifuged to the bottom of the well and activates the scintillant. The [$^{35}$S]GTPγS assay results parallel the results obtained in traditional second messenger assays of receptors.

Figure 10:
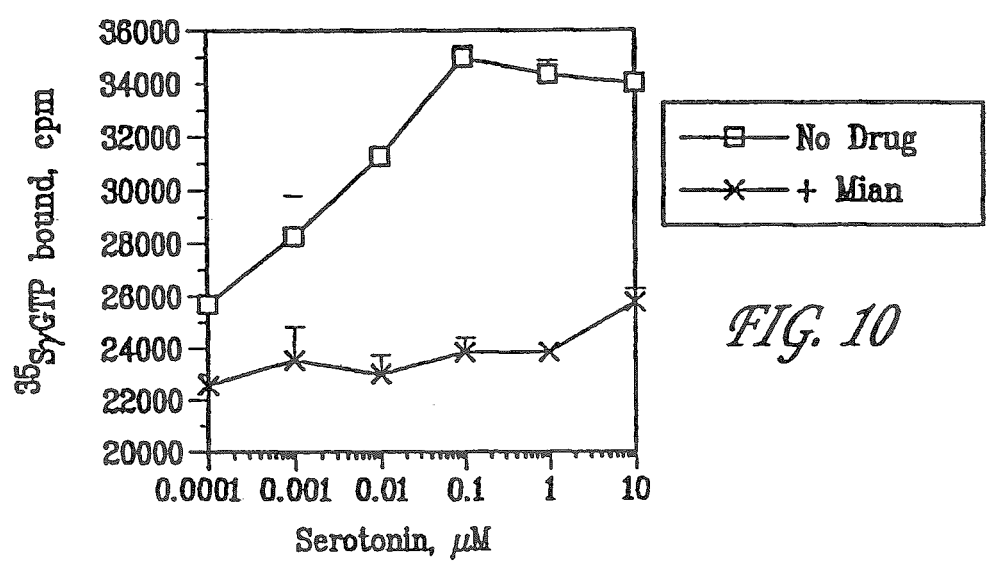
FIG. 10 is a diagram showing serotonin stimulation of ($^{35}$S)GTPγS binding to membranes expressing AP-1 receptors in 293T cells and the inhibition by 30 μM mianserin on Wallac™ scintistrips.

As shown in FIG. 10, serotonin stimulates the binding of [$^{35}$S]GTPγS to the endogenous human 5-HT$_{2C}$ receptor, while mianserin inhibits this response; furthermore, mianserin acts as a partial inverse agonist by inhibiting the basal constitutive binding of [$^{35}$S]GTPγS to membranes expressing the endogenous human 5-HT$_{2C}$ receptor. As expected, there is no agonist response in the absence of GDP since there is no GDP present to exchange for [$^{35}$S]GTPγS. Not only does this assay system demonstrate the response of the native 5HT$_{2C}$ receptor, but it also measures the constitutive activation of other receptors.

Figure 11A:
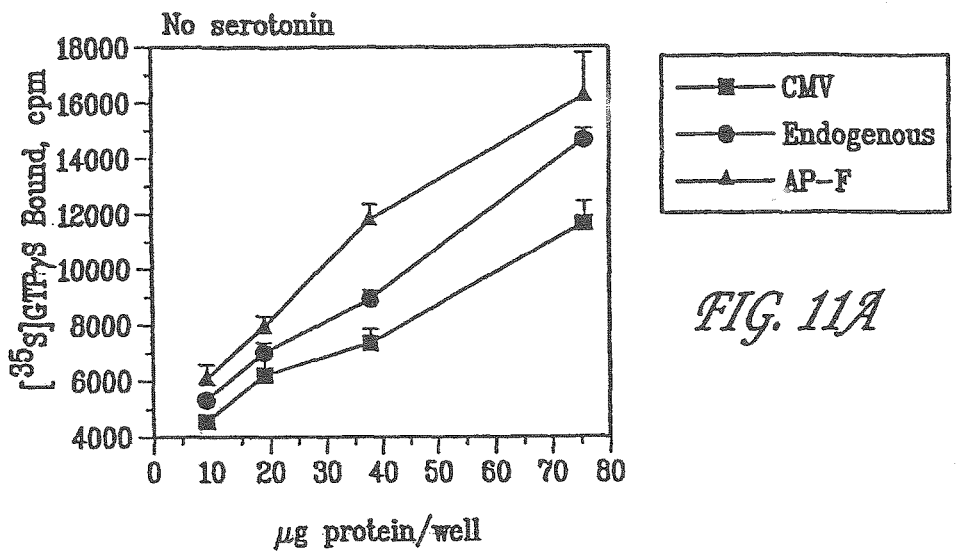
FIG. 11A is a diagram showing the effects of protein concentration on ($^{35}$S)GTPγS binding in membranes prepared from 293T cells transfected with the endogenous human 5-HT$_{2C}$ receptors and AP-1 receptors compared to cells transfected with the control vector (pCMV) alone in the absence of 10 μM serotonin. The radiolabeled concentration of ($^{35}$S)GTPγS was held constant at 0.3 nM, and the GDP concentration was held constant at 1 μM. The assay was performed on 96-well format on Wallac™ scintistrips.
Figure 11B:
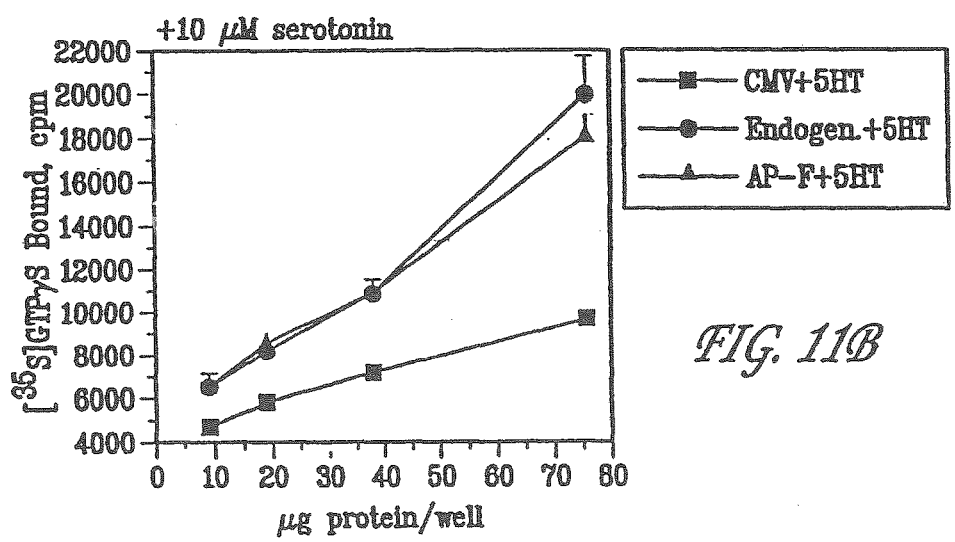
FIG. 11B is a diagram showing the effects of protein concentration on ($^{35}$S)GTPγS binding in membranes prepared from 293T cells transfected with the endogenous human 5-HT$_{2C}$ receptors and AP-1 receptors compared to cells transfected with the control vector (pCMV) alone in the presence of 10 μM serotonin. The radiolabeled concentration of ($^{35}$S)GTPγS was held constant at 0.3 nM, and the GDP concentration was held constant at 1 μM. The assay was performed on 96-well format on Wallac™ scintistrips.

FIG. 11A and FIG. 11B demonstrate the enhanced binding of [$^{35}$S]GTPγS to membranes prepared from 293T cells expressing the control vector alone, the native human 5-HT$_{2C}$ receptor or the AP-1 receptor was observed (data not shown). The total protein concentration used in the assay affects the total amount of [$^{35}$S]GTPγS binding for each receptor. The c.p.m. differential between the CMV transfected and the constitutively active mutant receptor increased from approximately 1000 c.p.m at 10 μg/well to approximately 6-8000 c.p.m. at 75 μg/well protein concentration, as shown in FIG. 11.

The AP-1 receptor showed the highest level of constitutive activation followed by the wild type receptor, which also showed enhanced [$^{35}$S]GTPγS binding above basal. This is consistent with the ability of the endogenous human 5-HT$_{2C}$ receptor to accumulate intracellular IP$_3$ in the absence of 5HT stimulation (Example 6) and is also consistent with published data claiming that the endogenous human 5-HT$_{2C}$ receptor has a high natural basal activity. Therefore, the AP-1 receptor demonstrates that constitutive activity may be measured by proximal [$^{35}$S]GTPγS binding events at the membrane interface.

Example 5

Serotonin Receptor Agonist/Antagonist Competitive Binding Assay

Membranes were prepared from transfected COS-7 cells (see Example 3) by homogenization in 20 mM HEPES and 10 mM EDTA, pH 7.4 and centrifuged at 49,000×g for 15 min. The pellet was resuspended in 20 mM HEPES and 0.1 mM EDTA, pH 7.4, homogenized for 10 sec. using a Polytron homogenizer (Brinkman) at 5000 rpm and centrifuged at 49,000×g for 15 min. The final pellet was resuspended in 20 mM HEPES and 10 mM MgCl$_2$, pH 7.4, homogenized for 10 sec. using polytron homogenizer (Brinkman) at 5000 rpm.

Assays were performed in triplicate 200 μl volumes in 96 well plates. Assay buffer (20 mM HEPES and 10 mM MgCl$_2$, pH 7.4) was used to dilute membranes, $^3$H-LSD, $^3$H-mesulergine, serotonin (used to define non-specific for LSD binding) and mianserin (used to define non-specific for mesulergine binding). Final assay concentrations consisted of 1 nM $^3$H-LSD or 1 nM $^3$H-mesulergine, 50 μg membrane protein and 100 m serotonin or mianserin. LSD assays were incubated for 1 hr at 37° C, while mesulergine assays were incubated for 1 hr at room temperature. Assays were terminated by rapid filtration onto Wallac Filtermat Type B with ice cold binding buffer using Skatron cell harvester. The radioactivity was determined in a Wallac 1205 BetaPlate counter.

Example 6

Intracellular IP$_3$ Accumulation Assay

For the IP$_3$ accumulation assay, a transfection protocol different from the protocol set forth in Example 3 was utilized. In the following example, the protocols used for days 1-3 were slightly different for the data generated for FIGS. 12 and 14 and for FIGS. 13 and 15; the protocol for day 4 was the same for all conditions.

A. COS-7 and 293 Cells

On day one, COS-7 cells or 293 cells were plated onto 24 well plates, usually 1×10$^5$ cells/well or 2×10$^5$ cells/well, respectively. On day two, the cells were transfected by first mixing 0.25 ug DNA (see Example 3) in 50 μl serum-free DMEM/well and then 2 μl lipofectamine in 50 μl serum-free DMEM/well. The solutions ("transfection media") were gently mixed and incubated for 15-30 minutes at room temperature. The cells were washed with 0.5 ml PBS and then 400 μl of serum free media was mixed with the transfection media and added to the cells. The cells were then incubated for 3-4 hours at 37° C/5% CO$_2$. Then the transfection media was removed and replaced with 1 ml/well of regular growth media. On day 3, the media was removed and the cells were washed with 5 ml PBS followed by aspiration. Then 2 ml of trypsin (0.05%) is added per plate. After 20-30 seconds, warm 293 media is added to plates, cells are gently resuspended, and cells are counted. Then a total of 55,000 cells are added to sterile poly-D-lysine treated 96 well microtiter plates and cells are allowed to attach over a six-hour incubation in an incubator. Then media is aspirated and 0.1 mL inositol-free/serum-free media (GIBCO BRL) was added to each well with 0.25 μCi of ³H-myo-inositol/well and the cells were incubated for 16-18 hours overnight at 37° C/5% $CO_2$. Protocol A.

B. 293 Cells

On day one, $13 \times 10^6$ 293 cells per 150 mm plate were plated out. On day two, 2 ml of serum OptimemI (Invitrogen Corporation) is added per plate followed by addition of 60 µL of lipofectamine and 16 µg of cDNA. Note that lipofectamine must be added to the OptimemI and mixed well before addition of cDNA. While complexes between lipofectamine and the cDNA are forming, media is carefully aspirated and cells are gently rinsed with 5 ml of OptimemI media followed by careful aspiration. Then 12 ml of OptimemI is added to each plate and 2 ml of transfection solution is added followed by a 5 hour incubation at 37° C in a 5% $CO_2$ incubator. Plates are then carefully aspirated and 25 mL of Complete Media are added to each plate and cells are then incubated until used. On day 3, cells are trypsinized with 2 ml of 0.05% trypsin for 20-30 seconds followed by addition of 10 mL of warmed media, gently titurated to dissociate cells, and then 13 additional ml of warmed media is gently added. Cells are then counted and then 55,000 cells are added to 96-well sterile poly-D-lysine trated plates. Cells are allowed to attach over a six hour incubation at 37° C in a 5% $CO_2$ incubator. Media is then carefully aspirated and 100 µL of warm inositol-free media plus 0.5 µCi ³H-inositol is added to each well and the plates are incubated for 18-20 hours at 37° C in a 5% $CO_2$ incubator.

On day 4, media is carefully aspirated and then 0.1 ml of assay medium is added containing inositol-free/serum free media, 10 µM pargyline, 10 mM lithium chloride, and test compound at indicated concentrations. The plates were then incubated for three hours at 37° C and then wells are carefully aspirated. Then 200 µL of ice-cold 0.1M formic acid is added to each well. Plates can then be frozen at this point at –80° C until further processed. Frozen plates are then thawed over the course of one hour, and the contents of the wells (approximately 220 µL) are placed over 400 µL of washed ion-exchange resin (AG 1-X8) contained in a Multi Screen Filtration plate and incubated for 10 minutes followed by filtration under vacuum pressure. Resin is then washed nine times with 200 µL of water and then tritiated inositol phosphates are eluted into a collecting plate by the addition of 200 ul of 1M ammonium formate and an additonal 10 minute incubation. The elutant is then transferred to 20 ml scintillation vials, 8 mL of SuperMix or Hi-Safe scintillation cocktails is added, and vials are counted for 0.5-1 minutes in a Wallac 1414 scintillation counter.

Figure 12:
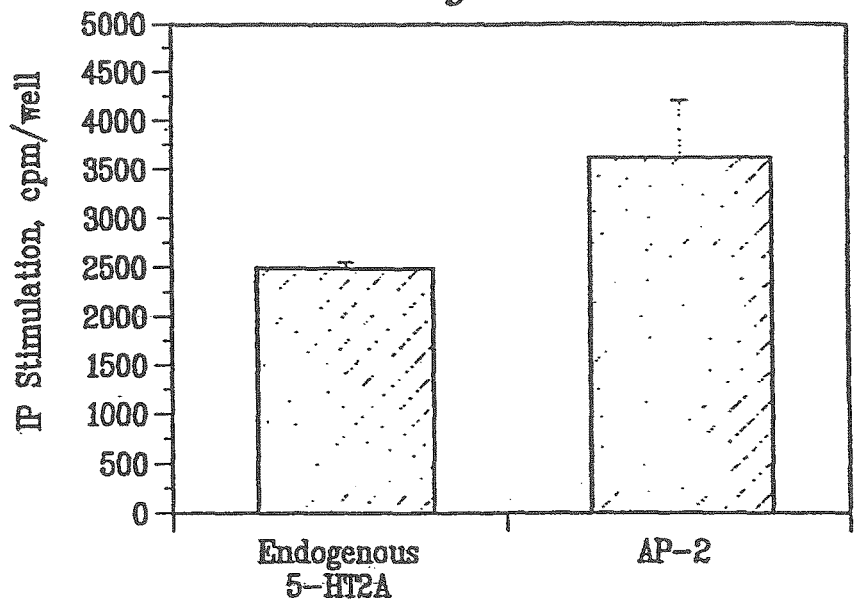
FIG. 12 provides bar-graph comparisons of inositol tris-phosphate ("IP3") production between the endogenous human 5HT$_{2A}$ receptor and AP-2, a mutated form of the receptor.

FIG. 12 is an illustration of IP3 production from the human 5-HT$_{2A}$ receptor which was mutated using the same point mutation as set forth in Casey, which rendered the rat receptor constitutively active. The results represented in FIG. 12, support the position that when the point mutation shown to activate the rat receptor is introduced into the human receptor, little activation of the receptor is obtained that would allow for appropriate screening of candidate compounds, with the response being only moderately above that of the endogenous human 5-HT$_{2A}$ receptor. Generally, a response of at least 2× above that of the endogenous response is preferred.

Figure 13:
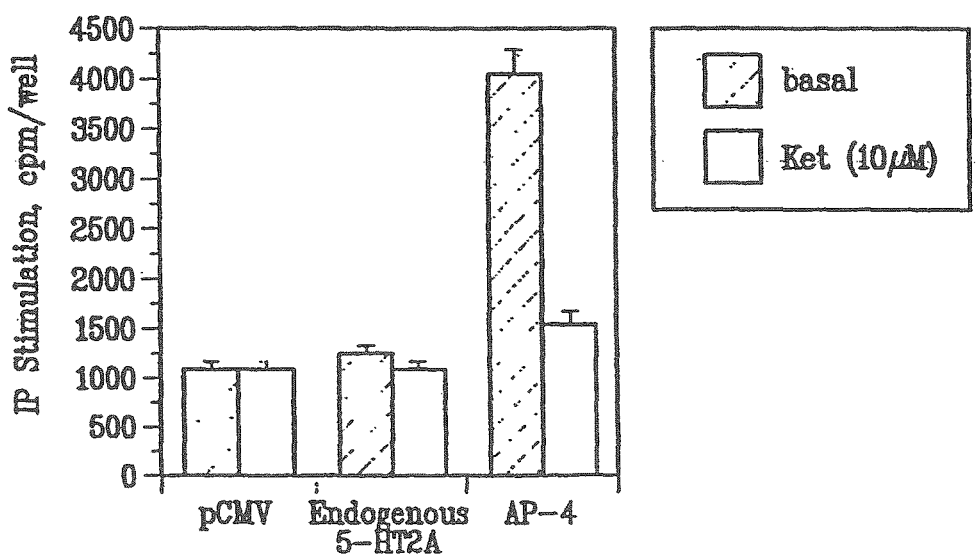
FIG. 13 provides bar-graph comparisons of inositol tris-phosphate ("IP3") production between the endogenous human 5HT$_{2A}$ receptor and AP-4, a mutated form of the receptor.

FIG. 13 provides an illustration comparing IP$_3$ production from endogenous 5-HT2$_A$ receptor and the AP4 mutation. The results illustrated in FIG. 13 support the position that when the novel mutation disclosed herein is utilized, a robust response of constitutive IP3 accumulation is obtained (e.g., over 2× that of the endogenous receptor).

Figure 14:
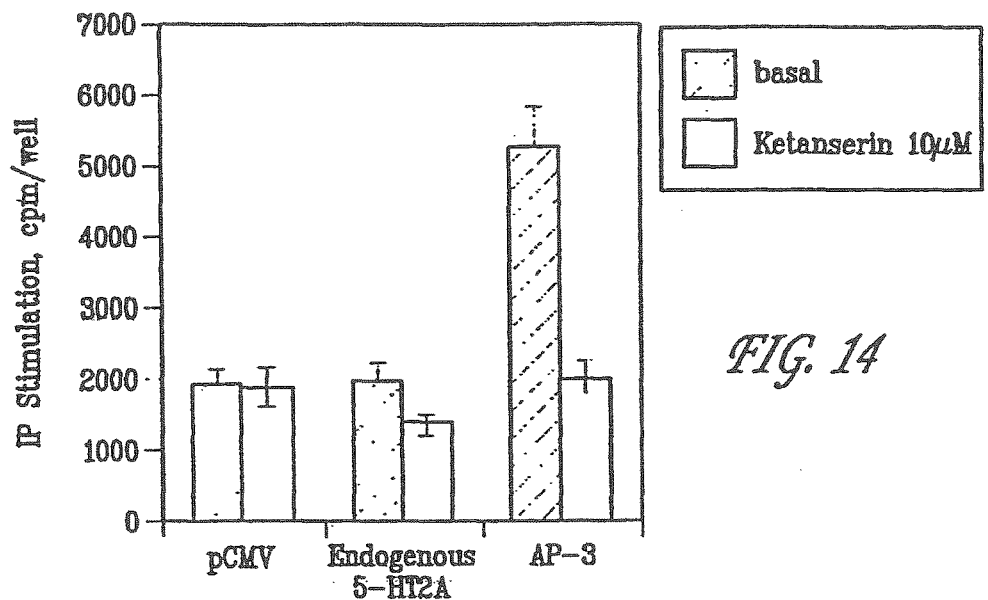
FIG. 14 provides bar graph comparisons of IP3 production between the endogenous human 5-HT$_{2A}$ receptor and AP-3, a mutated form of the receptor.

FIG. 14 provides an illustration of IP3 production from AP3. The results illustrated in FIG. 14 support the position that when the novel mutation disclosed herein is utilized, a robust response of constitutive IP3 accumulation is obtained.

Figure 15:
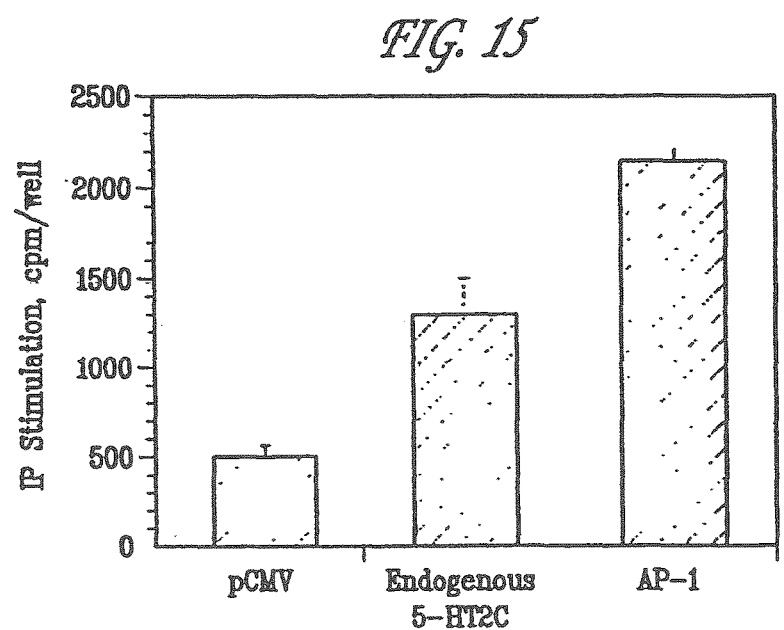
FIG. 15 provides bar-graph comparisons of IP3 production between the endogenous human 5-HT$_{2C}$ receptor and AP-1.

FIG. 15 provides bar-graph comparisons of IP3 accumulation between endogenous human 5-HT$_{2C}$ receptor and AP-1. Note that the endogenous receptor has a high degree of natural constitutive activity relative to the control CMV transfected cells (i.e., the endogenous receptor appears to be constitutively activated).

Example 7

In Vitro Binding of 5HT$_{2A}$ Receptor

Animals:

Animals (Sprague-Dawley rats) were sacrificed and brains were rapidly dissected and frozen in isopentane maintained at –42° C. Horizontal sections were prepared on a cryostat and maintained at –20° C.

LSD Displacement Protocol:

Lysergic acid diethylamide (LSD) is a potent 5HT$_{2A}$ receptor and dopamine D2 receptor ligand. An indication of the selectivity of compounds for either or both of these receptors involves displacement of radiolabeled-bound LSD from pre-treated brain sections. For these studies, radiolabeled $^{125}$I-LSD (NEN Life Sciences, Boston, Mass., Catalogue number NEX-199) was utilized; spiperone (RBI, Natick, Mass. Catalogue number s-128) a 5HT$_{2A}$ receptor and dopamine D2 receptor antagonist, was also utilized. Buffer consisted of 50 nanomolar TRIS-HCl, pH 7.4.

Brain sections were incubated in (a) Buffer plus 1 nanomolar $^{125}$I-LSD; (b) Buffer plus 1 nanomolar $^{125}$I-LSD and 1 micromolar spiperone; or Buffer plus 1 nanomolar $^{125}$I-LSD and 1 micromolar Compound 1 for 30 minutes at room temperature. Sections were then washed 2×10 minutes at 4° C in Buffer, followed by 20 seconds in distilled $H_2O$. Slides were then air-dried.

After drying, sections were apposed to x-ray film (Kodak Hyperfilm) and exposed for 4 days.

Figure 16A:
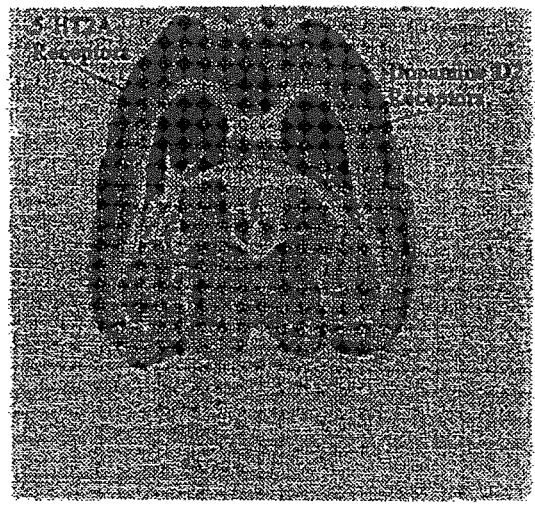
FIGS. 16A, 16B and 16C shows a grey-scale reproduction of representative autoradiograms demonstrating displacement of $^{125}$I-LSD from brain sections by spiperone and an early lead compound identified by the Inventors, referred to herein as S-1610 and has the following name: [3-(4-Bromo-2-methyl-2H-pyrazol-3-yl)-phenyl]-carbamic acid 4-methoxy-phenyl ester.
Figure 16B:
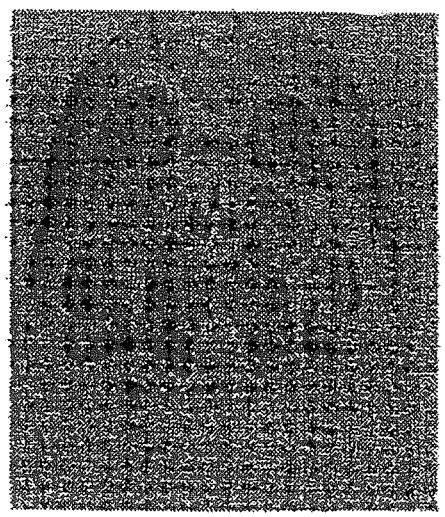
Figure 16C:
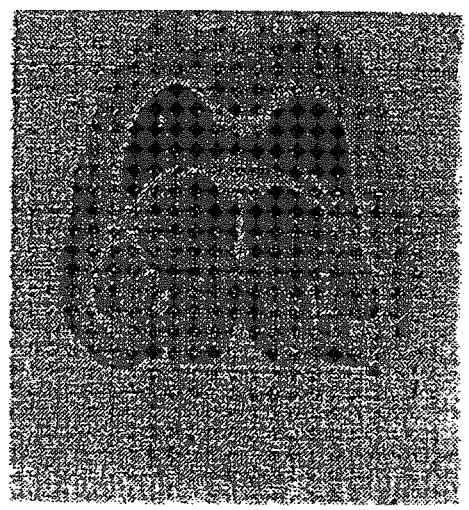
Figure 17:
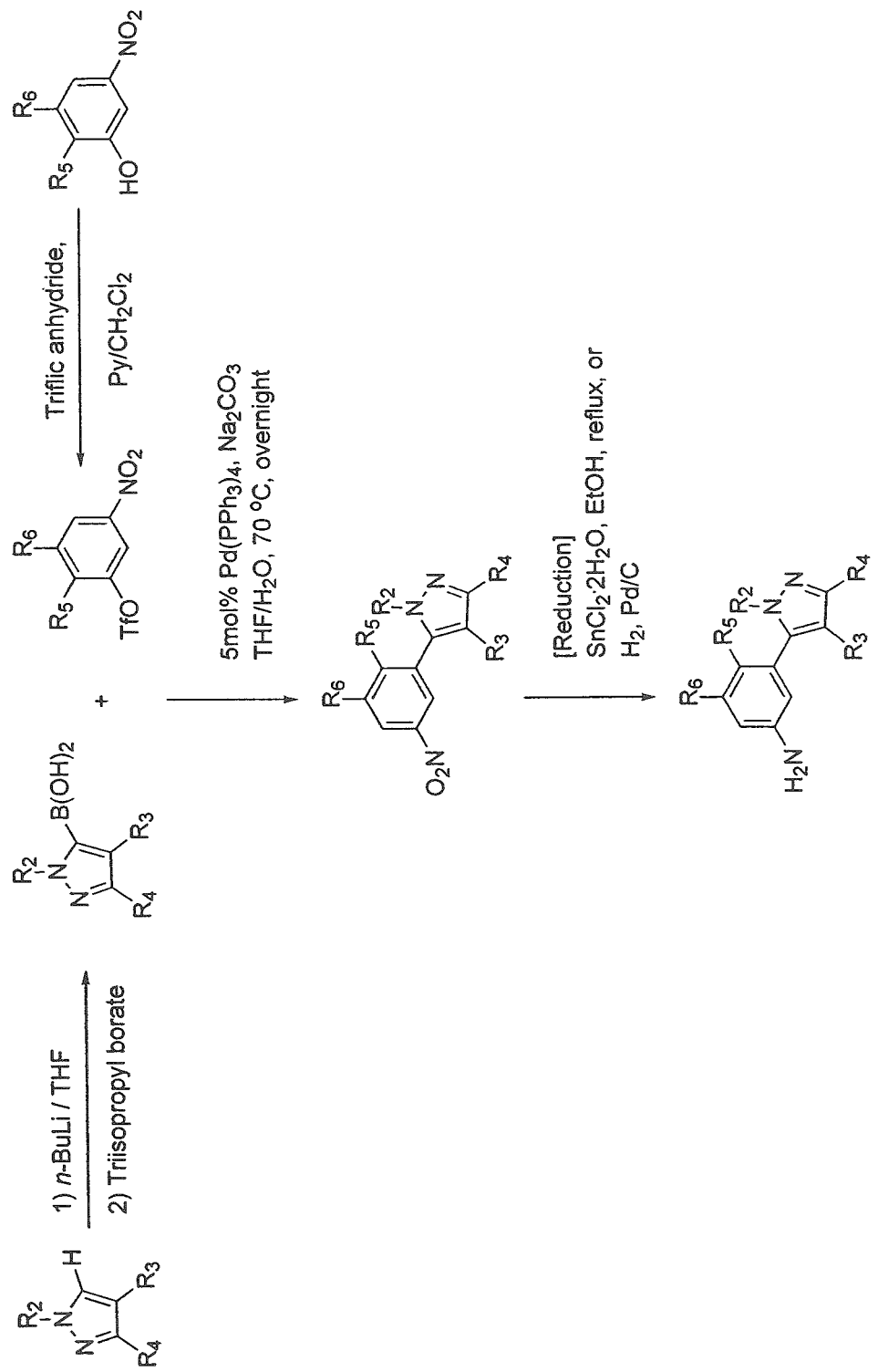
FIG. 17 shows the general synthetic scheme for the preparation of intermediate compounds of the present invention.
Figure 18:
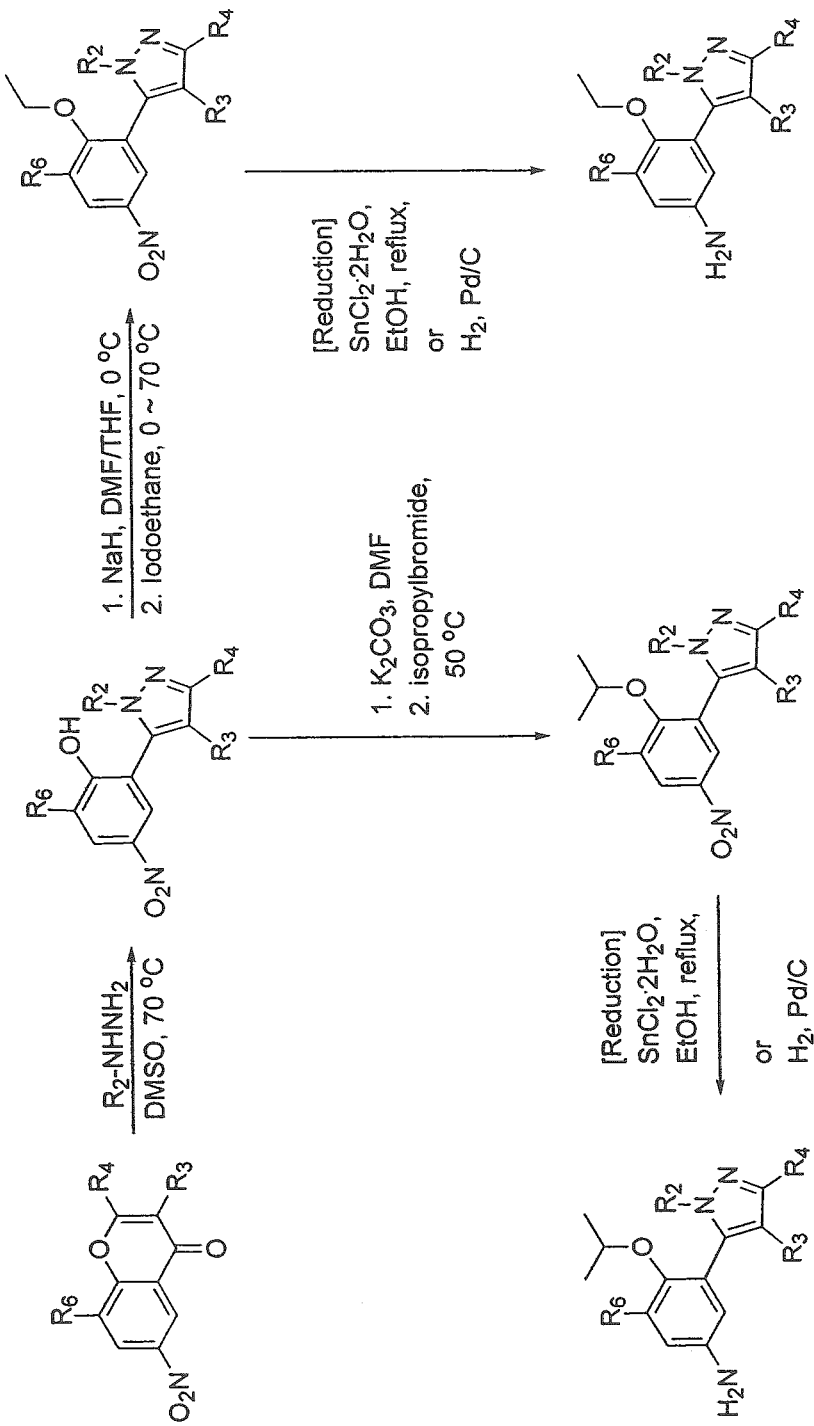
FIG. 18 shows the general synthetic scheme for the preparation of intermediate compounds of the present invention.
Figure 19:
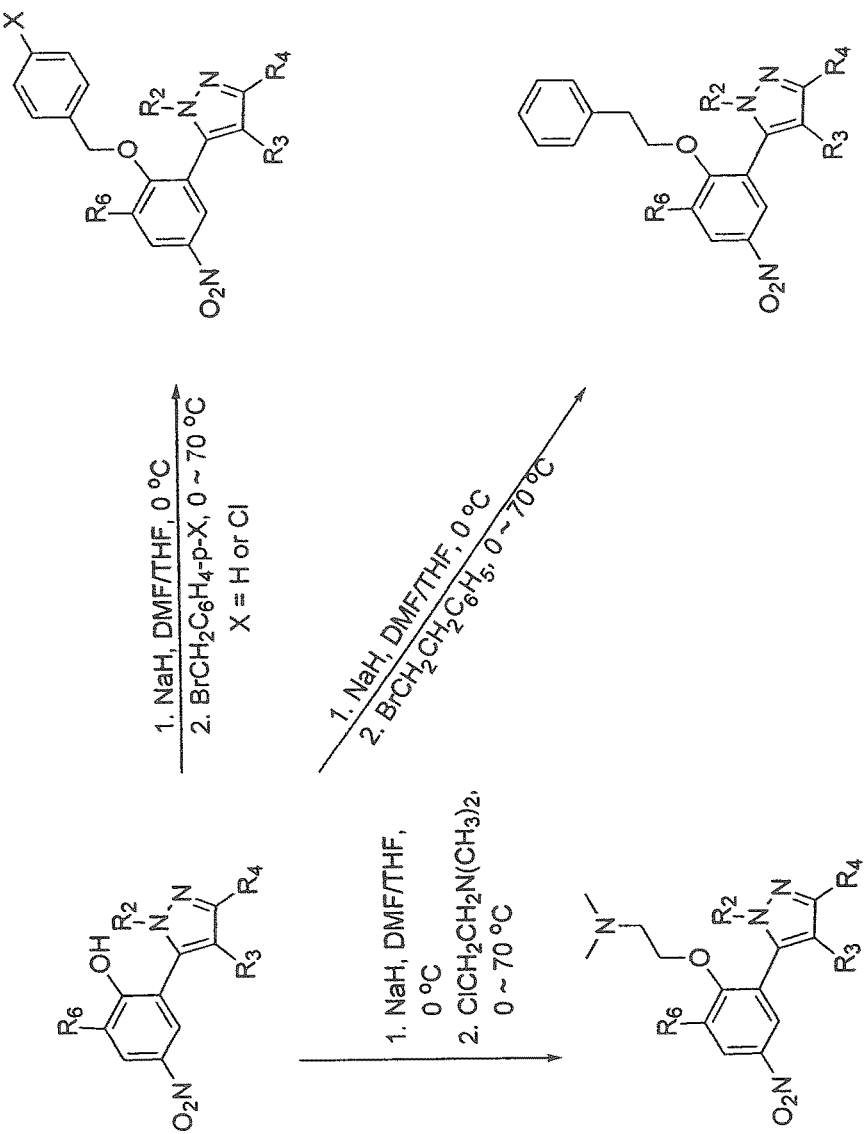
FIG. 19 shows the general synthetic scheme for the preparation of intermediate compounds useful in the preparation of compounds of the present invention.
Figure 20:
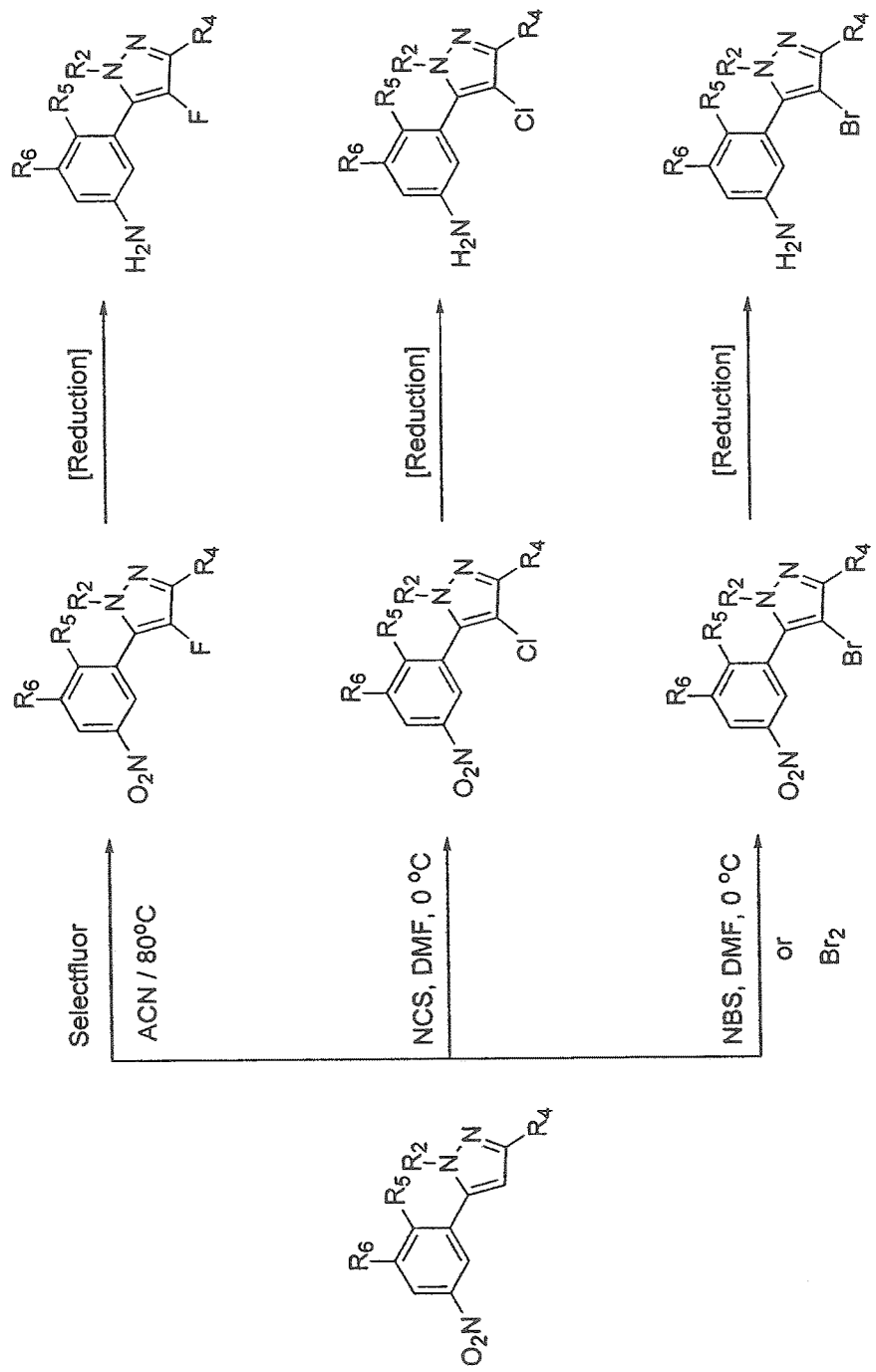
FIG. 20 shows the general synthetic scheme for the preparation of intermediate compounds useful in the preparation of compounds of the present invention.
Figure 21:
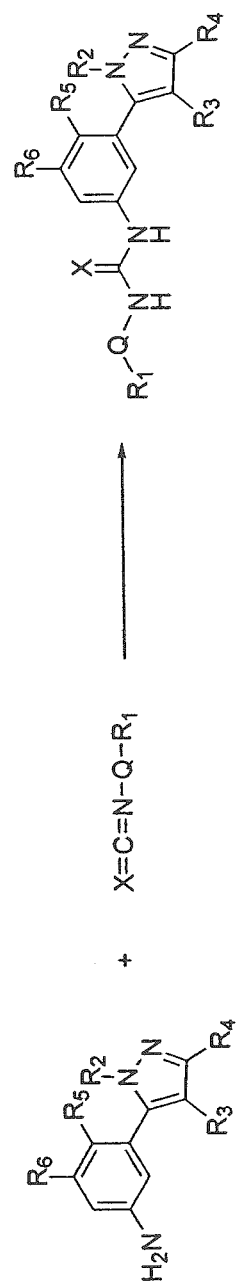
FIG. 21 shows the general synthetic scheme for the preparation of compounds of the present invention.

Analysis:

FIGS. 16A-C provide grey-scale representative autoradiographic sections from this study. FIG. 16A evidences darker bands (derived from $^{125}$I-LSD binding) primarily in both the fourth layer of the cerebral cortex (primarily 5HT$_{2A}$ receptors), and the caudate nucleus (primarily dopamine D2 receptors and some 5HT$_{2A}$ receptors). As can be seen from FIG. 16B, spiperone, which is a 5HT$_{2A}$ and dopamine D2 antagonist, displaces the I$^{125}$-LSD from these receptors on both the cortex and the caudate. As can be further seen from FIG. 16C, Compound S-1610, [3-(4-Bromo-2-methyl-2H-pyrazol-3-yl)-phenyl]-carbamic acid 4-methoxy-phenyl ester, appears to selectively displace the $^{125}$P-LSD from the cortex (5HT$_{2A}$) and not the caudate (dopamine D2).

Example 7

Screening Compounds Known to have 5-HT$_{2C}$ Antagonist Activity Against Non-Endogenous, Constitutively Activated Human Serotonin Receptor: AP-1

A final concentration of 12.5 µg membranes prepared from COS7 cells (see Example 3) transiently expressing constitutively active mutant human 5HT$_{2C}$ receptor AP-1 were incubated with binding buffer (20 mM HEPES, pH 7.4, 100 mM NaCl, 20 mM MgCl$_2$○6H$_2$0, 0.2% saponin, and 0.2 mM ascobate), GDP(1 μM) and compound in a 96-well plate format for a period of 60 minutes at ambient room temperature. Plates were then centrifuged at 4,000 rpm for 15 minutes followed by aspiration of the reaction mixture and counting for 1 minute in a Wallac™ MicroBeta plate scintillation counter. A series of compounds known to possess reported 5HT$_{2C}$ antagonist activity were determined to be active in the [$^{35}$S]GTPγS binding assay using AP-1. IC$_{50}$ determinations were made for these commercially available compounds (RBI, Natick, Mass.). Results are summarized in TABLE 5. For each determination, eight concentrations of test compounds were tested in triplicate. The negative control in these experiments consisted of AP-1 receptor without test compound addition, and the positive control consisted of 12.5 μg/well of COS7 cell membranes expressing the CMV promoter without expressed AP-1 receptor.

TABLE 5

| Test Compound | Known Pharmacology | IC$_{50}$ (nM) in GTP-γ-[$^{35}$S] Assay |
| --- | --- | --- |
| Metergoline | 5HT2/IC antagonist | 32.0 |
| Mesulergine | 5HT2/IC antagonist | 21.2 |
| Methysergide | 5HT2/IC antagonist | 6.1 |
| Methiothepin | 5HTI antagonist | 20.4 |
| Normethylclozapin | 5HT2/IC antagonist | 21.4 |
| Fluoxetine | 5HT reuptake inhibitor | 114.0 |
| Ritanserin | 5HT2/IC antagonist | 19.4 |

The IC$_{50}$ results confirm that the seven tested compounds showed antagonist activity at the AP-1 receptor.

Example 8

Receptor Binding Assay

In addition to the methods described herein, another means for evaluating a test compound is by determining binding affinities to the 5-HT$_{2A}$ receptor. This type of assay generally requires a radiolabelled ligand to the 5-HT$_{2A}$ receptor. Absent the use of known ligands for the 5-HT$_{2A}$ receptor and radiolabels thereof, compounds of the present invention can be labelled with a radioisotope and used in an assay for evaluating the affinity of a test compound to the 5-HT$_{2A}$ receptor.

A radiolabelled 5-HT$_{2A}$ compound of Formula (I) can be used in a screening assay to identify/evaluate compounds. In general terms, a newly synthesized or identified compound (i.e., test compound) can be evaluated for its ability to reduce binding of the "radiolabelled compound of Formula (I)" to the 5-HT$_{2A}$ receptor. Accordingly, the ability to compete with the "radiolabelled compound of Formula (I)" or Radiolabelled 5-HT$_{2A}$ Ligand for the binding to the 5-HT$_{2A}$ receptor directly correlates to its binding affinity of the test compound to the 5-HT$_{2A}$ receptor.
Assay Protocol for Determining Receptor Binding for 5-HT$_{2A}$:
  A. 5-HT$_{2A}$ RECEPTOR PREPARATION
  293 cells (human kidney, ATCC), transiently transfected with 10 μg human 5-HT$_{2A}$ receptor and 60 ul Lipofectamine (per 15-cm dish), are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C, until used in binding assay. When used in the assay, membranes are thawed on ice for 20 minutes and then 10 mL of incubation buffer (20 mM Hepes, 1 mM MgCl$_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.
  B. Binding Assay
  For total binding, a total volume of 50 ul of appropriately diluted membranes (diluted in assay buffer containing 50 mM Tris HCl (pH 7.4), 10 mM MgCl$_2$, and 1 mM EDTA; 5-50 μg protein) is added to 96-well polyproylene microtiter plates followed by addition of 100 μl of assay buffer and 50 μl of Radiolabelled 5-HT$_{2A}$ Ligand. For nonspecific binding, 50 μl of assay buffer is added instead of 100 μl and an additional 50 μl of 10 μM cold 5-HT$_{2A}$ is added before 50 μl of Radiolabelled 5-HT$_{2A}$ Ligand is added. Plates are then incubated at room temperature for 60-120 minutes. The binding reaction is terminated by filtering assay plates throh a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 μl of Optiphase Supermix is added to each well, the top of the plates are sealed, and plates are counted in a Trilux MicroBeta scintillation counter. For compound competition studies, instead of adding 100 μl of assay buffer, 100 μl of appropriately diluted test compound is added to appropriate wells followed by addition of 50 μl of Radiolabelled 5-HT$_{2A}$ Ligand.
  C. Calculations
  The test compounds are initially assayed at 1 and 0.1 μM and then at a range of concentrations chosen such that the middle dose would cause about 50% inhibition of a Radio-5-HT$_{2A}$ Ligand binding (i.e., IC$_{50}$). Specific binding in the absence of test compound (Bo) is the difference of total binding (B$_T$) minus non-specific binding (NSB) and similarly specific binding (in the presence of test compound) (B) is the difference of displacement binding (B$_D$) minus non-specific binding (NSB). IC$_{50}$ is determined from an inhibition response curve, logit-log plot of % B/Bo vs concentration of test compound.

K$_i$ is calculated, for example, by the Cheng and Prustoff transformation:

$$K_i = IC_{50}/(1+[L]/K_D)$$

where [L] is the concentration of a Radio-5-HT$_{2A}$ Ligand used in the assay and K$_D$ is the dissociation constant of a Radio-5-HT$_{2A}$ Ligand determined independently under the same binding conditions.

Example 9

Activity of Compounds of the Present Invention in the IP$_3$ Accumulation Assay

Certain compounds of the present invention and their corresponding activities in the IP Accumulation Assay are shown in TABLE 6.

TABLE 6

| Compound No. | 5-HT$_{2A}$ (IC$_{50}$)*<br>IP$_3$ Accumulation Assay (nM) |
|---|---|
| 20 | 0.45 |
| 60 | 1.10 |
| 61 | 8.57 |
| 79 | 13.0 |
| 84 | 12.2 |

*Reported values are averages of at least two trials.

The majority of the other compounds of the Examples were tested at least once and they showed IC$_{50}$ activities in the 5-HT$_{2A}$ IP$_3$ Accumulation Assay of at least about 10 μM.

Example 10

Efficacy of Compounds of the Invention in the Attenuation of DOI-Induced Hypolocomotion in Rats In this example, compounds of the invention, such as Compound 1 and Compound 26, were tested for inverse agonist activity by determining whether these compounds could attenuate DOI-induced hypolocomotion in rats in a novel environment. DOI is a potent 5HT2A/2C receptor agonist that crosses the blood-brain barrier.

Animals:

Male Sprague-Dawley rats (Harlan, San Diego, Calif.) weighing between 200-300 g were used for all tests. Rats were housed three to four per cage. These rats were naïve to experimental testing and drug treatment. Rats were handled one to three days before testing to acclimate them to experimental manipulation. Rats were fasted overnight prior to testing.

Compounds:

(R)-DOI HCl (C$_{11}$H$_{16}$INO$_2$.HCl) was obtained from Sigma-Aldrich, and was dissolved in 0.9% saline. Compounds of the invention were synthesized at Arena Pharmaceuticals Inc. and were dissolved in 100% PEG400. DOI was injected s.c. in a volume of 1 ml/kg, while compounds of the invention were administered p.o. in a volume of 2 ml/kg.

Procedure:

The "Motor Monitor" (Hamilton-Kinder, Poway, Calif.) was used for all activity measurement. This apparatus recorded rears using infrared photobeams.

Locomotor activity testing was conducted during the light cycle (0630-1830) between 9:00 a.m. and 4:00 p.m. Animals were allowed 30 min acclimation to the testing room before testing began.

In determining the effects of compounds of the invention on DOI-induced hypoactivity, animals were first injected with vehicle or the compound of the invention (50 μmol/kg) in their home cages. Sixty minutes later, saline or DOI (0.3 mg/kg salt) was injected. 10 min after DOI administration, animals were placed into the activity apparatus and rearing activity was measured for 10 minutes.

Figure 22:
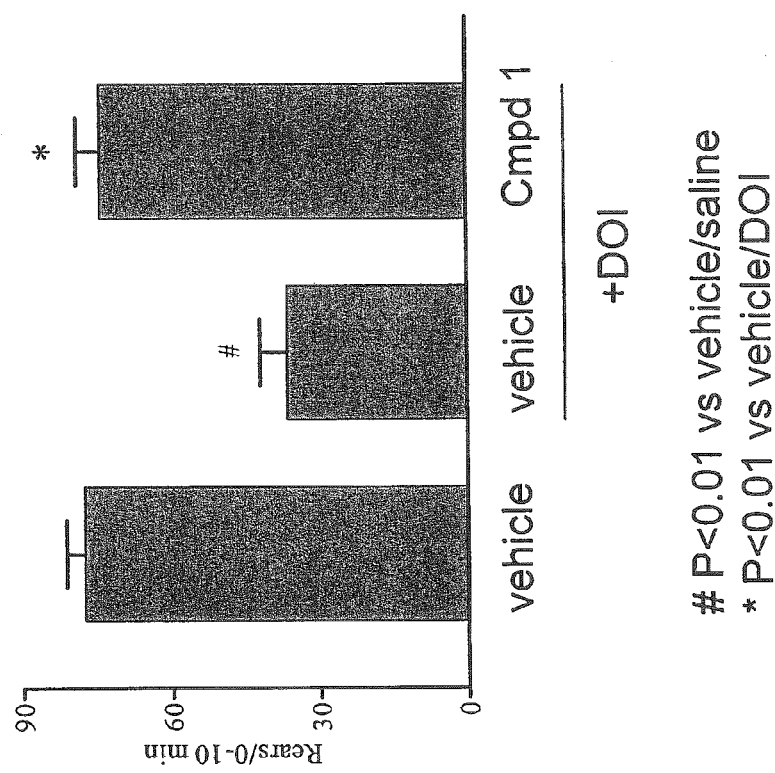
FIG. 22 shows the effect of Compound 1 on DOI-induced hypolocomotion in rats.
Figure 23:
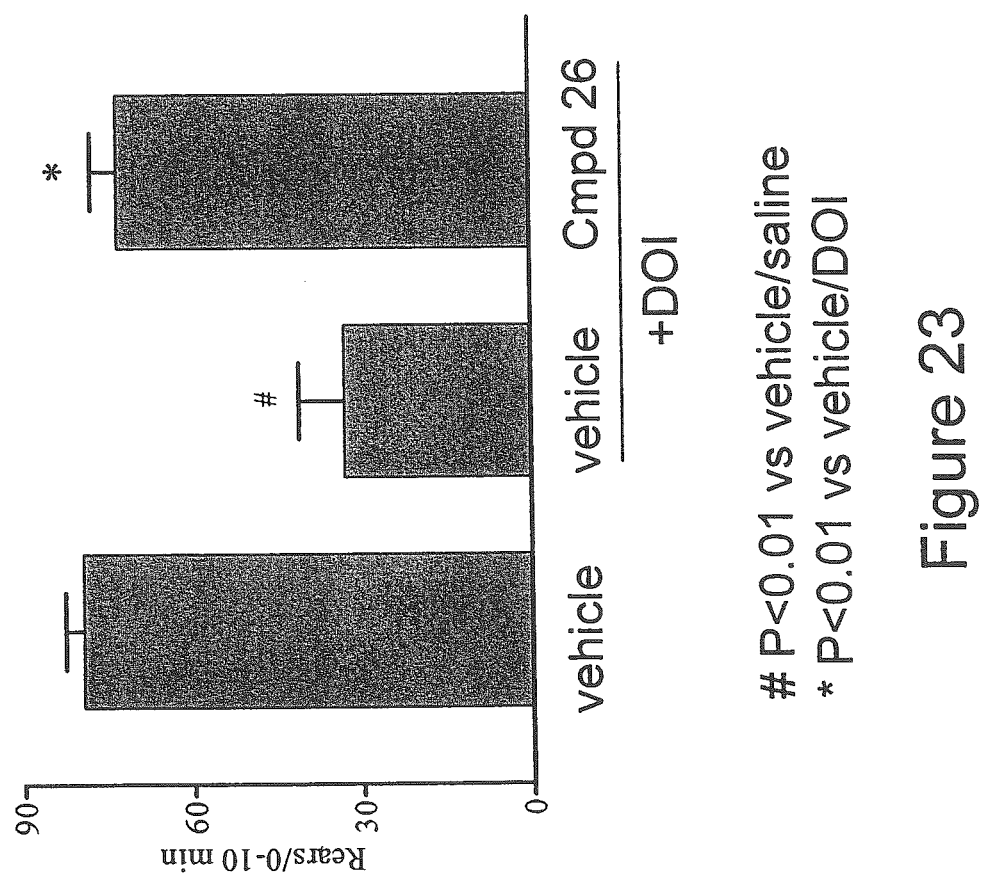
FIG. 23 shows the effect of Compound 26 on DOI-induced hypolocomotion in rats.
Figure 25:
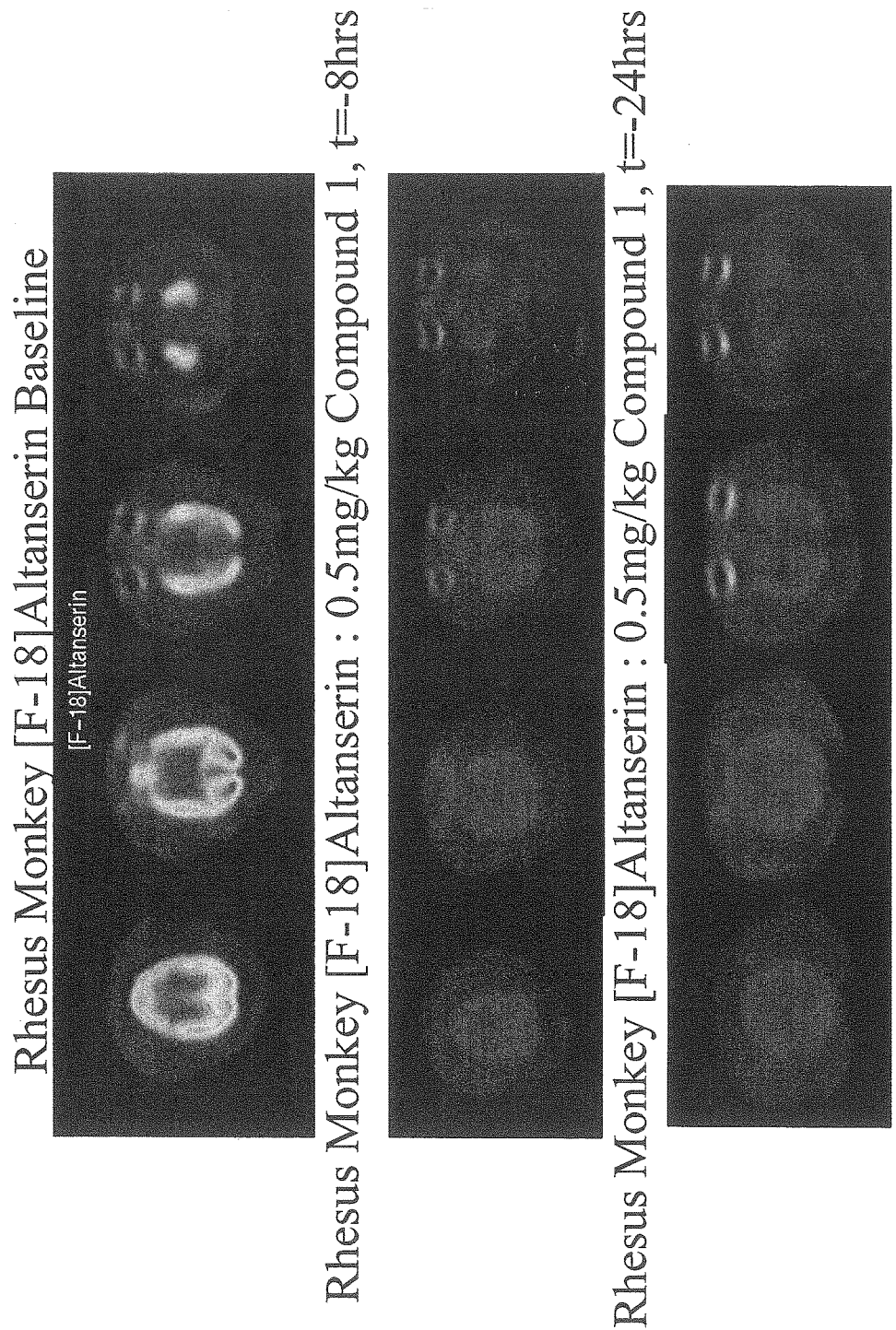
FIG. 25 shows PET scan images of monkey brains 8 or 24 hours after treatment with Compound 1 compared to a baseline PET scan (transaxial view).

Statistics and Results:

Results (total rears over 10 minutes) were analyzed by t-test. P<0.05 was considered significant. As shown in FIG. 22, Compound 1 attenuated DOI-induced hypolocomotion in rats. In addition, as shown in FIG. 23, Compound 26 also attenuated DOI-induced hypolocomotion in rats.

Example 11

Serotonin 5-HT2A Receptor Occupancy Studies in Monkey

In this example, the 5HT2A receptor occupancy of a compound of the invention, Compound 1, was measured. The study was carried out in rhesus monkeys using PET and $^{18}$F-altanserin.

Radioligand: The PET radioligand used for the occupancy studies was $^{18}$F-altanserin. Radiosynthesis of $^{18}$F-altanserin is achieved in high specific activities and is suitable for radiolabeling 5HT2a receptors in vivo (see Staley et al., Nucl. Med. Biol., 28:271-279 (2001) and references cited within). Quality control issues (chemical and radiochemical purity, specific activity, stability etc) and appropriate binding of the radioligand were verified in rat brain slices prior to use in PET experiments.

Drug Doses and Formulations:

Briefly, the radiopharmaceutical was dissolved in sterile 0.9% saline, pH approx 6-7. The compounds of the invention (Compound 1) were dissolved in 60% PEG 400-40% sterile saline on the same day of the PET experiment.

Serotonin 5HT2a occupancy studies in humans have been reported for M100,907 (Grunder et al., Neuropsychopharmacology, 17:175-185 (1997), and Talvik-Lofti et al., Psychophamacology, 148:400-403 (2000)). High occupancies of the 5HT2a receptors have been reported for various oral doses (doses studied ranged from 6 to 20 mg). For example, an occupancy of >90% was reported for a dose of 20 mg (Talvik-Lofti et al., supra), which translates to approx. 0.28 mg/kg. It may therefore be anticipated that an i.v. dose of 0.1 to 0.2 mg/kg of M100,907 is likely to provide high receptor occupancy. A 0.5 mg/kg dose of Compound 1 was used in these studies.

PET Experiments:

The monkey was anesthetized by using ketamine (10 mg/kg) and was maintained using 0.7 to 1.25% isoflurane. Typically, the monkey had two i.v. lines, one on each arm. One i.v. line was used to administer the radioligand, while the other line was used to draw blood samples for pharmacokinetic data of the radioligand as well as the cold drugs. Generally, rapid blood samples were taken as the radioligand is administered which then taper out by the end of the scan. A volume of approximately 1 ml of blood was taken per time point, which was spun down, and a portion of the plasma was counted for radioactivity in the blood.

An initial control study was carried out in order to measure baseline receptor densities. PET scans on the monkey were separated by at least two weeks. Unlabeled drug (Compound 1) was administered intravenously, dissolved in 80% PEG 400:40% sterile saline.

PET Data Analysis:

PET data were analyzed by using cerebellum as the reference region and using the distribution volume region (DVR) method. This method has been applied for the analysis of $^{18}$F-altanserin PET data in nonhuman primate and human studies (Smith et al., Synapse, 30:380-392 (1998).

The 5HT2A occupancy (rhesus monkey experimental methods) of Compound 1 is shown in FIGS. 24-27. The results of both an 8 hour and 24 hour study are shown. The test compound was administered via i.v. infusion in 5.0 ml of 80% PEG400. For the 8 hour study, venous blood samples were drawn at 5 minutes post Compound 1 and 15 minutes before PET scan. For the 24 hour study, venous blood samples were drawn at 5 minutes post Compound 1 and 10 minutes before PET scan.

The results show that 5HT2A receptor occupancy of Compound 1 at the dose of 0.5 mg/kg after 8 hours following drug administration was approximately 90% in the cortical regions, which is an area of high 5HT2A receptor density. This occupancy dropped to approximately 80% at 24 hours post-injection although no measurable test drug concentrations were apparent in plasma samples after 8 hours.

Example 12

The Effect of Compounds of the Invention and Zolpidem on Delta Power in Rats

In this example, the effect of Compounds of the Invention, such as Compound 1 and Compound 26, on sleep and wakefullness was compared to the reference drug zolpidem. Drugs were administered during the middle of the light period (inactivity period).

Briefly, four compounds of the invention, including Compound 1 (1.0 mg/kg) and Compound 26 (1.4 mg/kg), were tested for their effects on sleep parameters and were compared to zolpidem (5.0 mg/kg, Sigma, St. Louis, Mo.) and vehicle control (80% Tween 80, Sigma, St. Louis, Mo.). A repeated measures design was employed in which each rat was to receive seven separate dosings via oral gavage.

The first and seventh dosings were vehicle and the second through sixth were the test compounds and zolpidem given in counter-balanced order. Since all dosings were administered while the rats were connected to the recording apparatus, 60% $CO_2$/40% $O_2$ gas was employed for light sedation during the oral gavage process. Rats appeared fully recovered within 60 seconds following the procedure. A minimum of three days elapsed between dosings. In order to test the effect of the compounds on slee consolidation, dosing occurred during the middle of the rats' normal inactive period (6 hours following lights on). Dosing typically occurred between 13:15 and 13:45 using a 24 hour notation. All dosing solutions were made fresh on the day of dosing. Following each dosing, animals were continuously recorded until lights out the following day (~30 hours).

Animal Recording and Surgical Procedures:

Animals were housed in a temperature controlled recording room under a 12/12 light/dark cycle (lights on at 7:00 am) and had food and water available ad libitum. Room temperature (24+2° C), humidity (50+20% relative humidity) and lighting conditions were monitored continuously via computer. Drugs were administered via oral gavage as described above, with a minimum of three days between dosings. Animals were inspected daily in accordance with NIH guidelines.

Eight male Wistar rats (300+25 g; Charles River, Wilmington, Mass.) were prepared with chronic recording implants for continuous electroencephalograph (EEG) and electromyograph (EMG) recordings. Under isoflurane anesthesia (1-4%), the fur was shaved from the top of the skull and the skin was disinfected with Betadine and alcohol. A dorsal midline incision was made, the temporalis muscle retracted, and the skull cauterized and thoroughly cleaned with a 2% hydrogen peroxide solution. Stainless steel screws (#000) were implanted into the skull and served as epidural electrodes. EEG electrodes were positioned bilaterally at +2.0 mm AP from bregma and 2.0 mm ML and at −6.0 mm AP and 3.0 mm ML. Multi-stranded twisted stainless steel wire electrodes were sutured bilaterally in the neck muscles for recording of the EMG. EMG and EEG electrodes were soldered to a head plug connector that was affixed to the skull with dental acrylic. Incisions were closed with suture (silk 4-0) and antibiotics administered topically. Pain was relieved by a long-lasting analgesic (Buprenorphine) administered intramuscularly once post-operatively. Post-surgery, each animal was placed in a clean cage and observed until it recovered. Animals were permitted a minimum of one week post-operative recovery before study.

For sleep recordings, animals were connected via a cable and a counter-balanced commutator to a Neurodata model 15 data collection system (Grass-Telefactor, West Warwick, R.I.). The animals were allowed an acclimation period of at least 48 hours before the start of the experiment and were connected to the recording apparatus continuously throughout the experimental period except to replace damaged cables. The amplified EEG and EMG signals were digitized and stored on a computer using SleepSign software (Kissei Comtec, Irvine Calif.).

Data Analysis:

EEG and EMG data were scored visually in 10 second epochs for waking (W), REMS, NREMS. Scored data were analyzed and expressed as time spent in each state per half hour. Slee bout length and number of bouts for each state were calculated in hourly bins. A "bout" consisted of a minimum of two consecutive epochs of a given state. EEG delta power (0.5-3.5 Hz) within NREMS was also analyzed in hourly bins. The EEG spectra during NREMS were obtained offline with a fast Fourier transform algorithm on all epochs without artifact. The delta power was normalized to the average delta power in NREMS between 23:00 and 1:00, a time when delta power is normally lowest.

Data were analyzed using repeated measures ANOVA. Light phase and dark phase data were analyzed separately. Both the treatment effect within each rat and the time by treatment effect within each rat was analyzed. Since two comparisons were made, a minimum value of $P<0.025$ was required for post hoc analysis. When statistical significance was found from the ANOVAs, t-tests were performed comparing all compounds to vehicle and the test compounds to zolpidem.

Results:

Three rats completed the entire dosing protocol of 7 conditions. The remaining 5 animals completed only 3 to 6 of the 7 conditions, primarily because of loss of the implant. However, all drug conditions were tested on a minimum of 5 rats.

Although duration of the effect varied with each test compound, delta power was significantly increased ($p<0.05$) initially after dosing for all test compounds as compared to vehicle (see FIG. 28). There was a trend, and statistical significance in some conditions, for all compounds to increase NREMS bout length, while the number of Waking bouts and NREMS bouts were decreased as compared to vehicle. No significant effects were observed on Waking bout length, REMS bout length and bout number, or total time spent in each state.

These results demonstrate that compounds of the invention promote sleep consolidation in rats during a time in their circadian sleep cycle that their sleep is naturally fragmented. This conclusion is supported by the trend for all compounds to increase NREMS bout length while the number of Waking and NREMS bouts decreased. Delta power during NREMS increased during the same period when sleep consolidation was facilitated, indicating that these compounds can promote "deeper" sleep as well as sleep consolidation. Hence, compounds of the invention can be effective treatments for slee disorders.

No significant differences between the treatments were found for waking, NREMS sleep, or REMS sleep. Delta power during NREMS, however, was significantly different between drug conditions and vehicle control. Compound 1 and Compound 26 significantly increased delta power during the second hour following dosing (15:00).

No significant effects were found on either waking sleep bout length or number of bouts. Significant differences were found, however, in both NREMS and REMS bout length. Compound 1 significantly increased NREMS bout length during the second hour. The number of NREMS bouts did not show significance. REMS bout length was significantly increased by Compound 1 and Compound 26 during the fourth hour. The number of REMS bouts did not show significance.

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

What is claimed is:

1. A method for prophylaxis or treatment of reducing the risk of blood clot formation in an individual suffering from atrial fibrillation, comprising administering to said individual in need thereof a therapeutically effective amount of a compound of Formula (I):

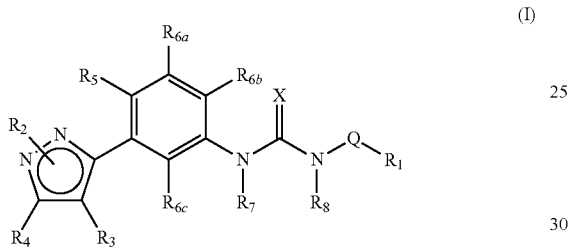

or a pharmaceutically acceptable salt, hydrate or solvate thereof;
wherein:
$R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

$R_2$ is selected from the group consisting of H, $C_{1-6}$ alkyl, $C_{2-6}$ alkenyl, $C_{2-6}$ alkynyl and $C_{3-7}$ cycloalkyl;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group is optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, amino, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl substituents are each optionally substituted with 1 to 5 further substituents selected from the group consisting of halogen and carbo-$C_{1-6}$-alkoxy;

$R_{6a}$, $R_{6b}$, and $R_{6c}$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_7$ and $R_8$ are independently H or $C_{1-8}$ alkyl;

X is O or S; and

Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

2. A method for prophylaxis or treatment of a sleep disorder in an individual comprising administering to said individual in need thereof a therapeutically effective amount of a compound of Formula (I):

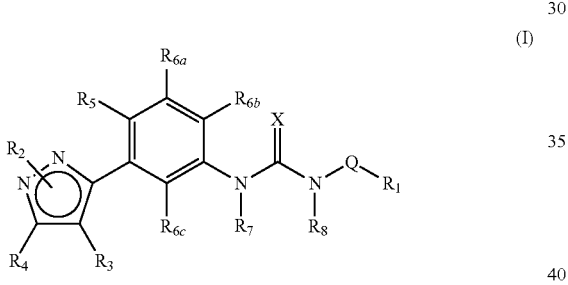

(I)

or a pharmaceutically acceptable salt, hydrate or solvate thereof;

wherein:

$R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{16}$ alkylthio, $C_{16}$ alkylureyl, amino, $C_{16}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

$R_2$ is selected from the group consisting of H, $C_{1-6}$ alkyl, $C_{2-6}$ alkenyl, $C_{2-6}$ alkynyl and $C_{3-7}$ cycloalkyl;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkyl sulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{16}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group is optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, amino, $C_{16}$ alkylamino, $C_{2-8}$ dialkylamino, $C_{1-4}$ alkylcarboxamide, $C_{2-6}$ alkynyl, $C_{1-4}$ alkyl sulfonamide, $C_{1-4}$ alkylsulfinyl, $C_{1-4}$ alkyl sulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl substituents are each optionally substituted with 1 to 5 further substituents selected from the group consisting of halogen and carbo-$C_{1-6}$-alkoxy;

$R_{6a}$, $R_{6b}$, and $R_{6c}$, are each independently selected from the group consisting of H, $C_{1-6}$ acyl, $C_{1-6}$ acyloxy, $C_{2-6}$ alkenyl, $C_{1-6}$ alkoxy, $C_{16}$ alkyl, $C_{1-6}$ alkylcarboxamide, $C_{2-6}$ alkynyl, $C_{1-6}$ alkyl sulfonamide, $C_{1-6}$ alkyl sulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_7$ and $R_8$ are independently H or $C_{1-8}$ alkyl;

X is O or S; and

Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

3. The method according to claim 2 wherein said sleep disorder comprises fragmented sleep architecture.

4. The method according to claim 2 wherein said effective amount of a compound of Formula (I) promotes sleep consolidation.

5. The method according to claim 2 wherein said effective amount of a compound of Formula (I) increases delta power.

6. The method according to claim 2 wherein said sleep disorder is a dyssomnia.

7. The method according to claim 6 wherein said dyssomnia is selected from the group consisting of psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome, inadequate sleep hygiene, environmental sleep disorder, altitude insomnia, adjustment sleep disorder, insufficient sleep syndrome, limit-setting sleep disorder, sleep-onset association disorder, nocturnal eating or drinking syndrome, hypnotic dependent sleep disorder, stimulant-dependent sleep disorder, alcohol-dependent sleep disorder, toxin-induced sleep disorder, time zone change (jet lag) syndrome, shift work sleep disorder, irregular sleep-wake pattern, delayed sleep phase syndrome, advanced sleep phase syndrome and non-24-hour sleep-wake disorder.

8. The method according to claim 2 wherein said sleep disorder is a parasomnia.

9. The method according to claim 8 wherein said parasomnia is selected from the group consisting of confusional arousals, sleepwalking and sleep terrors, rhythmic movement disorder, sleep starts, sleep talking and nocturnal leg cramps.

10. The method according to claim 2 wherein said sleep disorder is associated with a medical or psychiatric disorder.

11. A method for treating agitation in a patient in need of such treatment comprising administering to said patient a composition comprising a 5-HT2A inverse agonist of formula of Formula (I):

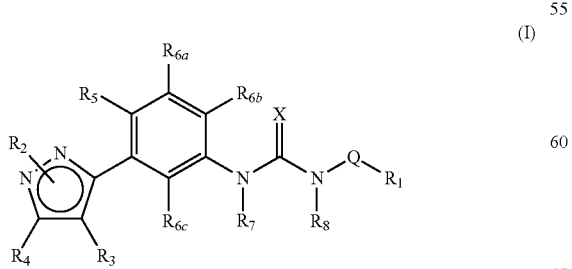

(I)

or a pharmaceutically acceptable salt, hydrate or solvate thereof;

wherein:

$R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkyl carb oxami de, $C_2$-6 alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl or Br; and wherein said $C_{2-6}$ alkenyl, $C_{1-6}$ alkyl, $C_{2-6}$ alkynyl, $C_{16}$ alkylamino, alkylimino, $C_{2-8}$ dialkylamino, heterocyclic, and phenyl are each optionally substituted with 1 to 5 substituents selected independently from the group consisting of $C_{1-6}$ acyl, $C_{16}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

$R_2$ is selected from the group consisting of H, $C_{1-6}$ alkyl, $C_{2-6}$ alkenyl, $C_{2-6}$ alkynyl and $C_{3-7}$ cycloalkyl;

$R_3$ is selected from the group consisting of H, $C_{2-6}$ alkenyl, $C_{16}$ alkyl, $C_{1-6}$ alkylcarboxamide, $C_{2-6}$ alkynyl, $C_{1-6}$ alkyl sulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{18}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{14}$ haloalkylthio, hydroxyl, nitro and sulfonamide;

$R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{16}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group is optionally substituted with 1 to 5 substituents selected independently from the group consisting of $C_{1-5}$ acyl, $C_1$5 acyloxy, $C_{2-6}$ alkenyl, $C_{1-4}$ alkoxy, $C_{1-8}$ alkyl, amino, $C_{1-6}$ alkylamino, $C_{2-8}$ dialkylamino, $C_{1-4}$ alkylcarboxamide, $C_{2-6}$ alkynyl, $C_{1-4}$ alkyl sulfonamide, $C_{1-4}$ alkylsulfinyl, $C_{1-4}$ alkyl sulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl substituents are each optionally substituted with 1 to 5 further substituents selected from the group consisting of halogen and carbo-$C_{1-6}$-alkoxy;

$R_{6a}$, $R_{6b}$, $R_{6b}$, and $R_{6c}$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_7$ and $R_8$ are independently H or $C_{1-8}$ alkyl;

X is O or S; and

Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

12. The method of claim 11, wherein the agitation is due to a psychiatric disorder other than dementia.

13. A method for the treatment of agitation or a symptom thereof in a patient suffering from dementia comprising administering to said patient a composition comprising a 5-HT2A inverse agonist of formula of Formula (I):

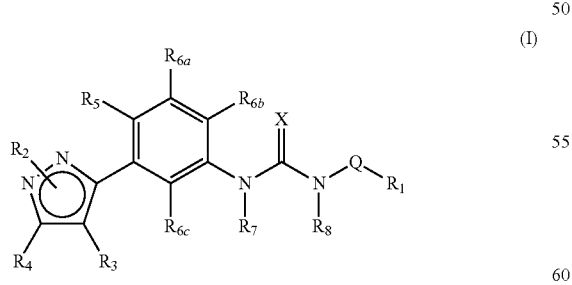

(I)

or a pharmaceutically acceptable salt, hydrate or solvate thereof;

wherein:

$R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{16}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

$R_2$ is selected from the group consisting of H, $C_{1-6}$ alkyl, $C_{2-6}$ alkenyl, $C_{2-6}$ alkynyl and $C_{3-7}$ cycloalkyl;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkylsulfonamide, carbo-$C_{1-6}$, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{16}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{18}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{37}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{16}$ haloalkylthio, hydroxyl, thiol, nitro and sulfonamide;

$R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{1-6}$ alkoxy group is optionally substituted with 1 to 5 substituents selected independently from the group consisting of $C_{1-5}$ acyl, $C_15$ acyloxy, $C_{2-6}$ alkenyl, $C_{1-4}$ alkoxy, $C_{18}$ alkyl, amino, $C_{1-6}$ alkylamino, $C_{2-8}$ dialkylamino, $C_{1-4}$ alkylcarboxamide, $C_{2-6}$ alkynyl, $C_{1-4}$ alkyl sulfonamide, $C_{1-4}$ alkylsulfinyl, $C_{1-4}$ alkyl sulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl substituents are each optionally substituted with 1 to 5 further substituents selected from the group consisting of halogen and carbo-$C_{1-6}$-alkoxy;

$R_{6a}$, $R_{6b}$, and $R_{6c}$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_7$ and $R_8$ are independently H or $C_{1-8}$ alkyl;

X is O or S; and

Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogen and oxo; or Q is a bond.

14. The method of claim 13, wherein the dementia is due to a degenerative disease of the nervous system.

15. The method of claim 13, wherein the dementia is selected from the group consisting of Alzheimer's disease, Lewy Body, Parkinson's disease, Huntington's disease, and dementia due to diseases that affect blood vessels, or any combination thereof.

16. A method of treating agitation or a symptom thereof in a patient in need of such treatment, where the patient is a cognitively intact elderly patient, comprising administering to said patient a composition comprising a 5-HT2A inverse agonist of Formula (I):

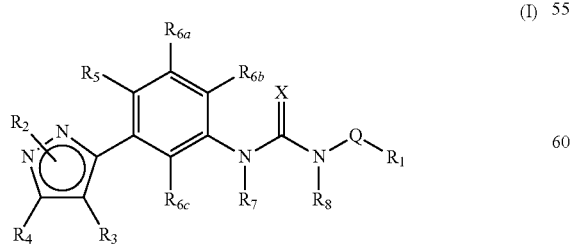

(I)

or a pharmaceutically acceptable salt, hydrate or solvate thereof;

wherein:

$R_1$ is aryl or heteroaryl each optionally substituted with $R_9$, $R_{10}$, $R_{11}$, $R_{12}$, $R_{13}$, $R_{14}$, and $R_{15}$ each selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, $C_{1-6}$ alkylimino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, heterocyclic, hydroxyl, thiol, nitro, phenoxy and phenyl, or two adjacent $R_9$, $R_{10}$, $R_{11}$, $R_{12}$, $R_{13}$, $R_{14}$, and $R_{15}$ together with the atoms to which they are attached form a $C_{5-7}$ cycloalkyl group or heterocyclic group each optionally substituted with F, Cl, or Br; and wherein said $C_{2-6}$ alkenyl, $C_{1-6}$ alkyl, $C_{2-6}$ alkynyl, $C_{1-6}$ alkylamino, $C_{1-6}$ alkylimino, $C_{2-8}$ dialkylamino, heterocyclic, and phenyl are each optionally substituted with 1 to 5 substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{-16}$-alkoxy, carboxamide, carboxy, cyano, $C_{3-7}$ cycloalkyl, $C_{2-8}$ dialkylcarboxamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol and nitro;

$R_2$ is selected from the group consisting of H, $C_{1-6}$ alkyl, $C_{2-6}$ alkenyl, $C_{2-6}$ alkynyl and $C_{37}$ cycloalkyl;

$R_3$ is selected from the group consisting of H, $C_{2-6}$ alkenyl, $C_{1-6}$ alkyl, $C_{1-6}$ alkylcarboxamide, $C_{2-6}$ alkynyl, $C_{1-6}$ alkyl sulfonamide, carbo-$C_{1-6}$-alkoxy, carboxamide, carboxy, cyano, $C_{3-7}$ cycloalkyl, $C_{2-8}$ dialkylcarboxamide, halogen, heteroaryl and phenyl; and wherein each of said $C_{2-6}$ alkenyl, $C_{1-6}$ alkyl, $C_{2-6}$ alkynyl, $C_{1-6}$ alkylsulfonamide, $C_{3-7}$ cycloalkyl, heteroaryl and phenyl groups can be optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-6}$ alkylamino, $C_{2-8}$ dialkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and sulfonamide;

$R_4$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_5$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{2-8}$ dialkylcarboxamide, $C_{2-8}$ dialkylsulfonamide, halogen, $C_{1-6}$ haloalkoxy, $C_{1-6}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide, wherein said $C_{16}$ alkoxy group is optionally substituted with 1 to 5 substituents selected independently from the group consisting of $C_{1-5}$ acyl, $C_{1-5}$ acyloxy, $C_{26}$ alkenyl, $C_{1-4}$ alkoxy, $C_{1-8}$ alkyl, amino, $C_{16}$ alkylamino, $C_{2-8}$ dialkylamino, $C_{1-4}$ alkylcarboxamide, $C_{2-6}$ alkynyl, $C_{1-4}$ alkyl sulfonamide, $C_{1-4}$ alkylsulfinyl, $C_{1-4}$ alkyl sulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{-26}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, nitro and phenyl, and wherein said amino and phenyl substituents are each optionally substituted with 1 to 5 further substituents selected from the group consisting of halogen and carbo-$C_{16}$-alkoxy;

$R_{ha}$, $R_{6b}$, and $R_{bc}$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylcarboxamide, $C_{2-6}$ alkynyl, $C_{1-6}$ alkyl sulfonamide, $C_{1-6}$ alkylsulfinyl, $C_{1-6}$ alkylsulfonyl, $C_{1-6}$ alkylthio, $C_{1-6}$ alkylureyl, amino, $C_{1-6}$ alkylamino, $C_{2-8}$ dialkylamino, carbo-$C_{1-6}$-alkoxy, carboxamide, carboxy, cyano, $C_{3-7}$ cycloalkyl, $C_{28}$ dialkylcarboxamide, $C_{2-8}$ dialkylsulfonamide, halogen, $C_{1-6}$ haloalkoxy, $C_{16}$ haloalkyl, $C_{1-6}$ haloalkylsulfinyl, $C_{1-6}$ haloalkylsulfonyl, $C_{1-6}$ haloalkylthio, hydroxyl, thiol, nitro and sulfonamide;

$R_7$ and $R_8$ are independently H or $C_{1-8}$ alkyl;

X is O or S; and

Q is $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl, halogennd oxo; or Q is a bond.

\* \* \* \* \*